(12) United States Patent
Clark et al.

(10) Patent No.: US 11,390,678 B2
(45) Date of Patent: Jul. 19, 2022

(54) COMPOSITIONS AND METHODS FOR THE TREATMENT OF IMMUNE RELATED DISEASES

(71) Applicant: Genentech, Inc., South San Francisco, CA (US)

(72) Inventors: Hilary Clark, San Francisco, CA (US); Dan Eaton, San Rafael, CA (US); Lino Gonzalez, Jr., Menlo Park, CA (US); Jane Grogan, San Francisco, CA (US); Jason A. Hackney, Palo Alto, CA (US); Kristin Bowles, Pacifica, CA (US); Xin Yu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 95 days.

(21) Appl. No.: 16/537,280

(22) Filed: Aug. 9, 2019

(65) Prior Publication Data

US 2020/0317773 A1 Oct. 8, 2020

Related U.S. Application Data

(60) Division of application No. 15/231,032, filed on Aug. 8, 2016, now abandoned, which is a division of application No. 13/648,191, filed on Oct. 9, 2012, now Pat. No. 9,499,596, which is a continuation of application No. 12/420,234, filed on Apr. 8, 2009, now abandoned.

(60) Provisional application No. 61/194,271, filed on Sep. 26, 2008, provisional application No. 61/123,530, filed on Apr. 9, 2008.

(51) Int. Cl.
| | |
|---|---|
| *C07K 16/28* | (2006.01) |
| *C07K 14/705* | (2006.01) |
| *C07K 16/18* | (2006.01) |
| *G01N 33/50* | (2006.01) |
| *G01N 33/564* | (2006.01) |
| *G01N 33/569* | (2006.01) |
| *C07K 14/47* | (2006.01) |
| *A61K 39/00* | (2006.01) |

(52) U.S. Cl.
CPC ...... *C07K 16/2803* (2013.01); *C07K 14/4702* (2013.01); *C07K 14/70503* (2013.01); *C07K 16/18* (2013.01); *G01N 33/505* (2013.01); *G01N 33/564* (2013.01); *G01N 33/56972* (2013.01); *A61K 2039/505* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/75* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,364,934 A | 11/1994 | Drayna et al. |
| 5,750,345 A | 5/1998 | Bowie |
| 5,989,811 A | 11/1999 | Veltri et al. |
| 6,518,033 B1 | 2/2003 | Gromeier et al. |
| 7,193,069 B2 | 3/2007 | Isogai et al. |
| 7,282,570 B2 | 10/2007 | Goddard et al. |
| 7,943,743 B2 | 5/2011 | Korman et al. |
| 8,431,350 B2 | 4/2013 | Baldwin et al. |
| 8,728,474 B2 | 5/2014 | Honjo et al. |
| 9,499,596 B2 | 11/2016 | Clark et al. |
| RE46,534 E | 9/2017 | Baldwin et al. |
| 9,873,740 B2 | 1/2018 | Grogan et al. |
| RE46,805 E | 4/2018 | Baldwin et al. |
| RE46,816 E | 5/2018 | Baldwin et al. |
| 10,017,572 B2 | 7/2018 | Grogan et al. |
| 10,047,158 B2 | 8/2018 | Grogan et al. |
| 2004/0005560 A1 | 1/2004 | Isogai et al. |
| 2004/0101876 A1 | 5/2004 | Mintz et al. |
| 2004/0121343 A1 | 6/2004 | Buechler et al. |
| 2004/0121370 A1 | 6/2004 | Baldwin et al. |
| 2004/0219521 A1 | 11/2004 | Tang et al. |
| 2004/0258678 A1 | 12/2004 | Bodary et al. |
| 2006/0105376 A1 | 5/2006 | Isogai et al. |
| 2006/0199181 A1 | 9/2006 | Bodary et al. |
| 2007/0041985 A1 | 2/2007 | Unger et al. |
| 2007/0054360 A1 | 3/2007 | Gao et al. |
| 2007/0243584 A1 | 10/2007 | West |
| 2007/0254339 A1 | 11/2007 | West et al. |
| 2008/0038264 A1 | 2/2008 | Bodary et al. |
| 2008/0050809 A1 | 2/2008 | Abuin et al. |
| 2009/0156495 A1 | 6/2009 | Gao et al. |

(Continued)

FOREIGN PATENT DOCUMENTS

| | | |
|---|---|---|
| CL | 2017000080 A1 | 6/2017 |
| CL | 2017000310 A1 | 8/2017 |

(Continued)

OTHER PUBLICATIONS

Progress in Autoimmune Diseases Research, 2005, pp. 1-126.*
"A study of Tiragolumab in Combination With Atezolizumab in Chemotherapy-Naïve Patients with Locally Advanced or Metastatic Non-Small Cell Lung Cancer," Jun. 20, 2018 (Jun. 20, 2018), XP002801580, Retrieved from the Internet: <URL:https://clinicaltrials.gov/ct2/show/NCT03563716> [retrieved on Jan. 11, 2021].
Avrillon et al., "First real life data on durvalumab after definitive concomitant chemoradiotherapy (cCRT) in unresectable stage (St) III non-small cell lung cancer (NSCLC) in France: Analysis of 591 patients (pts) enrolled in the French cohort (c) temporary authorization of use (ATU)," Annals of Oncology. 30(S5):v597 (2019).

(Continued)

*Primary Examiner* — Amy E Juedes
(74) *Attorney, Agent, or Firm* — Clark & Elbing LLP; Karen L. Elbing

(57) ABSTRACT

The present invention relates to compositions and methods of using those compositions for the diagnosis and treatment of immune related diseases.

20 Claims, 60 Drawing Sheets

Specification includes a Sequence Listing.

(56) References Cited

U.S. PATENT DOCUMENTS

| | | |
|---|---|---|
| 2009/0181024 A1 | 7/2009 | Baldwin et al. |
| 2009/0258013 A1 | 10/2009 | Clark et al. |
| 2010/0075377 A1 | 3/2010 | West et al. |
| 2010/0316646 A1 | 12/2010 | Gao et al. |
| 2011/0104170 A1 | 5/2011 | Baldwin et al. |
| 2012/0219540 A1 | 8/2012 | Gao et al. |
| 2013/0095102 A1 | 4/2013 | Levin et al. |
| 2013/0251720 A1 | 9/2013 | Clark et al. |
| 2014/0186380 A1 | 7/2014 | Gurney et al. |
| 2014/0341902 A1 | 11/2014 | Maecker et al. |
| 2015/0216970 A1 | 8/2015 | Grogan et al. |
| 2016/0152720 A1 | 6/2016 | Kim et al. |
| 2016/0176963 A1 | 6/2016 | Maurer et al. |
| 2017/0037127 A1 | 2/2017 | Grogan et al. |
| 2017/0044256 A1 | 2/2017 | Grogan et al. |
| 2017/0088613 A1 | 3/2017 | Grogan et al. |
| 2017/0143825 A1 | 5/2017 | Grogan |
| 2017/0145093 A1 | 5/2017 | Clark et al. |
| 2018/0169239 A1 | 6/2018 | Grogan |
| 2019/0016807 A1 | 1/2019 | Irving et al. |
| 2019/0119376 A1 | 4/2019 | Grogan et al. |

FOREIGN PATENT DOCUMENTS

| | | |
|---|---|---|
| CL | 2017001660 A1 | 3/2018 |
| CL | 2017003021 A1 | 6/2018 |
| CL | 2018000744 A1 | 7/2018 |
| CN | 1720336 A | 1/2006 |
| CN | 101035807 A | 9/2007 |
| CN | 103073644 A | 5/2013 |
| CN | 105492025 A | 4/2016 |
| CN | 108290946 A | 7/2018 |
| CN | 110079599 A | 8/2019 |
| CN | 110662552 A | 1/2020 |
| CN | 110799541 A | 2/2020 |
| CN | 111050788 A | 4/2020 |
| EP | 1516629 A2 | 3/2005 |
| EP | 2279412 | 2/2011 |
| EP | 1516629 B1 | 4/2013 |
| EP | 3126394 | 2/2017 |
| GB | 2408508 A | 6/2005 |
| JP | 2006-508649 A | 3/2006 |
| JP | 2006-521082 A | 9/2006 |
| JP | 2011-523034 A | 8/2011 |
| RU | 2016/104880 A | 8/2017 |
| RU | 2016/142476 A | 5/2018 |
| WO | WO-99/63063 A1 | 12/1999 |
| WO | WO-00/53758 A2 | 9/2000 |
| WO | WO-00/58334 A1 | 10/2000 |
| WO | WO-01/05972 A1 | 1/2001 |
| WO | WO-01/29221 A2 | 4/2001 |
| WO | WO-01/75116 A2 | 10/2001 |
| WO | WO-01/75166 A2 | 10/2001 |
| WO | WO-01/94413 A2 | 12/2001 |
| WO | WO-02/099062 A2 | 12/2002 |
| WO | WO-03/054152 A2 | 7/2003 |
| WO | WO-03/068943 A2 | 8/2003 |
| WO | WO-03/072035 A2 | 9/2003 |
| WO | WO-2004/024068 A2 | 3/2004 |
| WO | WO-2004/024072 A2 | 3/2004 |
| WO | WO-2004/074324 A2 | 9/2004 |
| WO | WO-2005/052005 A1 | 6/2005 |
| WO | WO-2006/042240 A2 | 4/2006 |
| WO | WO-2006/121168 A1 | 11/2006 |
| WO | WO-2006/124667 A2 | 11/2006 |
| WO | WO-2007/124383 A2 | 11/2007 |
| WO | WO-2009/126688 A2 | 10/2009 |
| WO | WO-2010/077634 A1 | 7/2010 |
| WO | WO-2011/066342 A2 | 6/2011 |
| WO | WO-2013/019906 A1 | 2/2013 |
| WO | WO-2013/119202 A1 | 8/2013 |
| WO | WO-2014/089113 A1 | 6/2014 |
| WO | WO-2014/116846 A2 | 7/2014 |
| WO | WO-2015/009856 A2 | 1/2015 |
| WO | WO-2015/037005 A1 | 3/2015 |
| WO | WO-2015/153513 A1 | 10/2015 |
| WO | WO-2015/153514 A1 | 10/2015 |
| WO | WO-2016/011264 A1 | 1/2016 |
| WO | WO-2016/028656 A1 | 2/2016 |
| WO | WO-2016/054555 A2 | 4/2016 |
| WO | WO-2016/073282 A1 | 5/2016 |
| WO | WO-2016/187546 A1 | 11/2016 |
| WO | WO-2016/191643 A2 | 12/2016 |
| WO | WO-2017/053748 A2 | 3/2017 |
| WO | WO-2018/129559 A1 | 7/2018 |
| WO | WO-2018/204363 A1 | 11/2018 |
| WO | WO-2019/165434 A1 | 8/2019 |
| WO | WO-2020/096915 A1 | 5/2020 |

OTHER PUBLICATIONS

Callahan et al., "At the Bedside: CTLA-4- and PD-1-blocking antibodies in cancer immunotherapy," J Leukoc Biol. 94(1):41-53 (2013) (13 pages).

Caruso, "Tiragolumab Impresses in Multiple Trials," Cancer Discov. 10(8):1086-1087 (2020) (3 pages).

Chen et al., "Molecular Pathways: Next-Generation Immunotherapy-Inhibiting Programmed Death-Ligand 1 and Programmed Death-1," Clin Cancer Res. 18(24): 6580-87 (2012) (9 pages).

Curran et al., "PD-1 and CTLA-4 combination blockade expands infiltrating T cells and reduces regulatory T and myeloid cells within 816 melanoma tumors," Proc Natl Acad Sci. 107(9): 4275-4280 (2010) (6 pages).

Dhupar et al., "Targeting Immune Checkpoints in Esophageal Cancer: A High Mutational Load Tumor," Ann Thorac Surg. 103(4):1340-1349 (2017) (10 pages).

Duan et al., "A nomogram-based immunoprofile predicts overall survival for previously untreated patients with esophageal squamous cell carcinoma after esohagectomy," J ImmunoTher Cancer. 6(1):100 (2018) (15 pages).

Duraiswamy et al., "Dual Blockade of PD-1 and CTLA-4 Combined with Tumor Vaccine Effectively Restores T-Cell Rejection Function in Tumors," Cancer Res. 73(12): 3591-603 (2013) (14 pages).

Hamid et al., "Anti-programmed death-1 and anti-programmed death-ligand 1 antibodies in cancer therapy," Expert Opin Biol Ther. 13(6): 847-61 (2013) (15 pages).

Hung et al., "TIGIT and PD-1 dual checkpoint blockade enhances antitumor immunity and survival in GBM," Oncoimmunology. 7(8) e1466769 (2018) (14 pages).

Inozume et al., Journal of Investigative Dermatology & International Investigative Dermatology Meeting, May 8-11, 2013, Edinburgh, United Kingdom.

Intlekofer et al., "At the Bench: Preclinical rationale for CTLA-4 and PD-1 blockade as cancer immunotherapy," Journal of Leukocyte Biology. 94(1): 25-39 (2013) (15 pages).

Jin et al., "CD226 hi CD8 + T Cells Are a Prerequisite for Anti-TIGIT Immunotherapy," Cancer Immunol Res. 8(7):912-925 (2020) (16 pages).

Johnston et al., "The checkpoint inhibitor TIGIT limits antitumor and antiviral CD8+ T cell responses," Oncoimmunology. 4.9:e1036214 (2015).

Malyguine et al., "ELISPOT Assay for Monitoring Cytotoxic T Lymphocytes (CTL) Activity in Cancer Vaccine Clinical Trials," Cells. 1(2):111-126 (2012) (16 pages).

Matsuzaki et al., "Tumor-infiltrating NY-ESO-1-specific CD8+ T cells are negatively regulated by LAG-3 and PD-1 in human ovarian cancer," Proc Natl Acad Sci. 107(17): 7875-7880 (2010) (6 pages).

McDermott et al., "PD-1 as a potential target in cancer therapy," Cancer Med. 2(5): 662-73 (2013) (12 pages).

Mullard, "New checkpoint inhibitors ride the immunotherapy tsunami," Nat Rev Drug Discov.12(7):489-492 (2013) (4 pages).

Nakamoto et al., "Synergistic Reversal of Intrahepatic HCV-Specific CD8 T Cell Exhaustion by Combined PD-1/CTLA-4 Blockade," PLoS Pathog. 5(2): e1000313 (2009) (13 pages).

Quezada et al., "Exploiting CTLA-4, PD-1 and PD-L 1 to reactivate the host immune response against cancer," Br J Cancer. 108(8):1560-1565 (2013) (6 pages).

(56) References Cited

OTHER PUBLICATIONS

Rodriguez-Abrez et al., "Primary analysis of a randomized, double-blind, phase II study of the anti-TIGIT antibody tiragolumab (tira) plus atezolizumab (atezo) versus placebo plus atezo as first-line (1L) treatment in patients with PD-L1-selected NSCLC (Cityscape)," J Clin One. 38(15S):A9503 (2020).

Selby et al., Antitumor activity of concurrent blockade of immune checkpoint molecules CTLA-4 and PD-1 in preclinical models, J Clin Onc. 31(15 suppl) Abstract 3061 (2013) (4 pages).

Stanietsky et al., "The interaction of TIGIT with PVR and PVRL2 inhibits human NK cell cytotoxicity," Proc Natl Acad Sci U S A. 106(42):17858-17863 (2009) (6 pages).

Villanueva et al., "New strategies in immunotherapy for lung cancer: beyond PD-1/PD-L1," Ther Adv Respir Dis. 12:1-29 (2018).

Yeo et al., "TIGIT/CD226 Axis Regulates Anti-Tumor Immunity," Pharmaceuticals (Basel). 14(3):200 (2021) (20 pages).

Zhang et al., "Prognostic Value of Lymphocyte Activation Gene-3 (LAG-3) Expression in Esophageal Squamous Cell Carcinoma," J Cancer. 9(22):4287-4293 (2018) (7 pages).

Zhao et al., "Orchestration of immune checkpoints in tumor immune contexture and their prognostic significance in esophageal squamous cell carcinoma," Cancer Manag Res. 10:6457-6468 (2018) (12 pages).

Zhu et al., "Cell Surface Signaling Molecules in the Control of Immune Responses: A Tide Model," Immunity. 34(4):466-478 (2011).

U.S. National Library of Medicine, Anonymous: "Safety and Pharmacokinetics (PK) of Escalating Doses of MTIG7192A as a Single Agent and in Combination With Atezolizumab With and Without Chemotherapy in Locally Advanced or Metastatic Tumors," Full Text View—ClinicalTrials.gov,Jun. 9, 2016 (Jun. 9, 2016), XP055758364, Retrieved from the Internet: <URL:https://clinicaltrials.gov/ct2/show/study/NCT02794571> [retrieved on Dec. 9, 2020] 'Study Description'; 'Arms and Interventions' (21 pages).

International Search Report and Written Opinion for International Application No. PCT/CN2020/096746, dated Feb. 24, 2021 (16 pages).

Extended European Search Report for European Patent Application No. 19181712.1, dated Jan. 8, 2020 (9 pages).

Notice of Reasons for Rejection for Japanese Patent Application No. 2018-188409, dated Sep. 3, 2019 (4 pages).

"FDA approves new, targeted treatment for bladder cancer," <http://www.fda.gov/NewsEvents/Newsroom/PressAnnouncements/ucm501762.htm>, retrieved on Sep. 19, 2016, dated May 18, 2016 (3 pages).

"VSTM3_HUMAN," <http://www.uniprot.org/uniprot/Q495A1.txt?version=27>, retrieved on Aug. 8, 2014 (3 pages).

Abbas et al., "Immune response in silico (IRIS): immune-specific genes identified from a compendium of microarray expression data," Genes Immun. 6(4):319-31 (2005).

Aebersold et al., "Perspective: a program to improve protein biomarker discovery for cancer," J Proteome Res. 4(4):1104-9 (2005).

Ahn et al., "Dendritic cells partially abrogate the regulatory activity of CD4+CD25+ T cells present in the human peripheral blood," Int Immunol. 19(3):227-37 (2007).

Baury et al., "Identification of secreted CD155 isoforms," Biochem Biophys Res Commun. 309(1):175-82 (2003).

Beers et al., Neurologic Disorders. *The Merck Manual of Diagnosis and Therapy*. Beers & Berkow, 1474-6 (1999).

Bergers et al., "Extrinsic regulators of epithelial tumor progression: metalloproteinases," Curr Opin Genet Dev. 10(1):120-7 (2000).

Blackburn et al., "Coregulation of CD8+ T cell exhaustion during chronic viral infection by multiple inhibitory receptors," available in PMC Jul. 1, 2009, published in final edited form as: Nat Immunol. 10(1):29-37 (2009) (22 pages).

Blalock et al., "Harnessing the power of gene microarrays for the study of brain aging and Alzheimer's disease: statistical reliability and functional correlation," Ageing Res Rev. 4(4):481-512 (2005).

Bolton, "Recent advances in the pharmacological control of experimental allergic encephalomyelitis (EAE) and the implications for multiple sclerosis treatment," Mult Scler. 1(3):143-9 (1995).

Bottino et al., "Identification of PVR (CD155) and Nectin-2 (CD112) as cell surface ligands for the human DNAM-1 (CD226) activating molecule," J Exp Med. 198(4):557-67 (2003).

Bruder et al., "Neuropilin-1: a surface marker of regulatory T cells," Eur J Immunol. 34(3):623-30 (2004).

Burshtyn et al., "A novel phosphotyrosine motif with a critical amino acid at position-2 for the SH2 domain-mediated activation of the tyrosine phosphatase SHP-1," J Biol Chem. 272(20):13066-72 (1997).

Butte et al., "Programmed death-1 ligand 1 interacts specifically with the B7-1 costimulatory molecule to inhibit T cell responses," Immunity. 27(1): 111-22 (2007).

Callahan et al., "Anti-CTLA-4 antibody therapy: immune monitoring during clinical development of a novel immunotherapy," Semin Oncol. 37(5):473-84 (2010).

Gasset et al., "A peptide mimetic of an anti-CD4 monoclonal antibody by rational design," Biochem Biophys Res Commun. 307(1):198-205 (2003).

Chan et al., "Receptors that interact with nectin and nectin-like proteins in the immunosurveillance and immunotherapy of cancer," Curr Opin Immunol. 24(2):246-51 (2012).

Chang et al., "Loop-sequence features and stability determinants in antibody variable domains by high-throughput experiments," Structure. 22(1):9-21 (2014).

Chauvin et al., "TIGIT and PD-1 impair tumor antigen-specific CD8+ T cells in melanoma patients," J Clin Invest. 125(5):2046-58 (2015) (13 pages).

Chien et al., "Significant structural and functional change of an antigen-binding site by a distant amino acid substitution: proposal of a structural mechanism," Proc Natl Acad Sci U S A. 86(14):5532-6 (1989).

Chin et al., "Immune intervention with monoclonal antibodies targeting CD152 (CTLA-4) for autoimmune and malignant diseases," Chang Gung Med J. 31(1):1-15 (2008).

Clarivate Analytics Integrity Database Entry No. 925174, <integrity.clarivate.com/integrity/xmlxsl/pk_qcksrch.show_records?sessionID=1&history=&query=MTIG-7192A%20%20&abbreviation=PR O&language=en > retrieved Jul. 29, 2019, (1 page).

Clarivate Analytics Integrity Database Entry No. 925174 update history, <https://integrity.clarivate.com/integrity xmlxslrecord_updates_ui_pkg.recordChangeLogFormp_subsystem=PR O&p subsystemId=925174> retrieved Jul. 29, 2019, (1 page).

Comps-Agrar et al., "TIGIT mediated T cell exhaustion in cancer is dependent on TIGIT/CD226 interaction (TUM2P.907)," Immunology 2014 Meeting Abstracts, J Immunol. 192(Suppl 1):71.31 (2014) (5 pages).

Correale et al., "Patterns of cytokine secretion by autoreactive proteolipid protein-specific T cell clones during the course of multiple sclerosis," J Immunol. 154(6):2959-68 (1995).

Danisch et al., "CD226 interaction with CD155 impacts on retention and negative selection of CD8 positive thymocytes as well as T cell differentiation to follicular helper cells in Peyer's Patches," Immunobiology. 218(2):152-8 (2013).

Dardalhon et al., "CD226 is specifically expressed on the surface of Th1 cells and regulates their expansion and effector functions," J Immunol. 175(3):1558-65 (2005).

De Pascalis et al., "Grafting of 'abbreviated' complementarity-determining regions containing specificity-determining residues essential for ligand contact to engineer a less immunogenic humanized monoclonal antibody," J Immunol. 169(6):3076-84 (2002).

Dennis, "Cancer: off by a whisker," Nature. 442(7104):739-41 (2006).

Dong et al., "Crystal structure of the V domain of human Nectin-like molecule-1/Syncam3/Tsll1/Igsf4b, a neural tissue-specific immunoglobulin-like cell-cell adhesion molecule," J Biol Chem. 281(15):10610-7 (2006).

Edgar, "T cell immunodeficiency," J Clin Pathol. 61(9):988-93 (2008).

Elder et al., "Growth factor and proto-oncogene expression in psoriasis," J Invest Dermatol. 95(5 Suppl):7S-9S (1990).

(56) References Cited

OTHER PUBLICATIONS

English Translation of Vyshkovsky (ed.), "Encyclopedia of medicines for radar therapy M. 2008 (16) Dakarbazin Medak," p. 278, col. 2 (2008) (1 page).

English Translation of Vyshkovsky (ed.), "Encyclopedia of medicines for radar, M. 2008 (16) Proleikin," p. 239, col. 3 (2008) (2 pages).

Fallarino et al., "Modulation of tryptophan catabolism by regulatory T cells," Nat Immunol. 4(12):1206-12 (2003).

Fehérvari et al., "Development and function of CD25+CD4+ regulatory T cells," Curr Opin Immunol. 16(2):203-8 (2004).

Finch et al., "Analysis of the cellular basis of keratinocyte growth factor overexpression in inflammatory bowel disease," Gut. 45(6):848-55 (1999).

Flies et al., "Blockade of the B7-H1/PD-1 pathway for cancer immunotherapy," Yale J Biol Med. 84(4):409-21 (2011).

Foks et al., "Agonistic anti-TIGIT treatment inhibits T cell responses in LDLr deficient mice without affecting atherosclerotic lesion development," PLoS One. 8(12):e83134 (2013) (7 pages).

Fuchs et al., "Cutting edge: CD96 (tactile) promotes NK cell-target cell adhesion by interacting with the poliovirus receptor (CD155)," J Immunol. 172(7):3994-8 (2004).

Fuchs et al., "The role of NK cell recognition of nectin and nectin-like proteins in tumor immunosurveillance," Semin Cancer Biol. 16(5):359-66 (2006).

Giusti et al., "Somatic diversification of S107 from an antiphosphocholine to an anti-DNA autoantibody is due to a single base change in its heavy chain variable region," Proc Natl Acad Sci USA. 84(9):2926-30 (1987).

Goding et al., "Restoring immune function of tumor-specific CD4+ T cells during recurrence of melanoma," J Immunol. 190(9):4899-909 (2013).

Greenwald et al., "The B7 family revisited," Annu Rev Immunol. 23:515-48 (2005).

Grogan et al., "TIGIT inhibits CD8+ T cell effector function during chronic viral infection and cancer (TUM7P.933)," J Immunol. 192(Suppl 1):203.15 (2014) (1 page) (Abstract Only).

Guo et al., "PD-1 blockade and OX40 triggering synergistically protects against tumor growth in a murine model of ovarian cancer," PLoS One. 9(2):e89350 (2014) (10 pages).

Gura, "Systems for identifying new drugs are often faulty," Science. 278(5340):1041-2 (1997).

Güssow et al., "Humanization of monoclonal antibodies," Methods Enzymol. 203:99-121 (1991).

He et al., "Complexes of poliovirus serotypes with their common cellular receptor, CD155," J Virol. 77(8):4827-35 (2003).

History of Changes for Study: NCT02794571: "Saftey and pharmacokinetics (PK) of escalating doses of MTIG7192A as a single agent and in combination with atezolizumab in locally advanced of metastic tumors," https://clinicaltrials.gov/ct2/history/NCT02794571?V_12=View#StudyPageTOP>, dated Feb. 1, 2018, retrieved Jul. 25, 2019 (9 pages).

Holm et al., "Functional mapping and single chain construction of the anti-cytokeratin 8 monoclonal antibody TS1," Mol Immunol. 44(6):1075-84 (2007).

Hori et al., "Control of regulatory T cell development by the transcription factor Foxp3," Science. 299(5609):1057-61 (2003).

Hou et al., "Recombinant soluble CD226 protein directly inhibits cancer cell proliferation in vitro," Int Immunopharmacol. 19(1):119-26 (2014).

Huang, "Structural chemistry and therapeutic intervention of protein-protein interactions in immune response, human immunodeficiency virus entry, and apoptosis," Pharmacol Ther. 86(3):201-15 (2000).

Inoue et al., "Cancer-associated fibroblast suppresses killing activity of natural killer cells through downregulation of poliovirus receptor (PVR/CD155), a ligand of activating NK receptor," Int J Oncol. 49(4):1297-304 (2016).

Inozume et al., "CD155 is highly expressed by melanoma tissues and it suppresses the activation of melanoma specific CTLs via interaction with TIGIT," Journal of Dermatological Science. 69(2):e67-e68, Abstract P10-01 (2013) (2 pages).

Inozume et al., "Development of a novel immunotherapy for melanoma which inhibits interaction between CD155 on melanoma cells and TIGIT on activated CTL," J Invest Dermatol. 133:S3 (2013) (1 page) (Abstract Only).

Inozume et al., "Melanoma Cells Control Antimelanoma CTL Responses via Interaction between TIGIT and CD155 in the Effector Phase," J Invest Dermatol. 136(1):255-63 (2016).

Issekutz et al., "Treatment of established adjuvant arthritis in rats with monoclonal antibody to CD18 and very late activation antigen-4 integrins suppresses neutrophil and T-lymphocyte migration to the joints and improves clinical disease," Immunology. 88(4):569-76 (1996).

Janeway et al., B-cell heterogeneity. Immunobiology, 3rd edition. Garland Publications Inc., 5:23-26, 8:3, and 9:23-9:27 (1997).

Jiang et al., "A novel peptide isolated from a phage display peptide library with trastuzumab can mimic antigen epitope of HER-2," J Biol Chem. 280(6):4656-62 (2005).

Jiang et al., "Disruption of E-cadherin-mediated adhesion induces a functionally distinct pathway of dendritic cell maturation," Immunity. 27(4):610-24 (2007).

Jin et al., "Cooperation of Tim-3 and PD-1 in CD8 T-cell exhaustion during chronic viral infection," Proc Natl Acad Sci U S A. 107(33):14733-8 (2010).

Johnston et al., "The immunoreceptor TIGIT regulates antitumor and antiviral CD8(+) T cell effector function," Cancer Cell. 26(6):923-37 (2014).

Joller et al., "Cutting edge: TIGIT has T cell-intrinsic inhibitory functions," J Immunol. 186(3):1338-42 (2011).

Joller et al., "Immune checkpoints in CNS autoimmunity," available in PMC Jul. 1, 2013, published in final edited form as: Immunol Rev. 248(1):122-39 (2012) (28 pages).

Ju et al., "Immunoglobulin-like transcripts ILT2, ILT3 and ILT7 are expressed by human dendritic cells and down-regulated following activation," Gene. 331:159-64 (2004).

Kashiwada et al., "Immunoreceptor tyrosine-based inhibitory motif of the IL-4 receptor associates with SH2-containing phosphatases and regulates IL-4-induced proliferation," J Immunol. 167(11):6382-7 (2001).

Kelland, "'Of mice and men': values and liabilities of the athymic nude mouse model in anticancer drug development," Eur J Cancer. 40(6):827-36 (2004).

Kisseleva et al., "Signaling through the JAK/STAT pathway, recent advances and future challenges," Gene. 285(1-2):1-24 (2002).

Klimka et al., "Human anti-CD30 recombinant antibodies by guided phage antibody selection using cell panning," Brit J Cancer. 83(2):252-60 (2000).

Kruisbeek et al., Proliferative Assays for T Cell Function. *Current Protocols in Immunology*. John Wiley & Sons, Inc. 3.12.1-3.12.14 (1991) (26 pages).

Kurtulus et al., "Mechanisms of TIGIT-driven immune suppression in cancer," J Immunother Cancer. 2(Suppl 3): O13 (2014) (1 page).

Lee et al., "Macrophage PD-L1 strikes back: PD-1/PD-L1 interaction drives macrophages toward regulatory subsets," Adv Biosci Biotechnol. 4:19-29 (2013).

Levin et al., "Identification and characterization of Vsig9 as an inhibitory member of the CD28 family," Keystone Symposia on Molecular and Cellular Biology: Tolerance in Transplantation and Autoimmunity, Jan. 29-Feb. 3, Keystone, Colorado. 74, Abstract 217 (2008).

Levin et al., "Vstm3 is a member of the CD28 family and an important modulator of T-cell function," available in PMC Aug. 5, 2013, published in final edited form as: Eur J Immunol. 41(4):902-15 (2011) (22 pages).

Liebman, "Biomedical informatics: the future for drug development," Drug Discov Today. 7(20 Suppl):S197-203 (2002).

Linsley et al., "Immunosuppression in vivo by a soluble form of the CTLA-4 T cell activation molecule," Science. 257(5071):792-5 (1992).

Lozano et al., "The TIGIT/CD226 Axis Regulates Human T Cell Function," J Immunol. 188(8):3869-75 (2012).

(56) References Cited

OTHER PUBLICATIONS

Luo et al., "Delayed-type hypersensitivity," Curr Protoc Immunolog. Chapter 4:Unit 4.5 (1993) (5 pages).
MacCallum et al., "Antibody-antigen interactions: contact analysis and binding site topography," J Mol Biol. 262(5):732-45 (1996).
Maier et al., "The adhesion receptor CD155 determines the magnitude of humoral immune responses against orally ingested antigens," Eur J Immunol. 37(8):2214-25 (2007).
Mariuzza et al., "The structural basis of antigen-antibody recognition," Annu Rev Biophys Biophys Chem. 16:139-59(1987).
Martinet et al., "Balancing natural killer cell activation through paired receptors," Nat Rev Immunol. 15(4):243-54 (2015).
McHugh et al., "CD4(+)CD25(+) immunoregulatory T cells: gene expression analysis reveals a functional role for the glucocorticoid-induced TNF receptor," Immunity. 16(2):311-23 (2002).
Melero et al., "Evolving synergistic combinations of targeted immunotherapies to combat cancer," Nat Rev Cancer. 15(8):457-72 (2015).
Mellman., "Developments in cancer immunotherapy," Nov. 2017, (20 pages).
Morales-Kastresana et al., "Combined immunostimulatory monoclonal antibodies extend survival in an aggressive transgenic hepatocellular carcinoma mouse model," Clin Cancer Res. 19(22):6151-62 (2013).
NCBI Blast for Accession No. gi256600228. Retrieved on Jun. 17, 2004 (1 page).
NCBI Blast for Accession No. gi57997171. Retrieved on Nov. 20, 2003 (1 page).
NCBI Blast for Accession No. Q8N877. Retrieved on Aug. 6, 2014 (2 pages).
NCBI Blast for Accession No. AL833175 GI:21733802. Retrieved on Aug. 6, 2014 (3 pages).
Nickoloff et al., "Severe combined immunodeficiency mouse and human psoriatic skin chimeras. Validation of a new animal model," Am J Pathol. 146(3):580-8 (1995).
Nobis et al., "Production of a monoclonal antibody against an epitope on HeLa cells that is the functional poliovirus binding site," J Gen Virol. 66(Pt 12):2563-9 (1985).
Norde et al., "PD-1/PD-L1 interactions contribute to functional T-cell impairment in patients who relapse with cancer after allogeneic stem cell transplantation," Cancer Res. 71 (15):5111-22 (2011).
Ota et al., "Complete sequencing and characterization of 21,243 full-length human cDNAs," Nat Genet. 36(1):40-5 (2004).
Pende et al., "Expression of the DNAM-1 ligands, Nectin-2 (CD112) and poliovirus receptor (CD155), on dendritic cells: relevance for natural killer-dendritic cell interaction," Blood. 107(5):2030-6 (2006).
Qiu et al., "CD155 is involved in negative selection and is required to retain terminally maturing CD8T cells in thymus," J Immunol. 184(4):1681-9 (2010).
Qu et al., "Loss of CD155 expression predicts poor prognosis in hepatocellular carcinoma," Histopathology. 66(5):706-14 (2015) Abstract only (2 pages).
Read et al., "Cytotoxic T lymphocyte-associated antigen 4 plays an essential role in the function of CD25(+)CD4(+) regulatory cells that control intestinal inflammation," J Exp Med. 192(2):295-302 (2000).
Redmond et al., "Combined targeting of co-stimulatory (OX40) and co-inhibitory (CTLA-4) pathways elicits potent effector T cells capable of driving robust antitumor immunity," available in PMC Feb. 1, 2015, published in final edited form as: Cancer Immunol Res. 2(2):142-53 (2014) (20 pages).
Reymond et al., "DNAM-1 and PVR regulate monocyte migration through endothelial junctions," J Exp Med. 199(10):1331-41 (2004).
Riemer et al., "Matching of trastuzumab (Herceptin®) epitope mimics onto the surface of Her-2/neu—a new method of epitope definition," Mol Immunol. 42(9):1121-4 (2005).
Rosenblatt et al., "Targetting the PD-L1/PD-1 axis holds promise in the treatment of malignancy," Transl Cancer Res. 1(4):283-6 (2012).
Rudikoff et al., "Single amino acid substitution altering antigen-binding specificity," Proc Natl Acad Sci U S A. 79(6):1979-83 (1982).
Saijo, "What are the reasons for negative phase III trials of molecular-target-based drugs?" Cancer Sci. 95(10):772-6 (2004).
Sakaguchi et al., "Immunologic self-tolerance maintained by activated T cells expressing IL-2 receptor alpha-chains (CD25). Breakdown of a single mechanism of self-tolerance causes various autoimmune diseases," J Immunol. 155(3):1151-64 (1995).
Sakisaka et al., "Biology and pathology of nectins and nectin-like molecules," Curr Opin Cell Biol. 16(5):513-21 (2004).
Sakuishi et al., "Targeting Tim-3 and PD-1 pathways to reverse T cell exhaustion and restore anti-tumor immunity," J Exp Med. 207(10):2187-94 (2010).
Satoh-Horikawa et al., "Nectin-3, a new member of immunoglobulin-like cell adhesion molecules that shows homophilic and heterophilic cell-cell adhesion activities," J Biol Chem. 275(14):10291-9 (2000).
Schaerli et al., "CXC chemokine receptor 5 expression defines follicular homing T cells with B cell helper function," J Exp Med. 192(11):1553-62 (2000).
Schneider, "A rational approach to maximize success rate in target discovery," Arch Pharm (Weinheim). 337(12):625-33 (2004).
Serra et al., "CD40 ligation releases immature dendritic cells from the control of regulatory CD4+CD25+T cells," Immunity. 19(6):877-89 (2003).
Seth et al., "The poliovirus receptor/CD155 is a potential modulator of the T cell response," Immunobiology. 210(6-8):542 (2005).
Shimizu et al., "Stimulation of CD25(+)CD4(+) regulatory T cells through GITR breaks immunological self-tolerance," Nat Immunol. 3(2):135-42 (2002).
Sicotte et al., "Onset of multiple sclerosis associated with anti-TNF therapy," Neurology. 57(10):1885-8 (2001).
Skolnick et al., "From genes to protein structure and function: novel applications of computational approaches in the genomic era," Trends Biotechnol. 18(1):34-9 (2000).
Smith, "Drug target validation: Hitting the target," Nature. 422(6929):341-7 (2003).
Stancovski et al., "Mechanistic aspects of the opposing effects of monoclonal antibodies to the ERBB2 receptor on tumor growth," Proc Natl Acad Sci U S A. 88(19):8691-5 (1991).
Stanietsky et al., "Mouse TIGIT inhibits NK-cell cytotoxicity upon interaction with PVR," Eur J Immunol. 43(8):2138-50 (2013).
Tahara-Hanaoka et al., "Functional characterization of DNAM-1 (CD226) interaction with its ligands PVR (CD155) and nectin-2 (PRR-2/CD112)," Int Immunol. 16(4):533-8 (2004).
Takahashi et al., "Immunologic self-tolerance maintained by CD25(+)CD4(+) regulatory T cells constitutively expressing cytotoxic T lymphocyte-associated antigen 4," J Exp Med. 192(2):303-9 (2000).
Tarbell et al., "CD25+ CD4+ T cells, expanded with dendritic cells presenting a single autoantigenic peptide, suppress autoimmune diabetes," J Exp Med. 199(11):1467-77 (2004).
Thaventhiran et al., "T cell co-inhibitory receptors: functions and signalling mechanisms," J Clin Cell Immunol. S12:004 (2012) (12 pages).
Thornton et al., "CD4+CD25+ immunoregulatory T cells suppress polyclonal T cell activation in vitro by inhibiting interleukin 2 production," J Exp Med. 188(2):287-96 (1998).
Vajdos et al., "Comprehensive functional maps of the antigen-binding site of an anti-ErbB2 antibody obtained with shotgun scanning mutagenesis," J Mol Biol. 320(2):415-28 (2002).
Velten et al., "A gene signature of inhibitory MHC receptors identifies a BDCA3(+) subset of IL-10-induced dendritic cells with reduced allostimulatory capacity in vitro," Eur J Immunol. 34(10):2800-11 (2004).
Vinuesa et al., "Follicular B helper T cells in antibody responses and autoimmunity," Nat Rev Immunol. 5(11):853-65 (2005).
Wang et al., "Regulatory T cells and cancer," Curr Opin Immunol. 19(2):217-23 (2007).
Whisstock et al., "Prediction of protein function from protein sequence and structure," Q Rev Biophys. 36(3):307-40 (2003).
Wiesmann et al., "Nerve growth factor: structure and function," Cell Mol Life Sci. 58(5-6):748-59 (2001).

(56) References Cited

OTHER PUBLICATIONS

Winkler et al., "Changing the antigen binding specificity by single point mutations of an anti-p24 (HIV-1) antibody," J Immunol. 165(8):4505-14 (2000).
Wolchok et al., "Nivolumab plus ipilimumab in advanced melanoma," N Engl J Med. 369(2):122-33 (2013).
Wu et al., "Humanization of a murine monoclonal antibody by simultaneous optimization of framework and CDR residues," J Mol Biol. 294(1):151-62 (1999).
Xia et al., "Suppression of interleukin-12 production through endogenously secreted interleukin-10 in activated dendritic cells: involvement of activation of extracellular signal-regulated protein kinase," Scand J Immunol. 58(1):23-32 (2003).
Xiao et al., "RGMb is a novel binding partner for PD-L2 and its engagement with PD-L2 promotes respiratory tolerance," J Exp Med. 211(5):943-59 (2014).
Xu et al., "A novel interface consisting of homologous immunoglobulin superfamily members with multiple functions," Cell Mol Immunol. 7(1):11-9 (2010).
Yamashita-Kanemaru et al., "CD155 (PVR/Necl5) mediates a costimulatory signal in CD4+ T cells and regulates allergic inflammation," J Immunol. 194(12):5644-53 (2015).
Yamazaki et al., "Effective expansion of alloantigen-specific Foxp3+ CD25+ CD4+ regulatory T cells by dendritic cells during the mixed leukocyte reaction," Proc Natl Acad Sci USA. 103(8):2758-63 (2006).
Yu et al., "Rationalization and design of the complementarity determining region sequences in an antibody-antigen recognition interface," PLoS One. 7(3):e33340 (2012) (15 pages).
Yu et al., "Simultaneous inhibition of two regulatory T-cell subsets enhanced Interleukin-15 efficacy in a prostate tumor model," Proc Natl Acad Sci USA. 109(16):6187-92 (2012).
Yu et al., "The surface protein TIGIT suppresses T cell activation by promoting the generation of mature immunoregulatory dendritic cells" Nat Immunol. 10(1):48-57 (2009).
Zhan et al., "From monoclonal antibodies to small molecules: the development of inhibitors targeting the PD-1/PD-L1 pathway," Drug Discov Today. 21(6):1027-36 (2016).
Zheng et al., "Human Cancer Immunotherapy with PD-1/PD-L1 Blockade," Biomark Cancer. 7(Suppl 2):15-8 (2015).
Zhou et al., "Coexpression of Tim-3 and PD-1 identifies a CD8+ T-cell exhaustion phenotype in mice with disseminated acute myelogenous leukemia," Blood. 117(17):4501-10 (2011).
Ziegler, "FOXP3: not just for regulatory! cells anymore," Eur J Immunol. 37(1):21-3 (2007).
Communication pursuant to Article 94(3) for European Patent Application No. 14750063.1, dated Oct. 18, 2017 (9 pages).
Communication pursuant to Article 94(3) for European Patent Application No. 15801009.0, dated Mar. 22, 2018 (6 pages).
English Translation of Office Action for Chinese Application No. 200980121734.2, dated Sep. 22, 2013 (2 pages).
Exam Report for Canadian Patent Application No. 2,905,334, dated Jun. 25, 2019 (5 pages).
Examination Report for Australian Application No. 2009233708, dated Sep. 6, 2013 (3 pages).
Examination Report for Australian Patent Application No. 2017221784, dated Nov. 1, 2018 (2 pages).
International Search Report and Written Opinion for International Application No. PCT/US2009/039868, dated Oct. 23, 2009 (25 pages).
International Search Report and Written Opinion for International Application No. PCT/US2014/046896, dated Mar. 2, 2015 (21 pages).
Invitation to Pay Additional Fees for International Patent Application No. PCT/US2015/058087, dated Jan. 27, 2016 (10 pages).
Invitation to Pay Additional Fees for International Patent Application No. PCT/US2016/053368, dated Feb. 2, 2017 (8 pages).
International Preliminary Report on Patentability for International Patent Application No. PCT/US2015/040770, dated Jan. 17, 2017 (11 pages).
International Preliminary Report on Patentability for International Patent Application No. PCT/US2016/053368, dated Mar. 27, 2018 (10 pages).
International Search Report and Written Opinion for International Patent Application No. PCT/US2015/040770, dated Oct. 16, 2015 (13 pages).
International Search Report and Written Opinion for International Patent Application No. PCT/US2015/058087, dated Apr. 8, 2016 (22 pages).
International Search Report and Written Opinion for International Patent Application No. PCT/US2016/053368, dated Mar. 31, 2017 (19 pages).
Notice of Preliminary Rejection for Korean Patent Application No. 10-2010-7025044, dated Nov. 13, 2015 (6 pages).
Notice of Preliminary Rejection for Korean Patent Application No. 10-2018-7034436, dated Jan. 22, 2019 (4 pages).
Notice of Reasons for Rejection for Japanese Patent Application No. 2016-527082, dated May 8, 2018 (18 pages).
Notification of Defects for Israeli Patent Application No. 264498, dated Jun. 23, 2019 (5 pages).
Office Action for Canadian Patent Application No. 2,719,189, dated Mar. 2, 2018 (4 pages).
Office Action for Chinese Patent Application No. 201510024034.9, dated Nov. 2, 2018 (8 pages).
Office Action for Indian Patent Application No. 6588/DELNP/2010, dated May 12, 2017 (9 pages).
Office Action for Russian Patent Application No. 2016104880, dated Jul. 3, 2018 (17 pages).
Office Action for U.S. Appl. No. 14/228,172, dated Feb. 12, 2015 (14 pages).
Office Action for U.S. Appl. No. 14/228,173, dated Mar. 11, 2015 (18 pages).
Office Action for U.S. Appl. No. 14/333,375, dated Sep. 23, 2016 (27 pages).
Office Action for U.S. Appl. No. 14/699,845, dated Jun. 9, 2016 (11 pages).
Office Action for U.S. Appl. No. 15/231,032, dated Oct. 29, 2018 (13 pages).
Search Report for Russian Patent Application No. 2016104880, dated Jun. 6, 2018 (6 pages).
Search Report for Singaporean Patent Application No. 11201600310Q, dated Mar. 9, 2017 (5 pages).
Search Report for Singaporean Patent Application No. 11201700258V, dated Jan. 18, 2018 (3 pages).
Search Report for Singaporean Patent Application No. 11201703376Q, dated Apr. 4, 2018 (5 pages).
Sequence Alignment with U.S. Appl. No. 14/236,064, filed Jan. 29, 2014 (2 pages).
Written Opinion for Singaporean Patent Application No. 10201402815V, dated Jan. 31, 2018 (7 pages).
Written Opinion for Singaporean Patent Application No. 10201402815V, dated May 10, 2019 (6 pages).
Written Opinion for Singaporean Patent Application No. 11201600310Q, dated Apr. 6, 2017 (10 pages).
Written Opinion for Singaporean Patent Application No. 11201700258V, dated Jan. 18, 2018 (6 pages).
Written Opinion for Singaporean Patent Application No. 11201703376Q, dated Apr. 4, 2018 (9 pages).
Tahara-Hanaoka et al., "Tumor rejection by the poliovirus receptor family ligands of the DNAM-1 (CD226) receptor," Blood. 107(4):1491-6 (2006) (7 pages).
Gothberg et al., "Identification of Tigit on Intra-Tumor T Cells As a New Target for Immune Checkpoint Blockade in Follicular Lymphoma," Blood. 128 (22): 7 pages (2016).
Jelinek et al., "Update on PD-1/PD-L1 Inhibitors in Multiple Myeloma," Front Immunol. 9(2413): 13 pages (2018).
Decision of Rejection for Japanese Patent Application No. 2018-514968, dated Jun. 23, 2020 (8 pages).
English Translation of Notice of Reasons for Rejection for Japanese Patent Application No. 2011-504145, dated Dec. 17, 2013.
English Translation of Search Report for Taiwan Application No. 104136746, dated Oct. 2, 2019.

(56) References Cited

OTHER PUBLICATIONS

Examination Report for Singaporean Application No. 11201802133W, dated Jul. 3, 2020 (5 pages).
International Preliminary Report on Patentability for International Patent Application No. PCT/US2015/058087, dated May 18, 2017.
International Preliminary Report on Patentability for International Patent Application No. PCT/US2019/019603, dated Aug. 27, 2020 (9 pages).
Invitation to Pay Additional Fees for International Application No. PCT/US2020/020135, dated Jun. 16, 2020 (13 pages).
Notice of Reasons for Rejection for Japanese Patent Application No. 2015-090362, dated Apr. 12, 2016 (7 pages).
Office Action for Canadian Application No. 2,905,334, dated Jun. 10, 2020 (5 pages).
Office Action for Ukrainian Application No. a 2018 01146, dated Jun. 15, 2020 (19 pages).
Search Report and Written Opinion for Brazilian Application No. PI0906550-4, dated Aug. 14, 2020 (4 pages).
Search Report for International Patent Application No. PCT/US2015/058087, dated Jan. 27, 2016.
Second Examination Report for Gulf Cooperation Council Application No. 2014/36982, dated Jun. 16, 2020 (4 pages).
Third Examination Report for Gulf Cooperation Council Application No. 2016/32074, dated Jun. 11, 2020 (3 pages).
Baldo et al., "Combined hexavalent diphtheria-tetanus-acellular pertussis-hepatitis B-inactivated poliovirus-*Haemophilus influenzae* type b vaccine-Infanrix™ hexa: Twelve years of experience in Italy," Human Vaccines & Immunotherapeutics.10(1):129-137 (2014).
Castro et al., "Cytokine Production and the Menstrual Cycle: Is There a Relationship?" Abstract Book, 2003 Annual Meeting American College of Allergy, Asthma & Immnology, November 7-12. 122 Abstract P5 (2003).
Gogas et al., "Cobimetinib Plus Atezolizumab in BRAFV600 Wild-Type Melanoma: Primary Results From the Randomized Phase III IMspire170 Study," European Society for Medical Oncology. 32(3):384-394 (2021).
Inozume et al., "Development of a novel immunotherapy for melanoma which inhibits interaction between CD155 on melanoma cells and TIGIT on activated CTL," Journal of Investigative Dermatology. 133(Suppl. 1):S3, Abstract 018 (2013).
Inozume et al., "Development of a novel immunotherapy for melanoma which inhibits interaction between CD155 on melanoma cells and TIGIT on activated CTL," Journal of Investigative Dermatology & International Investigative Dermatology Meeting, May 8-11, Edinburgh, United Kingdom (2013).
Kulczycki et al., "Unknown lung pathology in patients with cystic fibrosis is becoming known," Annals of Diagnostic Paediatric Pathology. 6(1-2):81-86 (2002) (6 pages).
Simpson et al., "Efficacy and safety of lebrikizumab (an anti-IL-13 monoclonal antibody) in adults with moderate-to-severe atopic dermatitis inadequately controlled by topical corticosteroids: A randomized, placebo-controlled phase II trial (TREBLE)," J Am Acad Dermatol. 78(5): 863-871.e11 (2018) (20 pages).
Swigris et al., "The RIFF Study (Cohort A): A Phase II, Randomized, Double-Blind, Placebo-Controlled Trial of Lebrikizumab as Monotherapy in Patients With Idiopathic Pulmonary Fibrosis," American Journal of Respiratory and Critical Care Medicine. 197:A6167 Abstract (2018).
Office Action for Chinese Application No. 201910073153.1, dated Dec. 3, 2021 (11 pages).

* cited by examiner

| | | | | | |
|---|---|---|---|---|---|
| Human | MRWCLLLIWAQGLRQAPLAS-GMMTGTIETTGNISAEKGGSIILQCHLSS | 49 | SEQ ID NO: 1 |
| Rhesus | MRWCLFLIWAQGLRQAPLAS-GMMTGTIETTGNISAKKGGSVILQCHLSS | | SEQ ID NO: 2 |
| Dog | MQWYLLLIWAQGLGQAPLPTSGAVSGRHMTMGNISAKEGGSVTLQCHLSS | | SEQ ID NO: 3 |
| Mouse | MHGWLLLVWVQGLIHQAAFLATGATAGTIDTKRNISAEEGGSVILQCHFSS | | SEQ ID NO: 4 |

TTAQVTQVNWEQQDQ--LLAICNADLGWHISPSFKDRVAPGPGLTLQSL 98 SEQ ID NO: 1
TMAQVTQVNWEQHDHSLLAIRNAELGWHIYPAFKDRVAPGPGLTLQSL SEQ ID NO: 2
TTANVTQVNWEKQDQ--LLAVHHTDLGWHIYPAFRERVAPGPNLGLTLQSL SEQ ID NO: 3
DTAEVTQVDWKQQDQ--LLAIYSVDLGWHVASVFSDRVVPGPSLGTFQSL SEQ ID NO: 4

TVNDTGEYFCIYHTYPDGTYTGRIFLEVLESSVAEHGARFQIPLLGAMAA 148 SEQ ID NO: 1
TMNDTGEYFCTYHTYPDGTYRGRIFLEVLESSVAEHSARFQIPLLGAMAM SEQ ID NO: 2
TRNDTGEYLCTYHTYPDGIHYRGTFFLEVLQSSVAERSAAFQIPLLGAMAS SEQ ID NO: 3
TMNDTGEYFCTYHTYPGGHYKGRIFLKVQESSVAQFQT--APLGTMAA SEQ ID NO: 4

TLVVICTAVIVVALTRKKKALRIHSVEGDLRRKSAGQEEWSPSAPSPPG 198 SEQ ID NO: 1
MLVVICHAVIVVVLARKKKSLRIHSVESGLQRKSTGQEEQIPSAPSPPG SEQ ID NO: 2
VLAVICVAVILGGLWTRKKKCRRVHCGESGLRTMTYEQEEQSPCILSSTG SEQ ID NO: 3
VLGLICLMVTGVTVLARKK-SIRMHSIESGLGRTEAEPQEWNLRSLSSPG SEQ ID NO: 4

SCVQAEAAPAGLCGEQRGEDCAELHDYFNVLSYRSLGNCSFFTETG 244 SEQ ID NO: 1
SCVQAEAAPAGLCGEQQGDDCAELHDVFNVLSYRSLGSCSFFTETG SEQ ID NO: 2
RAIQVEMVPVGLYTEQRADDYAEPHDYFNVLSYRSLGSFSFLAETG SEQ ID NO: 3
SPVQTQTAPAGPCGEQAEDDYADPQEYFNVLSYRSLESFIAVSKTG SEQ ID NO: 4

| | | | | | |
|---|---|---|---|---|---|
| TIGIT | 18 | LASG:M:MTGTIETTGNISAE--KGGSIILQCHLSST------TAQVTQNWEQQ | 62 | SEQ ID NO: 5 |
| PVR | 22 | PPPGTGDVVVQAPTOVPGF--LGDSVTLPCYLQVPNMEVTHVSQLTWARH | 69 | SEQ ID NO: 6 |
| CD96 | 18 | FVKGVWEKTVNTEENVYAT--LGSDVNLTCQTQTVG----FFVQMQWSKV | 61 | SEQ ID NO: 7 |
| PVRL2 | 27 | LETGAQDVRVQVLPEVRGQ--LGGTVELPCHLLPP-VPGLYISLVTWQRP | 73 | SEQ ID NO: 8 |
| PVRL1 | 24 | FLPGVHSQVVQVNDSM:YGF--IGTDVVLHCSFANP-LPSVKITQVTWQKS | 70 | SEQ ID NO: 9 |
| PVRL3 | 51 | RLCGALAGPIIVEPHVTAV--WGKNVSLKCLIEVN---ETITQISWEKI | 94 | SEQ ID NO: 10 |
| PVRL4 | 25 | FTGRCPAGELGTSDVTVV--LGQDAKLPCFYRGD--SGEQVGQVAWARV | 70 | SEQ ID NO: 11 |
| CD226 | 10 | LLHVYRALCEEVLWHTSVP--FAEN:M:SLECVYPSMG---ILTQVEWFKI | 53 | SEQ ID NO: 12 |

V/I - S/T - Q

| | | | | | |
|---|---|---|---|---|---|
| VSIG2 | 18 | CIISGLAVEVKVPTEPLSTP--LGKTAELTCTYSTS----VGDSFALEWSFV | 62 | SEQ ID NO: 13 |
| IGSF11 | 16 | TGVAASLEVSESPGSIQVA--RGQTAVLPCTFTTS---AALINLNVIWMVT | 61 | SEQ ID NO: 14 |
| TREML1 | 11 | LGLEGQGIVGSLPEVLQAP--VGSSILVQCHYRLQ---DVKAQKVWCRF | 54 | SEQ ID NO: 15 |
| PSG5 | 26 | NFWNLPITAQVTIEALPPKVSEGKDVLLVHNLPQ---NLAGYIWYKG | 70 | SEQ ID NO: 16 |
| SCN1B | 16 | SACGGCVEVDSETEAVYIGM--TFKILCISCKRRSE--TNAETFTEWTFR | 60 | SEQ ID NO: 17 |
| B7-H4 | 27 | IGFGISGRHSITVTTTVASAGNIGEDGIQSCTFEPD--IKLSDIVIQWLKE | 74 | SEQ ID NO: 18 |

A - X(6) - G

| | | | | | |
|---|---|---|---|---|---|
| TIGIT | 63 | D--Q----LLAICNADLGWHISP--SFKDRVAP-GPGLG------ | 92 | SEQ ID NO: 5 |
| PVR | 70 | GESG----SM:AVFHQTQGPSYSE--SKRLEFVAARLG------ | 105 | SEQ ID NO: 6 |
| CD96 | 62 | TNKID---LHAVYHPQYGFYCAYGRPCES-LVTFTETPENGS----K | 100 | SEQ ID NO: 7 |
| PVRL2 | 74 | DAPANH-QNVAAFHPKMGPSFPSPKPGSERLSFVSAKQSTGQDTEAELQD | 122 | SEQ ID NO: 8 |
| PVRL1 | 71 | TNGSK--QNVAIYNPSMGVYGF-YREREVEFLRPSFT------D | 106 | SEQ ID NO: 9 |
| PVRL3 | 95 | HGKSS--QTVAVHHPQYGF SVQG--EYQGRVLFKNYSLN------D | 130 | SEQ ID NO: 10 |
| PVRL4 | 71 | DAGEGA-QELALLHSKYGLHVSP--AYEGRVEQPPPPRN--P-LD | 109 | SEQ ID NO: 11 |
| CD226 | 54 | GTQQD--SIAIFSPTHGMVIRKP--YAERVYFLNSTM:ASN------N | 90 | SEQ ID NO: 12 |

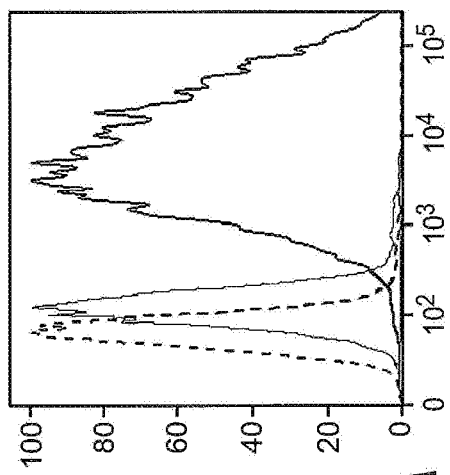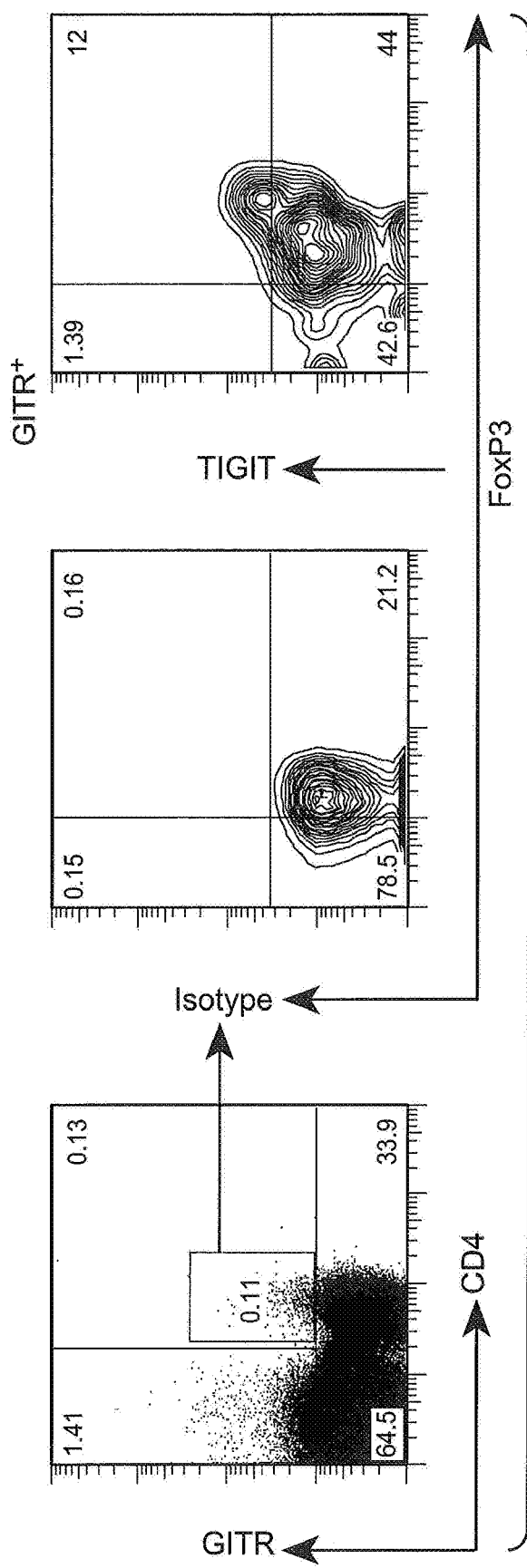
FIG. 9A
FIG. 9B

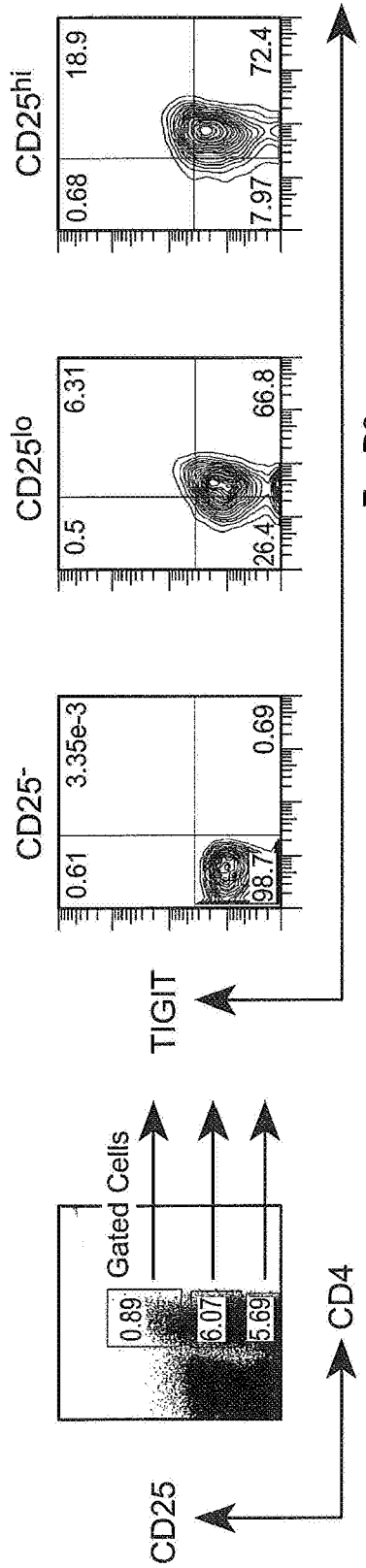
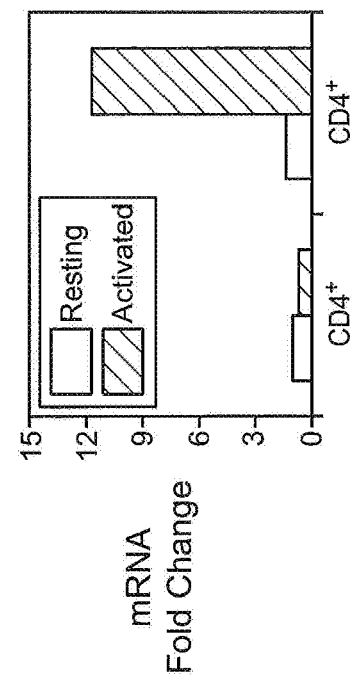
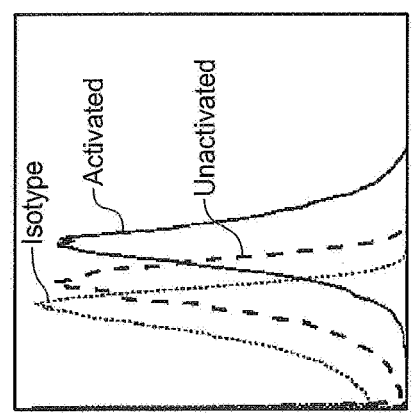
FIG. 10E
FIG. 10F

FIG. 12A

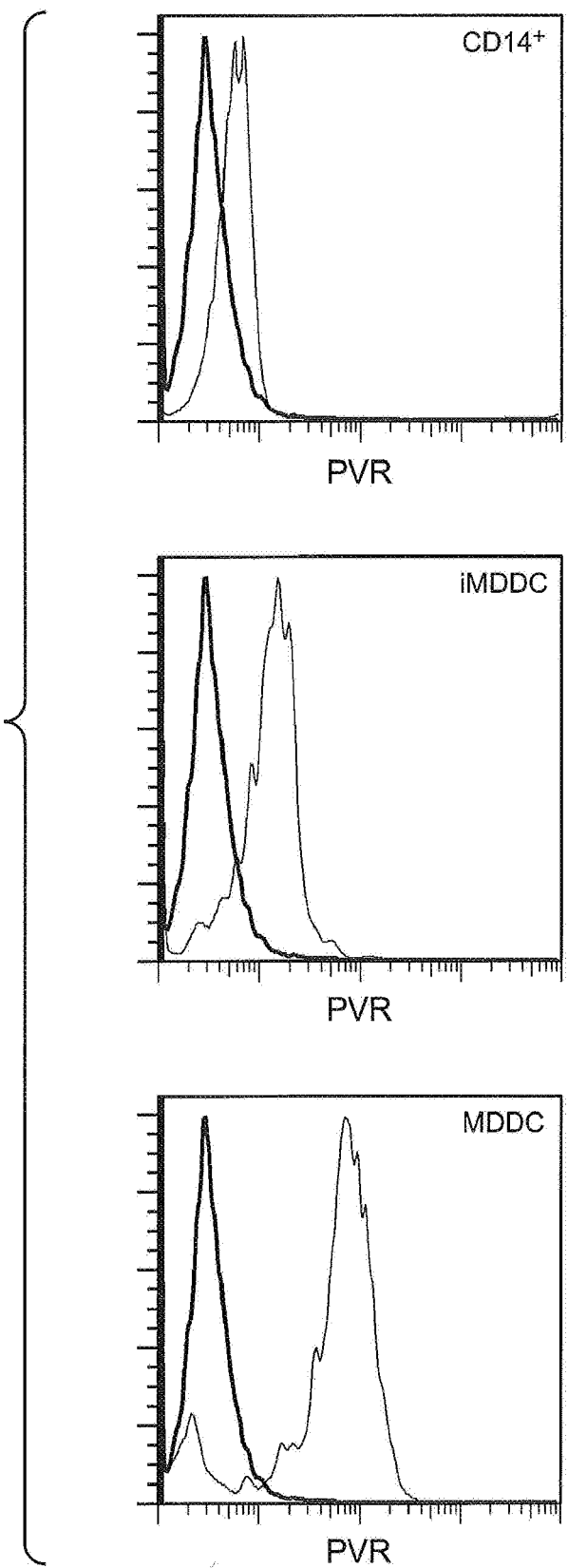

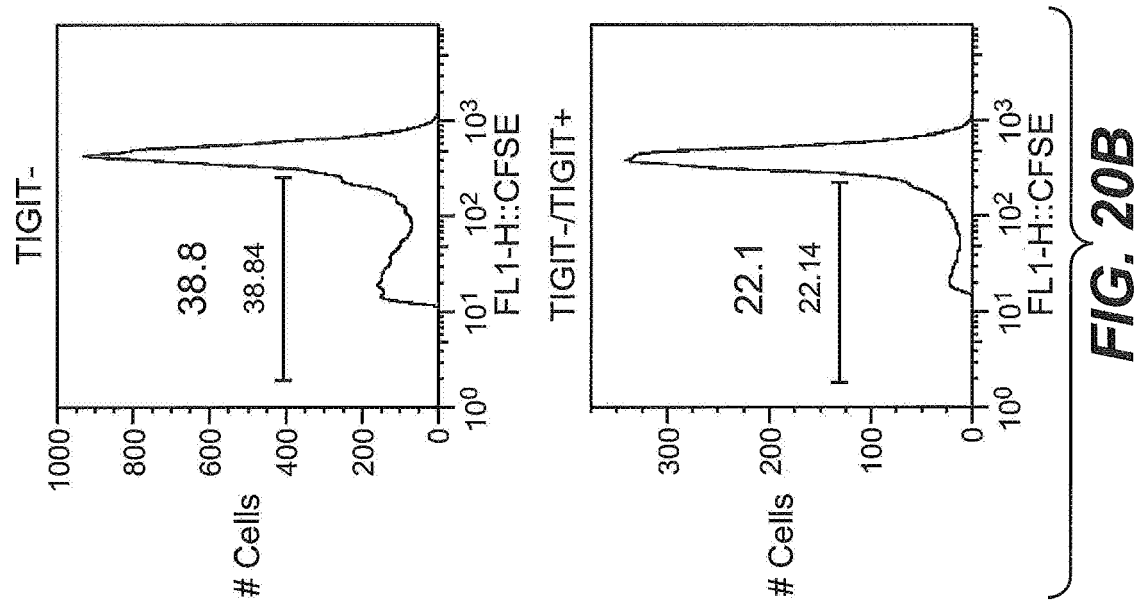
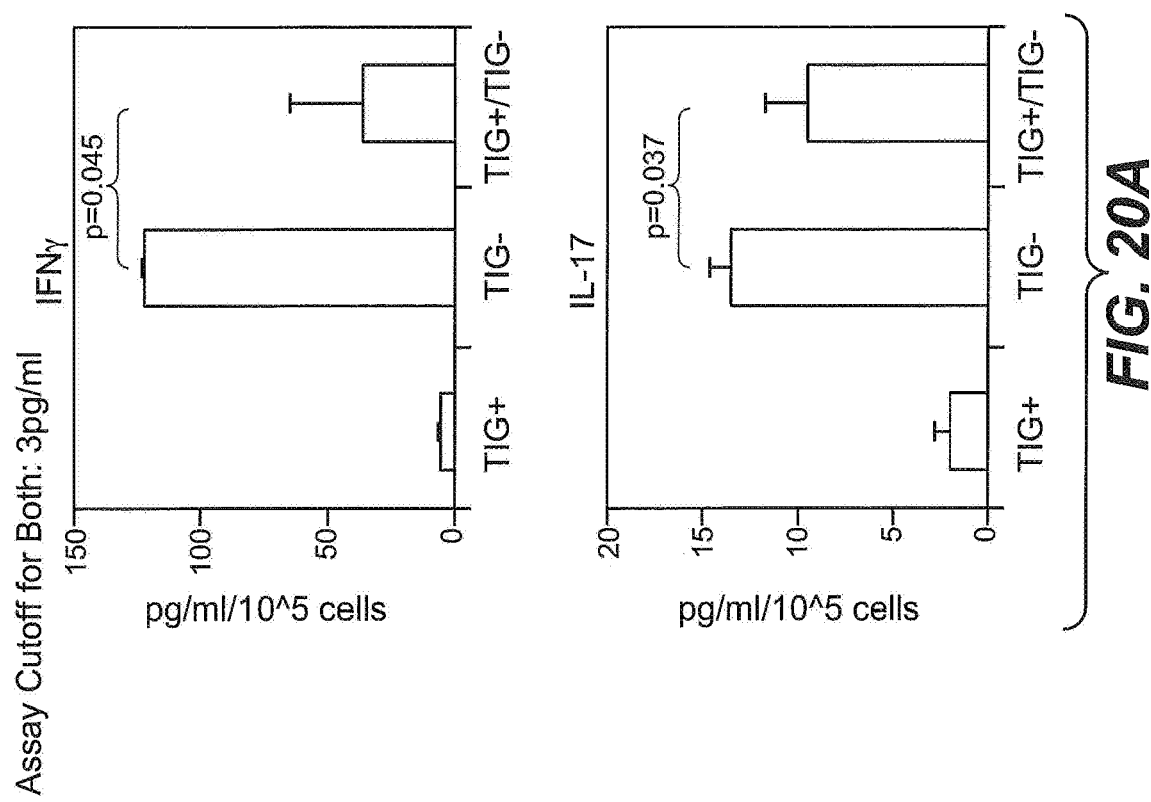
FIG. 20A
FIG. 20B

FIG. 23A     FIG. 23B

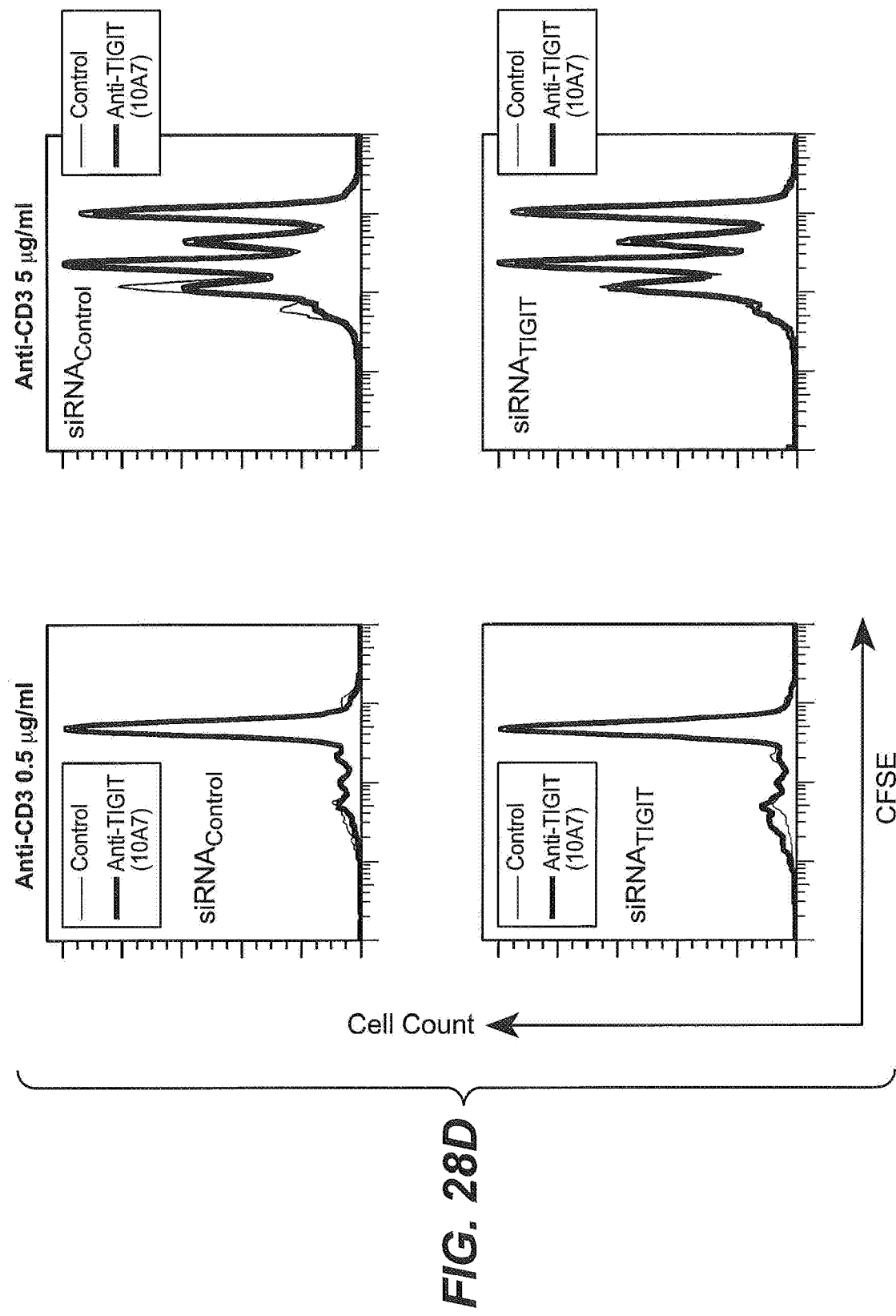

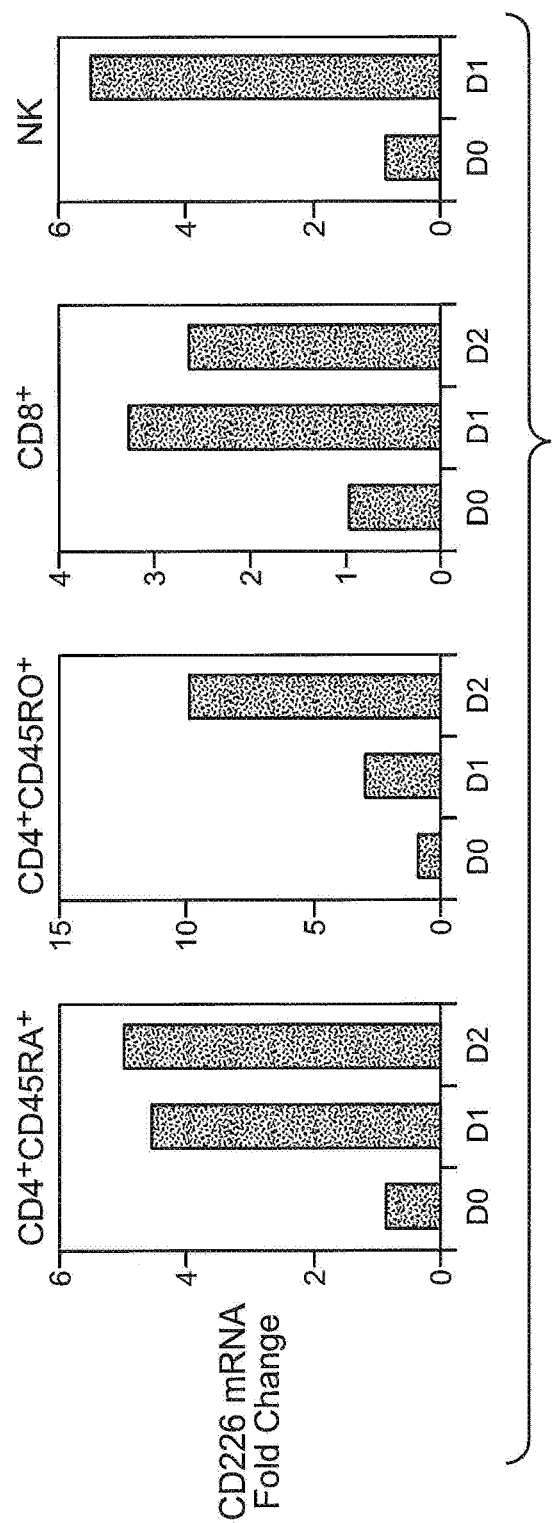
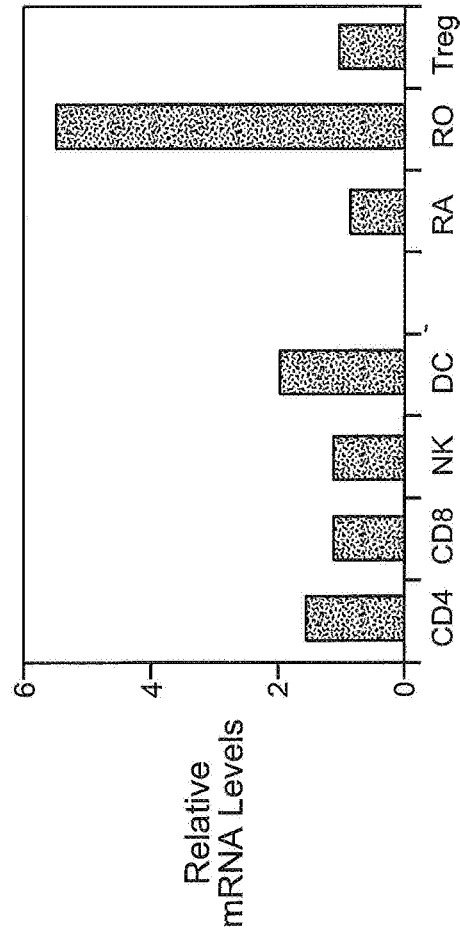
FIG. 29B
FIG. 29C

COMPOSITIONS AND METHODS FOR THE TREATMENT OF IMMUNE RELATED DISEASES

RELATED APPLICATIONS

This application is a divisional application of U.S. application Ser. No. 15/231,032, filed Aug. 8, 2016, which is a divisional application of U.S. application Ser. No. 13/648,191, filed Oct. 9, 2012, now U.S. Pat. No. 9,499,596, which is a continuation of U.S. patent application Ser. No. 12/420,234, filed Apr. 8, 2009, now abandoned, which claims priority under 35 U.S.C. § 119(e) to U.S. Provisional Application No. 61/123,530, filed Apr. 9, 2008, and to U.S. Provisional Application No. 61/194,271, filed Sep. 26, 2008, the contents of which are incorporated in their entirety herein by reference.

FIELD OF THE INVENTION

The present invention relates to compositions and methods useful for the diagnosis and treatment of immune related diseases.

BACKGROUND OF THE INVENTION

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases, non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response. Another subcategory of helper T cells are the follicular helper T cells ($T_{Fh}$) (for review, see Vineusa et al., Nat. Rev. Immunol. 5: 853-865 (2005)). Detectable by their characteristic expression of CXC- chemokine receptor 5 (Schaerli et al., J. Exp. Med. 192: 1553-62 (2000)), these cells have been found to produce IL-10 and possibly IL-21. $T_{Fh}$ cells provide assistance to germinal-center B cells, particularly aiding the survival and propagation of B cells and potently inducing antibody production during coculture with B cells. They have also been implicated in tolerogenesis.

Regulatory T cells ($T_{reg}$) are a subset of helper T cells that play a critical role in inhibition of self-reactive immune responses and are often found in sites of chronic inflammation such as in tumor tissue (Wang, H. Y. & Wang, R. F., Curr Opin Immunol 19, 217-23 (2007)). $T_{regs}$ are defined phenotypically by high cell surface expression of CD25, CLTA4, GITR, and neuropilin-1 (Read, S., Malmstrom, V. & Powrie, F., J Exp Med 192, 295-302 (2000); Sakaguchi, S., et al., J Immunol 155, 1151-64 (1995); Takahashi, T. et al., J Exp Med 192, 303-10 (2000); McHugh, R. S. et al., Immunity 16, 311-23 (2002); Bruder, D. et al., Eur J Immunol 34, 623-30 (2004)), and are under the control of the transcription factor FOXP3 (Hori, S., Nomura, T. & Sakaguchi, S., Science 299, 1057-61 (2003)). $T_{regs}$ perform their suppressive function on activated T cells through contact-dependent mechanisms and cytokine production (Fehervari, Z. & Sakaguchi, Curr Opin Immunol 16, 203-8 (2004)). $T_{regs}$ also modulate immune responses by direct interaction with ligands on dendritic cells (DC), such as CTLA4 interaction with B7 molecules on DC that elicits the induction of indoleamine 2,3-dioxygenase (IDO) (Fallarino, F. et al., Nat Immunol 4, 1206-12 (2003)), and CD40L ligation (Serra, P. et al., Immunity 19, 877-89 (2003)). DCs are professional antigen-presenting cells capable of inducing immunity or tolerance against self or non-self antigens. DC-expanded $T_{regs}$ suppress alloreactivity responses in vitro (Yamazaki, S. et al., Proc Natl Acad Sci USA 103, 2758-63 (2006); Ahn, J. S., Krishnadas, D. K. & Agrawal, Int Immunol 19, 227-37 (2007)), and when adoptively transferred, appropriate $T_{regs}$ inhibited diabetes in NOD.scid mice (Tarbell, K. V. et al., J Exp Med 199, 1467-77 (2004)) or experimentally induced asthma (Lewkowich, I. P. et al. J Exp Med 202, 1549-61 (2005)). Specific interactions of ligands on DC with $T_{regs}$ can also abrogate their suppressive function, such as engagement of GITR in mice (Shimizu, J., et al., Nat Immunol 3, 135-42 (2002)), suggesting DC may have a pluralistic role in modulating $T_{reg}$ function.

The molecules CTLA4 and GITR are representative of ligands defined within the CD28-B7 and TNF-superfamilies of co-stimulatory/-inhibitory molecules, respectively (Greenwald, R. J., et al., Annu Rev Immunol 23, 515-48 (2005)). These molecules are high on $T_{regs}$ but are also typically upregulated on activated T cells. In order to search for new co-stimulatory molecules expressed in $T_{reg}$ cells searches were performed to identify genes specifically expressed in T cells (Abbas, A.R. et al., Genes Immun 6, 319-31 (2005)) that had both Ig domains and immunoreceptor tyrosine-based activation or inhibition (ITAM/ITIM) motifs. Through the intersection of these two genome-wide bioinformatics search strategies a novel cell surface-bound protein with the protein encoding an IgV domain, a transmembrane domain, and two putative immunoreceptor tyrosine inhibitory motifs was identified (see US patent publication no. US20040121370, incorporated herein by reference). The protein designated TIGIT (for T-Cell-Ig and ITIM domain) was shown to be expressed on T cells—particularly $T_{reg}$ and memory cell subsets—as well as NK cells. There is a need for new therapeutics and methods of treatment to address immune disorders, particularly autoimmune disorders. Herein, Applicants identify TIGIT binding partners and provide new compositions, detection methods, and methods of treatment for immune disorders modulated by TIGIT interaction with those binding partners and the elucidated TIGIT effects on T cell maturation and activity.

SUMMARY OF THE INVENTION

The present invention concerns compositions and methods useful for the diagnosis and treatment of immune related disease in mammals, including humans. The present invention is based on the identification of proteins involved in the negative regulation of proliferation and function of certain types of immune cells. Immune related diseases can be treated by suppressing or enhancing the immune response. Molecules that enhance the immune response stimulate or potentiate the immune response to an antigen. Molecules which stimulate the immune response can be used therapeutically where enhancement of the immune response would be beneficial. Alternatively, molecules that suppress the immune response attenuate or reduce the immune response to an antigen (e.g., neutralizing antibodies) can be used therapeutically where attenuation of the immune response would be beneficial (e.g., inflammation). Herein, Applicants demonstrate that TIGIT (for "T-Cell-Ig and ITIM domain") protein specifically binds to poliovirus receptor (PVR, also known as CD155) and several other members of a newly elucidated protein family, and that this TIGIT-PVR interaction negatively regulates T cell activation and proliferation. Accordingly, TIGIT polypeptides, agonists thereof, and antagonists thereof, as well as PVR polypeptides, agonists thereof and antagonists thereof are useful to prepare medicines and medicaments for the treatment of immune-related and inflammatory diseases. The invention also provides methods of treating immune-related and inflammatory diseases and methods and compositions for detecting and assessing the status of immune-related and inflammatory diseases.

In one embodiment, the invention provides an isolated polypeptide comprising an amino acid sequence comprising one or more of the following amino acids: an alanine at amino acid position corresponding to amino acid position 67 of human TIGIT, a glycine at an amino acid position corresponding to amino acid position 74 of human TIGIT, a proline at an amino acid position corresponding to amino acid position 114 of human TIGIT, and a glycine at an amino acid position corresponding to amino acid position 116 of human TIGIT. In one aspect, the polypeptide is not PVR, PVRL1, PVRL2, PVRL3, PVRL4, TIGIT, CD96, or CD226. In another aspect, the polypeptide further comprises one or more of: an amino acid selected from valine, isoleucine, and leucine at an amino acid position corresponding to amino acid position 54 of human TIGIT, an amino acid selected from serine and threonine at an amino acid position corresponding to amino acid position 55 of human TIGIT, a glutamine at an amino acid position corresponding to amino acid position 56 of human TIGIT, a threonine at an amino acid position corresponding to amino acid position 112 of human TIGIT, and an amino acid selected from phenylalanine and tyrosine at an amino acid position corresponding to amino acid position 113 of human TIGIT. In another aspect, the polypeptide further comprises one or more structural submotifs selected from the following:

a. an amino acid selected from valine and isoleucine at amino acid position 54-an amino acid selected from serine and threonine at amino acid position 55-a glutamine at amino acid position 56;

b. an alanine at position 67-any amino acid at each of amino acid positions 68-73-a glycine at amino acid position 74; and c. a threonine at amino acid position 112-an amino acid selected from phenylalanine and tyrosine at amino acid position 113-a proline at amino acid position 114-any amino acid at amino acid position 115-a glycine at amino acid position 116, wherein the numbering of the amino acid positions corresponds to the amino acid positions of human TIGIT, although the absolute numbering of the amino acids in the polypeptide may differ.

In another embodiment, the invention provides a method of determining whether a test polypeptide is a member of the TLP family of polypeptides comprising aligning the amino acid sequence of the test polypeptide with an amino acid sequence of one or more members of the TLP family of polypeptides and assessing the presence or absence in the test polypeptide amino acid sequence of one or more of an alanine at amino acid position corresponding to amino acid position 67 of human TIGIT, a glycine at an amino acid position corresponding to amino acid position 74 of human TIGIT, a proline at an amino acid position corresponding to amino acid position 114 of human TIGIT, and a glycine at an amino acid position corresponding to amino acid position 116 of human TIGIT. In another embodiment, the invention provides a method for identifying one or more members of the TLP protein family by identifying proteins in one or more sequence databases whose amino acid sequences comprise at least one amino acid selected from an alanine at amino acid position corresponding to amino acid position 67 of human TIGIT, a glycine at an amino acid position corresponding to amino acid position 74 of human TIGIT, a proline at an amino acid position corresponding to amino acid position 114 of human TIGIT, and a glycine at an amino acid position corresponding to amino acid position 116 of human TIGIT.

In another embodiment, the invention provides an isolated agent that specifically interacts with one or more conserved or substantially conserved regions of TLP family members. In one aspect, the agent is an antagonist of the expression and/or activity of a TLP family member. In another aspect, the antagonist is selected from a small molecule inhibitor, an inhibitory antibody or antigen-binding fragment thereof, an aptamer, an inhibitory nucleic acid, and an inhibitory polypeptide. In another aspect, the agent is an agonist of the expression and/or activity of a TLP family member. In another aspect, the agonist is selected from an agonizing antibody or antigen-binding fragment thereof, an agonizing peptide, and a small molecule or protein that activates TIGIT binding to PVR and/or TIGIT intracellular signaling mediated by PVR. In another embodiment, the invention provides a method of identifying or detecting one or more TLP family members by contacting a putative TLP family member polypeptide with at least one of the above agents and determining the binding of the at least one agent to the putative TLP family member.

In another embodiment, the invention provides a method of determining whether a test immune cell is an activated or normal $T_{reg}$, memory T cell, NK cell, or $T_{Fh}$ cell, comprising assessing the level of expression of TIGIT in the test immune cell and comparing it to the level of expression of TIGIT in a known activated or normal Treg, memory T cell, NK cell, or TFh cell, or by comparing the level of expression of TIGIT in the test immune cell to known standard TIGIT expression value(s). In another embodiment, the invention provides a method for modulating immune system function and/or activity comprising modulating the binding of TIGIT to one or more of PVR, PVRL3, and PVRL2.

In another embodiment, the invention provides an anti-TIGIT antibody or a fragment thereof comprising at least one HVR comprising an amino acid sequence selected from the amino acid sequences set forth in SEQ ID NOs: 23-28. In another embodiment, the invention provides an anti-TIGIT antibody or a fragment thereof comprising at least one HVR comprising an amino acid sequence selected from the amino acid sequences set forth in SEQ ID NOs: 31-36. In another embodiment, the invention provides an anti-TIGIT antibody or a fragment thereof wherein the antibody light chain comprises the amino acid sequence set forth in SEQ ID NO: 21. In another embodiment, the invention provides an anti-TIGIT antibody or a fragment thereof wherein the antibody light chain comprises the amino acid sequence set forth in SEQ ID NO: 29. In another embodiment, the invention provides an anti-TIGIT antibody or a fragment thereof wherein the antibody heavy chain comprises the amino acid sequence set forth in SEQ ID NO: 22 or a portion thereof. In another embodiment, the invention provides an anti-TIGIT antibody or a fragment thereof wherein the antibody heavy chain comprises the amino acid sequence set forth in SEQ ID NO: 30 or a portion thereof. In another embodiment, the invention provides an anti-TIGIT antibody or a fragment thereof wherein the antibody light chain comprises the amino acid sequence set forth in SEQ ID NO: 21 or a portion thereof and the antibody heavy chain comprises the amino acid sequence set forth in SEQ ID NO: 22 or a portion thereof. In another embodiment, the invention provides an anti-TIGIT antibody or a fragment thereof wherein the antibody light chain comprises the amino acid sequence set forth in SEQ ID NO: 29 or a portion thereof and the antibody heavy chain comprises the amino acid sequence set forth in SEQ ID NO: 30 or a portion thereof. In another embodiment, the invention provides an anti-TIGIT antibody or a fragment thereof wherein the antibody light chain is encoded by the nucleotide sequence of SEQ ID NO: 50 or a portion thereof. In another embodiment, the invention provides an anti-TIGIT antibody or a fragment thereof wherein the antibody heavy chain is encoded by the nucleotide sequence of SEQ ID NO: 51 or a portion thereof. In one aspect, an antibody or antigen-binding fragment thereof of the invention is selected from a humanized antibody, a chimeric antibody, a bispecific antibody, a heteroconjugate antibody, and an immunotoxin.

In another aspect, the at least one HVR of the invention is at least 90%, 91%, 92%, 93%, 94%, 95%, 96%, 97%, 98%, or 99% identical to an HVR set forth in any of SEQ ID NOs: 23-28. In another aspect, the at least one HVR of the invention is at least 90%, 91%, 92%, 93%, 94%, 95%, 96%, 97%, 98%, or 99% identical to an HVR set forth in any of SEQ ID NOs: 31-36. In another aspect, the light chain of an antibody or antigen-binding fragment of the invention comprises an amino acid sequence at least 90%, 91%, 92%, 93%, 94%, 95%, 96%, 97%, 98%, or 99% identical to the amino acid sequence set forth in SEQ ID NO: 21. In another aspect, the light chain of an antibody or antigen-binding fragment of the invention comprises an amino acid sequence at least 90%, 91%, 92%, 93%, 94%, 95%, 96%, 97%, 98%, or 99% identical to the amino acid sequence set forth in SEQ ID NO: 29. In another aspect, the heavy chain of an antibody or antigen-binding fragment of the invention comprises an amino acid sequence at least 90%, 91%, 92%, 93%, 94%, 95%, 96%, 97%, 98%, or 99% identical to the amino acid sequence set forth in SEQ ID NO: 22. In another aspect, the heavy chain of an antibody or antigen-binding fragment of the invention comprises an amino acid sequence at least 90%, 91%, 92%, 93%, 94%, 95%, 96%, 97%, 98%, or 99% identical to the amino acid sequence set forth in SEQ ID NO: 30. In another aspect, an antibody or antigen-binding fragment of the invention comprises a light chain comprising an amino acid sequence at least 90%, 91%, 92%, 93%, 94%, 95%, 96%, 97%, 98%, or 99% identical to the amino acid sequence set forth in SEQ ID NO: 21 and a heavy chain comprising an amino acid sequence at least 90%, 91%, 92%, 93%, 94%, 95%, 96%, 97%, 98%, or 99% identical to the amino acid sequence set forth in SEQ ID NO: 22. In another aspect, an antibody or antigen-binding fragment of the invention comprises a light chain comprising an amino acid sequence at least 90%, 91%, 92%, 93%, 94%, 95%, 96%, 97%, 98%, or 99% identical to the amino acid sequence set forth in SEQ ID NO: 29 and a heavy chain comprising an amino acid sequence at least 90%, 91%, 92%, 93%, 94%, 95%, 96%, 97%, 98%, or 99% identical to the amino acid sequence set forth in SEQ ID NO: 30.

In another embodiment, the invention provides a method of modulating a CD226-PVR interaction and/or a CD96-PVR interaction comprising administering at least one of TIGIT, an agonist of TIGIT expression and/or activity, or an antagonist of TIGIT expression and/or activity in vivo or in vitro. In one aspect, TIGIT or an agonist of TIGIT expression and/or activity is administered and the CD226-PVR interaction and/or the CD96-PVR interaction is inhibited or blocked. In another aspect, an antagonist of TIGIT expression and/or activity is administered and the CD226-PVR interaction and/or the CD96-PVR interaction is stimulated.

In another embodiment, the invention provides a method of modulating immune cell function and/or activity by modulating TIGIT and/or PVR expression and/or activity, or by modulating the intracellular signaling mediated by TIGIT binding to PVR. In one aspect, the modulating is decreasing or inhibiting proliferation of one or more immune cells or proinflammatory cytokine release by one or more immune cells by treating the cells in vitro or in vivo with TIGIT, an agonist of TIGIT expression and/or activity, an agonist of PVR expression and/or activity, or by stimulating intracellular signaling mediated by TIGIT binding to PVR. In another aspect, the modulating is increasing or stimulating proliferation of one or more immune cells or proinflammatory cytokine release by one or more immune cells by treating the cells in vitro or in vivo with an antagonist of TIGIT expression and/or activity, an antagonist of PVR expression and/or activity, or by inhibiting intracellular signaling mediated by TIGIT binding to PVR.

In another embodiment, the invention provides a method of inhibiting an immune response by administering in vitro or in vivo TIGIT, an agonist of TIGIT expression and/or activity, an agonist of PVR expression and/or activity, or by stimulating intracellular signaling mediated by TIGIT binding to PVR. In another embodiment, the invention provides a method of increasing or stimulating an immune response by administering in vitro or in vivo an antagonist of TIGIT expression and/or activity, an antagonist of PVR expression and/or activity, or by inhibiting intracellular signaling mediated by TIGIT binding to PVR. In another embodiment, the invention provides a method of modulating the type and/or amount of cytokine production from an immune cell by modulating TIGIT or PVR expression and/or activity in vitro or in vivo. In one aspect, proinflammatory cytokine production is stimulated and/or increased by administration of an antagonist of TIGIT expression and/or activity, an antagonist of PVR expression and/or activity, or by inhibiting intracellular signaling mediated by TIGIT binding to PVR. In another aspect, proinflammatory cytokine production is inhibited by administration of an agonist of TIGIT expression and/or activity, an agonist of PVR expression and/or activity, or by stimulating intracellular signaling mediated by TIGIT binding to PVR.

In another embodiment, the invention provides a method of stimulating ERK phosphorylation and/or intracellular signaling through the ERK pathway in one or more immune cells comprising treating the one or more immune cells with TIGIT, an agonist of TIGIT expression and/or activity, or an agonist of PVR expression and/or activity.

In another embodiment, the invention provides a method of diagnosing an immune-related disease relating to aberrant immune cell response in a subject comprising assessing the expression and/or activity of TIGIT in a sample from the subject and comparing the expression and/or activity of TIGIT to a reference amount of TIGIT expression and/or activity or the amount of TIGIT expression and/or activity in a sample from a normal subject. In one aspect, the immune-related disease is selected from psoriasis, arthritis, inflammatory bowel disease or cancer. In another aspect, the cancer is breast cancer. In another embodiment, the invention provides a method of assessing the severity of an immune-related disease relating to aberrant immune cell response in a subject comprising assessing the expression and/or activity of TIGIT in a sample from the subject and comparing the expression and/or activity of TIGIT to a reference amount of TIGIT expression and/or activity or the amount of TIGIT expression and/or activity in a sample from a normal subject. In one aspect, the immune-related disease is selected from psoriasis, arthritis, inflammatory bowel disease or cancer. In another aspect, the cancer is breast cancer. In another embodiment, the invention provides a method of preventing an immune-related disease relating to aberrant immune cell response in a subject comprising modulating the expression and/or activity of TIGIT in the subject. In one aspect, the immune-related disease is selected from psoriasis, arthritis, inflammatory bowel disease or cancer. In another aspect, the cancer is breast cancer. In another embodiment, the invention provides a method of treating or lessening the severity of an immune-related disease relating to aberrant immune cell response in a subject comprising modulating the expression and/or activity of TIGIT in the subject. In one aspect, the immune-related disease is selected from psoriasis, arthritis, inflammatory bowel disease or cancer. In another aspect, the cancer is breast cancer.

BRIEF DESCRIPTION OF THE DRAWINGS

FIGS. 2A and 2B depict an alignment of protein sequences of IgV domains of the indicated PVR family proteins. Side chains that share similarity across sequences are marked according to property. V-frame fingerprint residues (black circle) and PVR-related fingerprint residues (thick line boxed residues) are indicated. For comparative purposes, six IgV domain sequences (set forth under the horizontal line) from non-PVR family members are also aligned.

FIGS. 4B-1 to 4B-6 depict the results of FACS analyses to assess the binding of biotinylated Fc-fusion proteins to receptor-expressing CHO stable transfectants, as described in Example 2.

FIG. 6 shows graphs depicting the results of competition binding studies among TIGIT, PVR, CD226 and CD96, as described in Example 2.

FIG. 7A depicts the binding of biotinylated PVR-Fc to CHO transfectants expressing CD226 or TIGIT in the presence (dotted line) or absence (solid line) of a 10-fold molar excess of antibody D171. The results from a matched isotype control antibody are indicated by the shaded area. FIG. 7B depicts the binding of PVR-Fc (top line) or buffer (bottom line) to biosensors loaded with CD226-Fc or TIGIT-Fc. The middle line indicates PVR-Fc binding to biosensor pre-loaded CD226-Fc or TIGIT-Fc that had been blocked with antibody D171 prior to exposure to PVR-Fc.

FIGS. 9A and 9B depict the results of experiments testing the ability of anti-TIGIT antibody 10A7 to bind to TIGIT at the surface of cells, as described in Example 3. FIG. 9A shows the binding of anti-TIGIT antibody 10A7 to stable 293-TIGIT cell lines (solid line) and the abrogation of that binding in the presence of PVR-Fc (dashed line). The grey region represents the binding of an isotype-matched control antibody. FIG. 9B shows the results of FACS analyses demonstrating that TIGIT co-expresses with FoxP3 in GITR$^+$ CD4 T-cells. The data shown is representative of two independent experiments.

FIGS. 10A-1, 10-A2, and 10B to 10F depict the results of experiments assessing TIGIT expression either by mRNA analysis or by binding studies at the cell surface, as described in Example 3. FIGS. 10A-1 and 10A-2 depict the results of flow cytometric experiments to determine the expression of TIGIT and CD226 on resting or activated (for one or two days) CD4$^+$CD45RA$^+$ (left panel) or CD4$^+$CD45RO$^+$ T cells (right panel), as described in Example 2(A). FIG. 10E depicts the results of FACS experiments assessing the cell surface expression of TIGIT on human PBMC cells expressing low or high amounts of CD25 and shows that expression of TIGIT correlates with expression of FOXP3. FIG. 10F depicts the results of FACS experiments assessing TIGIT expression in sorted CD4+CD25$^{hi}$T cells activated with anti-CD3 and anti-CD28 for 24 hours (left panel) and complementary RT-PCR analyses of TIGIT mRNA levels in resting or activated CD25−or CD25$^{hi}$CD4+ cells.

FIG. 12A depicts the results of flow cytometry experiments to assess the stability of TIGIT expression on T cells, as described in Example 3.

FIGS. 19A-19D depict the results of experiments assessing the effect of TIGIT on T cell activation, as described in Example 4. FIG. 19A depicts the results of FACS assays assessing PVR expression on CD14+ monocytes, iMDDC and MDDC. Anti-PVR experiments are shown without shading and isotype-matched controls are shown in grey. FIG. 19B depicts the results of in vitro MLR assays using TNFα-matured DC and isolated CD4+ T cells assessing the effect of TIGIT-Fc on T cell proliferation. The data indicated with the asterisk has a p<0.001. FIG. 19C depicts the results of experiments assessing T cell proliferation by [$^3$H]-thymidine incorporation (cpm) (left panel) and IFN-γ production by ELISA (right panel) in CD4+ T cells activated with soluble anti-CD3 in the presence of autologous CD11c+DCs and anti-TIGIT antibody 10A7 (black bars) or isotype control (white bars). A single asterisk indicates a p<0.01; a double asterisk indicates a p<0.001. FIG. 19D depicts the results of experiments assessing proliferation and IFN-γ production in naïve CD4+CD25− T cells activated with autologous CD11c+DC and soluble anti-3 in the presence of 100 μg/mL TIGIT-Fc (grey bars) or isotype control (white bars). A single asterisk indicates a p<0.01; a double asterisk indicates a p<0.001.

FIGS. 20A and 20B depict the results of experiments assessing the ability of sorted TIGIT T cells to inhibit TIGIT− T cell proliferation in an MLR assay, as described in Example 4.

FIGS. 22A-1 to 22A-3 show the results of ELISA assays measuring IL-10 or IL-12p40 production in iMDDC, iMDDC stimulated with TNFα, iMDDC stimulated with CD40L, iMDDC stimulated with LPS, or iMDDC stimulated with Pam3CSK4. The results shown are averages from three experiments. Lines in each panel represent data from each of three different donors. FIG. 22B shows the results of FACS analyses to measure the expression of cell surface maturation markers HLA-DR, CD80, CD83, and CD86 in treated cells. Values are represented as mean fluorescence intensity (MFI), and the data shown is representative of three donors. FIG. 22C shows data from experiments measuring TIGIT effects on other proinflammatory cytokine production from TNFα-matured or LPS-matured MDDC. The data shown are representative of three experiments. IL-6, IL12p70, and IL-18 levels were determined by LUMINEX analysis, as described in Example 5. FIG. 22D shows a graph representing the relative amounts of TGFβ secretion in iMDDC in response to TIGIT.Fc or an isotype-matched control, as described in Example 5.

FIGS. 23A-23C depict the results of experiments assessing the effect of TIGIT treatment on activation of downstream signaling by PVR, as described in Example 6. FIG. 23A shows Western blot analyses of the tyrosine phosphorylation state of PVR treated with TIGIT or a control. FIG. 23B shows Western blot analyses of ERK dimerization state upon treatment of iMDDC with TIGIT-Fc, TIGIT-Fc-DANA, or control. FIG. 23C shows Western blot analyses of active versus total β-catenin in TIGIT-treated versus control-treated iMDDC.

FIG. 24A shows graphs of results from experiments testing the impact of a MAPK kinase inhibitor on TIGIT-Fc or TIGIT-Fc-DANA-induced decreases in IL-12p40 production. FIG. 24B shows graphs of results from experiments assessing the impact of an anti-TIGIT antibody (10A7), an anti-IL-10 antibody, or an anti-CD32 antibody on TIGIT-mediated decreases in IL-12p40 production from TNFα-matured MDDC.

FIG. 27A shows a graph representing ear swelling data from wild-type or IL-10 knockout mice treated with anti-ragweed antibody, TIGIT-Fc, or CTLA4. FIG. 27B shows data representing the proliferation response of spleen cells from TIGIT-Fc–, CTLA4-Fc-, or control-treated mice to KLH restimulation. The data shows as response±standard deviation (n=3 per group; the in vitro recall assay was performed in triplicate wells). FIG. 27C shows a graph representing ear swelling data from wild-type mice treated with TIGIT-Fc, TIGIT-Fc-DANA, or anti-TIGIT antibody 10A7. FIGS. 27D and 27E depict graphs indicating the proliferation response of spleen cells from wild-type (FIG. 27D) or IL-10 knockout (FIG. 27E) TIGIT-Fc-treated mice to KLH restimulation. FIGS. 27F and 27G depict graphs indicating the IL-2 or IFN-γ levels in culture supernatants from splenocytes isolated from wild-type (FIG. 27F) or IL-10 knockout (FIG. 27G) TIGIT-Fc-treated mice that had been reactivated with KLH for two days. Data are shown as mean±s.d. (n=3 per group; in vitro recall was performed in triplicate wells). An asterisk indicates p<0.001. FIG. 27H depicts graphs showing the relative mRNA levels of IL-10 (left panel), IL-12/23p40 (center panel), and IL-12p35 (right panel) from CD11c+ splenocytes of TIGIT-Fc and isotype control-treated wild-type or IL-10-deficient mice, as determined by qRT-PCR (n=8). IL-10 mRNA levels from WT CD11c− depleted splenocytes were also determined as a control. Data represent arbitrary mRNA levels relative to corresponding mRNA levels from unimmunized mice. An asterisk indicates p<0.05.

FIGS. 28A-28E depict the results of experiments assessing the effects of knock-down of TIGIT expression by TIGIT-specific siRNA, as described in Example 4(B). FIG. 28A shows the results of qRT-PCR analysis of TIGIT knock down efficiency versus control siRNA. CTLA4 mRNA levels were determined as a non-target control. FIG. 28B shows FACS analyses of surface TIGIT expression in siRNA$_{control}$ and siRNA$_{TIGIT}$-treated cells (summarized in Table 7). FIGS. 28C and 28D show the results of FACS analyses of cell proliferation of CD4+CD45RO+ human T cells activated with plate-bound anti-CD3 alone or in conjunction with anti-CD28 in the presence of siRNA$_{control}$ or siRNA$_{TIGIT}$ (FIG. 27C) or anti-TIGIT antibody 10A7 (FIG. 27D). FIG. 28E depicts the results of analyses of cytokine production from the cells used in the assays in FIG. 28C after two days of culture. The data shown is representative of four individual donors and experiments.

FIGS. 29A-29E depict the results of experiments assessing the expression of CD226 on various cell types and upon various treatments. FIG. 29A depicts the results of FACS analyses showing the surface expression of CD226 on resting and anti-CD3 and anti-CD28 activated (day 1 and 2) sorted naïve CD4+CD45RA+cells (top panels) or memory CD4+CD45RO+ cells (bottom panels) using anti-CD226. FIG. 29B provides graphs showing the fold-increase in mRNA levels on sorted CD4+CD45RO+, CD4+CD45RA+ and CD8+ cells activated with anti-CD3 plus anti-CD28 for 1 or 2 days, and sorted CD56+ NK cells activated with IL-2 plus IL-15 for one day, as compared to unstimulated cells. FIG. 29C shows the relative mRNA levels of a variety of cell markers on cells sorted directly ex vivo from PBMC as determined by qRT-PCR, as an indicator of the populations of CD4+, CD8+, CD4+CD45RO+, CD4+CD25$^{hi}$T$_{regs}$, NK and CD11c+DC cells relative to naïve CD4+CD45RA+ cells. Data shown represents an average of data from three donors. FIG. 29D depicts the results of FACS analyses to determine the co-expression of CD226 and CD25 on gated CD4+ cells taken from a population of total human PBMC stained with anti-CD4, anti-CD25, and anti-CD226. The plot shown is one representative from two donors. FIG. 29E shows a graph depicting TIGIT and CD226 mRNA levels in activated and resting CD4+CD25− and CD4+CD25$^{hi}$ cells isolated from PBMC. mRNA levels are representated as fold-change over the resting CD4+CD25− cells and are an average of data from two donors.

FIG. 30A shows graphs comparing the proliferation of TIGIT-deficient (TIGIT.KO) T cells versus wild-type T cells in the absence (left panel) or presence (middle panel) of wild-type antigen-presenting cells. The right panel shows graphs comparing the proliferation of TIGIT.KO T cells to wild-type T cells in the presence of TIGIT.KO antigen-presenting cells. FIG. 30B shows the results of FACS assays assessing IFNγ and IL-4 levels in TIGIT.KO versus wild-type T cells. FIG. 30C are graphs showing the measured levels of the indicated cytokines in the supernatants of TIGIT.KO or wild-type T cells.

DETAILED DESCRIPTION OF THE PREFERRED EMBODIMENTS

Figure 2B:
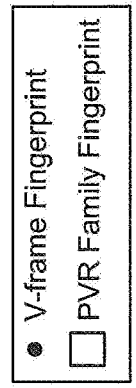

TIGIT had previously been identified as a putative modulator of immune function (see, e.g., US patent publication no. US20040121370, incorporated herein by reference). Herein, Applicants demonstrate that TIGIT is a member of a newly described family of immune-related proteins that includes poliovirus receptor (PVR, also known as NECL5 or CD155), PVR-like proteins 1-4 (PVRL1-4), CD96, and CD226. Applicants provide the conserved structural elements of this new family, whose members play roles in immune regulation and function, and provide methods to identify further family members.

Applicants show that TIGIT binds tightly to PVR, and binds with lesser Kd to PVRL3 (also known as nectin-3 or CD113) and PVRL2 (also known as nectin-2 or CD112). PVR is a cell surface receptor highly expressed on dendritic cells (DC), as well as FDC, fibroblasts, endothelial cells, and some tumor cells (Sakisaka, T. & Takai, Y., *Curr Opin Cell Biol* 16, 513-21 (2004); Fuchs, A. & Colonna, M., *Semin Cancer Biol* 16, 359-66 (2006)). Applicants show by mRNA and FACS analyses that TIGIT is predominantly expressed on a variety of activated T cells, particularly regulatory T cells (T$_{reg}$), memory T cells, NK cells, and follicular T helper cells (T_{fh}). The studies described herein demonstrate the interaction of TIGIT with PVR on DC, and show that this binding interaction modulates DC function, particularly cytokine production. TIGIT-bound human DC secreted high levels of IL-10 and fewer pro-inflammatory cytokines (such as IL-12p40 and IL-12p70). TIGIT binding to immature T cells (as assessed using TIGIT fusion constructs) inhibited T cell activation and proliferation. Notably, this inhibition was reversed in the presence of an ERK inhibitor, indicating that ERK activation may be an important step in the functioning of TIGIT to modulate DC activity. Applicants show herein that TIGIT T cells suppress proliferation of not only other TIGIT⁻T cells, but also antigen presenting cells when present in a mixed population of immune cells, and that TIGIT itself is responsible for this suppressive effect, since inclusion of a blocking anti-TIGIT antibody in the mixture greatly reduces the observed suppression.

TIGIT is increased in expression in arthritis, psoriasis, inflammatory bowel disorder, and breast cancer tissues relative to normal control tissues, as is shown herein. Applicants also directly demonstrate the ability of TIGIT to modulate immune response by showing that a TIGIT fusion protein inhibited human T cell responses in vitro and murine T cell activation in a delayed-type hypersensitivity in vivo assay. TIGIT significantly modified mature DC, and to a lesser extent immature DC, suggesting the TIGIT-PVR interaction may be important in fine-tuning a regulatory immune response once DC become fully activated antigen-presenting cells. The experiments presented herein suggest a mechanism by which TIGIT inhibits T cell activation through an inhibitory feedback loop via the induction of IL-10 in DC. Accordingly, the invention further provides novel methods of modulating immune function by modulating particular subsets of cytokines or particular subsets of immune cells. These and other aspects of the invention are described in greater detail hereinbelow.

I. Definitions

The terms "TIGIT polypeptide", "TIGIT protein" and "TIGIT" are used interchangeably herein and refer to specific polypeptide sequences as described herein. The TIGIT polypeptides described herein may be isolated from a variety of sources, such as from human tissue or tissue from a nonhuman organism, or prepared by recombinant or synthetic methods. In one embodiment, a TIGIT polypeptide has the amino acid sequence set forth in any of SEQ ID NO: 1-4. All disclosures in this specification which refer to the "TIGIT polypeptide" refer to each of the polypeptides individually as well as jointly. For example, descriptions of the preparation of, purification of, derivation of, formation of antibodies to or against, administration with, etc., pertain to each polypeptide of the invention individually. The terms "TIGIT polypeptide", "TIGIT protein", or "TIGIT" also include variants of the TIGIT polypeptides disclosed herein or known in the art.

A "native sequence TIGIT polypeptide" comprises a polypeptide having the same amino acid sequence as the corresponding TIGIT polypeptide derived from nature. Such native sequence TIGIT polypeptides can be isolated from nature or can be produced by recombinant or synthetic means. The term "native sequence TIGIT polypeptide" specifically encompasses naturally-occurring truncated or secreted forms of the specific TIGIT polypeptide (e.g., an extracellular domain sequence), naturally-occurring variant forms (e.g., alternatively spliced forms) and naturally-occurring allelic variants of the polypeptide. In various embodiments of the invention, the native sequence TIGIT polypeptides disclosed herein are mature or full-length native sequence polypeptides comprising the full-length amino acid sequences. However, while the TIGIT polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TIGIT polypeptides.

The TIGIT polypeptide "extracellular domain" or "ECD" refers to a form of the TIGIT polypeptide which is essentially free of the transmembrane and cytoplasmic domains. Ordinarily, a TIGIT polypeptide ECD will have less than 1% of such transmembrane and/or cytoplasmic domains and preferably, will have less than 0.5% of such domains. It will be understood that any transmembrane domains identified for the TIGIT polypeptides of the present invention are identified pursuant to criteria routinely employed in the art for identifying that type of hydrophobic domain. The exact boundaries of a transmembrane domain may vary but most likely by no more than about 5 amino acids at either end of the domain as identified herein. Optionally, therefore, an extracellular domain of a TIGIT polypeptide may contain from about 5 or fewer amino acids on either side of the transmembrane domain/extracellular domain boundary and such polypeptides, with or without the associated signal peptide, and nucleic acid encoding them, are contemplated by the present invention. In one embodiment, the TIGIT ECD encompasses amino acids 1-139 of the human TIGIT protein set forth in SEQ ID NO: 1.

The approximate locations of the "signal peptides" of the various TIGIT polypeptides disclosed herein can be identified using art-known methods. For example, the signal sequence of the human TIGIT polypeptide set forth in SEQ ID NO: 1 is predicted to span amino acids 1-15 (see, e.g., U.S. patent publication no. US20040121370). It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1-6 (1997) and von Heinje et al., Nucl. Acids. Res. 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TIGIT polypeptide variant" means an active TIGIT polypeptide as defined above or below having at least about 80% amino acid sequence identity with a full-length native sequence TIGIT polypeptide sequence as disclosed herein, a TIGIT polypeptide sequence lacking the signal peptide as disclosed herein, an extracellular domain of a TIGIT polypeptide, with or without the signal peptide, as disclosed herein or any other fragment of a full-length TIGIT polypeptide sequence. Such TIGIT polypeptide variants include, for instance, TIGIT polypeptides wherein one or more amino acid residues are added, or deleted, at the N- or C-terminus of the full-length native amino acid sequence. Ordinarily, a TIGIT polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence TIGIT polypeptide sequence as disclosed herein, a TIGIT polypeptide sequence lacking the signal peptide as disclosed herein, an extracellular domain of a TIGIT polypeptide, with or without the signal peptide, as disclosed herein or any other specifically defined fragment of a full-length TIGIT polypeptide sequence. Ordinarily, TIGIT variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the TIGIT polypeptide sequences identified herein is defined as the percentage of amino acid residues in a candidate sequence that are identical with the amino acid residues in the specific TIGIT polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is publicly available. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is also publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 1 and 2 demonstrate how to calculate the % amino acid sequence identity of the amino acid sequence designated "Comparison Protein" to the amino acid sequence designated "TIGIT", wherein "TIGIT" represents the amino acid sequence of a hypothetical TIGIT polypeptide of interest, "Comparison Protein" represents the amino acid sequence of a polypeptide against which the "TIGIT" polypeptide of interest is being compared, and "X, "Y" and "Z" each represent different hypothetical amino acid residues.

TABLE 1

Protein of interest   XXXXXXXXXXXXXXX   (Length = 15 amino acids)

Comparison Protein    XXXXXYYYYYYY      (Length = 12 amino acids)

% amino acid sequence identity = (the number of identically matching amino acid residues between the two polypeptide sequences as determined by ALIGN-2) divided by (the total number of amino acid residues of the protein of interest) = 5 divided by 15 = 33.3%

TABLE 2

Protein of interest   XXXXXXXXXX         (Length = 10 amino acids)

Comparison Protein    XXXXXYYYYYYZZYZ    (Length = 15 amino acids)

% amino acid sequence identity = (the number of identically matching amino acid residues between the two polypeptide sequences as determined by ALIGN-2) divided by (the total number of amino acid residues of the protein of interest) = 5 divided by 10 = 50%

Unless specifically stated otherwise, all % amino acid sequence identity values used herein are obtained as described in the immediately preceding paragraph and Tables 1 and 2 using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the TIGIT polypeptide of interest having a sequence derived from the native TIGIT polypeptide and the comparison amino acid sequence of interest (i.e., the sequence against which the TIGIT polypeptide of interest is being compared which may be a TIGIT variant polypeptide) as determined by WU-BLAST-2 by (b) the total number of amino acid residues of the TIGIT polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the TIGIT polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The terms "TIGIT polynucleotide" and "TIGIT nucleotide sequence" are used interchangeably herein and refer to specific polynucleotide sequences encoding a TIGIT polypeptide. These polynucleotides may comprise DNA or RNA or both DNA and RNA. The TIGIT polynucleotides described herein may be isolated from a variety of sources, such as from human tissue or tissue from a nonhuman organism, or prepared by recombinant or synthetic methods.

All disclosures in this specification which refer to a "TIGIT polynucleotide" refer to each of the polynucleotides individually as well as jointly. For example, descriptions of the preparation of, purification of, derivation of, administration of, compositions containing, treatment of a disease with, etc., pertain to each polynucleotide of the invention individually as well as collectively. The terms "TIGIT polynucleotide" and "TIGIT nucleotide sequence" also include variants of the TIGIT polynucleotides disclosed herein.

A "native sequence TIGIT polynucleotide" comprises a polynucleotide having the same nucleic acid sequence as the corresponding TIGIT polynucleotide derived from nature. Such native sequence TIGIT polynucleotides can be isolated from nature or can be produced by recombinant or synthetic means. The term "native sequence TIGIT polynucleotide" specifically encompasses polynucleotides encoding naturally-occurring truncated or secreted forms of the specific TIGIT polypeptide (e.g., an extracellular domain sequence), naturally-occurring variant forms (e.g., alternatively spliced forms) and naturally-occurring allelic variants of the polypeptide. In various embodiments of the invention, the native sequence TIGIT polynucleotides disclosed herein are mature or full-length native sequence polynucleotides comprising the full-length nucleic acid sequences.

A "TIGIT variant polynucleotide" or "TIGIT variant nucleic acid sequence" means a nucleic acid molecule which encodes an active TIGIT polypeptide as defined below and which has at least about 80% nucleic acid sequence identity with a nucleotide acid sequence encoding a full-length native sequence TIGIT polypeptide sequence as disclosed herein, a full-length native sequence TIGIT polypeptide sequence lacking the signal peptide as disclosed herein, an extracellular domain of a TIGIT polypeptide, with or without the signal peptide, as disclosed herein or any other fragment of a full-length TIGIT polypeptide sequence. Ordinarily, a TIGIT variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence TIGIT polypeptide sequence, a full-length native sequence TIGIT polypeptide sequence lacking the signal peptide, an extracellular domain of a TIGIT polypeptide, with or without the signal sequence, or any other fragment of a full-length TIGIT polypeptide sequence. Variants do not encompass the native nucleotide sequence.

Ordinarily, TIGIT variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to TIGIT-encoding nucleic acid sequences identified herein is defined as the percentage of nucleotides in a candidate sequence that are identical with the nucleotides in the TIGIT nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the publicly available source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 3 and 4, demonstrate how to calculate the % nucleic acid sequence identity of the nucleic acid sequence designated "Comparison DNA" to the nucleic acid sequence designated "TIGIT-DNA", wherein "TIGIT-DNA" represents a hypothetical TIGIT-encoding nucleic acid sequence of interest, "Comparison DNA" represents the nucleotide sequence of a nucleic acid molecule against which the "TIGIT-DNA" nucleic acid molecule of interest is being compared, and "N", "L" and "V" each represent different hypothetical nucleotides.

TABLE 3

| DNA of interest | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the DNA of interest) = 6 divided by 14 = 42.9%

TABLE 4

| DNA of interest | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the DNA of interest) = 4 divided by 12 = 33.3%

Unless specifically stated otherwise, all % nucleic acid sequence identity values used herein are obtained as described in the immediately preceding paragraph and Tables 3 and 4 using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the TIGIT polypeptide-encoding nucleic acid molecule of interest having a sequence derived from the native sequence TIGIT polypeptide-encoding nucleic acid and the comparison nucleic acid molecule of interest (i.e., the sequence against which the TIGIT polypeptide-encoding nucleic acid molecule of interest is being compared which may be a variant TIGIT polynucleotide) as determined by WU-BLAST-2 by (b) the total number of nucleotides of the TIGIT polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the TIGIT polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, TIGIT variant polynucleotides are nucleic acid molecules that encode an active TIGIT polypeptide and which are capable of hybridizing, preferably under stringent hybridization and wash conditions, to nucleotide sequences encoding a full-length TIGIT polypeptide as disclosed herein. TIGIT variant polypeptides may be those that are encoded by a TIGIT variant polynucleotide.

"Isolated," when used to describe the various polypeptides disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide natural environment will not be present. Ordinarily, however, isolated polypeptide will be prepared by at least one purification step.

An "isolated" TIGIT polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-TIGIT monoclonal antibodies or antibodies that specifically bind to any of the other polypeptides described herein (including agonist, antagonist, and neutralizing antibodies), anti-TIGIT or antibody compositions with polyepitopic specificity, single chain anti-TIGIT or other antibodies, and fragments of anti-TIGIT or other antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of interest (as one nonlimiting example, a TIGIT polypeptide) fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a polypeptide (as a nonlimiting example, a TIGIT polypeptide) which retain a biological and/or an immunological activity of native or naturally-occurring form of that polypeptide (in the previous example, a TIGIT activity), wherein "biological" activity refers to a biological function (either inhibitory or stimulatory) caused by a native or naturally-occurring polypeptide other than the ability to induce the production of an antibody against an antigenic epitope possessed by a native or naturally-occurring polypeptide and an "immunological" activity refers to the ability to induce the production of an antibody against an antigenic epitope possessed by a native or naturally-occurring polypeptide (in the previous example, a TIGIT antigenic epitope).

The term "aptamer" refers to a nucleic acid molecule that is capable of binding to a target molecule, such as a polypeptide. For example, an aptamer of the invention can specifically bind to a TIGIT polypeptide, or to a molecule in a signaling pathway that modulates the expression of TIGIT. The generation and therapeutic use of aptamers are well established in the art. See, e.g., U.S. Pat. No. 5,475,096, and the therapeutic efficacy of Macugen® (Eyetech, N.Y.) for treating age-related macular degeneration.

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

The terms "TIGIT antagonist" and "antagonist of TIGIT activity or TIGIT expression" are used interchangeably and refer to a compound that interferes with the normal functioning of TIGIT, either by decreasing transcription or translation of TIGIT-encoding nucleic acid, or by inhibiting or blocking TIGIT polypeptide activity, or both. Examples of TIGIT antagonists include, but are not limited to, antisense polynucleotides, interfering RNAs, catalytic RNAs, RNA-DNA chimeras, TIGIT-specific aptamers, anti-TIGIT antibodies, TIGIT-binding fragments of anti-TIGIT antibodies, TIGIT-binding small molecules, TIGIT-binding peptides, and other polypeptides that specifically bind TIGIT (including, but not limited to, TIGIT-binding fragments of one or more TIGIT ligands, optionally fused to one or more additional domains), such that the interaction between the TIGIT antagonist and TIGIT results in a reduction or cessation of TIGIT activity or expression. It will be understood by one of ordinary skill in the art that in some instances, a TIGIT antagonist may antagonize one TIGIT activity without affecting another TIGIT activity. For example, a desirable TIGIT antagonist for use in certain of the methods herein is a TIGIT antagonist that antagonizes TIGIT activity in response to one of PVR interaction, PVRL3 interaction, or PVRL2 interaction, e.g., without affecting or minimally affecting any of the other TIGIT interactions.

The terms "PVR antagonist" and "antagonist of PVR activity or PVR expression" are used interchangeably and refer to a compound that interferes with the normal functioning of PVR, either by decreasing transcription or translation of PVR-encoding nucleic acid, or by inhibiting or blocking PVR polypeptide activity, or both. Examples of PVR antagonists include, but are not limited to, antisense polynucleotides, interfering RNAs, catalytic RNAs, RNA-DNA chimeras, PVR-specific aptamers, anti-PVR antibodies, PVR-binding fragments of anti-PVR antibodies, PVR-binding small molecules, PVR-binding peptides, and other polypeptides that specifically bind PVR (including, but not limited to, PVR-binding fragments of one or more PVR ligands, optionally fused to one or more additional domains), such that the interaction between the PVR antagonist and PVR results in a reduction or cessation of PVR activity or expression. It will be understood by one of ordinary skill in the art that in some instances, a PVR antagonist may antagonize one PVR activity without affecting another PVR activity. For example, a desirable PVR antagonist for use in certain of the methods herein is a PVR antagonist that antagonizes PVR activity in response to TIGIT interaction without impacting the PVR-CD96 and/or PVR-CD226 interactions.

The terms "TIGIT agonist" and "agonist of TIGIT activity or TIGIT expression" are used interchangeably and refer to a compound that enhances or stimulates the normal functioning of TIGIT, by increasing transcription or translation of TIGIT-encoding nucleic acid, and/or by inhibiting or blocking activity of a molecule that inhibits TIGIT expression or TIGIT activity, and/or by enhancing normal TIGIT activity (including, but not limited to, enhancing the stability of TIGIT or enhancing binding of TIGIT to one or more target ligands). For example, the TIGIT agonist can be selected from an antibody, an antigen-binding fragment, an aptamer, an interfering RNA, a small molecule, a peptide, an antisense molecule, and another binding polypeptide. In another example, the TIGIT agonist can be a polynucleotide selected from an aptamer, interfering RNA, or antisense molecule that interferes with the transcription and/or translation of a TIGIT-inhibitory molecule. It will be understood by one of ordinary skill in the art that in some instances, a TIGIT agonist may agonize one TIGIT activity without affecting another TIGIT activity. For example, a desirable TIGIT agonist for use in certain of the methods herein is a TIGIT agonist that agonizes TIGIT activity in response to one of PVR interaction, PVRL3 interaction, or PVRL2 interaction, e.g., without affecting or minimally affecting any of the other TIGIT interactions.

The terms "PVR agonist" and "agonist of PVR activity or PVR expression" are used interchangeably and refer to a compound that enhances or stimulates the normal functioning of PVR, by increasing transcription or translation of PVR-encoding nucleic acid, and/or by inhibiting or blocking activity of a molecule that inhibits PVR expression or PVR activity, and/or by enhancing normal PVR activity (including, but not limited to, enhancing the stability of PVR or enhancing binding of PVR to one or more target ligands). For example, the PVR agonist can be selected from an antibody, an antigen-binding fragment, an aptamer, an interfering RNA, a small molecule, a peptide, an antisense molecule, and another binding polypeptide. In another example, the PVR agonist can be a polynucleotide selected from an aptamer, interfering RNA, or antisense molecule that interferes with the transcription and/or translation of a PVR-inhibitory molecule. It will be understood by one of ordinary skill in the art that in some instances, a PVR agonist may agonize one PVR activity without affecting another PVR activity. For example, a desirable PVR agonist for use in certain of the methods herein is a PVR agonist that agonizes PVR activity in response to TIGIT interaction, or which mimics TIGIT in interacting with PVR, e.g., without affecting or minimally affecting PVR-CD96 or PVR-CD226 binding interactions.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multi-specific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, N.Y., pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using a dye or stain such as, but not limited to, Coomassie blue or silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen. An "agonist antibody," as used herein, is an antibody which partially or fully mimics at least one of the functional activities of a polypeptide of interest.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include, but are not limited to, those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a polypeptide described herein or antibody thereto) to a mammal. The components of the liposome are commonly arranged in a bilayer formation, similar to the lipid arrangement of biological membranes.

A "small molecule" is defined herein to have a molecular weight below about 500 Daltons.

The term "immune-related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means an immune-related disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disorder (IBD) (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections also may have immune and/or inflammatory components and/or etiology.

Several diseases of the skin are correlated with an aberrant immune response and to autoimmunity. Diseases such as psoriasis are hallmarked by skin blistering, skin flaking, edema and the presence of autoantibodies that bind to skin proteins. In this application, experiments determine that TIGIT expression is upregulated in psoriatic skin vs. normal skin. Modulation of TIGIT expression and/or activity may be useful in treating the symptoms or underlying causes of psoriasis.

The term inflammatory bowel disorder ("IBD") describes a group of chronic inflammatory disorders of unknown causes in which the intestine (bowel) becomes inflamed, often causing recurring cramps or diarrhea. The prevalence of IBD in the US is estimated to be about 200 per 100,000 population. Patients with IBD can be divided into two major groups, those with ulcerative colitis ("UC") and those with Crohn's disease ("CD").

In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately, this situation typically progresses to epithelial damage with loss of epithelial cells resulting in multiple ulcerations, fibrosis, dysplasia and longitudinal retraction of the colon. CD differs from UC in that the inflammation extends through all layers of the intestinal wall and involves mesentery as well as lymph nodes. CD may affect any part of the alimentary canal from mouth to anus. The disease is often discontinuous, i.e., severely diseased segments of bowel are separated from apparently disease-free areas. In CD, the bowel wall also thickens which can lead to obstructions. In addition, fistulas and fissures are not uncommon.

Clinically, IBD is characterized by diverse manifestations often resulting in a chronic, unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD also have an increased risk of colon carcinomas compared to the general population. During acute "attacks" of IBD, work and other normal activity are usually impossible, and often a patient is hospitalized.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

Further, the risk of colon cancer is highly elevated in patients with severe ulcerative colitis, particularly if the disease has existed for several years. About 20-25% of patients with IBD eventually require surgery for removal of the colon because of massive bleeding, chronic debilitating illness, perforation of the colon, or risk of cancer. Surgery is also sometimes performed when other forms of medical treatment fail or when the side effects of steroids or other medications threaten the patient's health. As surgery is invasive and drastically life altering, it is not a highly desirable treatment regimen, and is typically the treatment of last resort. In order to better understand this disease and possibly treat it, experiments determined that TIGIT was upregulated both in CD and UC when compared to normal tissue. Modulation of the expression and/or activity of TIGIT may prove useful in the treatment of one or more forms of IBD.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

The term "effective amount" is a concentration or amount of a polypeptide and/or agonist/antagonist which results in achieving a particular stated purpose. An "effective amount" of a polypeptide or agonist or antagonist thereof may be determined empirically. Furthermore, a "therapeutically effective amount" is a concentration or amount of a polypeptide and/or agonist/antagonist which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found, for example, in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

The term "cytokine" is a generic term for proteins released by one cell population which act on another cell as intercellular mediators. Certain examples of such cytokines are lymphokines, monokines, and traditional polypeptide hormones. Included among the cytokines are, e.g., growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and-β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and-II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2, IgG3, or IgG4 subtypes, IgA (including IgA-1 and IgA-2), IgE, IgD or IgM.

As used herein, the term "inflammatory cells" designates cells that enhance the inflammatory response such as mononuclear cells, eosinophils, macrophages, and polymorphonuclear neutrophils (PMN).

II. Compositions and Methods of the Invention

TIGIT had previously been identified as a putative modulator of immune function (see, e.g., US patent publication no. US20040121370, incorporated herein by reference). Herein, Applicants demonstrate that TIGIT is a member of a newly described family of immune-related proteins termed the "TIGIT-like protein" (TLP) family that includes poliovirus receptor (PVR, also known as NECL5 or CD155), PVR-like proteins 1-4 (PVRL1-4), CD96, and CD226. Applicants provide the conserved structural elements of this new TLP family, whose members play roles in immune regulation and function, and provide methods to identify further family members. PVRL1-4 and PVR share a common domain architecture (IgV-IgC-IgV), whereas CD226 and CD96 lack the membrane proximal IgV domain. The intracellular segments of these eight proteins show only a limited similarity with each other outside of the afadin binding motif shared between PVRL1-3; PVRL4 lacks this sequence but still is known to bind afadin. Based on the crystal structure of the related IgV domain of NECL-1 (Dong et al., J. Biol. Chem. 281: 10610-17 (2006)) the first and third motifs are predicted to lie in hairpin loops between the B and C and the F and G beta-strands, respectively. These two loops are adjacent to each other at one end of the IgV fold. The second motif comprises the C' and C" beta-strands that are involved in forming part of the homodimeric interface for NECL-1. Thus, these sequence motifs may play a role in specific homo- and heterotypic interactions observed between PVR family members.

The TLP family members comprise a number of absolutely conserved amino acids, including alanine$^{67}$, glycine$^{74}$, proline$^{114}$, and glycine$^{116}$. Additionally, TLP family members comprise several amino acids which are substantially conserved (e.g., found in the majority of family members, but not in every family member), including an amino acid selected from valine, isoleucine, and leucine at position 54, an amino acid selected from serine and threonine at position 55, a glutamine at position 56, a threonine at position 112, and an amino acid selected from phenylalanine and tyrosine at position 113. Members of the TLP family also comprise three structural submotifs: valine/isoleucine$^{54}$-serine/threonine$^{55}$-glutamine$^{56}$; alanine$^{67}$-X$^{68-73}$-glycine$^{74}$ (where X is any amino acid); and threonine$^{112}$-phenylalanine/tyrosine$^{113}$-proline$^{114}$-x$^{115}$-glycine$^{116}$ (where X is any amino acid). It will be understood by one of ordinary skill in the art that the numbering used above is with respect to the human TIGIT protein sequence, and while the relative position of these conserved residues and motifs in different members of the TLP protein family are identical to the position of those amino acids in the human TIGIT sequence, the absolute numbering of those residues in other TLP family members may differ.

Given the involvement of the identified TLP family members in immune regulation and function, other members of this protein family are also likely to be involved in immune regulation and function. Accordingly, the invention provides methods of determining whether a given protein is a member of the TLP family by aligning the sequence of the protein to the sequences of one or more of the above-identified family members and assessing the presence or absence in the given protein sequence of the above-identified absolutely conserved residues, the above-identified substantially conserved residues, and/or the above-identified structural submotifs. The invention also provides methods of identifying other members of the TLP protein family by searching one or more sequence databases for proteins whose amino acid sequences comprise the above-identified absolutely conserved residues, the above-identified substantially conserved residues, and/or the above-identified structural submotifs.

The identification of the TLP family by Applicants herein also presents the possibility that the common structural features of the TLP family members may permit two or more members of the TLP family to be similarly modulated. For example, if the conserved and substantially conserved amino acid residues and submotifs in each TLP family member give rise to similar three-dimensional structures in those family members in one or more domains of each protein, then those similar three-dimensional structures may be targeted in order to simultaneously modulate more than one TLP family member, or even all TLP family members at the same time. The invention thus also provides agents ("TLP-interacting agents") that specifically interact with such conserved or substantially conserved regions of TLP family members. Such agents may be used to identify one or more further members of the TLP family by assessing whether a candidate protein interacts with a TLP-interacting agent. Interaction of the candidate protein with the TLP-interacting agent may indicate that the protein may also be a TLP family member. TLP-interacting agents may modulate TLP activity. For example, a TLP-interacting agent may be an antagonist of TLP activity, including, but not limited to, a small molecule inhibitor, an inhibitory antibody or antigen-binding fragment thereof, an aptamer, and an inhibitory peptide. In another example, a TLP-interacting agent may be an agonist of TLP activity, including, but not limited to, an agonizing antibody or antigen-binding fragment thereof, an agonizing peptide, and a small molecule that stabilizes a TLP protein structure to facilitate TLP protein activity. TLP-interacting agents may be identified in a variety of art-known ways, for example by using the screening methods described herein.

Applicants show by mRNA and FACS analyses that TIGIT is predominantly expressed on a variety of activated T cells, particularly regulatory T cells ($T_{reg}$), memory T cells, NK cells, and follicular B cell helper T cells ($T_{fh}$) isolated from tonsillar tissue. The invention thus provides methods of identifying whether or not a selected cell is a $T_{reg}$, memory T cell, NK cell, or TFh cell based on whether or not the cell expresses TIGIT. The invention also provides methods of using TIGIT to purify $T_{reg}$, memory T cells, NK cells, and $T_{Fh}$ cells away from other types of immune cells that do not express TIGIT using any of the purification methods known in the art and/or described herein (as one nonlimiting example, by flow cytometry). Applicants also demonstrate that the highest expression of TIGIT in these cell populations occurs in activated $T_{regs}$. Thus, the invention also provides methods of identifying whether a given cell is an activated $T_{reg}$ based on its expression level of TIGIT relative to TIGIT expression levels in one or more control samples (where the control samples may be predetermined values from exemplary T cell subset populations, or the control samples may be other samples from known T cell subpopulations such as activated $T_{reg}$, unactivated $T_{reg}$, naïve T cells, memory T cells, NK cells, $T_{Fh}$ cells, or other T cell populations). Also provided are methods of determining whether a given $T_{reg}$ cell is activated, by determining its expression level of TIGIT relative to TIGIT expression levels in one or more control activated or unactivated $T_{reg}$ samples or relative to predetermined TIGIT expression values in known activated or unactivated $T_{reg}$ cell populations. Further provided are methods of separately isolating activated $T_{reg}$ from other T cells using any of the purification methods known in the art and/or described herein where the quantity of TIGIT expressed in the cell can be used to separate the cell from other cells (as one nonlimiting example, by flow cytometry).

Applicants demonstrate herein that TIGIT binds tightly to PVR, and binds with lesser Kd to PVRL3 (also known as nectin-3 or CD113) and PVRL2 (also known as nectin-2 or CD112). As exemplified by Applicants, TIGIT binding to PVR blocks the interaction of PVR with two other ligands, CD226 and CD96, and CD226 is a less effective inhibitor of the TIGIT-PVR interaction than TIGIT is of the PVR-CD226 interaction. Applicants produced anti-TIGIT antibodies (for example, the anti-TIGIT antibody 10A7 described herein) which inhibited the binding of TIGIT or a TIGIT fusion protein to cell surface-expressed PVR. Applicants further produced other antibodies, such as the antibody 1F4 described herein, with different epitope specificities on TIGIT than 10A7. Notably, CD226 is not significantly expressed in $T_{regs}$ or $T_{Fh}$, two cell types that highly express TIGIT.

Supported by these findings, the invention provides agonists and antagonists of the TIGIT-PVR interaction, the TIGIT-PVRL2 interaction, and the TIGIT-PVRL3 interaction, and methods of modulating TIGIT-PVR binding, TIGIT-PVRL2 binding and TIGIT-PVRL3 binding in vitro or in vivo using such agonists and antagonists. Also provided are methods of modulating the CD226-PVR interaction and/or the CD96-PVR interaction by administering TIGIT (a competitor for PVR binding) or an anti-TIGIT antibody or antigen-binding fragment thereof in vitro or in vivo. The invention further includes anti-TIGIT antibodies and fragments thereof, both agonizing and antagonizing, and in particular anti-TIGIT antibodies 10A7 and 1F4 and alternate types of antibodies comprising the CDRs of anti-TIGIT antibody 10A7 and/or 1F4.

The studies described herein demonstrate the interaction of TIGIT with PVR on DC, and show that this binding interaction modulates DC function, particularly cytokine production. PVR is a cell surface receptor known to be highly expressed on dendritic cells (DC), as well as FDC, fibroblasts, endothelial cells, and some tumor cells (Sakisaka, T. & Takai, Y., Curr Opin Cell Biol 16, 513-21 (2004); Fuchs, A. & Colonna, M., Semin Cancer Biol 16, 359-66 (2006)). TIGIT-bound human DC secreted high levels of IL-10 and fewer pro-inflammatory and other cytokines (such as IL-12p40, IL-12p70, IL-6, IL-18, and IFNγ). TIGIT had no effect on production of certain cytokines such as IL-23. This cytokine skewing upon TIGIT binding was only observed in cells that had been stimulated by TNFα or CD40/LPS, and not in TLR2- or Pam3CSK4-stimulated cells, suggesting that TIGIT is one means by which the immune system may fine-tune DC function. TIGIT binding to immature T cells (as assessed using TIGIT fusion constructs) inhibited T cell activation and proliferation. However, TIGIT treatment did not affect the ability of immature monocyte-derived DC (iMDDC) to mature, nor did it directly induce maturation of those cells. Notably, this inhibition was reversed in the presence of an ERK inhibitor, indicating that ERK activation may be an important step in the functioning of TIGIT to modulate DC activity. In fact, Applicants demonstrate that binding of TIGIT to PVR results in phosphorylation of PVR and increased phosphorylation of pERK dimer but not pERK monomer. This was not a generalized effect, since, for example, the p38 intracellular signaling pathway was not modulated by TIGIT-Fc treatment of cells. Applicants show herein that TIGIT$^+$ T cells suppress proliferation of not only other TIGIT$^-$ T cells, but also antigen presenting cells when present in a mixed population of immune cells. Applicants further demonstrate that the TIGIT-PVR interaction mediates the above observed effects, since inclusion of an anti-TIGIT antibody or an anti-PVR antibody in the experiments greatly reduced the observed inhibition of proliferation, modulation of DC cytokine production, and suppression of proliferation of other immune cells. Overall, the data provided by Applicants herein suggests that TIGIT provides an immune system feedback mechanism by negatively regulating immune response.

Accordingly, the invention provides methods of modulating immune cell (e.g., DC) function by modulating TIGIT or PVR expression and/or activity. For example, methods are provided for decreasing or inhibiting proliferation of immune cells (for example, DC or antigen-presenting cells) by treating immune cells in vitro or in vivo with TIGIT, an agonist of TIGIT expression and/or activity, or an agonist of PVR expression and/or activity. Methods are also provided for increasing proliferation of immune cells (for example, DC or antigen-presenting cells) by treating immune cells in vitro or in vivo with an antagonist of TIGIT expression and/or activity or an antagonist of PVR expression and/or activity. The invention also provides methods for increasing/stimulating an immune response by administering an antagonist of TIGIT expression and/or activity or an antagonist of PVR expression and/or activity. Similarly provided are methods for decreasing/inhibiting an immune response by administering TIGIT, an agonist of TIGIT expression and/or activity or an agonist of PVR expression and/or activity.

Also provided by the invention are methods of modulating the type and/or amount of cytokine production from an immune cell (e.g., DC) by modulating TIGIT or PVR expression and/or activity. Specifically, the invention provides methods of increasing IL-10 production by immune cells, for example DC, by treating cells in vitro or in vivo with TIGIT, an agonist of TIGIT expression and/or activity, or an agonist of PVR expression and/or activity. Also provided are methods of decreasing proinflammatory cytokine production and/or release by immune cells, for example DC, by treating cells in vitro or in vivo with TIGIT, an agonist of TIGIT expression and/or activity, or an agonist of PVR expression and/or activity. Similarly, methods of decreasing IL-10 production by immune cells, for example DC, by treating cells in vitro or in vivo with an antagonist of TIGIT expression and/or activity or an antagonist of PVR expression and/or activity are also provided. The invention further provides methods of increasing proinflammatory cytokine production and/or release by immune cells, for example, DC, by treating cells in vitro or in vivo with an antagonist of TIGIT expression and/or activity or an antagonist of PVR expression and/or activity. Also provided are methods of stimulating ERK phosphorylation and/or intracellular signaling through the ERK pathway in one or more cells by treating the cells with TIGIT, an agonist of TIGIT expression and/or activity, or an agonist of PVR expression and/or activity. Similarly, the invention provides methods of inhibiting or decreasing ERK phosphorylation and/or intracellular signaling through the ERK pathway in one or more cells by treating the cells with an antagonist of TIGIT expression and/or activity or an antagonist of PVR expression and/or activity.

TIGIT is increased in expression in arthritis, psoriasis, inflammatory bowel disorder, and breast cancer tissues relative to normal control tissues, as is shown herein. With regard to the breast cancer tissues, Applicants show that TIGIT expression does not correlate with tumor cells per se, but rather with $CD4^+$ immune cell infiltrates in tumors. Applicants also directly demonstrate the ability of TIGIT to modulate immune response by showing that a TIGIT fusion protein inhibited human T cell responses in vitro and murine T cell activation in a delayed-type hypersensitivity in vivo assay. Accordingly, the invention provides methods of diagnosing diseases/disorders involving aberrant immune cell response in a subject by assessing the expression and/or activity of TIGIT in a sample from the subject and comparing the expression and/or activity to a reference amount of TIGIT expression and/or activity or the amount of TIGIT expression and/or activity in a sample from a normal subject. The invention also provides methods of assessing the severity of a disease or disorder involving aberrant immune cell response (i.e., an immune-related disease) in a subject by assessing the expression and/or activity of TIGIT in a sample from the subject and comparing the expression and/or activity to a reference amount of TIGIT expression and/or activity or the amount of TIGIT expression and/or activity in a sample from a normal subject. Also provided are methods of preventing a disease or disorder involving aberrant immune cell response (i.e., an immune-related disease) by modulating TIGIT expression and/or activity. Further provided are methods of treating or lessening the severity of a disease or disorder involving aberrant immune cell response (i.e., an immune-related disease) by modulating TIGIT expression and/or activity. Modulation of TIGIT expression and/or activity may take the form of inhibiting TIGIT activity and/or expression (i.e., with a TIGIT antagonist or a PVR antagonist) when the negative regulatory activities of TIGIT are contributing to the disease state. For example, antagonizing TIGIT expression and/or activity may be desirable when an increase in proliferation of DC and/or increased production of proinflammatory cytokines by DC is desirable. Modulation of TIGIT expression and/or activity may take the form of activating or increasing TIGIT expression and/or activity (i.e., by administering TIGIT, a TIGIT agonist or a PVR agonist) when the negative regulatory activities of TIGIT are desirable to control a disease state. For example, agonizing TIGIT expression and/or activity may be desirable when a decrease in proliferation of DC and/or decreased release of proinflammatory cytokines by DC is desirable. These and other aspects of the invention are described in greater detail hereinbelow.

A. Full-Length TIGIT Polypeptides

The present invention provides isolated nucleotide sequences encoding polypeptides referred to in the present application as TIGIT polypeptides. In particular, cDNAs encoding various TIGIT polypeptides have been identified and isolated, as disclosed in further detail in the specification and Examples below. It will be understood by one of ordinary skill in the art that the invention also provides other polypeptides useful in the methods of the invention (i.e., PVR) and that any of the description herein drawn specifically to the method of creation, production, labeling, post-translational modification, use or other aspects of TIGIT polypeptides will also be applicable to other non-TIGIT polypeptides.

B. TIGIT Polypeptide Variants

In addition to the full-length native sequence TIGIT polypeptides described herein, it is contemplated that TIGIT variants can be prepared. TIGIT variants can be prepared by introducing appropriate nucleotide changes into the TIGIT polynucleotide, and/or by synthesis of the desired TIGIT polypeptide. Those skilled in the art will appreciate that amino acid changes may alter post-translational processes of the TIGIT, such as changing the number or position of glycosylation sites or altering the membrane anchoring characteristics of the polypeptide.

Variations in the native full-length sequence TIGIT or in various domains of the TIGIT described herein, can be made, for example, using any of the techniques and guidelines for conservative and non-conservative mutations set forth, for instance, in U.S. Pat. No. 5,364,934. Variations may be a substitution, deletion and/or insertion of one or more codons encoding the TIGIT that results in a change in the amino acid sequence of the TIGIT as compared with the native sequence TIGIT. Optionally, the variation is by substitution of at least one amino acid with any other amino acid in one or more of the domains of the TIGIT. Guidance in determining which amino acid residues may be inserted, substituted or deleted without adversely affecting the desired activity may be found by comparing the sequence of the TIGIT with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

TIGIT polypeptide fragments are also provided herein. Such fragments may be truncated at the N-terminus or C-terminus, or may lack internal residues, for example, when compared with a full length native protein. Certain fragments lack amino acid residues that are not essential for a desired biological activity of the TIGIT polypeptide.

TIGIT fragments may be prepared by any of a number of conventional techniques. Desired peptide fragments may be chemically synthesized. An alternative approach involves generating TIGIT fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, TIGIT polypeptide fragments share at least one biological and/or immunological activity with the native TIGIT polypeptide disclosed herein.

In certain embodiments, conservative substitutions of interest are shown in Table 5 under the heading of preferred substitutions. If such substitutions result in a change in biological activity, then more substantial changes, denominated exemplary substitutions in Table 5, or as further described below in reference to amino acid classes, are introduced and the products screened.

TABLE 5

| Original Residue | Exemplary Substitutions | Preferred Substitutions |
|---|---|---|
| Ala (A) | val; leu; ile lys; gln; asn | val lys |
| Arg (R) | gln; his; lys; arg | gln |
| Asn (N) | | glu |
| Asp (D) | glu | ser |

TABLE 5-continued

| Original Residue | Exemplary Substitutions | Preferred Substitutions |
|---|---|---|
| Cys (C) | ser | asn |
| Gln (Q) | asn | asp |
| Glu (E) | asp | ala |
| Gly (G) | pro; ala | arg |
| His (H) | | |
| Ile (I) | asn; gln; lys; arg leu; val; met; ala; phe; | leu |
| Leu (L) | norleucine norleucine; ile; val; | ile arg |
| Lys (K) | met; ala; phe | leu |
| Met (M) | arg; gln; asn | leu |
| Phe (F) | leu; phe; ile | ala |
| Pro (P) | leu; val; ile; ala; tyr | thr |
| Ser (S) | ala | ser |
| Thr (T) | thr | tyr |
| Trp (W) | ser | phe |
| Tyr (Y) | tyr; phe | |
| Val (V) | trp; phe; thr; ser ile; leu; met; phe; ala; norleucine | leu |

Substantial modifications in function or immunological identity of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081-1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1

(1976)]. If alanine substitution does not yield adequate amounts of variant, an isoteric amino acid can be used.

C. Modifications of TIGIT

Covalent modifications of TIGIT are included within the scope of this invention. One type of covalent modification includes reacting targeted amino acid residues of a polypeptide with an organic derivatizing agent that is capable of reacting with selected side chains or the N-or C-terminal residues of the TIGIT polypeptide. Derivatization with bifunctional agents is useful, for instance, for crosslinking TIGIT polypeptide to a water-insoluble support matrix or surface for use in the method for purifying anti-TIGIT antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-34(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the TIGIT polypeptides included within the scope of this invention comprises altering the native glycosylation pattern of the polypeptide. "Altering the native glycosylation pattern" is intended for purposes herein to mean deleting one or more carbohydrate moieties found in a native sequence TIGIT (either by removing the underlying glycosylation site or by deleting the glycosylation by chemical and/or enzymatic means), and/or adding one or more glycosylation sites that are not present in the native sequence TIGIT. In addition, the phrase includes qualitative changes in the glycosylation of the native proteins, involving a change in the nature and proportions of the various carbohydrate moieties present. Addition of glycosylation sites to a polypeptide may be accomplished by altering the amino acid sequence. The alteration may be made, for example, by the addition of, or substitution by, one or more serine or threonine residues to the native sequence polypeptide (for O-linked glycosylation sites). The polypeptide's amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on the polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of a polypeptide disclosed herein comprises linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The polypeptides of the present invention may also be modified in a way to form a chimeric molecule comprising a polypeptide fused to another, heterologous polypeptide or amino acid sequence.

In one embodiment, such a chimeric molecule comprises a fusion of the polypeptide of interest with a tag polypeptide which provides an epitope to which an anti-tag antibody can selectively bind. The epitope tag is generally placed at the amino- or carboxyl-terminus of the polypeptide of interest. The presence of such epitope-tagged forms of the polypeptide of interest can be detected using an antibody against the tag polypeptide. Also, provision of the epitope tag enables the polypeptide of interest to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include, but are not limited to, the Flag-peptide [Hopp et al., *BioTechnology*, 6:1204-1210 (1988)]; the KT3 epitope peptide [Martin et al., *Science*, 255:192-194 (1992)]; an alpha-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a polypeptide in place of at least one variable region within an Ig molecule. In one embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Polypeptide Preparation

The description below relates primarily to production of polypeptides by culturing cells transformed or transfected with a vector containing nucleic acid encoding the polypeptide of interest. It is, of course, contemplated that alternative methods, which are well known in the art, may be employed to prepare polypeptides. For instance, the polypeptide sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation.

Automated synthesis may be accomplished, for instance, using an Applied Biosystems Peptide Synthesizer (Foster City, Calif.) using manufacturer's instructions. Various portions of the polypeptide may be chemically synthesized separately and combined using chemical or enzymatic methods to produce the full-length polypeptide.

1. Isolation of DNA Encoding the Polypeptide

DNA encoding a polypeptide of interest may be obtained from a cDNA library prepared from tissue believed to possess the polypeptide mRNA and to express it at a detectable level. Accordingly, human DNA encoding the polypeptide can be conveniently obtained from a cDNA library prepared from human tissue. The polypeptide-encoding gene may also be obtained from a genomic library or by known synthetic procedures (e.g., automated nucleic acid synthesis).

Libraries can be screened with probes (such as antibodies to the polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the polypeptide is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for polypeptide-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982). Suitable host cells for the expression of glycosylated polypeptide are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

Examples of suitable selectable markers for mammalian cells are those that enable the identification of cells competent to take up the polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)].

Promoters for use in bacterial systems also will contain a Shine-Dalgarno (S.D.) sequence operably linked to the DNA encoding polypeptides.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide.

Still other methods, vectors, and host cells suitable for adaptation to the synthesis of a polypeptide of interest in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to DNA encoding the polypeptide and encoding a specific antibody epitope.

5. Purification of Polypeptide

Forms of a polypeptide of interest may be recovered from culture medium or from host cell lysates. If membrane-bound, it can be released from the membrane using a suitable detergent solution (e.g. Triton-X 100) or by enzymatic cleavage. Cells employed in expression of the polypeptide can be disrupted by various physical or chemical means, such as freeze-thaw cycling, sonication, mechanical disruption, or cell lysing agents.

It may be desired to purify the polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the polypeptide. Various methods of protein purification may be employed and such methods are known in the art and described for example in Deutscher, *Methods in Enzymology*, 182 (1990); Scopes, *Protein Purification: Principles and Practice*, Springer-Verlag, N.Y. (1982). The purification step(s) selected will depend, for example, on the nature of the production process used and the particular polypeptide produced.

E. Tissue Distribution

The location of tissues expressing the polypeptide can be identified by determining mRNA expression in various human tissues. The location of such genes provides information about which tissues are most likely to be affected by the stimulating and inhibiting activities of the polypeptides. The location of a gene in a specific tissue also provides sample tissue for the activity blocking/activating assays discussed below.

As noted before, gene expression in various tissues may be measured by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide or against a synthetic peptide based on the DNA sequences encoding the polypeptide or against an exogenous sequence fused to a DNA encoding a polypeptide and encoding a specific antibody epitope. General techniques for generating antibodies, and special protocols for Northern blotting and in situ hybridization are provided below.

F. Antibody Binding Studies

The activity of a polypeptide of the invention can be further verified by antibody binding studies, in which the ability of anti-polypeptide antibodies to inhibit the effect of the polypeptide on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. See, e.g., Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

G. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are more commonly used in the art. Techniques to derive continuous cell lines from transgenic animals are well known in the art (see, e.g., Small et al., *Mol. Cell. Biol.* 5: 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, above, 3.15, 6.3.

A proliferative T cell response in an MLR assay may be due to direct mitogenic properties of an assayed molecule or to external antigen induced activation. Additional verification of the T cell stimulatory activity of the polypeptide can be obtained by a costimulation assay. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a T cell deactivating effect. Chambers, C. A. and Allison, J. P., *Curr. Opin. Immunol.* (1997) 9:396. Schwartz, R. H., *Cell* (1992) 71:1065; Linsey, P. S. and Ledbetter, J. A., *Annu. Rev. Immunol.* (1993) 11:191; June, C. H. et al, *Immunol. Today* (1994) 15:321; Jenkins, M. K., *Immunity* (1994) 1:405. In a costimulation assay, the polypeptides are assayed for T cell costimulatory or inhibitory activity.

Direct use of a stimulating compound as in the invention has been validated in experiments with 4-1BB glycoprotein, a member of the tumor necrosis factor receptor family, which binds to a ligand (4-1BBL) expressed on primed T cells and signals T cell activation and growth. Alderson, M. E. et al., *J. Immunol.* (1994) 24:2219.

The use of an agonist stimulating compound has also been validated experimentally. As one example, activation of 4-1BB by treatment with an agonist anti-4-1BB antibody enhances eradication of tumors. Hellstrom, I. and Hellstrom, K. E., *Crit. Rev. Immunol.* (1998) 18:1. Immunoadjuvant therapy for treatment of tumors, described in more detail below, is another example of the use of the stimulating compounds of the invention.

Alternatively, an immune stimulating or enhancing effect can also be achieved by administration of a polypeptide which has vascular permeability enhancing properties. Enhanced vascular permeability would be beneficial to disorders which can be attenuated by local infiltration of immune cells (e.g., monocytes, eosinophils, PMNs) and inflammation.

On the other hand, TIGIT polypeptides, as well as other compounds of the invention, which are direct inhibitors of T cell proliferation/activation, proinflammatory cytokine secretion, and/or vascular permeability can be directly used to suppress the immune response. These compounds are useful to reduce the degree of the immune response and to treat immune related diseases characterized by a hyperactive, superoptimal, or autoimmune response. This use of the compounds of the invention has been validated by the experiments described above in which CTLA-4 binding to receptor B7 deactivates T cells. The direct inhibitory compounds of the invention function in an analogous manner. The use of a compound which suppresses vascular permeability would be expected to reduce inflammation. Such uses would be beneficial in treating conditions associated with excessive inflammation.

Similarly, compounds, e.g., antibodies, which bind to TIGIT-inhibitory polypeptides and block the effect of these TIGIT-inhibitory polypeptides produce a net inhibitory effect and can also be used to suppress the T cell mediated immune response by leaving TIGIT free to inhibit T cell proliferation/activation and/or lymphokine secretion. Blocking the inhibitory effect of the polypeptides suppresses the immune response of the mammal.

Alternatively, for conditions associated with insufficient T cell mediated immune response and/or inflammation, inhibiting or lessening TIGIT activity and/or expression or interfering with TIGIT's ability to bind to and/or signal through PVR may be beneficial for treatment. Such inhibition or lessening may be provided by administration of an antagonist of TIGIT expression and/or activity and/or an antagonist of PVR expression and/or activity.

H. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, above, unit 4.4. Other transplant rejection models which can be used to test the compounds of the invention are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19 (1): 37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A.C. et al., *Immunology* (1996) 88:569.

The collagen-induced arthritis (CIA) model is considered a suitable model for studying potential drugs or biologics active in human arthritis because of the many immunological and pathological similarities to human rheumatoid arthritis (RA), the involvement of localized major histocompatibility, complete class-II-restricted T helper lymphocyte activation, and the similarity of histological lesions. Features of this CIA model that are similar to that found in RA patients include: erosion of cartilage and bone at joint margins (as can be seen in radiographs), proliferative synovitis, symmetrical involvement of small and medium-sized peripheral joints in the appendicular, but not the axial, skeleton. Jamieson et al., *Invest.Radiol.* 20: 324-9 (1985). Furthermore, IL-1 and TN-α appear to be involved in CIA as in RA. Joosten et al., *J. Immunol.* 163: 5049-5055 (1999). TNF-neutralizing antibodies and separately, TNFR:Fc reduced the symptoms of RA in this model (Williams et al., *PNAS*, 89:9784-9788 (1992); Wooley et al., *J. Immunol.*151: 6602-6607 (1993)).

In this model for RA, type II collagen is purified from bovine articular cartilage (Miller, *Biochemistry* 11:4903 (1972)) and used to immunized mice (Williams et al, *Proc. Natl. Acad. Sci. USA* 91:2762 (1994)). Symptoms of arthritis include erythema and/or swelling of the limbs as well as erosions or defects in cartilage and bone as determined by histology. This widely used model is also described, for example, by Holmdahl et al., *APMIS* 97:575 (1989) and in *Current Protocols in Immunology*, supra, units 15.5, and in Issekutz et al., *Immunology,* 88:569 (1996), as well as in the Examples hereinbelow.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al, *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path.* (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene in such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cel. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to a polypeptide of the invention, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the polypeptide.

I. ImmunoAdjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., (1996) *Proc. Natl. Acad. Sci. USA,* 93:7149. It has been shown that costimulation of T cells induces tumor regression and an antitumor response both in vitro and in vivo. Melero, I. et al., Nature Medicine (1997) 3:682; Kwon, E. D. et al., *Proc. Natl. Acad. Sci. USA* (1997) 94: 8099; Lynch, D. H. et al, *Nature Medicine* (1997) 3:625; Finn, O. J. and Lotze, M. T., *J. Immunol.* (1998) 21:114. The data provided herein demonstrates that TIGIT expression correlates with immune cell infiltrate in breast cancer tumors. TIGIT is also demonstrated herein to inhibit proliferation of DC and other immune cells and to inhibit proinflammatory cytokine production from such cells. Thus, TIGIT overexpression in tumor immune infiltrate cells may be aberrant, since decreased T cell activity in tumors would be undesirable. TIGIT antagonists and/or antagonists of the TIGIT-PVR signaling interaction (i.e., PVR antagonists) may be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the TIGIT-antagonistic and TIGIT activity-antagonistic compounds of the invention allows reduced amounts of the growth regulating, cytotoxic, or chemotherapeutic agents thereby potentially lowering the toxicity to the patient.

J. Screening Assays for Drug Candidates

Screening assays for drug candidates are designed to identify compounds that bind to or complex with the polypeptides encoded by the genes identified herein or a biologically active fragment thereof, or otherwise interfere with the interaction of the encoded polypeptides with other cellular proteins. Such screening assays include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* (*London*) 340, 245-246 (1989); Chien et al., *Proc. Natl. Acad. Sci. USA* 88, 9578-9582 (1991)] as disclosed by Chevray and Nathans, *Proc. Natl. Acad. Sci. USA* 89, 5789-5793 (1991). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

K. Compositions and Methods for the Treatment of Immune Related Diseases

The compositions useful in the treatment of immune related diseases include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed above and/or by any other screening techniques well known for those skilled in the art.

L. Anti-TIGIT Antibodies

The present invention further provides anti-TIGIT antibodies. Exemplary antibodies include polyclonal, monoclonal, humanized, bispecific, and heteroconjugate antibodies. It will be understood by one of ordinary skill in the art that the invention also provides antibodies against other polypeptides (i.e., anti-PVR antibodies) and that any of the description herein drawn specifically to the method of creation, production, varieties, use or other aspects of anti-TIGIT antibodies will also be applicable to antibodies specific for other non-TIGIT polypeptides.

1. Polyclonal Antibodies

The anti-TIGIT antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the TIGIT polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-TIGIT antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the TIGIT polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-TIGIT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for TIGIT, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. As one nonlimiting example, trispecific antibodies can be prepared. See, e.g., Tutt et al., J. Immunol. 147:60 (1991).

Exemplary bispecific antibodies may bind to two different epitopes on a given TIGIT polypeptide herein. Alternatively, an anti-TIGIT polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular TIGIT polypeptide. Bispecific antibodies may also be used to localize cytotoxic agents to cells which express a particular TIGIT polypeptide. These antibodies possess a TIGIT-binding arm and an arm which binds a cytotoxic agent or a radionuclide chelator, such as EOTUBE, DPTA, DOTA, or TETA. Another bispecific antibody of interest binds the TIGIT polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10): 2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARGTM (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; US Patent Nos. 4970198; 5079233; 5585089; 5606040; 5693762; 5739116; 5767285; 5773001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, *Aleurites fordii* proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{122}$Bi, $^{131}$I, $^{131}$In, $^{90}$Y and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

a. Maytansine and Maytansinoids

In some embodiments, the immunoconjugate comprises an antibody (full length or fragments) conjugated to one or more maytansinoid molecules. Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3 x 10$^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

b. Auristatins and dolastatins In some embodiments, the immunoconjugate comprises an antibody conjugated to dolastatins or dolostatin peptidic analogs and derivatives, the auristatins (U.S. Pat. Nos. 5635483; 5780588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (US 5663149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5635483; U.S. Pat. No. 5780588; Pettit et al (1989) J. Am. Chem. Soc. 111:5463-5465; Pettit et al (1998) Anti-Cancer Drug Design 13:243-277; Pettit, G.R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", US Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

c. Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714, 586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α3I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

d. Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), Momordica charantia inhibitor, curcin, crotin, Sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase). For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal,CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

e. Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \quad \quad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

M. Pharmaceutical Compositions

The active molecules of the invention (e.g., TIGIT polypeptides, anti-TIGIT antibodies, variants of each, TIGIT agonists, TIGIT antagonists, PVR agonists and PVR antagonists) as well as other molecules identified by the screening assays disclosed above, can be administered for the treatment of immune related diseases, in the form of pharmaceutical compositions.

Therapeutic formulations of an active molecule, for example a polypeptide or antibody of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine;

preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol);

low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN', PLURONICS™ or polyethylene glycol (PEG).

Compounds identified by the screening assays disclosed herein can be formulated in an analogous manner, using standard techniques well known in the art.

Lipofections or liposomes can also be used to deliver the active molecule into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations of the active molecules may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

N. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased cytokine production, and/or increased or decreased vascular permeability or the inhibition thereof. Given the disclosures herein of TIGIT's role in modulating T cell proliferation and cytokine production, modulation of TIGIT expression and/or activity may be efficacious in preventing and/or treating these diseases.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the $CD8^+$ T lymphocyte, a cell which targets antigen presented by class I MHC molecules. $CD8^+$ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a $CD8^+$ T cells response. As shown herein, TIGIT is expressed in $CD8^+$ T cells, and modulation of TIGIT expression and/or activity in those cells may modulate the symptoms of and/or prevent this disease.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including biliary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual endorgan dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barré syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e., as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer.

Molecules that inhibit the lymphocyte response in the MLR (i.e., TIGIT) also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g., polypeptides, small molecules or antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous, subcutaneous or inhaled administration of polypeptides and antibodies are most commonly used.

In immunoadjuvant therapy, other therapeutic regimens, such administration of an anti-cancer agent, may be combined with the administration of the proteins, antibodies or compounds of the instant invention. For example, the patient to be treated with, e.g., an immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M.C. Perry, Williams & Wilkins, Baltimore, Md. (1992). The chemotherapeutic agent may precede, or follow administration of the immunoadjuvant or may be given simultaneously therewith. Additionally, an anti-estrogen compound such as tamoxifen or an anti-progesterone such as onapristone (see, EP 616812) may be given in dosages known for such molecules.

It may be desirable to also administer antibodies against other immune disease associated or tumor associated antigens, including, but not limited to antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. For example, in one embodiment, the TIGIT polypeptides are coadministered with a growth inhibitory agent. For example, the growth inhibitory agent may be administered first, followed by a TIGIT polypeptide. However, simultaneous administration or administration first is also contemplated. Suitable dosages for the growth inhibitory agent are those presently used and may be lowered due to the combined action (synergy) of the growth inhibitory agent and the, e.g., TIGIT polypeptide.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound may be suitably administered to the patient at one time or over a series of treatments.

For example, depending on the type and severity of the disease, about 1 μg/kg to 15 mg/kg (e.g., 0.1-20 mg/kg) of polypeptide or antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

O. Articles of Manufacture

In another embodiment of the invention, an article of manufacture containing materials (e.g., comprising a TIGIT molecule, TIGIT agonist, TIGIT antagonist, PVR agonist, or PVR antagonist) useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

P. Diagnosis and Prognosis of Immune Related Disease

Cell surface proteins, such as proteins which are overexpressed in certain immune related diseases (i.e., TIGIT), are excellent modulation targets for drug candidates or disease treatment. The same proteins along with secreted proteins encoded by the genes amplified in immune related disease states find additional use in the diagnosis and prognosis of these diseases. For example, antibodies directed against the protein products of genes amplified in rheumatoid arthritis or other immune related diseases can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection. Other techniques are also well known in the art, for example fluorescence-assisted cell sorting (FACS).

The following examples are offered for illustrative purposes only, and are not intended to limit the scope of the present invention in any way.

All patent, patent publication and literature references cited in the present specification are hereby incorporated by reference in their entirety.

EXAMPLES

Example 1

Further Characterization of TIGIT

Figure 4A:
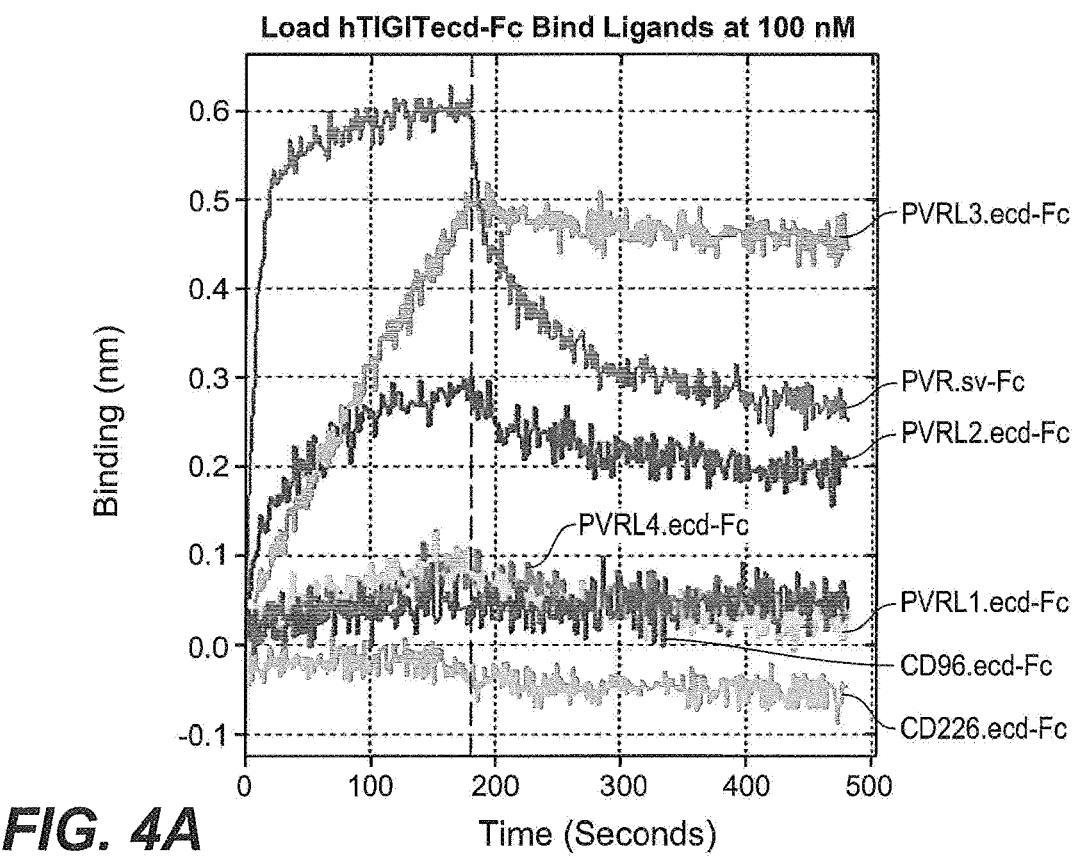
FIG. 4A depicts the results of biosensor assays to assess the binding of various Fc fusion proteins to immobilized TIGIT-Fc, as described in Example 2.
Figures 1, 4B:
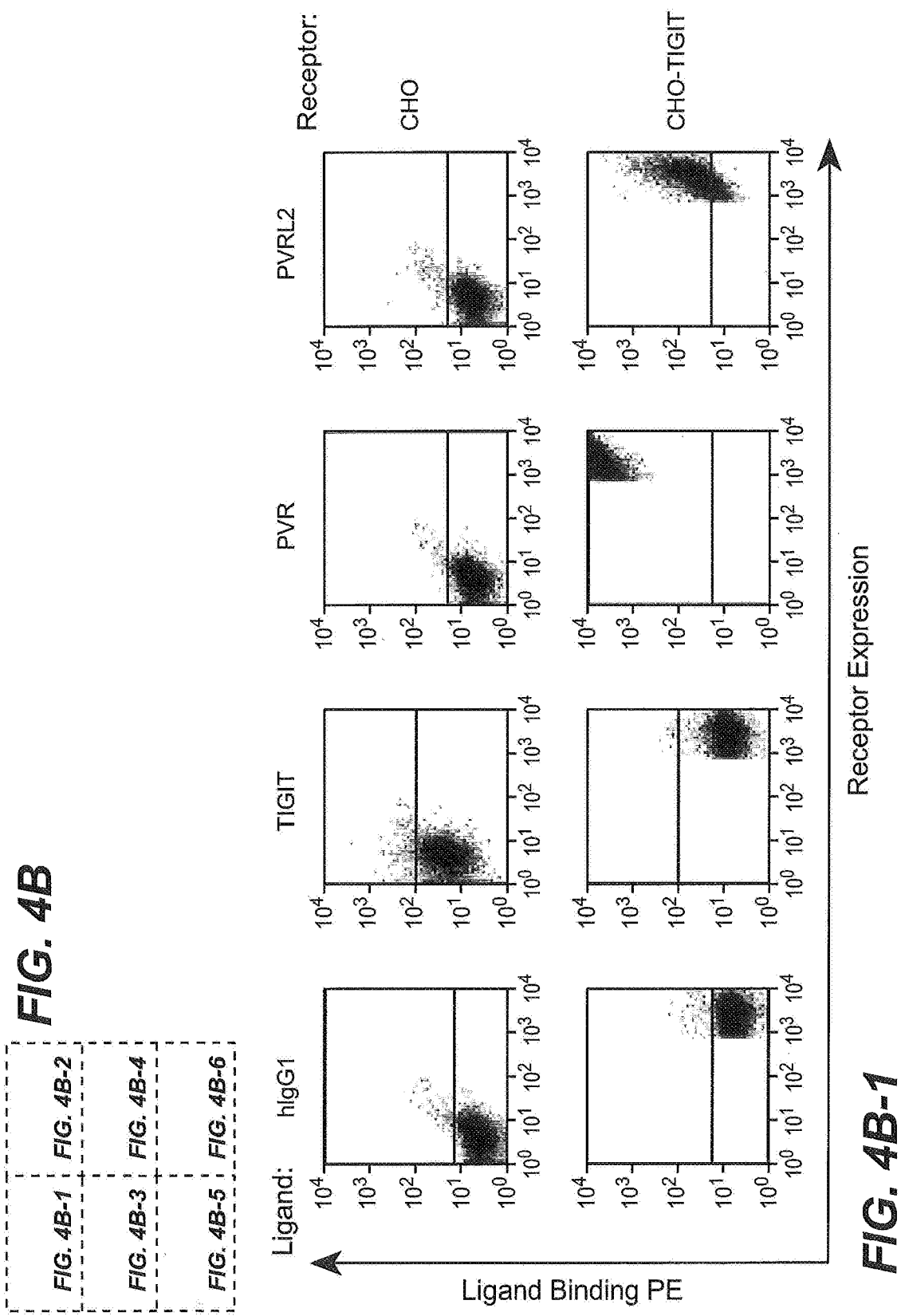

TIGIT had been previously identified (see, e.g., US patent publication no. US20040121370, incorporated herein by reference in its entirety) in genome-wide search strategies targeting genes specifically expressed by immune cells which have a domain structure consisting of extracellular Ig domains, a type one transmembrane region, and an intracellular immunoreceptor tyrosine-based activation or inhibition (ITAM/ITIM) motif(s) (Abbas, A. R. et al. *Genes Immun* 6, 319-31 (2005); Burshtyn, D. N. et al., *J Biol Chem* 272, 13066-72 (1997); Kashiwada, M. et al., *J Immunol* 167, 6382-7 (2001)). The sequence of human TIGIT and homologues from mouse (submitted to Genbank), rhesus monkey (Genbank accession no. XP_001107698) and dog (Genbank accession no. XP_545108) are shown in FIG. 1. To further elucidate the role of TIGIT in immune function, a homology search was performed which identified the TIGIT Ig domain as being similar to the N-terminal IgV domains of the poliovirus receptor (PVR) protein and PVR-like proteins 1-4 (PVRL1-4), as well as the N-terminal IgV domains of CD96 and CD226 (see FIGS. 2A and 2B). The alignment of these proteins showed that the highly conserved residues that define the canonical IgV domain were conserved in TIGIT, and further suggested that those eight proteins may comprise a related subset of the Ig family. The conserved V-frame residues have been shown to be important for establishing the V-frame fold (Wiesmann, C. & de Vos, A. M. *Cell Mol Life Sci* 58, 748-59 (2001)). A number of residues were identified near the V-frame fold that were conserved among the eight proteins, including four absolutely conserved residues ($A^{67}$, $G^{74}$, $P^{114}$, and $G^{116}$) and five conserved residues ($V/I/L^{54}$, $S/T^{55}$, $Q^{56}$, $T^{112}$ and $F/Y^{113}$) that comprise three submotifs ($V/I^{54}$-$S/T^{55}$-$Q^{56}$), ($A^{67}$-X(6)-$G^{74}$) and ($T^{112}$-$F/Y^{113}$-$P^{114}$-X-$G^{116}$). In the case of TIGIT, these submotifs appear to be conserved across species (see FIG. 1) and are not present in other currently described IgV domain containing proteins. Those conserved residues may define a class of PVR-like proteins including PVR, PVR-like proteins 1-4, CD96, CD226, and TIGIT.

PVRL1-4 and PVR share a common domain architecture (IgV-IgC-IgV), whereas CD226 and CD96 lack the membrane proximal IgV domain. TIGIT is the most economical member of the family, consisting of a single IgV domain. The intracellular segments of these eight proteins show only a limited similarity with each other outside of the afadin binding motif shared between PVRL1-3. Based on the crystal structure of the related IgV domain of NECL-1 (Dong, X. et al., *J Biol Chem* 281, 10610-7 (2006)), the first and third motifs are predicted to lie in hairpin loops between the B and C and the F and G beta-strands, respectively. These two loops are adjacent to each other at one end o the IgV fold. The second motif comprises the C' and C" beta strands that are involved in forming part of the homodimeric interface for NECL-1. Thus, the observed sequence motifs in the TIGIT/PVR family may play a role in specific homo- and heterotypic interactions observed between PVR family members. PVR has previously been characterized as a nectin-like protein, but the above sequence analysis suggests that it should instead be considered a PVR family member, with certain nectins (i.e., PVRL1-4) being categorized as a branch of the PVR family.

Example 2

Identification of PVR Ligand

Figure 3:
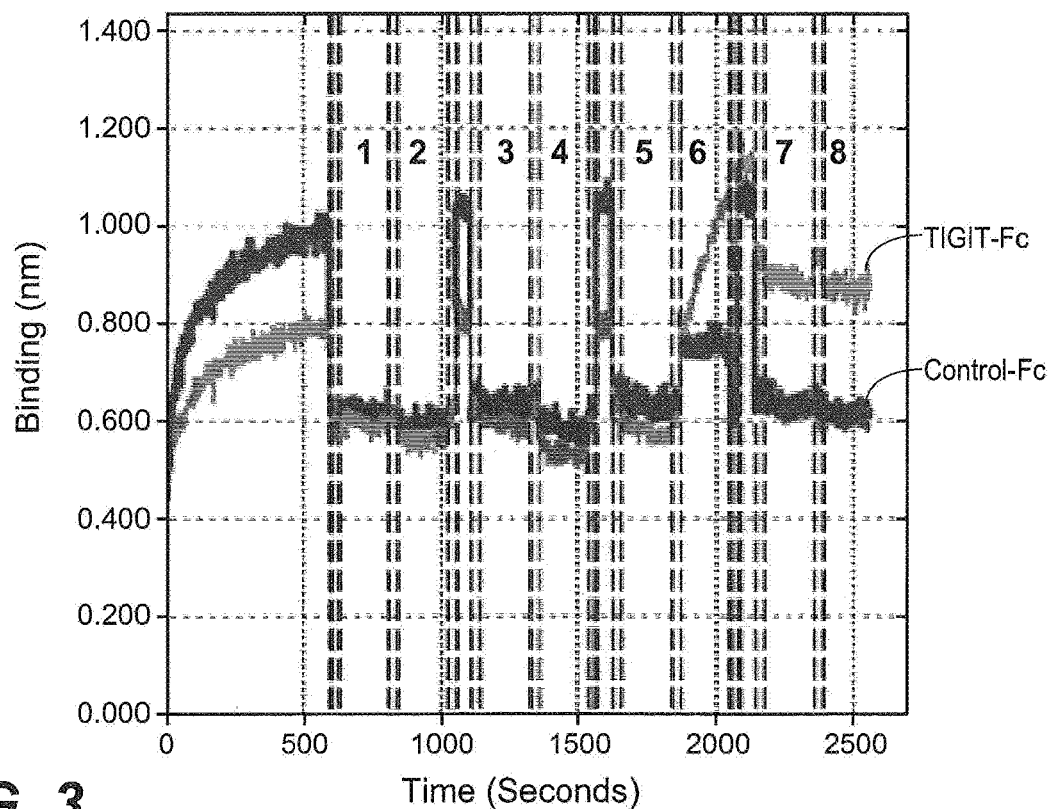
FIG. 3 depicts the results of biosensor analyses to assess the ability of TIGIT-Fc (light grey line) or a control-Fc protein (black line) to bind to various proteins, as described in Example 2. The numbers 1-8 represent, respectively, ESAM, OTOR, TEK, TNFRSF10C, IGFBP4, PVR, IL-19, and TEK.

Potential binding partners for TIGIT were identified by screening a large library of secreted proteins to look for proteins that bound immobilized TIGIT. Briefly, an Fc fusion of TIGIT (TIGIT-Fc) was constructed by cloning amino acids 1-138 of human TIGIT into a vector immediately preceding the Fc region of human IgG1 (TIGIT-Fc). An alternate version of TIGIT-Fc in which FcγR binding was abolished was also constructed by introducing two mutations into the Fc tail of TIGIT-Fc at D256A and N297A using standard site-directed mutagenesis techniques (TIGIT-Fc-DANA). The resulting fusion protein was transiently expressed in and purified from CHO cells using standard affinity chromatography techniques. A library of individual secreted proteins fused to hexahistidine or Fc tags were screened for binding to TIGIT-Fc using the Octet system (ForteBio). Proteins were tested for binding in HBS-P (10 mM Hepes, pH 7.4; 0.15M NaCl; 0.005% Surfactant P20). TIGIT-Fc or a control Fc fusion protein was loaded onto anti-human Fc biosensors to saturation. The biosensors were washed in buffer (30 seconds), placed into wells containing 5 μg/mL protein for three minutes, and washed again for 30 seconds. The sensors were reloaded and washed after every two binding cycles. Binding was indicated as an increase in response level greater than 0.2 nm, and specificity was determined by comparison to a control Fc fusion protein. A single protein that bound TIGIT was identified in over 1000 proteins analyzed. As shown in FIG. 3, a TIGIT-Fc fusion protein immobilized onto an anti-human Fc biosensor specifically interacted with a PVR-Fc fusion protein. The specificity of this interaction was supported by the lack of specific interaction of TIGIT with any other protein in the library, and further by the fact that biosensors loaded with other Ig domain-containing proteins did not elicit a response to PVR.

Because it had previously been known that PVR, PVRL1-4, CD96, and CD226 interact with one another (He, Y. et al., *J Virol* 77, 4827-35 (2003); Satoh-Horikawa, K. et al., *J Biol Chem* 275, 10291-9 (2000); Bottino, C. et al. *J Exp Med* 198, 557-67 (2003); Fuchs, A. et al., *J Immunol* 172, 3994-8 (2004); Reymond, N. et al., *J Exp Med* 199, 1331-41 (2004)), the interaction of TIGIT with each of these proteins was assessed using the biosensor system described above. Fc fusion proteins were constructed and purified for each of the proteins to be tested as described above for TIGIT-Fc. Specifically, amino acids 1-343 of PVR-like protein 1 (PVRL1), amino acids 1-360 of PVR-like protein 2 (PVRL2), amino acids 1-411 of PVR-like protein 3 (PVRL3), amino acids 1-349 of PVR-like protein 4 (PVRL4), amino acids 1-259 of CD226, or amino acids 1-500 of CD96 were fused immediately preceding the Fc region of human IgG1. The resulting Fc fusion proteins were tested for binding to TIGIT-Fc. PVR-Fc, PVRL3-Fc and PVRL2-Fc bound TIGIT-Fc, whereas CD226-Fc, CD96-Fc, PVRL1-Fc, and PVRL4-Fc did not bind TIGIT-Fc (FIG. 4A). Of the three observed binders, PVR-Fc showed the greatest binding to TIGIT-Fc, followed by PVRL3-Fc, and the least amount of binding of the three to TIGIT-Fc was observed with PVRL2-Fc.

FACS analyses were also performed to assess the binding of the PVR family member Fc fusions constructed above to CHO cells expressing TIGIT. Fc fusion proteins were biotinylated via amine coupling using NHS-PEO4-Biotin (Pierce) in PBS. Binding of biotin-ligands was detected using phycoerythrin-conjugated streptavidin (Caltag).

Mouse monoclonal antibody to gD tag (Genentech) was conjugated to AlexaFluor 647 (Invitrogen). Antibodies were conjugated to appropriate fluor labels using standard techniques. Cells were stained per the manufacturer's instructions. Prior to staining, cells were blocked with appropriate sera or purified IgG. Acquisition was performed on a FACSCalibur (BD Biosciences) and analyzed with JoFlo software (Tree Star, Inc.). Forward and side scatter gated viable cells. The results are set forth in FIGS. 4B-1 to 4B-6, and show that the binding pattern observed in the artificial biosensor assay was the same as that observed in a more physiological setting at the cell surface. To determine the strength of the PVR-TIGIT, PVRL2-TIGIT and PVRL3-TIGIT binding interactions, direct radioligand binding assays were performed using CHO cells stably transfected with those proteins. For CHO cell surface expression, TIGIT, PVR, PVRL2, PVRL3, CD226 and CD96 full-length DNAs were cloned into a vector immediately following a gD signal sequence (MGGTAARLGAVILFV-VIVGLHGVRG (SEQ ID NO: 19)) and the gD tag (KY-ALADASLKMADPNRFRGKDLPVL (SEQ ID NO: 20)). Plasmids were transfected into CHO cells using Lipofectamine LTX (Invitrogen). Expression of gD-tagged proteins was verified by flow cytometry using the Alexa-647 anti-gD conjugate. Stably-transfected cell lines were sorted twice by FACS for purity before use. Fc-fusion proteins constructed as described above were iodinated ($^{125}$I) using the Iodogen method. Binding studies were carried out on stable transfectants in triplicate with 0.1-3 nM iodinated ligand. Iodinated proteins were incubated with $1\times10^5$-$2\times10^5$ cells in the presence of a dilution series of unlabeled competitor protein (25 pM-5 µM) for four hours at 4° C. Cell suspensions were harvested onto nitrocellulose membranes (Millipore) and washed extensively. Dried filters were counted and Scatchard analyses were performed using New-Ligand 1.05 software (Genentech) to determine binding affinity ($K_d$).

Figure 5A:
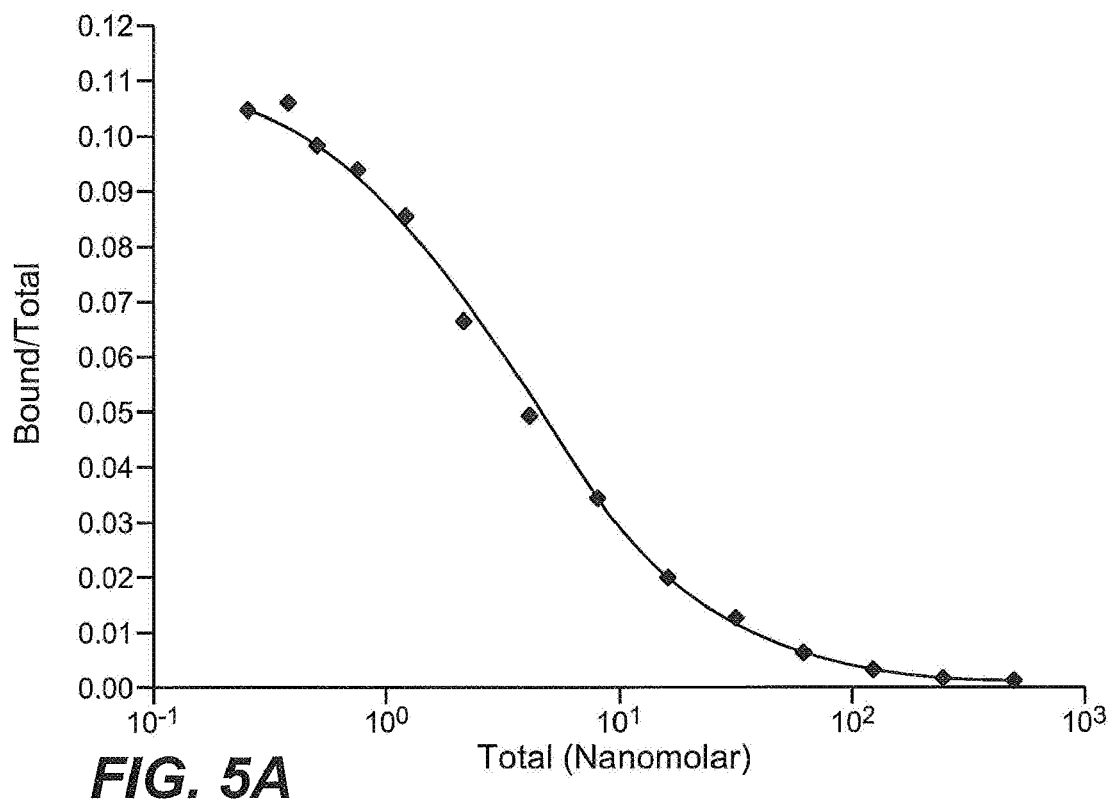
FIGS. 5A and 5B depict the results of one representative radioligand binding assay to determine the Kd for binding between TIGIT-Fc and PVR-expres sing CHO cells, as described in Example 2.
Figure 5B:
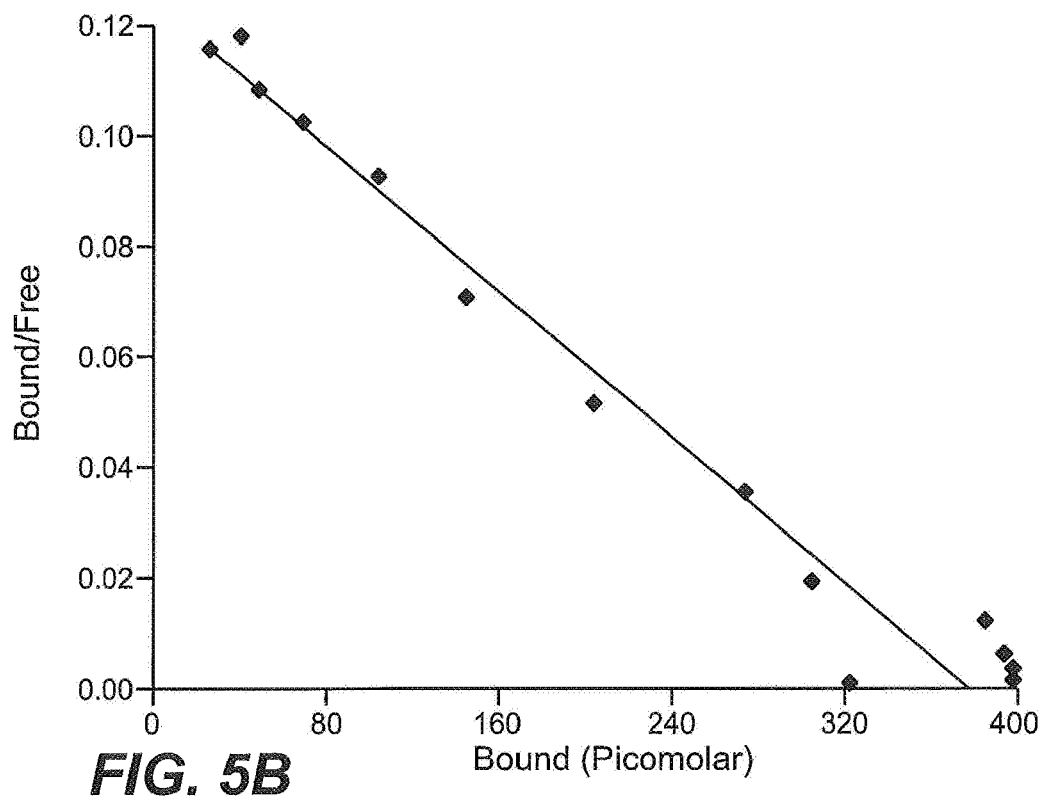
Figure 6:
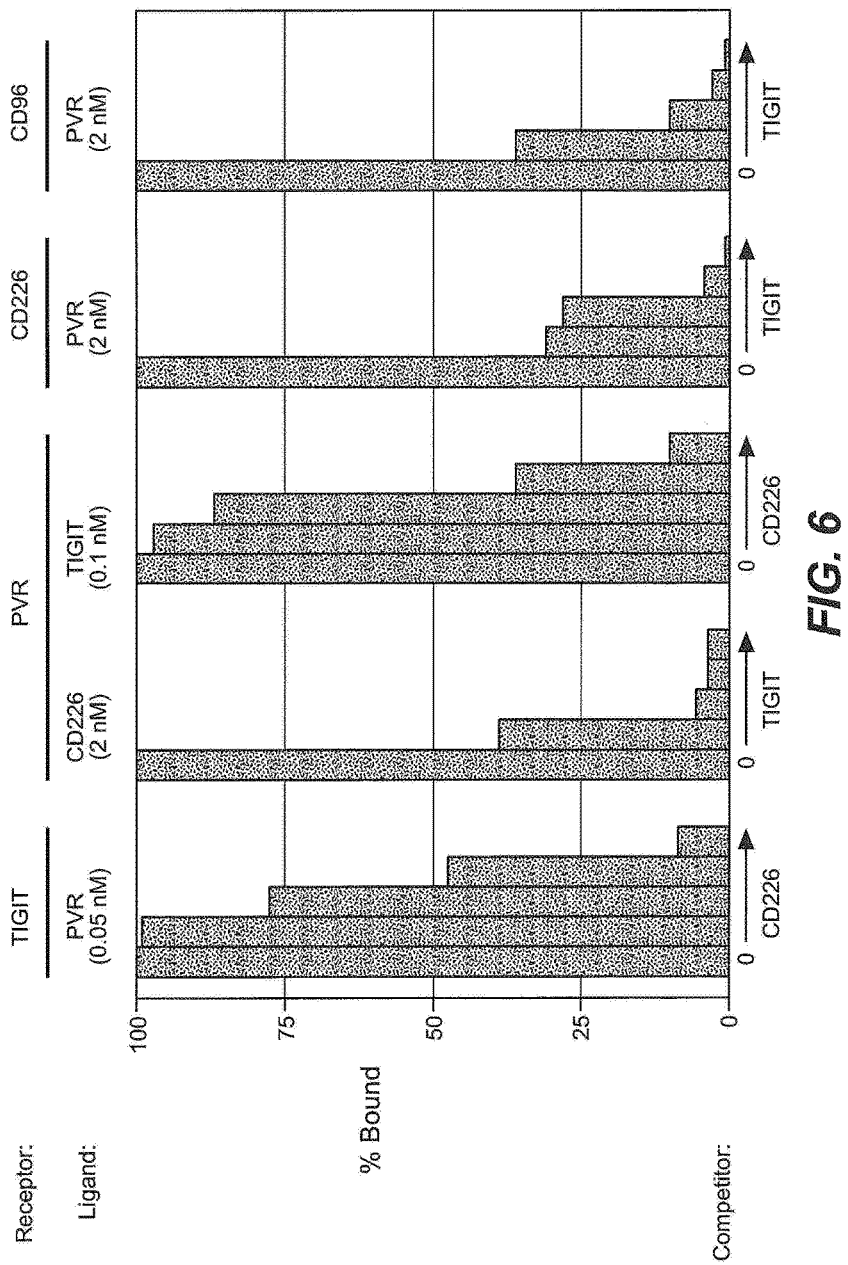

FIGS. 5A and 5B show the binding of the radiolabeled TIGIT-Fc protein to PVR-expressing CHO cells. The average Kd for the TIGIT-Fc-PVR interaction over four experiments was 3.15 nM. Table 6 shows the results of all the analyses in tabular form.

Figures 2, 4B:
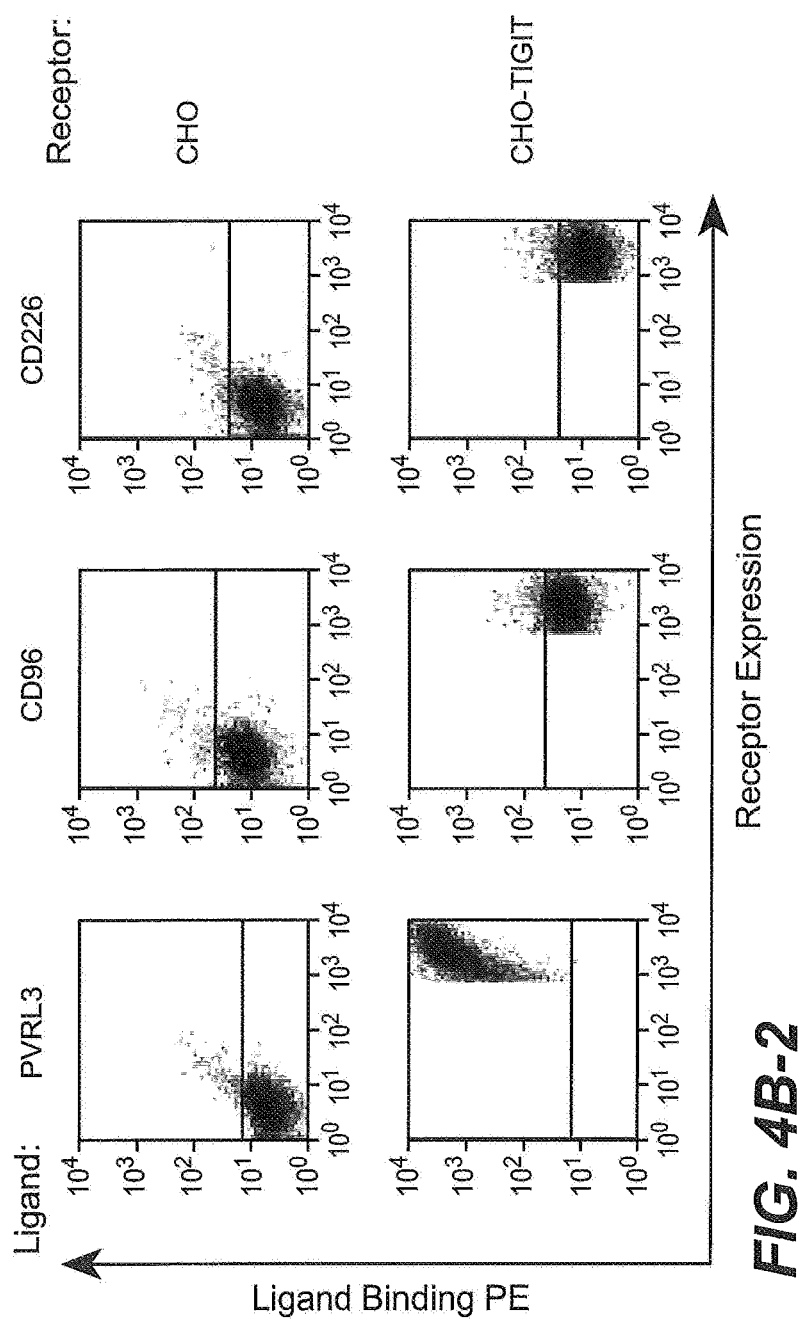
Figures 3, 4B:
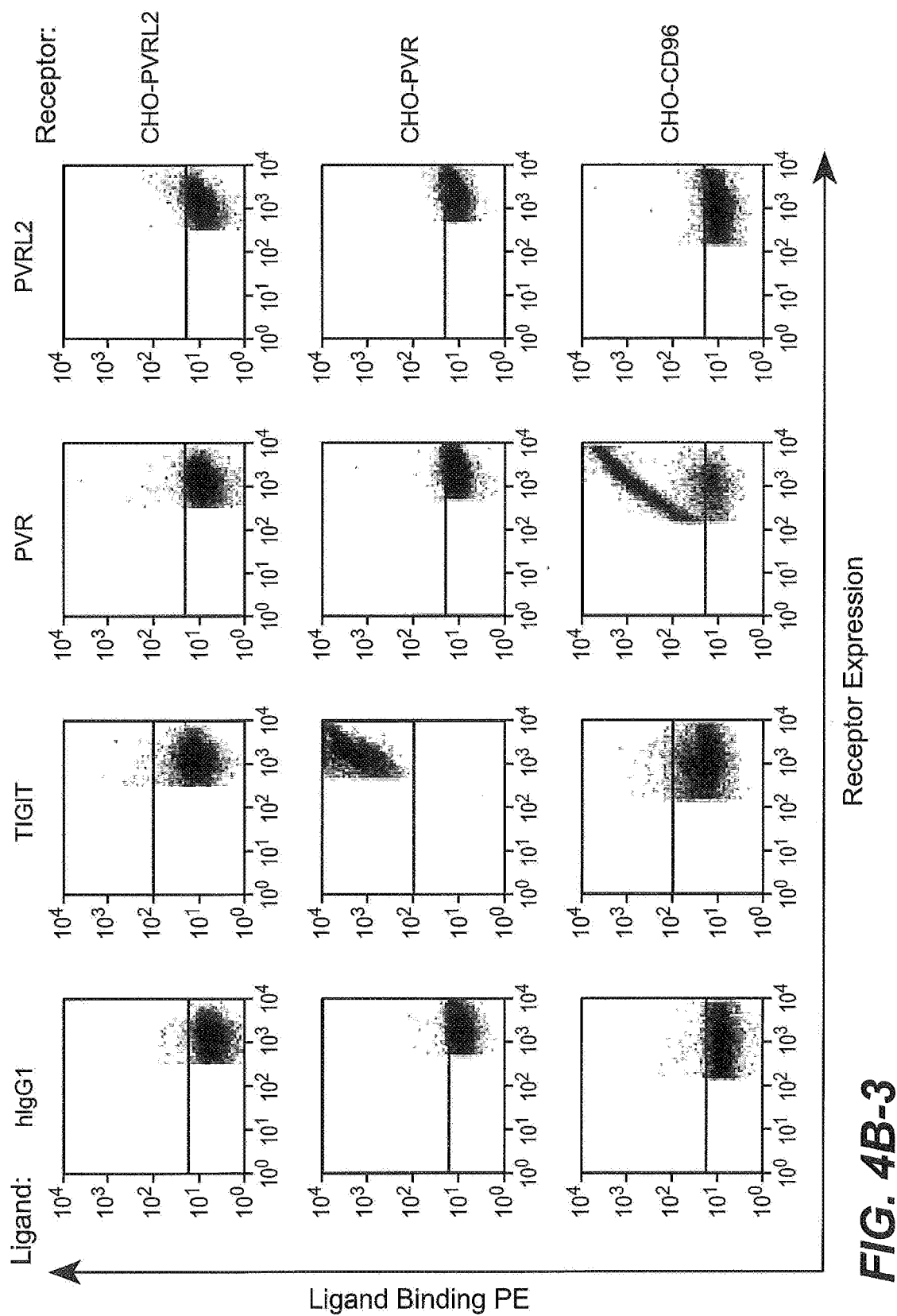
Figures 4, 4B:
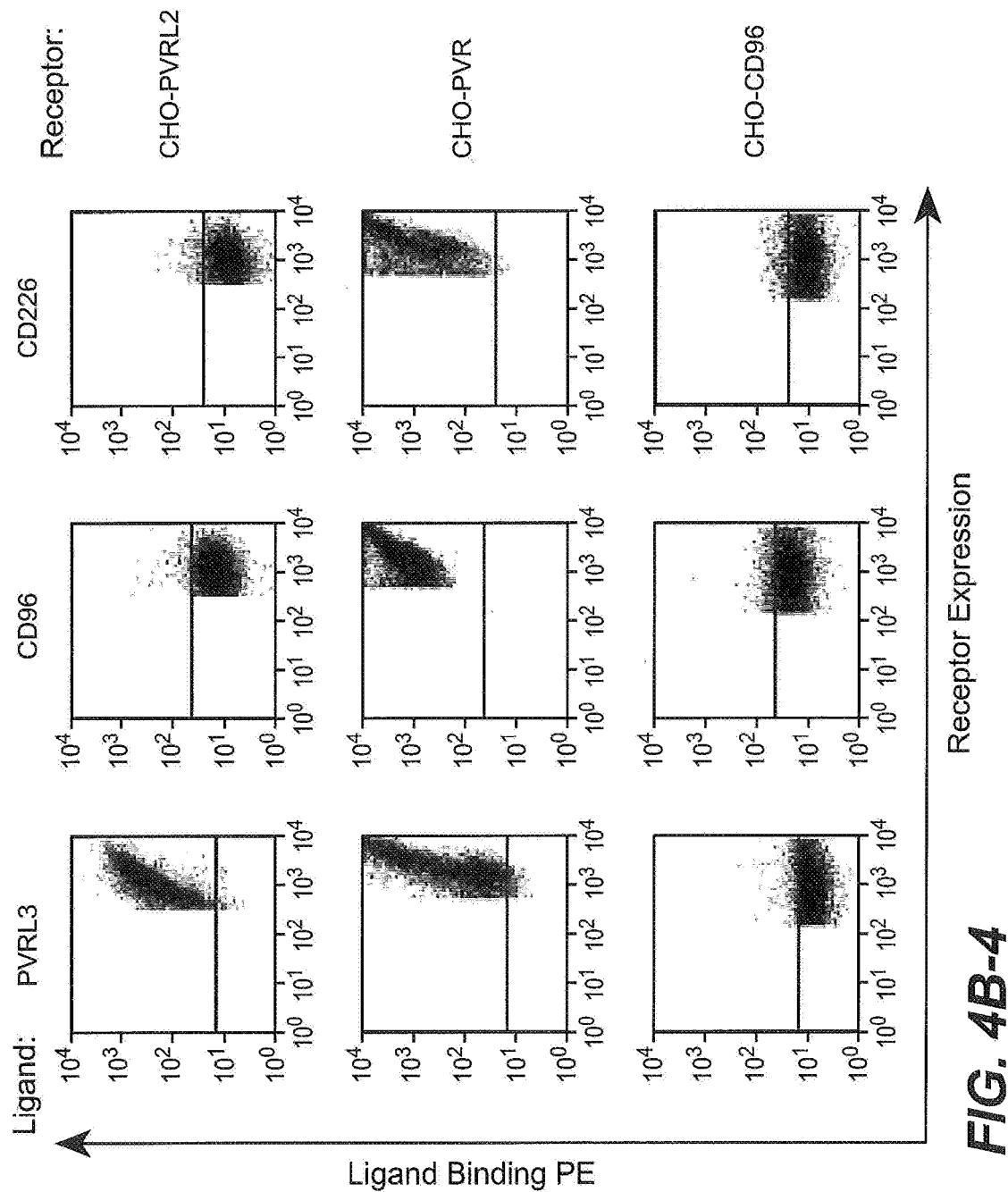
Figures 4, 4B, 5:
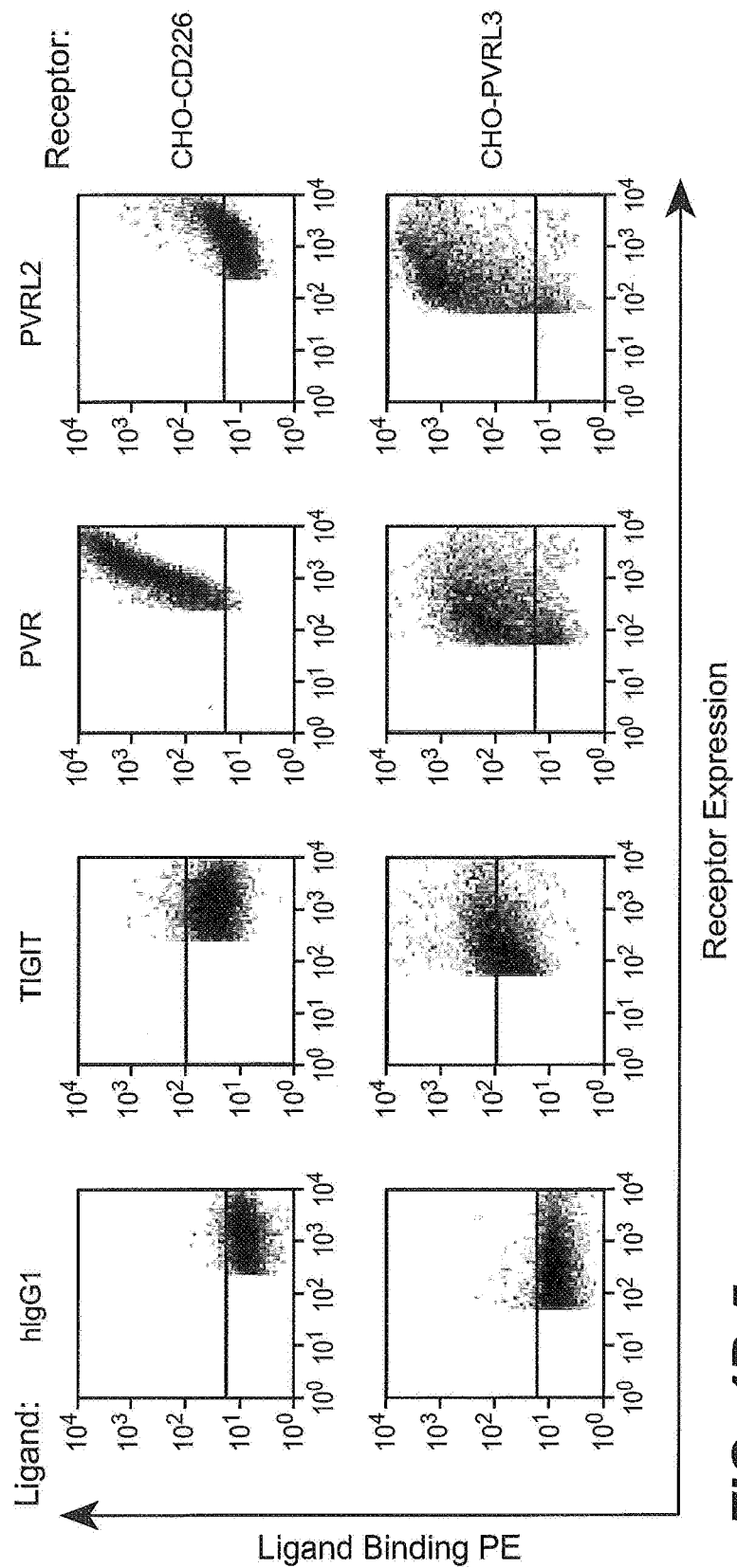
Figures 4, 4B, 5, 6:
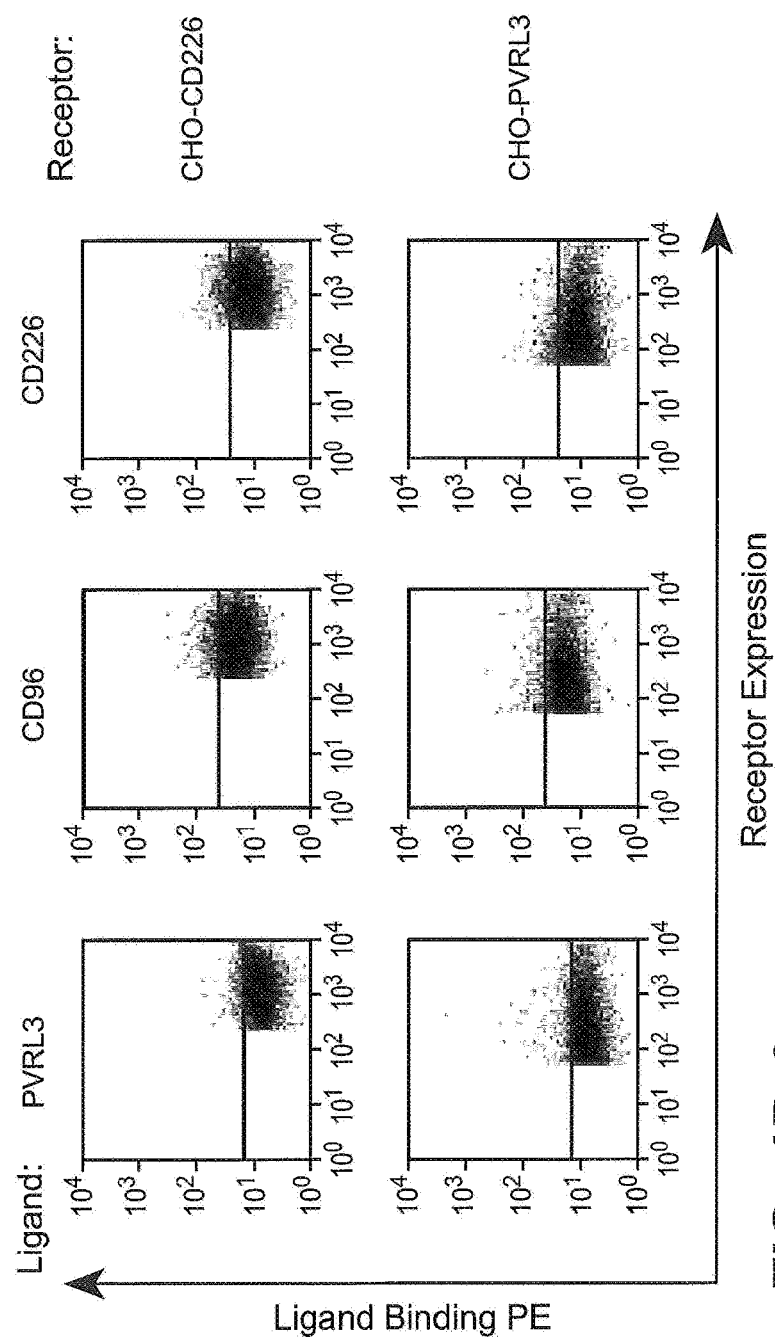
Figure 7A:
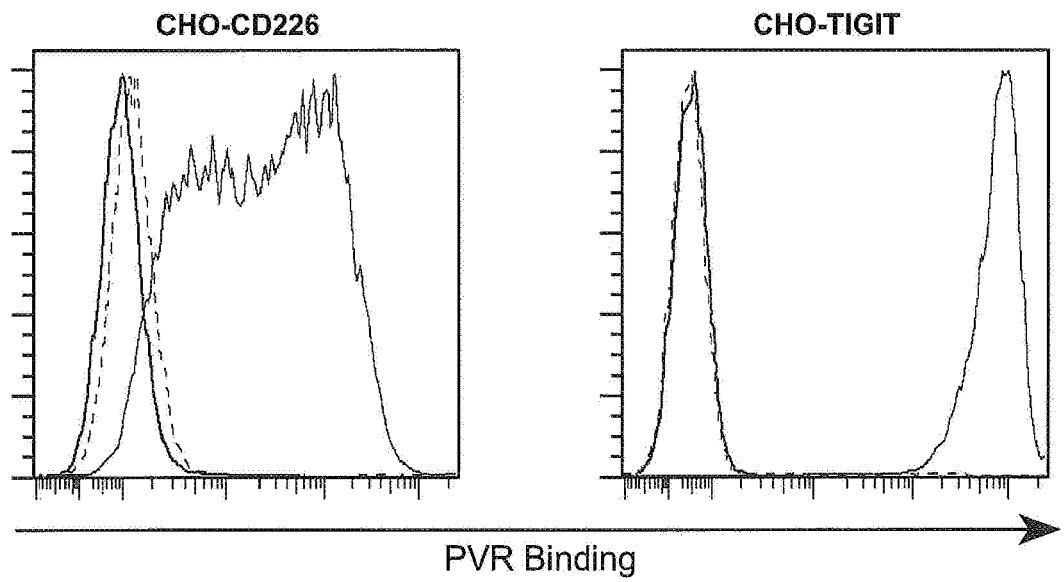
FIGS. 7A and 7B show the results of experiments assessing the ability of an anti-PVR antibody to block PVR binding to TIGIT or CD226, as described in Example 2.
Figure 7B:
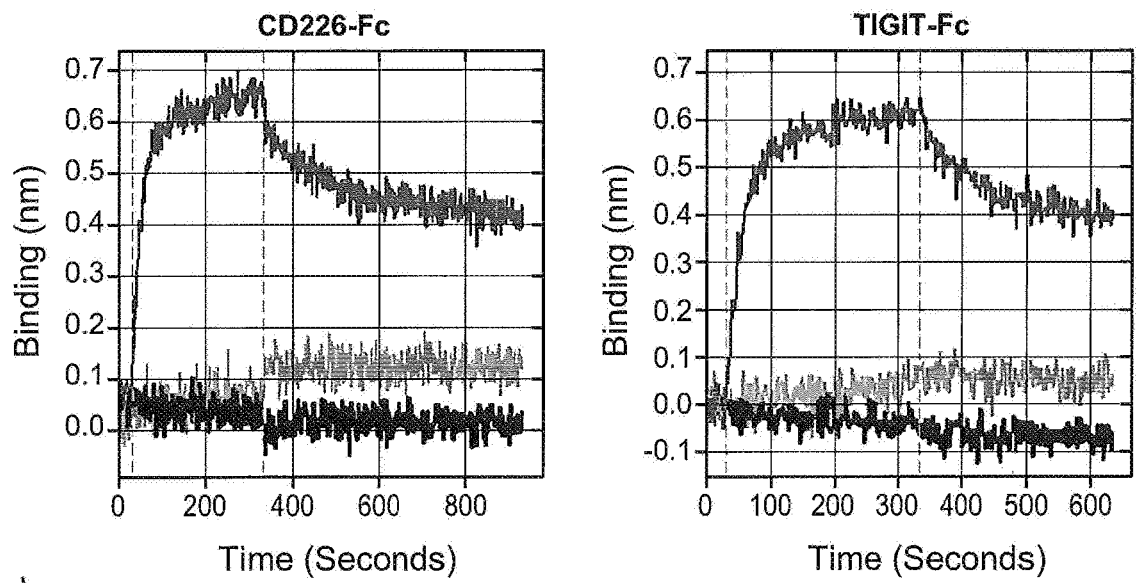

The interaction of TIGIT with PVR exhibited the highest affinity (Kd=1-3 nM) while the affinity of TIGIT binding to PVRL3 was approximately 10-30-fold lower (Kd=38.9 nM) (see Table 6). Due to poor curve fitting in the radioligand assay the binding constant for the PVRL2-TIGIT interaction could not be determined, but specific binding was nonetheless observed and was consistent with the above-described FACS data showing modest binding of PVRL2-Fc to CHO-TIGIT, and further bolstered the finding that binding between PVRL2 and TIGIT is a low-affinity interaction. Iodinated Fc fusion protein (ligand) was bound to receptor-expressing CHO cells at the indicated concentration, and competed with 10-fold serial dilutions of CD226-Fc (8 µM on CHO-TIGIT; 5 µM on CHO-PVR), TIGIT-Fc (2 µM on CHO-PVR; 6 µM on CHO-CD226 and CHO-CD96). Nonspecific binding was determined using 2000-fold excess cold ligand and subtracted from total binding. The competition studies showed that TIGIT effectively blocked the interaction of PVR to its other co-receptors CD226 and CD96, whereas CD226 was a less effective inhibitor of the TIGIT-PVR interaction (FIG. 6). This data was in agreement with the higher observed affinity of the PVR-TIGIT interaction (1-3 nM) as compared to the PVR-CD226 interaction (approximately 115 nM, according to Tahara-Hanaoka, S. et al. Int Immunol 16, 533-8 (2004)). Direct competition studies with CD96 were not possible due to low expression of that protein, although TIGIT completely inhibited PVR binding to CD96-expressing CHO cells. The foregoing competition studies demonstrated that TIGIT, CD226, and CD96 share a common binding site or overlapping binding sites on PVR. This finding was further supported by the observation that the anti-PVR antibody D171, which binds to the N-terminal IgV domain of PVR, blocks the binding of TIGIT and CD226 to PVR (FIG. 7).

Example 3

Expression of TIGIT and PVR (A) Expression of TIGIT and PVR on Resting and Activated Immune Cells The relative distribution and expression of TIGIT and PVR on immune cells was assessed as an

TABLE 6

Cell binding of PVR family proteins. Receptors were expressed on CHO cells, and all ligands were-Fc constructs. MFI was determined by flow cytometry with biotinylated Fc-ligands, after gating on receptor-positive cells. Binding affinity (Kd) was determined by competition radioligand binding assay. Kd is indicated (nM) and is the average value from at least 3 independent assays, except where indicated (*).

| | Ligand | | | | | | | | | | |
|---|---|---|---|---|---|---|---|---|---|---|---|
| | PVR | | TIGIT | | PVRL2 | | PVRL3 | | CD226 | | CD96 |
| Receptor | MFI | Kd | MFI | Kd | MFI | Kd | MFI | Kd | MFI | Kd | MFI |
| PVR | – | – | +++ | 1.02 | – | – | +++ | 70.8 | +++ | 114* | +++ |
| TIGIT | ++++ | 3.15 | – | – | ++ | & | +++ | 38.9 | – | – | – |
| PVRL2 | – | – | – | – | – | – | ++ | 14-30 | – | – | – |
| PVRL3 | ++ | – | ++ | – | +++ | 3-13 | – | – | – | – | – |
| CD226 | +++ | 119 | – | – | + | & | – | – | – | – | – |
| CD96 | +++ | 37.6 | – | – | – | – | – | – | – | – | – |

Figure 8A:
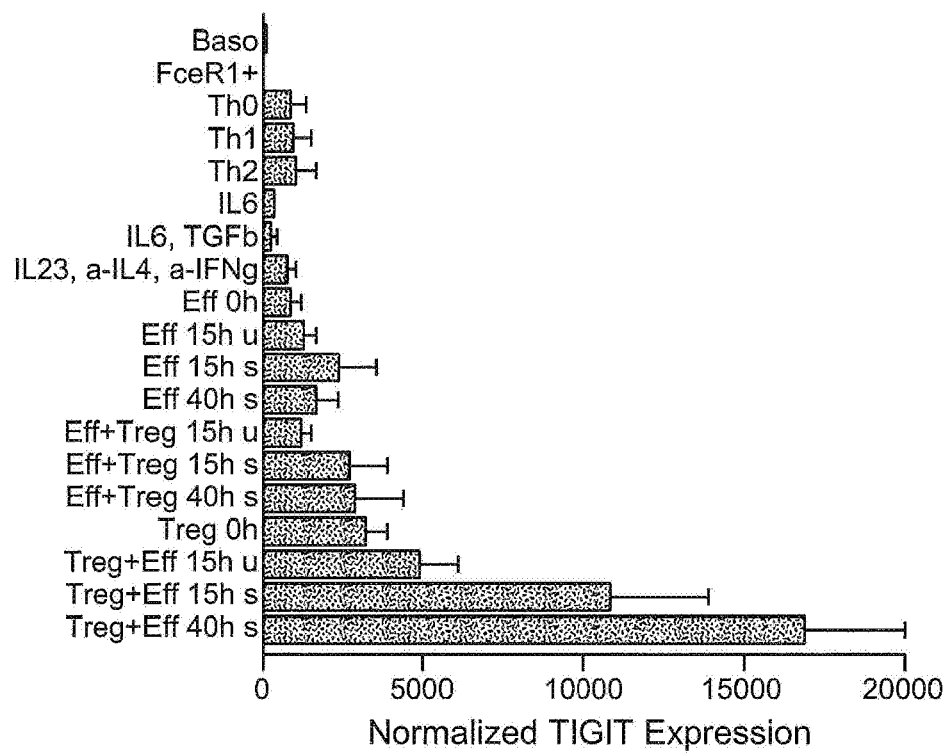
FIG. 8A depicts TIGIT expression data (left panel) or CD226 expression data (right panel) in a variety of immune cell types, as described in Example 2(A).
Figure 8A:
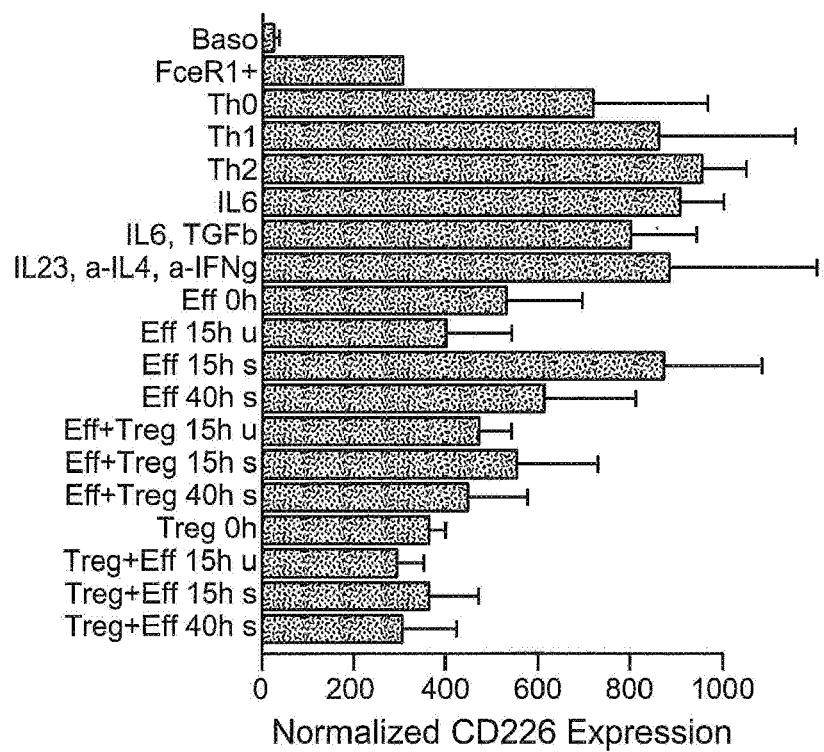
Figure 8B:
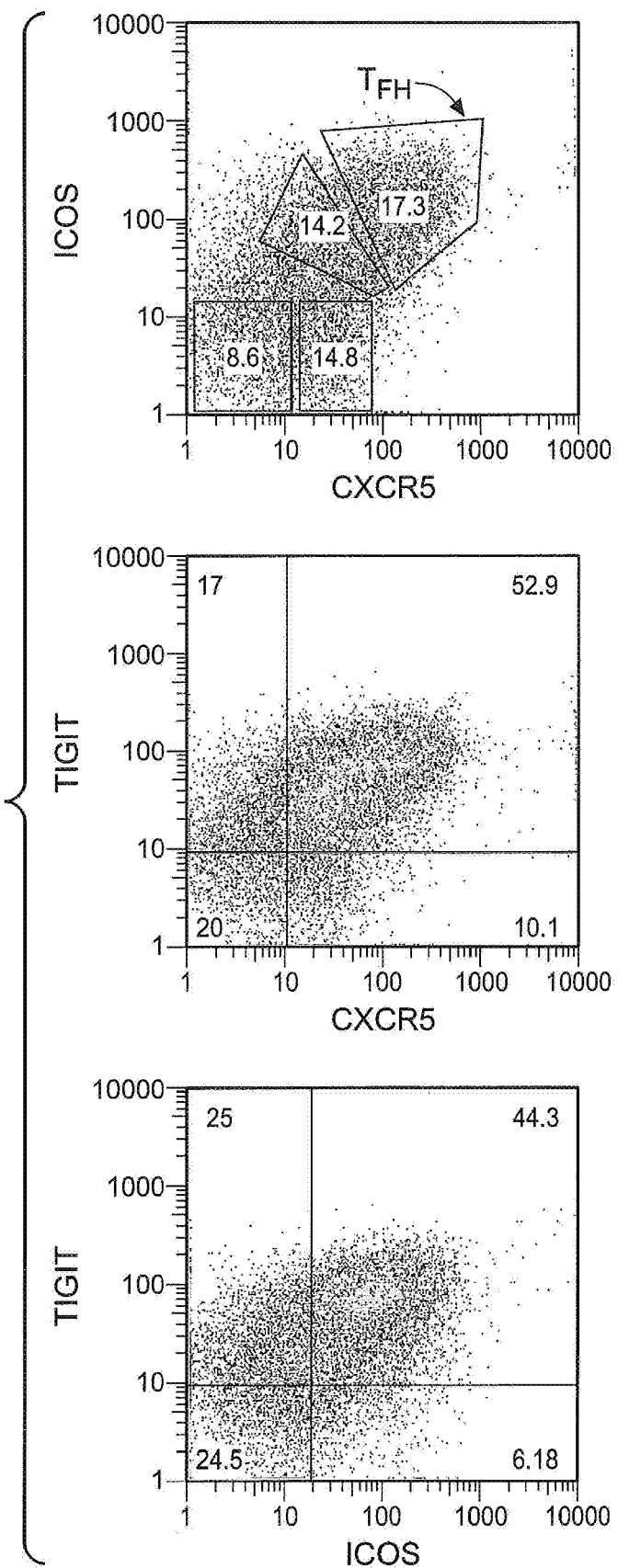
FIG. 8B depicts RT-PCR analyses of TIGIT and ICOS mRNA expression in tonsillar $T_{fh}$ cells, as described in Example 2(A).

++++ MFI > 5000
+++ MFI = 1000-4999
++ MFI = 100-999
+ MFI < 100
– No binding
& Specific binding but Kd not elucidated
*average of two assays indicator of the role of these two molecules in normal immune function, and was compared to the expression of CD226, a molecule known previously and shown in Example 2 to interact with PVR in vivo. An earlier study had shown that the expression of TIGIT was specific to T and NK cells, across multiple immune cell types as well as an array of tissues (Abbas, A.R. et al., Genes Immun 6, 319-31 (2005)). A further analysis of the expression of TIGIT in a variety of immune cells and tissues ex vivo and after activation was performed. As shown in FIGS. 8A and 8B, TIGIT is most strongly expressed in regulatory T cells ($T_{reg}$), and is also highly expressed in NK cells and $T_{fh}$ cells from human tonsillar tissue. TIGIT is expressed to a lesser extent in unstimulated NK cells, in activated and resting memory T cells, in CD8$^+$ T cells and in Th2 and Th1 cells. This data correlates with the data shown in US patent publication no. US20040121370, where TIGIT was shown to be significantly overexpressed in isolated CD4$^+$ T cells activated by anti-CD3/ICAM-1 and anti-CD3/anti-CD28 as compared to isolated resting CD4$^+$ T cells. By contrast, PVR has been reported to be expressed in endothelial cells, fibroblasts, osteoclasts, follicular dendritic cells, dendritic cells, and tumor cells (Sakisaka, T. & Takai, Y., Curr Opin Cell Biol 16, 513-21 (2004); Fuchs, A. & Colonna, M., Semin Cancer Biol 16, 359-66 (2006)). This data highlights that TIGIT is associated with T cells that produce regulatory cytokines that may suppress the immune response.

Complementary flow cytometric analyses were also performed, using the same methods as described in Example 2. Human ex vivo T cells were examined after activation for surface TIGIT expression using a hamster anti-murine TIGIT antibody (10A7) that cross-reacts to human TIGIT and blocks TIGIT interaction with PVR (see FIG. 9). Anti-TIGIT antibodies were generated by immunizing hamsters with murine TIGIT-Fc fusion protein and obtaining hamster-anti-mouse antibodies therefrom using standard techniques. Two antibodies, 10A7 and 1F4, also specifically bound to human TIGIT (data not shown) and were used for further experiments. Notably, 10A7 and 1F4 bind to different epitopes on human TIGIT, as evidenced by the fact that 1F4 binding to TIGIT does not block 10A7 binding to TIGIT on the surface of 293 cells expressing TIGIT (data not shown). The amino acid sequences of the light and heavy chains of the 10A7 antibody were determined using standard techniques. The light chain sequence of this antibody is: DIVMTQSPSSLAVSPGEKVTMTCKSSQSLYYSGVK-ENLLAWYQQKPGQS PKLLIYYASIRFTGVPDRFTG-SGSGTDYTLTITSVQAEDMGQYFCQQGINNPLTFG-DGT KLEIKR (SEQ ID NO: 21) and the heavy chain sequence of this antibody is: EVQLVESGGGLTQP-GKSLKLSCEAS GFTFSSFTMHWVRQSPGKGLEWVA-FIRSGSGIV FYADAVRGRFTISRDNAKNLLFLQMN-DLKSEDTAMYYCARRPLGHNTFDSWGQGTLV TVSS (SEQ ID NO: 22), where the complementarity determining regions (CDRs) of each chain are represented by bold text. Thus, CDR1 of the 10A7 light chain has the sequence KSSQSLYYSGVKENLLA (SEQ ID NO: 23), CDR2 of the 10A7 light chain has the sequence ASIRFT (SEQ ID NO: 24), and CDR3 of the 10A7 light chain has the sequence QQGINNPLT (SEQ ID NO: 25). CDR1 of the 10A7 heavy chain has the sequence GFTFSSFTMH (SEQ ID NO: 26), CDR2 of the 10A7 heavy chain has the sequence FIRSGS-GIVFYADAVRG (SEQ ID NO: 27), and CDR3 of the 10A7 heavy chain has the sequence RPLGHNTFDS (SEQ ID NO: 28).

The amino acid sequences of the light and heavy chains of the 1F4 antibody were determined using 5' RACE (see, e.g., Ozawa et al., BioTechniques 40(4): 469-478 (2006)). The light chain sequence of this antibody is: DV-VLTQTPLSLSVSFGDQVSISCRSSQSLVNSYGNTFLS-WYLHKPGQSPQLLIFGISNRF SGVPDRFSGSGSGTD-FTLKISTIKPEDLGMYYCLQGTHQPPTFGPGTKLEVK (SEQ ID NO: 29) and the heavy chain sequence of this antibody is: EVQLQQSGPELVKPGTSMKISCKASGY-SFTGHLMNWVKQSHGKNLEWIGLIIPYNGGT SYNQ-KFKGKATLTVDKSSSTAYMELLSLTSDDSAVYFCSR-GLRGFYAMDYWGQGTSV TVSS (SEQ ID NO: 30), where the complementarity determining regions (CDRs) of each chain are represented by bold text. Thus, CDR1 of the 1F4 light chain has the sequence RSSQSLVNSYGNTFLS (SEQ ID NO: 31), CDR2 of the 1F4 light chain has the sequence GISNRFS (SEQ ID NO: 32), and CDR3 of the 1F4 light chain has the sequence LQGTHQPPT (SEQ ID NO: 33). CDR1 of the 1F4 heavy chain has the sequence GYSFTGHLMN (SEQ ID NO: 34), CDR2 of the 1F4 heavy chain has the sequence LIIPYNGGTSYNQKFKG (SEQ ID NO: 35), and CDR3 of the 1F4 heavy chain has the sequence GLRGFYAMDY (SEQ ID NO: 36). The primers used for the RACE sequencing methodology were as follows: RT-PCR gene-specific primers: (i) heavy chain: IgGRace4: TTTYTTGTCCACCKTGGTGCTGC (SEQ ID NO: 37); IgGRace2: CTGGACAGGGATCCAGAGTTCC (SEQ ID NO: 38); IgGRace7: CARGTCAMDGTCACTGRCTCAG (SEQ ID NO: 39); IgGRace1: GAARTARCCCT-TGACCAGGC (SEQ ID NO:64); (ii) light chain: KapRace3: GTAGAAGTTGTTCAAGAAG (SEQ ID NO: 40); KapRace2: GAGGCACCTCCAGATGTTAAC (SEQ ID NO: 41); KapRace7: CTGCTCACTGGATGGTGG-GAAG (SEQ ID NO: 42); KapRace1: GAAGATGGATA-CAGTTGGTGC (SEQ ID NO: 43); and 5' RACE tail PCR primers: ODC2: GATTCAAATCTCAATTATATAAT-CCGAATATGTTTACCGGCTCGCTCATGGACCCCC CCCCCCDN (SEQ ID NO: 44); ODC3: GAAT-TCCCCCCCCCCCCC (SEQ ID NO: 45); ODC4: CTCATGGACCCCCCCCCCC (SEQ ID NO: 46); ODC5: AAATATAATACCCCCCCCCCCCC (SEQ ID NO: 47); ADCS: AAATATAATACCCCCCC (SEQ ID NO: 48), and ADC5X: CTCATGGACCCCCC (SEQ ID NO: 49).

The nucleotide sequence encoding the 1F4 light chain was determined to be GATGTTGTGTTGACTCAAACTC-CACTCTCCCTGTCTGTCAGCTTTGGAGATCAAGTTT CTATCTCTTGCAGGTCTAGTCAGAGTCTTGTAAAC-AGTTATGGGAACACCTTTTTGTCTTGGTACCTGCA-CAAGCCTGGCCAGTCTCCACAGCTCCTCATCTT-TGGGATTTCCAA CAGATTTTCTGGGGTGCCAGAC-AGGTTCAGTGGCAGTGGTTCAGGGACAGATTTCAC ACTCAAGATCAGCACAATAAAGCCTGAGGACTT-GGGAATGTATTACTGCTTACAAG GTACGCATCAG-CCTCCCACGTTCGGTCCTGGGACCAAGCTGGAG-GTGAAA (SEQ ID NO: 50) and the nucleotide sequence encoding the 1F4 heavy chain was determined to be GAGGTCCAGCTGCAACAGTCTGGACCTGAGCTG-GTGAAGCCTGGAACTTCAATGAAGATATCCTGC-AAGGCTTCTGGTTACTCATTCACTGGCCATCTTAT-GAACTGGGTGAA GCAGAGCCATGGAAAGAACCTT-GAGTGGATTGGACTTATTATTCCTTACAATGGTGG TACAAGCTATAACCAGAAGTTCAAGGGCAAGGC-CACATTGACTGTAGACAAGTCATCCAGCACAGCC-TACATGGAGCTCCTCAGTCTGACTTCTGATGACT-CTGCAGTCTATTT CTGTTCAAGAGGCCTTAGGGG-CTTCTATGCTATGGACTACTGGGGTCAAGGAACCTC AGTCACCGTCTCCTCA (SEQ ID NO: 51).

Human peripheral blood mononuclear cells (PBMC) were isolated from buffy coats by centrifugation over Ficoll- Paque Plus (Amersham Biosciences). Indicated subsets of cells were purified with corresponding MACS kits (Miltenyi). Purity of sorted cells was verified by flow cytometry and ranged from greater than 93% for cells purified by magnetic cell sorting to greater than 98% for cells purified by flow cytometry. All cells were blocked with 10-20% of the appropriate sera or purified IgG prior to staining. Quantitative PCR analyses were performed to assess the mRNA levels of proteins of interest in the sorted cell populations. Total RNA of the sorted cells was isolated with an RNeasy kit (Qiagen) and digested with DNAse I (Qiagen). Total cellular RNA was reverse-transcribed and analyzed by real-time TaqMan™ PCR in triplicate according to the manufacturer's instructions using a 7500 Sequence Detection System (Applied Biosystems). Arbitrary expression units are given as fold-expression over unstimulated cells. The forward and reverse primers used to detect TIGIT were: TGCCAGGTTCCAGATTCCA (SEQ ID NO: 52) and ACGATGACTGCTGTGCAGATG (SEQ ID NO: 53), respectively, and the TIGIT probe sequence used was AGC-CATGGCCGCGACGCT (SEQ ID NO: 54).

Figures 1, 10A:
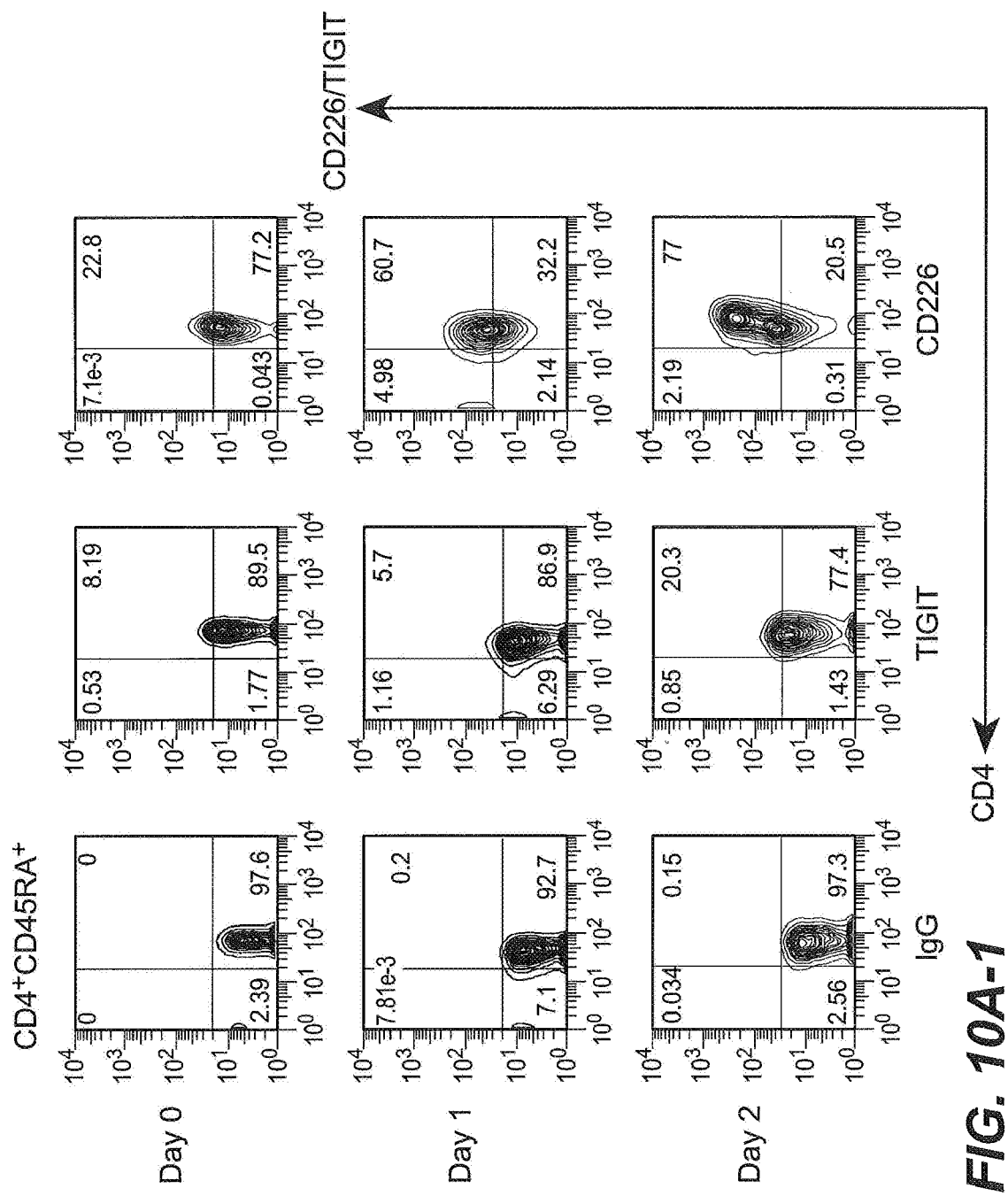
Figures 2, 10A:
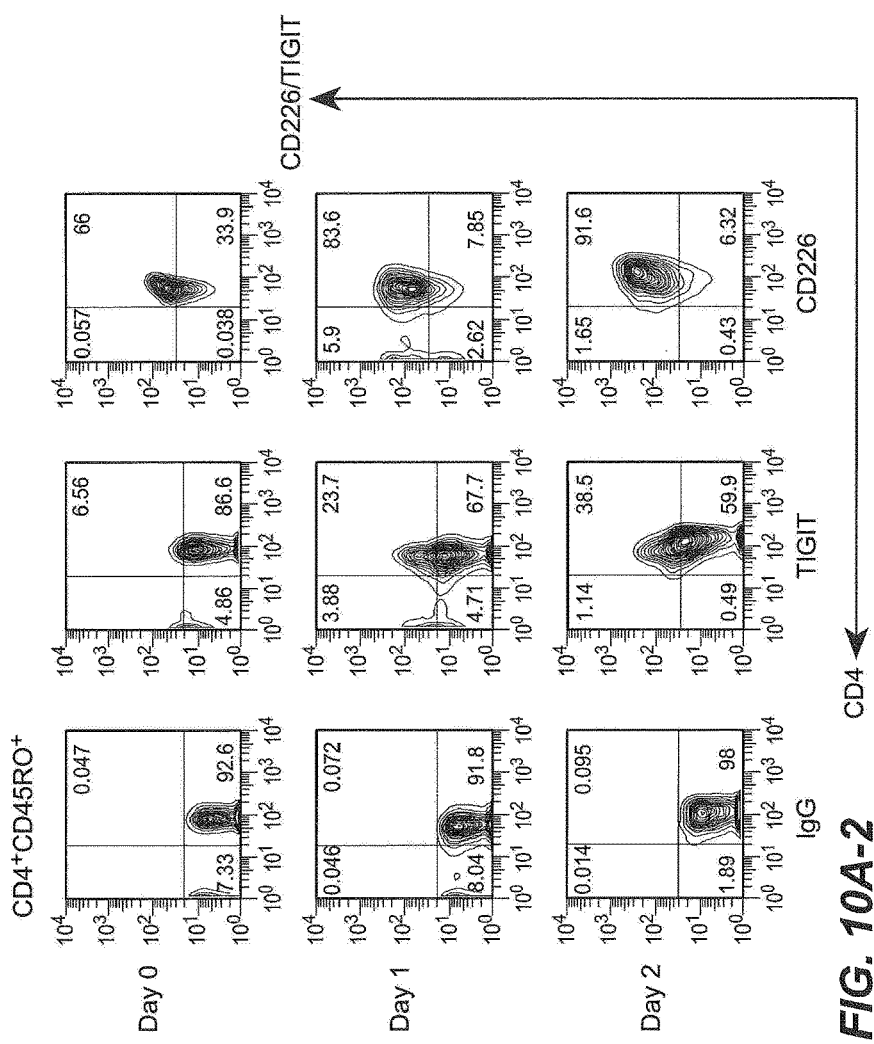
Figure 10B:
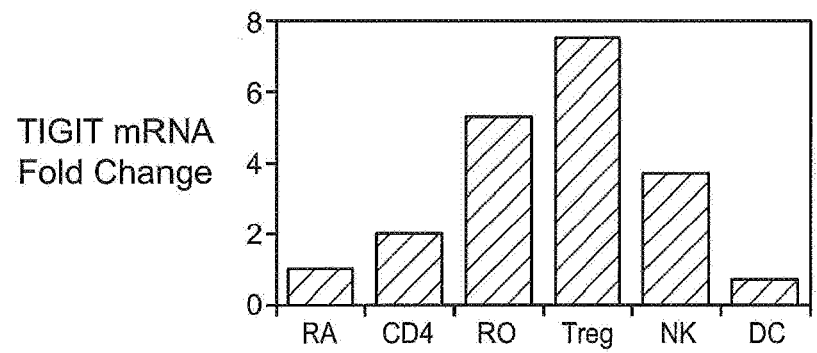
FIG. 10B shows a bar graph indicating the fold-change in TIGIT mRNA in different types of immune cells sorted directly ex vivo from PBMC, as compared to the TIGIT mRNA levels in naïve CD4$^+$CD45RA$^+$ cells.
Figure 10D:
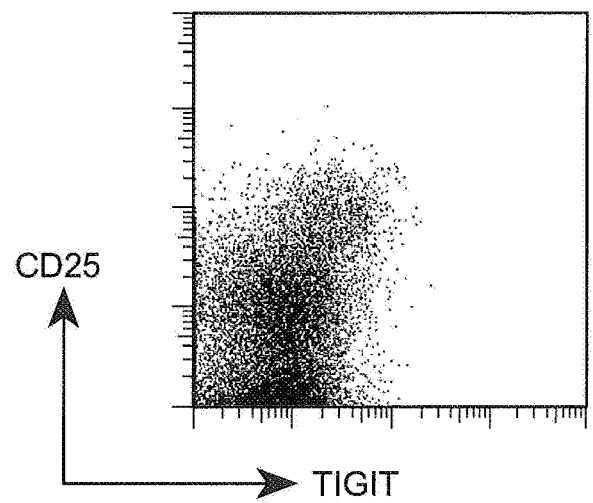
FIG. 10D shows the results of FACS assays showing that CD25− human PBMC cells lack TIGIT expression.
Figure 10C:
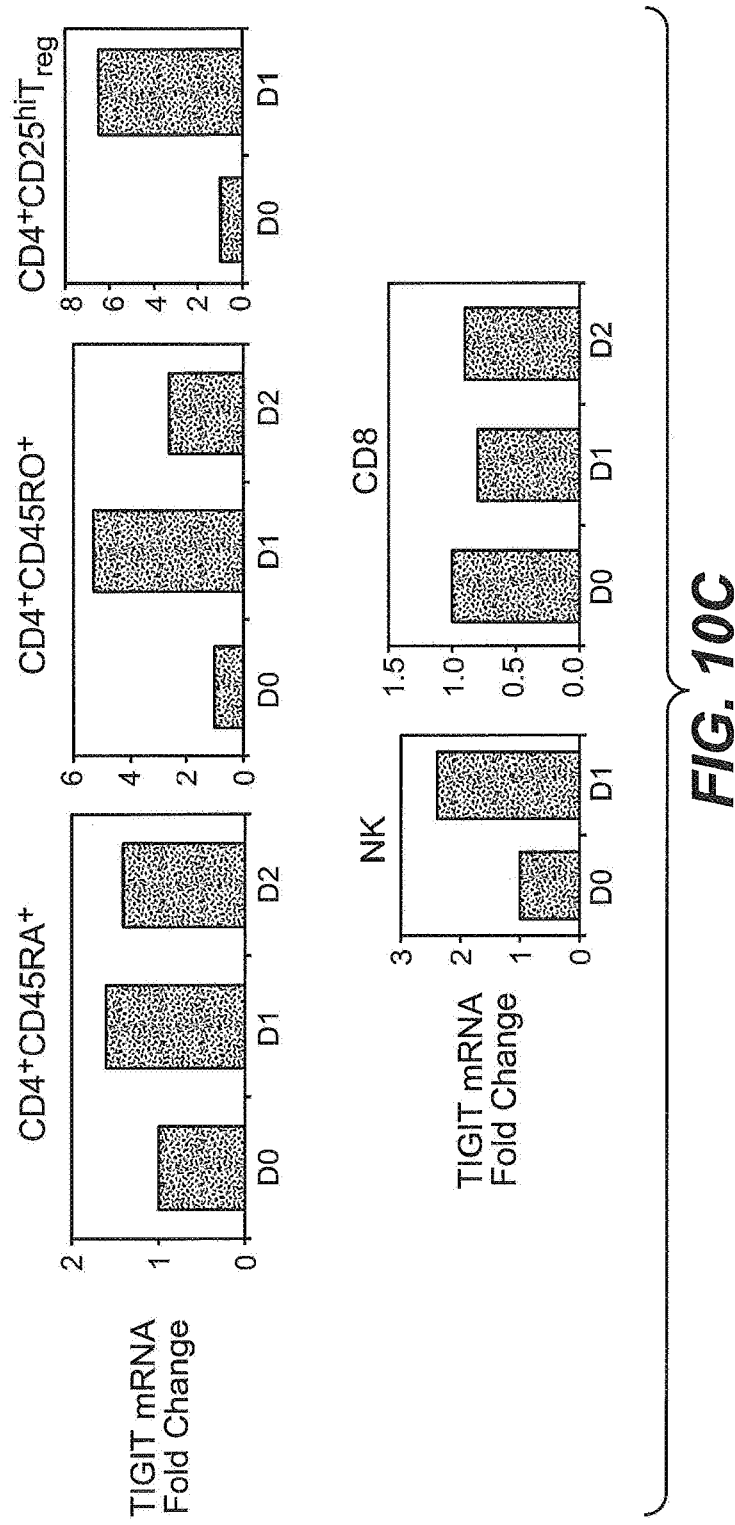
FIG. 10C shows bar graphs indicating the—fold increase in TIGIT mRNA levels on sorted CD4$^+$CD45RO$^+$, CD4$^+$CD45RA$^+$ and CD4$^+$CD25$^{hi}$T$_{reg}$ cells activated with anti-CD3 and anti-CD28 for 1 or 2 days or sorted CD56+ NK cells activated with IL-2 for one day, as compared to unstimulated cells. The FACS plots shown are from one representative experiment and the RT-PCR values are an average of three donors.

CD4$^+$ T cells were isolated from PBMC and activated with anti-CD3 and anti-CD8. Cell surface-expressed TIGIT was undetectable in unstimulated naïve CD4$^+$CD45RA$^+$ cells, whereas unstimulated CD4$^+$CD45RO$^+$ cells had low but detectable expression (FIGS. 10A-1 to 10A-2). As shown in FIGS. 10A-1 to 10A-2, TIGIT expression differed significantly from CD226 expression in RA$^+$ vs. RO$^+$ subsets of CD4 T cells. Analysis of mRNA in immune cell populations sorted directly ex vivo from PBMC showed greater expression of TIGIT in $T_{reg}$, RO, and NK cells than in other cell types studied relative to TIGIT expression in naïve CD4$^+$CD45RA$^+$ cells (FIG. 10B). After activation with anti-CD3 and CD28, cell surface-expressed TIGIT was upregulated in both naïve and memory T cell populations, as shown in FIGS. 10A-1 to 10A-2. CD4$^+$CD45RO$^+$ memory cells had significantly higher levels of expression at 24 and 48 hours post-activation as compared to CD4$^+$CD45RA$^+$ naïve cells (FIGS. 10A-1 to 10A-2). The CD4$^+$CD45RO$^+$ memory cells expressed 5.3-fold more TIGIT mRNA at day 1 than on day 0, whereas naïve cells only increased expression of TIGIT by 1.4-fold relative to day 0 (FIG. 10C). TIGIT expression was not detectable by day 6.

Figure 12A:
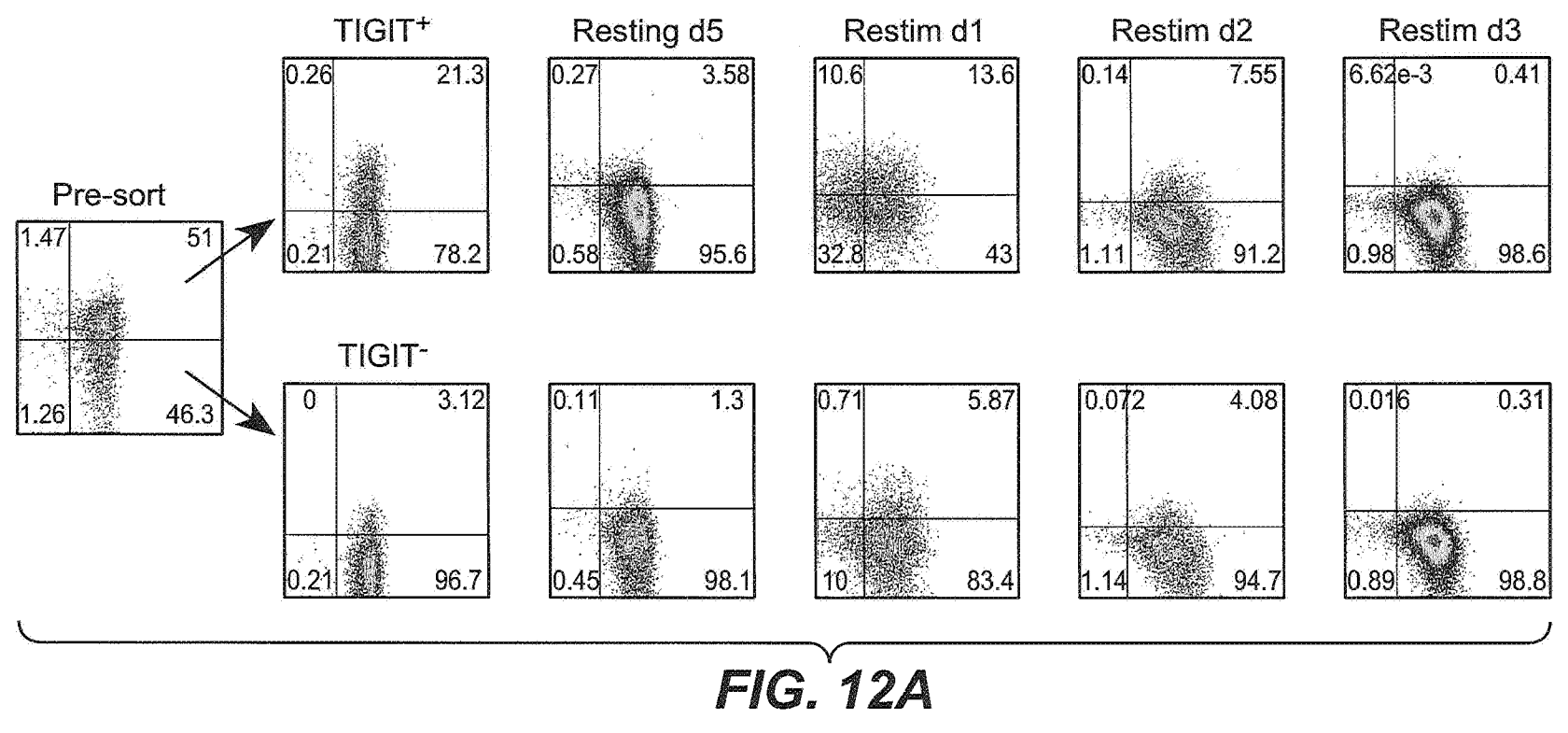
Figure 12B:
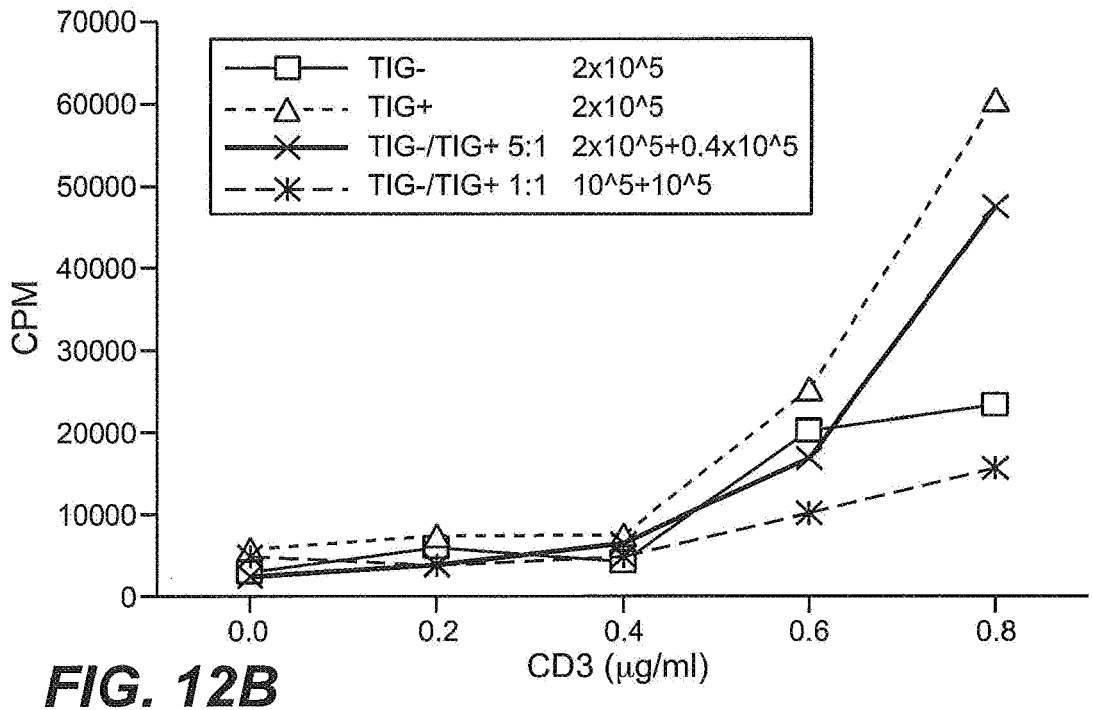
FIG. 12B depicts the results of plate-based assays to assess TIGIT expression in sorted TIGIT+ and TIGIT− cells exposed to varying concentrations of anti-CD3, as described in Example 3.

The stability of TIGIT expression on T cells was also assessed. Briefly, CD4$^+$CD45RO$^+$ cells were isolated and activated with anti-CD3/anti-CD28 for one day. The cells were flow sorted by FACS for CD4$^+$ and CD4$^+$TIGIT$^+$ populations. After resting for five days post-sorting, cells were restimulated with anti-CD3/anti-CD28 for up to three days and the cell surface TIGIT expression was determined by FACS. In a separate experiment, sorted TIGIT cells and CD4$^+$ cells were plated at a density of 2×10$^5$ cells/well onto 96-well plates coated with various concentrations of anti-CD3 (0-0.8 μg/mL), 100 μL volume and cultured for 4 days under standard conditions. $^3$H-thymidine was added for the final 18 hours of incubation, followed by washing. At the end of four days, the cells were solubilized and the radioactivity associated with each sample was measured by scintillation counting. As shown in FIGS. 12A and 12B, TIGIT expression was induced in both TIGIT cells and TIGIT$^-$cells, indicating that TIGIT$^-$ cells can express TIGIT under certain circumstances and that TIGIT cells are not a fixed cell population.

Given the higher level of TIGIT expression on effector memory cells, expression in T cell subsets was further dissected. Given that co-stimulatory or co-inhibitory molecules expressed on activated effector/memory T cells are often expressed on induced $T_{regs}$, TIGIT expression in $T_{regs}$ was assessed. $T_{regs}$ are phenotypically defined as CD25$^{hi}$ cells, and are known to express the transcription factor FoxP3 (Fontenot, J. D. et al., Immunity 22, 329-41 (2005)). In mice, the transcription factor FoxP3 is used to co-define $T_{reg}$ populations (Linsley, P. S. et al., Science 257, 792-5 (1992)). However, this association is not maintained in human T cells, since all activated human T cells express FoxP3 (Ziegler S F., Eur J Immunol. 37(1):21-3 (2007))). Ex vivo freshly isolated CD4$^+$CD25$^{hi}$ cells expressed TIGIT, whereas CD25$^-$ cells were negative for cell surface expression of TIGIT (FIG. 10E). TIGIT T cells also co-expressed FoxP3 and GITR (FIGS. 9 and 10E). Activation of sorted CD25$^+$ cells resulted in an upregulation of TIGIT protein expression (FIG. 10F) and a 6.5-fold increase in mRNA levels (FIGS. 10C and 10F). The fold-increase in TIGIT mRNA was equivalent in $T_{reg}$ and memory T cells.

Figure 11:
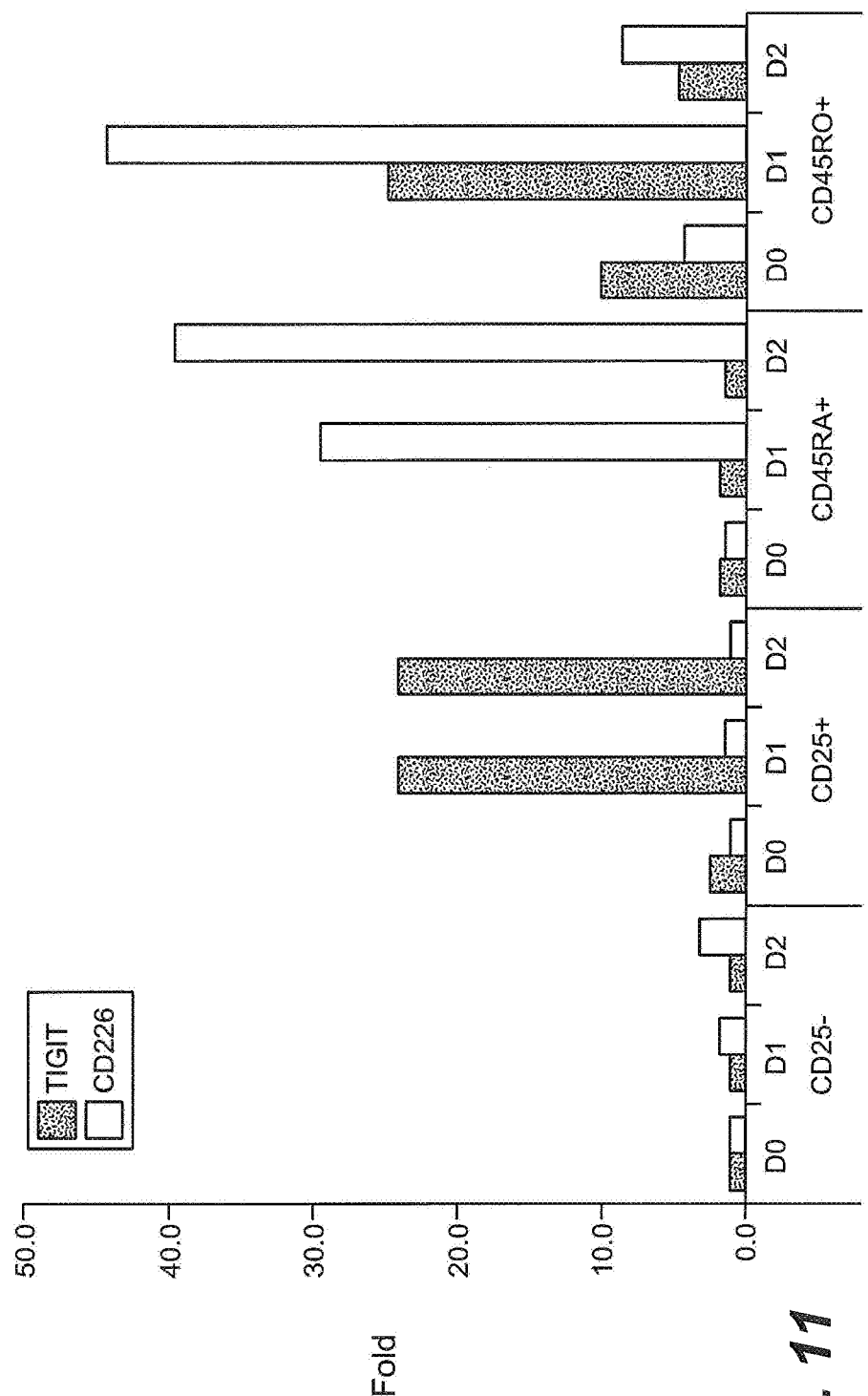
FIG. 11 provides graphs showing the fold-change in TIGIT or CD226 expression on resting or activated (for one or two days) CD25, CD25+, CD45RA+, CD45RO+ cells, as described in Example 2(A).

Comparison of mRNA levels from immune cells sorted directly ex vivo from donor PBMC showed that CD4$^+$CD25$^{hi}$ $T_{regs}$, CD4$^+$CD45RO$^+$, and NK cells each had significant TIGIT expression, with $T_{regs}$ exhibiting the highest expression (FIG. 10C). TIGIT expression was not observed in resting or activated B cells or monocytes (FIG. 10C and data not shown). Notably, CD226, another co-receptor for PVR, was not upregulated in CD4$^+$CD25$^{hi}$ $T_{reg}$ cells, suggesting divergent regulatory roles of TIGIT versus CD226 (FIG. 11).

Figure 14:
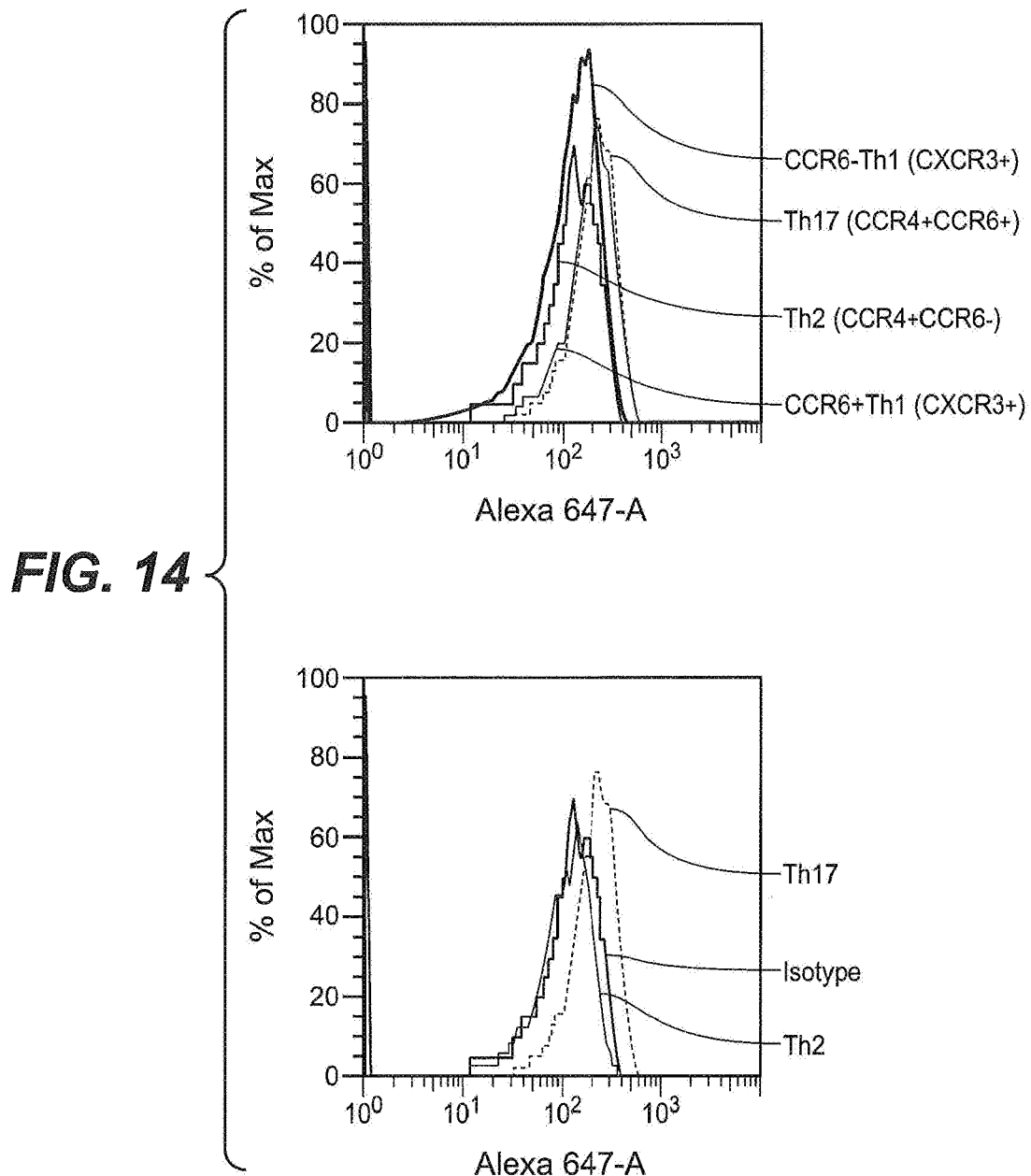
FIG. 14 depicts the results of flow cytometric experiments to assess TIGIT expression on IL-17-producing versus IL-2-producing T-helper cells, as described in Example 2(A). The data in each panel is representative of an experiment using PBMC from a different donor.

In other experiments, TIGIT expression on human tonsil T ($T_{FH}$) cells was examined using flow cytometry, following standard protocols as described above, with the exception that for assays involving FoxP3, cells were stained with antibodies following the above protocol, followed by fixation and permeabilization of the cells and staining with anti-FoxP3 or control IgG. TIGIT expression correlated with high levels of co-expression of CXCR5 and ICOS in T cells, markers which are typically observed in $T_{FH}$ cells (FIG. 8A). By contrast, CD226 (DNAM) expression in those cells was low to nonexistent (FIG. 8A). High levels of TIGIT expression were also observed in CD4$^+$CCR4$^+$CCR$^+$ IL-17-producing Th cells (FIG. 14). Overall, TIGIT was shown to be expressed by resting and activated T regulatory cells, human tonsillar $T_{fh}$ cells, IL17-producing helper T cells, resting and activated effector/memory T helper cells (CD4$^+$CD45RO$^+$ cells) and NK cells, and can be further upregulated upon activation of these cells. CD8$^+$ cells also express TIGIT and this expression is only slightly upregulated upon cellular activation. CD226 is shown herein and is known in the art to be expressed by CD8$^+$ T cells, on CD45RA$^+$ T cells, mast cells, platelets, natural killer (NK) cells, activated CD4$^+$CD45RA$^+$ T cells, and CD4$^+$CD45RO$^+$ T cells. TIGIT is specifically expressed on $T_{reg}$ and $T_{Fh}$ and resting effector/memory CD4$^+$CD45RO$^+$ cells; whereas CD226 is not expressed in these cells.

(B) Expression of TIGIT and PVR in Human Disease

Figure 15:
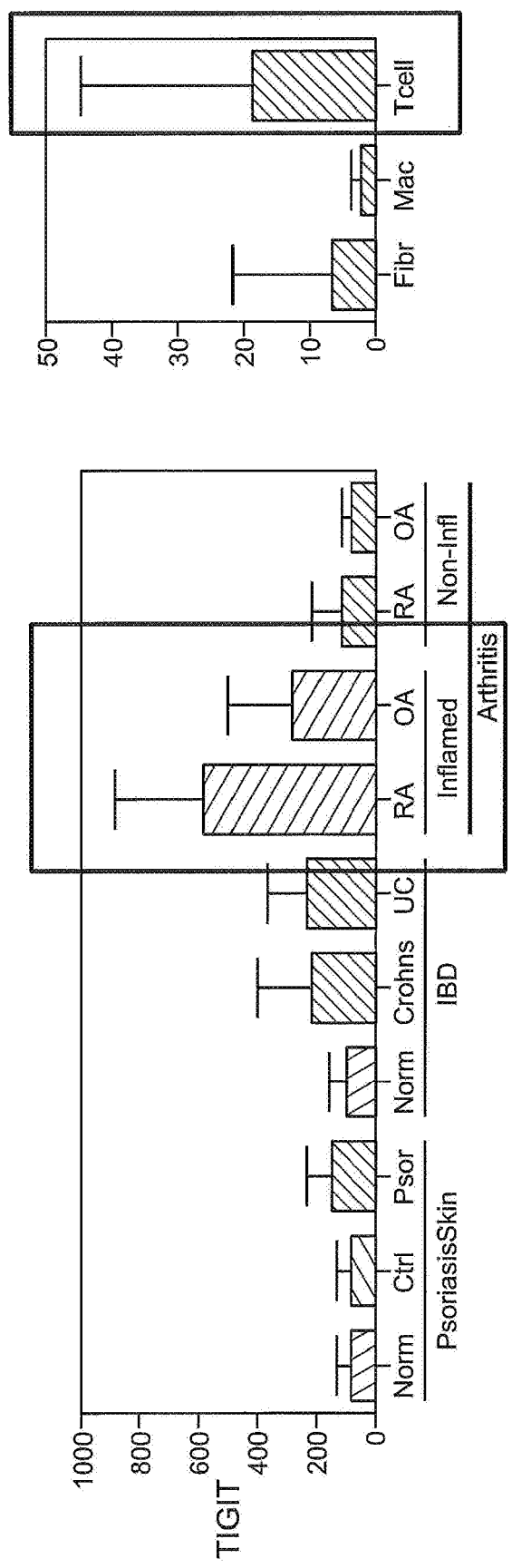
FIG. 15 depicts the results of mRNA analyses assessing the expression levels of TIGIT in disease tissue samples, as described in Example 3. The rightmost panel provides expression data from sorted cells taken from rheumatoid arthritis synovial tissue. PVR and CD226 expression were undetectable in these samples.
Figure 16:
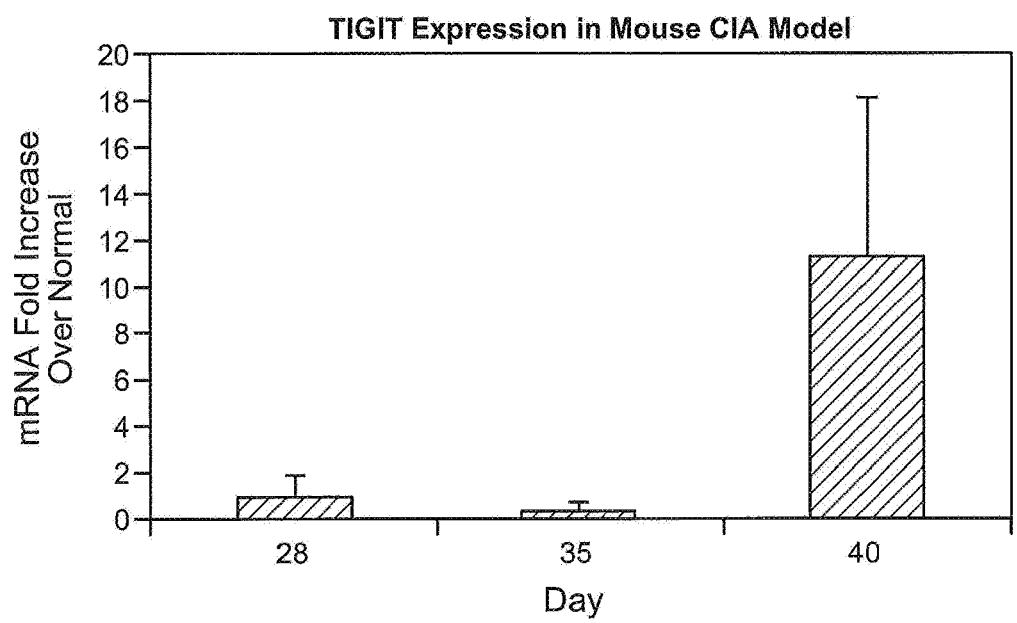
FIG. 16 depicts the results of RT-PCR experiments assessing the expression of TIGIT (top panel) or CD226 (lower panel) in tissues taken at various time points from mouse models of collagen-induced arthritis relative to normal samples.
Figure 16:
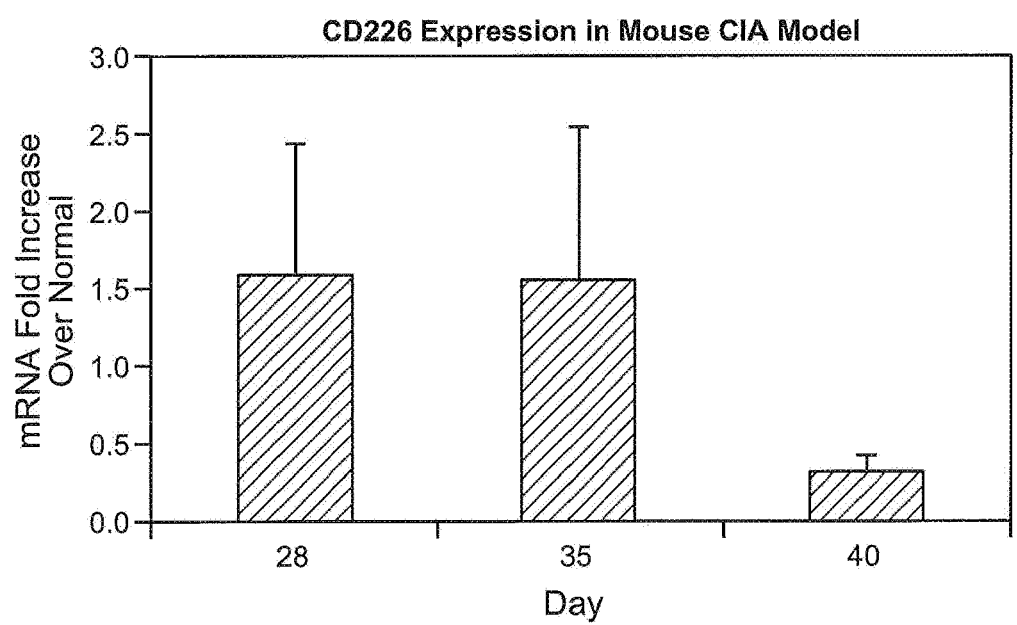

Having determined that TIGIT is highly expressed on selected populations of immune cells, the expression levels of TIGIT, PVR, and CD226 were next assessed in tissues from different immune-related disease states, including psoriasis, inflammatory bowel disorder, arthritis, asthma, and cancer. A microarray-based system was used for the studies, and description of the appropriate microarray protocol can be found in the literature, for example in US patent publication no. US20080038264, incorporated herein by reference. As shown in FIG. 15, significant expression of TIGIT was observed in inflamed human synovial tissue relative to uninflamed tissue, particularly notable in the case of rheumatoid arthritis tissue. Within the inflamed arthritis tissue samples, TIGIT expression was correlated mainly with T cells as opposed to macrophages or fibroblasts (see FIG. 15, right panel). This data was further confirmed in murine collagen-induced arthritis (CIA) models by RT-PCR analysis of TIGIT mRNA levels (see FIG. 16). In the CIA model used herein, DBA-1J mice were immunized with 100 µg bovine collagen type II in 100 µL of Complete Freund's Adjuvant (CFA) on Day 0 and Day 21 intradermally. RNA was extracted from joints from hind paws on days 28, 30 and 40 and assessed for TIGIT and CD226 expression as described above. As seen in FIG. 16, increased TIGIT expression was observed at day 40, while CD226 expression was significantly downregulated by day 40.

Figure 17:
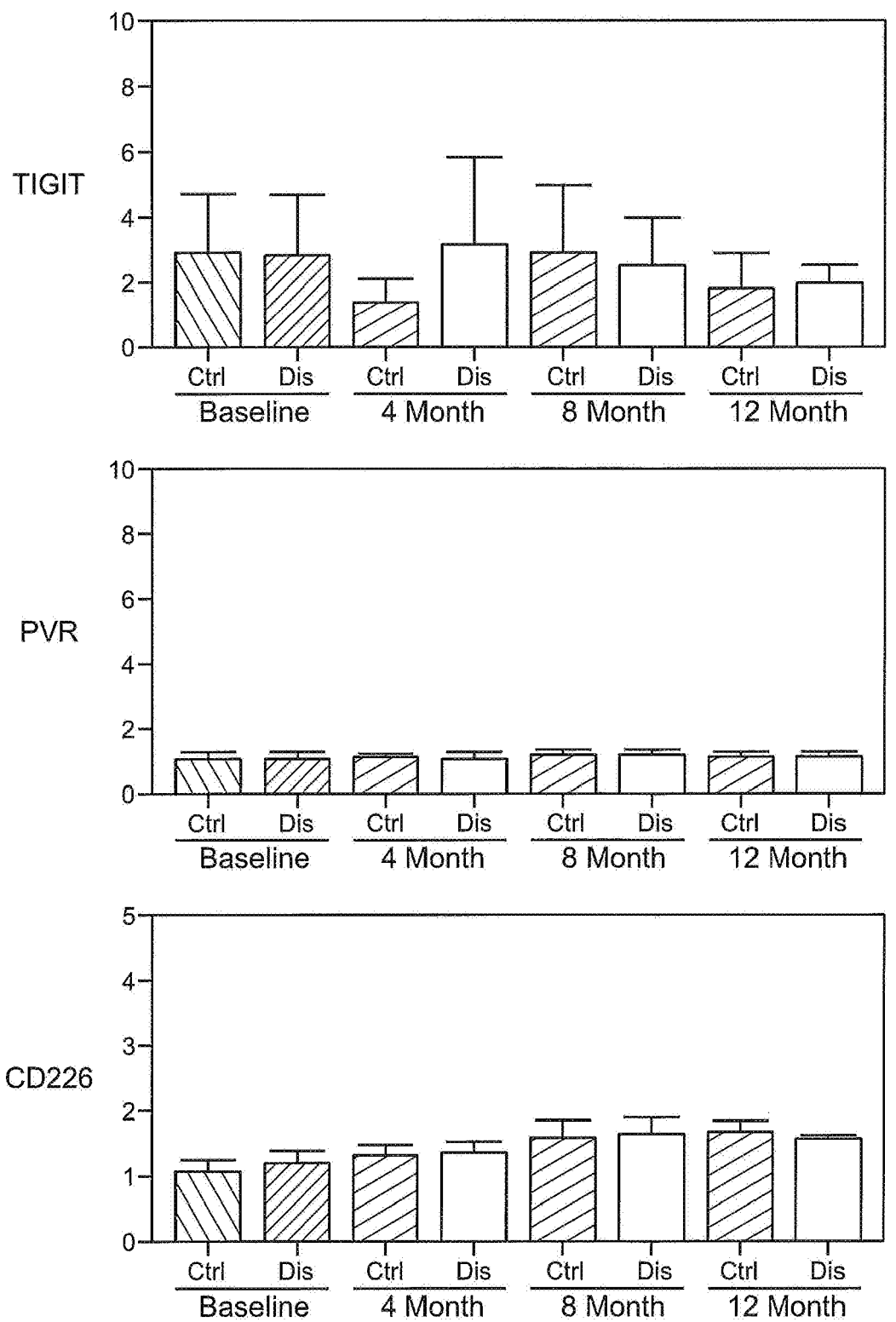
FIG. 17 depicts the results of mRNA analyses assessing the expression levels of TIGIT, PVR, and CD226 in tissue samples from asthmatic and control rhesus monkeys, as described in Example 3.
Figure 18A:
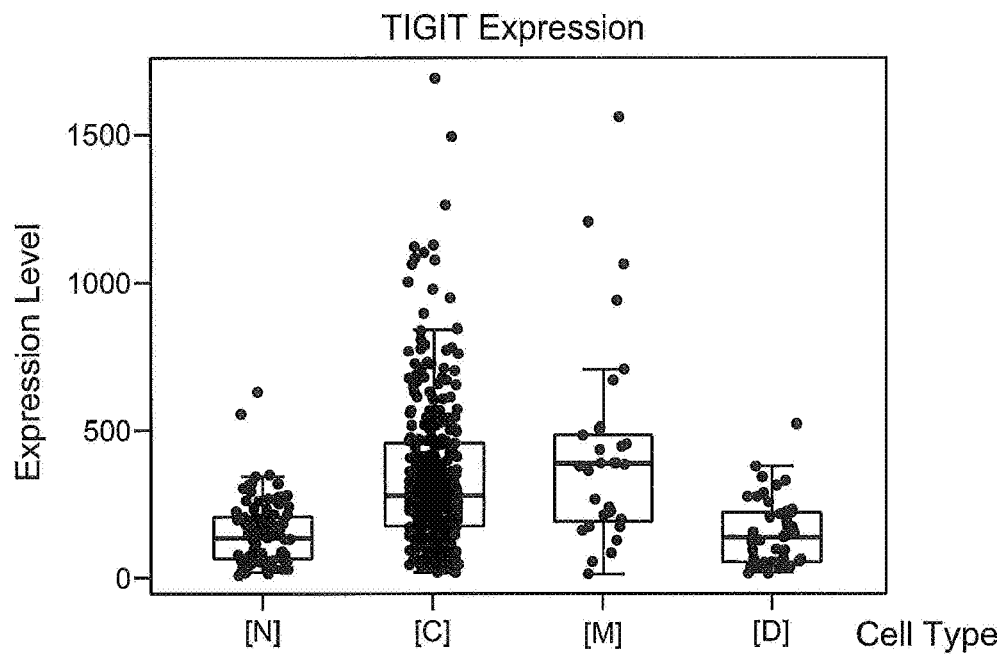
FIG. 18A depicts the results of mRNA analyses assessing the expression levels of TIGIT (upper panel) in normal or cancerous cells or the expression of CD4 in various breast tumor samples (lower panel).
Figure 18A:
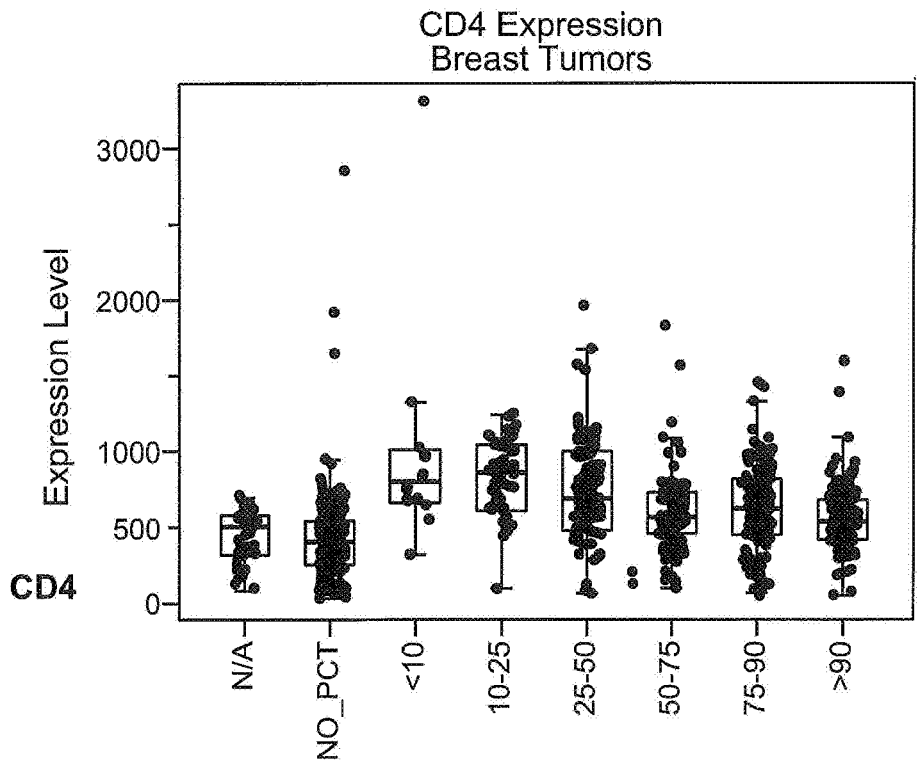
Figure 18B:
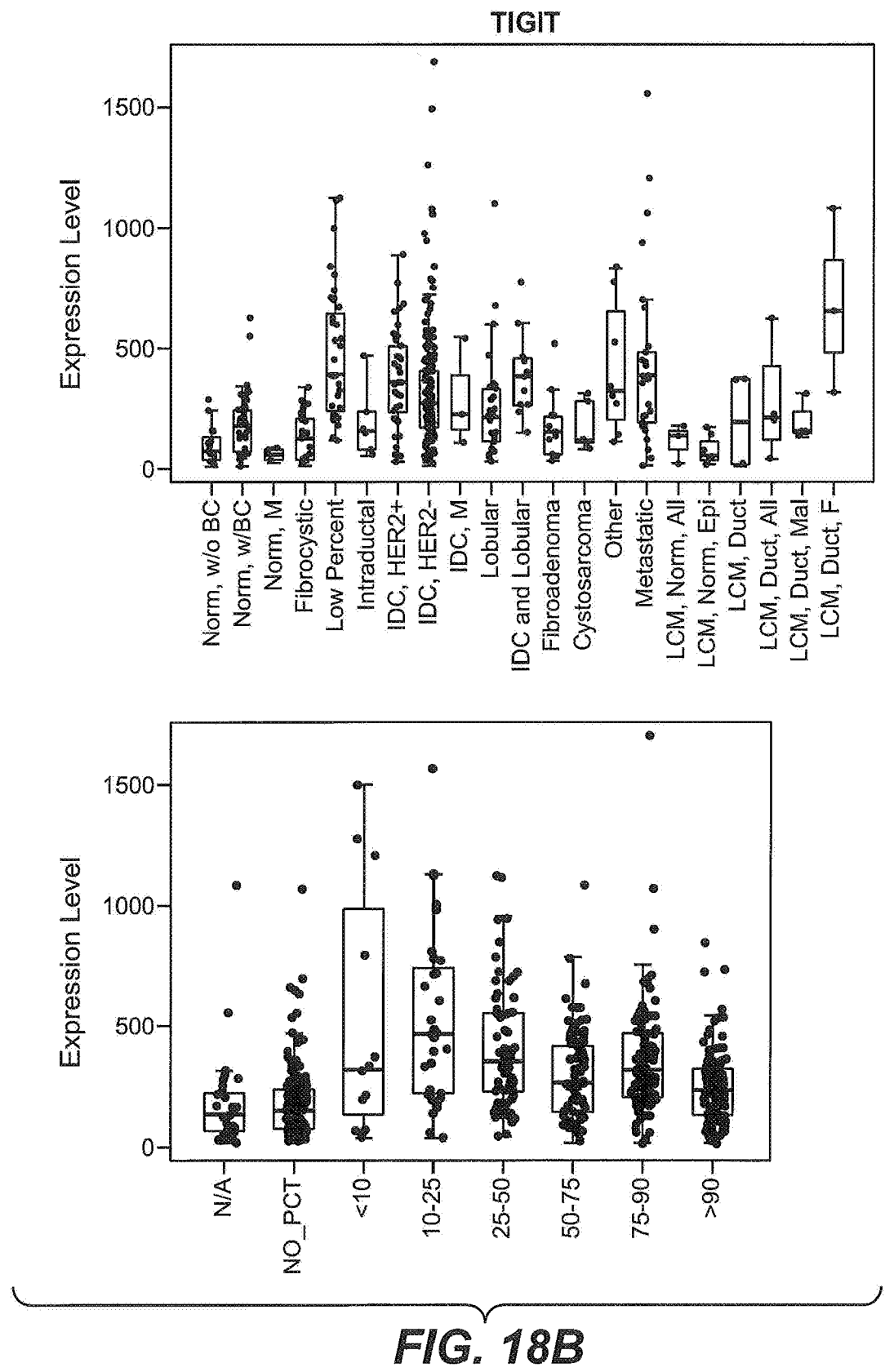
FIGS. 18B-18D depict the results of mRNA analyses assessing the expression levels of TIGIT (FIG. 18B), PVR (FIG. 18C), and CD226 (FIG. 18D) in various cancer samples, as described in Example 3. The lower panels in each of FIGS. 18B, 18C, and 18D show levels of TIGIT, PVR, or CD226 expression, respectively, in cancer samples containing various percentages of tumor cells. Boxes in all panels represent statistically significant data.
Figure 18C:
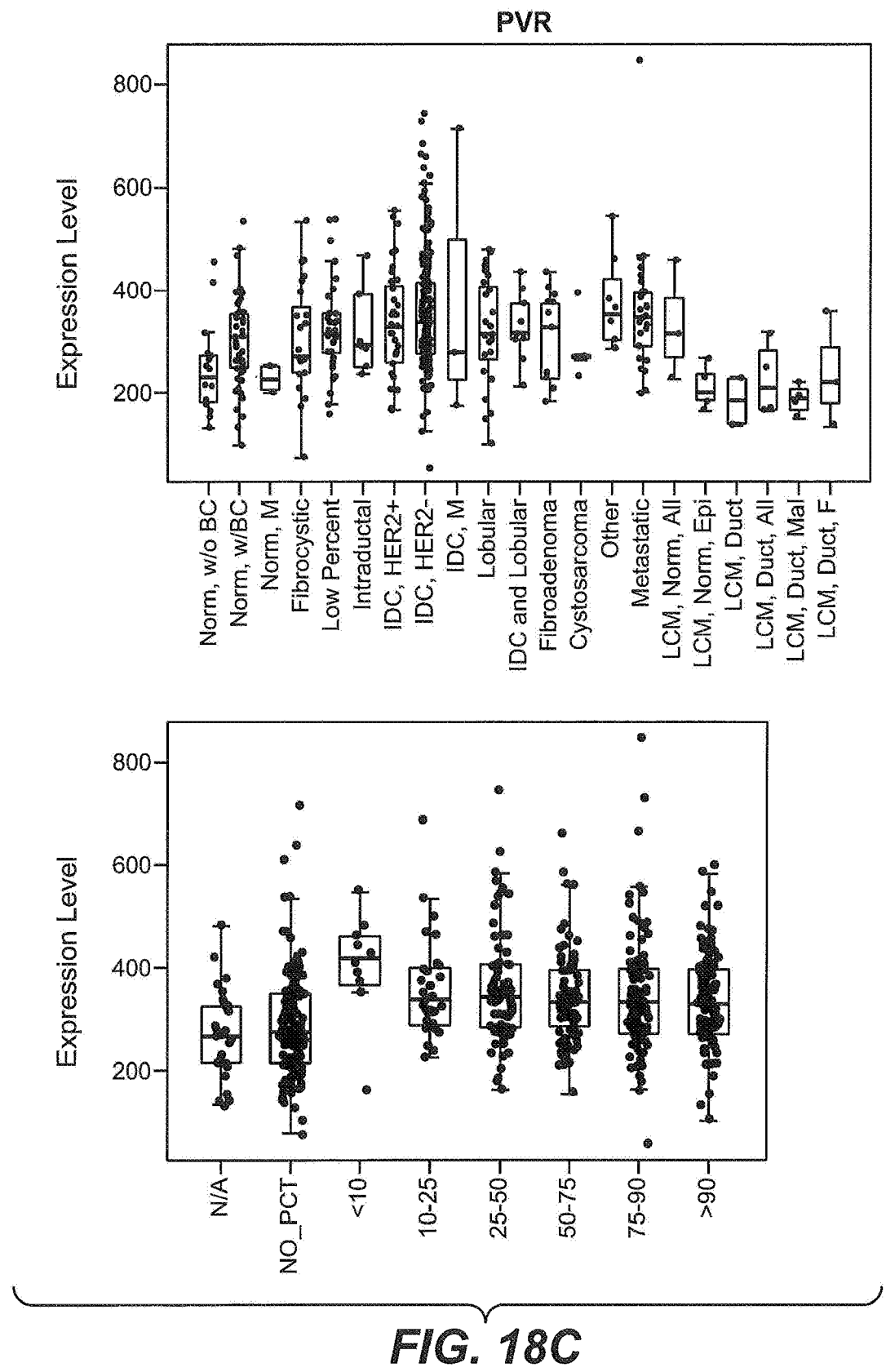
Figure 18D:
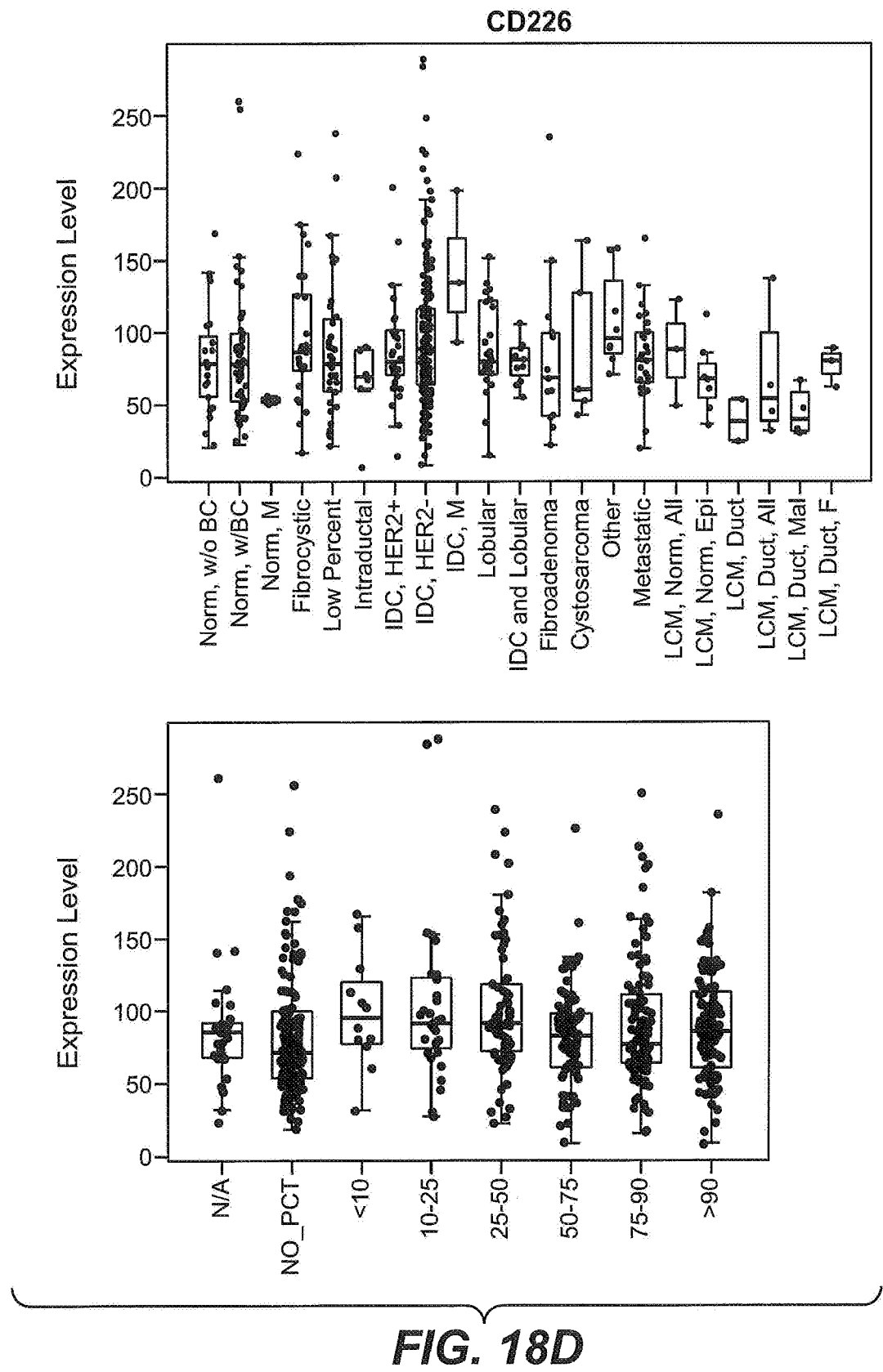

Lesser increases in expression of TIGIT relative to normal tissues were observed in psoriasis tissue samples and inflammatory bowel disease tissue samples. Similar analyses in asthma tissue samples from rhesus monkeys showed that TIGIT expression is significantly elevated in diseased tissue as compared to normal control tissue (FIG. 17). Breast cancer samples also exhibited greatly increased expression of TIGIT relative to normal breast tissue, with varying amounts in different types of breast cancer tissue. As shown in the upper panel of FIG. 18B, the largest expression of TIGIT is observed in tumor samples with the lowest percentage of tumor cells, suggesting that TIGIT expression is correlated with other cells infiltrating the tumor rather than with the tumor cells themselves. The lower panel of FIG. 18A indicates that $CD4^+$ cells are increased in tumor samples having low percentages of tumor cells. Given the data presented herein regarding expression of TIGIT on $T_{reg}$ and other T cell subsets, the observed high levels of TIGIT expression in the breast tumor samples with the lowest percentages of tumor cells suggests that TIGIT is being expressed by immune cell tumor infiltrates, most likely $T_{reg}$ infiltrates. The correlation of TIGIT expression with T cells in breast cancer samples suggests that TIGIT may play a role in tumor regulation. For example, a tumor may evade the immune response of the host by recruiting/activating $TIGIT^+$ $T_{regs}$.

Example 4

Role of TIGIT in T-cell Activation

Given the high levels of expression of TIGIT by $T_{reg}$ and memory T cells shown above, and the known expression of PVR on dendritic cells (Pende, D. et al., *Blood* 107, 2030-6 (2006)), the possibility that TIGIT might modify DC function and effect T cell activation was investigated.

(A) Function of TIGIT in Modulating T Cell Proliferation

The effect of TIGIT-Fc in a mixed lymphocyte reaction (MLR) proliferation assay was assessed using monocyte-derived human DCs matured with TNFα. Briefly, monocytes were isolated by negative selection of human total PBMC (Miltenyi Biotec). Immature monocyte-derived DC (iMDDC) were generated by incubating monocytes ($3 \times 10^5$ cells/ml) in complete RPMI 1640 medium containing 10% FBS, penicillin and streptomycin, supplemented with human recombinant IL-4 (125 ng/mL, R&D Biosystems) and human recombinant GM-CSF (50 ng/mL, R&D Biosystems) in a humidified atmosphere at 37° C., 5% $CO_2$ for 5 days. GM-CSF and IL-4 were added again on day 2 and day 4 with fresh complete RPMI 1640 medium. After five days of culture, over 90% of the cells exhibit an immature DC phenotype ($CD14^-$, MHC class $II^+$, $CD80^+$, $CD86^+$ and $CD83^{low}$) as verified by FACS analysis. These immature DC were used here for treatment with LPS, CD40L, TNFα, Pam3CSK4 and TSLP, and the indicated fusion proteins to induce their maturation. Phenotypic analysis of MDDCs and cell lines was carried out by immunofluorescence. Monoclonal antibodies used for cell surface staining included PE-labeled anti-CD83, FITC-HLA-DR, PE-anti-CD86, and FITC-anti-CD80. All incubations were performed in the presence of 10% human AB serum to prevent binding through the Fc portion of the fusions/antibodies. Inhibitor studies were performed by preincubation of the indicated molecules with 10 µM of a MEK1 inhibitor (PD98059), 1 µg/mL anti-IL-10 antibody, 10 µg/ml anti-CD32 antibody or 10 µg/ml anti-TIGIT antibody prior to stimulation with TNFα (0.1 µg/mL). The solvent DMSO or human IgG was used as a control. Cell culture supernatants were collected after 16 hours and assayed for production of IL-12 p40 by ELISA. The effect of the blocking anti-TIGIT antibody 10A7 on T cell proliferation and activation was assessed. No effect was observed upon incubation of anti-CD3-activated $CD4^+$ $CD45RO^+$ T cells with 10A7. When T cells were cultured with anti-CD3 together with autologous $CD11c^+$ DC, T cell proliferation increased two-fold (p<0.01) and IFNγ production increased four-fold (p<0.001) (FIG. 19C). This exacerbation of T cell activity was observed to a lesser degree in total PBMC. In contrast, TIGIT-Fc significantly inhibited T cell activation (p<0.01) and IFNγ production (p<0.001) in the presence of $CD11c^+DC$ (FIG. 19D). When total PBMC were activated with anti-CD3, TIGIT-Fc had a milder effect than that observed in the previous experiment, suggesting that the amount of PVR present on the cells may be important for activity. No effect was observed on T cells alone, as expected, given that TIGIT does not bind to such cells. Anti-TIGIT antibody treatment was also found to block $T_{reg}$ suppression of T cell proliferation only in the presence of APC. TIGIT.Fc was further found to regulate $CD11c^+$ cell function and to inhibit naïve T cell proliferation in transwell assays, indicating that the observed modifications in cellular behavior and proliferation were due specifically to TIGIT binding. Taken together, these data suggested that TIGIT regulates T cell activation via interaction with a ligand on APC, most likely PVR.

Figure 19B:
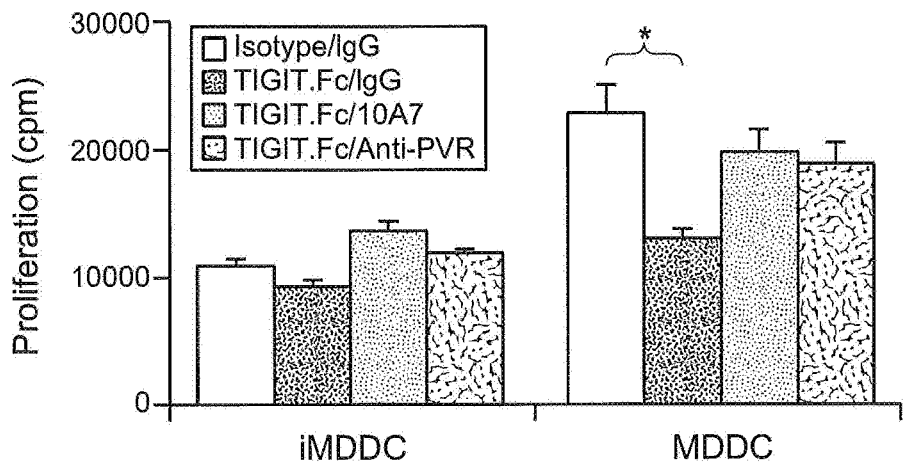
Figure 19C:
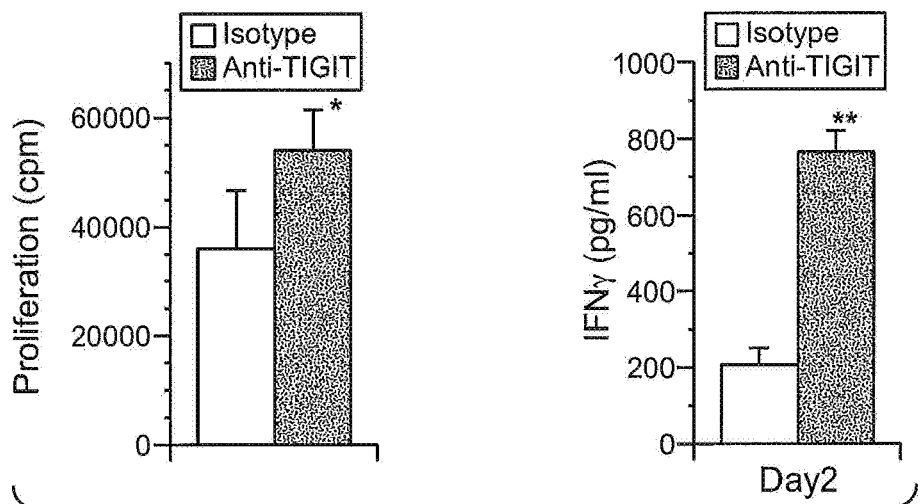
Figure 19D:
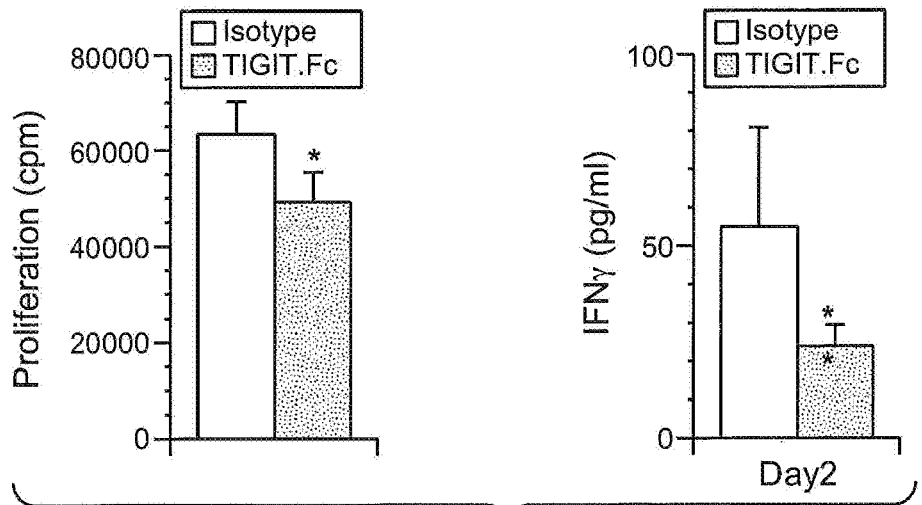

Both iMDDC and TNFα-matured MDDC expressed surface PVR, with the MDDC expressing higher levels of PVR than the iMDDC (FIG. 19A). TNFα-matured MDDC also increased proliferation of T cells over unstimulated iMDDC (FIG. 19B). In the MLR assays, the addition of TIGIT-Fc resulted in a modest yet significant decrease in proliferation, while TIGIT-Fc added to TNFα matured MDDC reduced proliferation to baseline levels. The TIGIT-induced inhibition of proliferation was prevented upon the further inclusion of anti-TIGIT antibody 10A7 or anti-PVR antibody TX21. Secreted IL-10 levels measured on day 3 were significantly higher in the cultures containing TIGIT-Fc than those containing the isotype control (45±5 pg/mL versus 29±8 pg/mL, respectively with a p=0.04). Inclusion of anti-TIGIT antibody or anti-PVR antibody also blocked the TIGIT-Fc-induced increase in secreted IL-10 (data not shown). IFNγ levels were reduced by TIGIT-Fc treatment (data not shown). Taken together, this data suggested that TIGIT modulates T cell activation.

To examine the effect of $TIGIT^+$ T cells on $TIGIT^-$ T cell proliferation in coculture, further MLR assays were performed. Briefly, $CD4^+CD45RO^+$ T cells were isolated from human PBMC and activated for five days. On day six, cells were restimulated with anti-CD3/anti-CD28 overnight and $TIGIT^+$ cells were separately sorted from $TIGIT^-$ cells by FACS. $TIGIT^-$ cells were CFSE labeled and mixed at a ratio of 10:1 with $CD11c^+$ cells isolated from a second donor with or without the same number of TIGIT⁺ cells in culture. Culture supernatants were collected at day seven for luminex analysis of cytokine production (IFNγ or IL-17). Cell proliferation was analyzed by FACS, gating for CFSE living cells, at day eight. The results are shown in FIGS. 20A and 20B. As shown in FIG. 20A, TIGIT⁺ T cells expressed lower levels of IFNγ and IL-17 than TIGIT⁻ T cells. When TIGIT⁺ T cells were mixed with TIGIT⁻ T cells, the resulting culture was significantly lower in production of these two cytokines, indicating that TIGIT⁺ T cells inhibit TIGIT⁻ T cell production of these two cytokines. TIGIT⁺ cells also inhibited proliferation of TIGIT⁻ T cells (FIG. 20B). This further supports the idea that TIGIT⁺ cells are indeed regulatory cells and can act on CD4+ cells to inhibit their response either directly through secretion of inhibitory cytokines or indirectly via engagement of PVR on antigen-presenting cells.

Figures 21A, 21B:
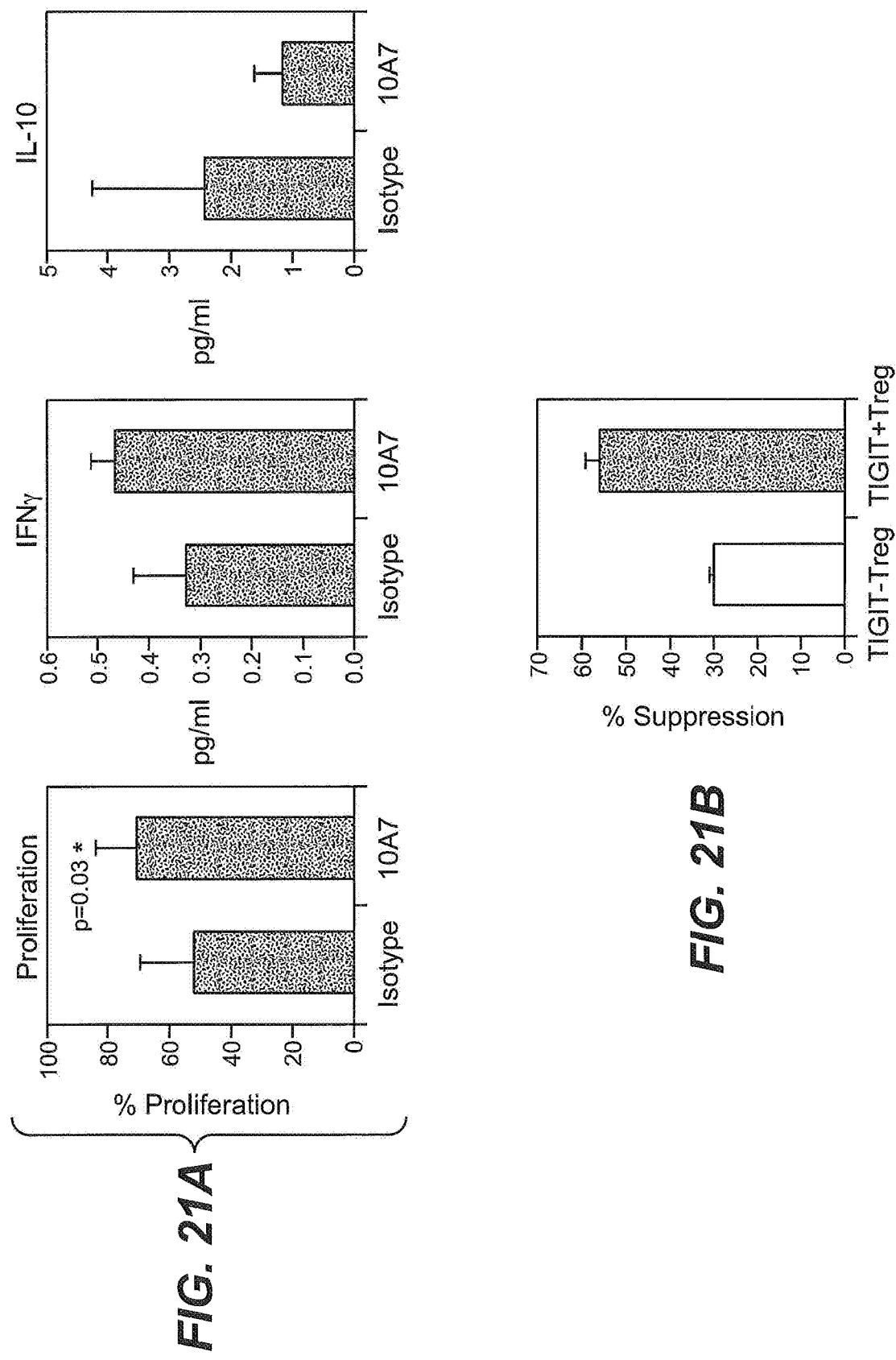
FIG. 21A depicts the results of proliferation assays assessing the effect of TIGIT $T_{reg}$ on proliferation of other T cells and APC in the presence and absence of anti-TIGIT antibody (10A7), as described in Example 4, as well as the production of IFNγ and IL-10 in those cell populations.
FIG. 21B depicts the results of proliferation assays assessing the effect of TIGIT+ $T_{regs}$ on naïve T cell proliferation in comparison with TIGIT− $T_{reg}$, as described in Example 4A.

Based on the observation in Example 3(A) that CD4⁺ CD25$^{hi}$ T$_{reg}$ cells in particular highly express TIGIT, assays were performed to examine the ability of the T$_{reg}$ T cell subset to inhibit proliferation of other immune cells. Briefly, CD4⁺CD25$^{hi}$ T$_{reg}$ cells were isolated from buffy coat with a MACS kit (Miltenyi) following the manufacturer's instructions. CD4⁺CD25⁻ cells were also prepared as the effector T cells to be used in the assay. Antigen-presenting cell (APC) populations were isolated by standard methods, by irradiating PBMC that had previously been depleted in T cells using MACS CD3 microbeads (Miltenyi). Isolated T$_{reg}$, effector T cells and APC were mixed together at a 1:4:4 ratio and incubated with 0.5 µg/ml soluble anti-CD3. The cell mixtures were plated into wells coated with 10 µg/mL of either anti-TIGIT antibody 10A7 or a control IgG and cultured for four days with [³H]-thymidine added for the final 18 hours of incubation. Cells from each well were solubilized and the amount of radioactivity in each cell sample quantitated. The indicated percent proliferation values were calculated relative to the amount of radioactivity observed in effector cells in the absence of T$_{reg}$ cells. The results are shown in FIG. 21A. In wells coated with the control IgG, approximately 55% cell proliferation was observed, in keeping with the above experimental finding that TIGIT T cells inhibited proliferation of TIGIT⁻ T cells. Inclusion of an anti-TIGIT antibody in the wells significantly increased the observed proliferation, confirming that TIGIT mediates the suppressive effect. This evidence further suggests that TIGIT T$_{reg}$ may act as negative regulators of immune cell proliferation and function. In fact, when CD4⁺CD25$^{hi}$TIGIT⁺T$_{reg}$ and CD4⁺CD25$^{hi}$TIGIT⁻T$_{reg}$ were isolated and examined separately for their ability to suppress naïve T cell proliferation, it was found that TIGIT T$_{reg}$ were more potent at suppressing naïve T cell proliferation than TIGIT⁻T$_{reg}$. Briefly, TIGIT⁺and TIGIT⁻T$_{reg}$ were isolated by FACS. CD11c⁺ cells were positively selected using CD11c-PE (BD Biosciences) and anti-PE microbeads (MACS). Naïve T cells were plated on U-bottom 96 well plate at a density of 4×10⁵, along with 2×10⁵T$_{reg}$ and 0.8×10⁵CD11c⁺ antigen presenting cells. As shown in FIG. 21B, TIGIT⁺ T$_{regs}$ were nearly twice as potent at suppressing naïve T cell proliferation as TIGIT⁻ T$_{reg}$ were, further supporting the finding that TIGIT⁺ T$_{reg}$ may act as negative regulators of immune cell proliferation and function.

(B) Knockdown of TIGIT

Using the stable cell line expressing gD-tagged TIGIT (293-TIGIT cells) constructed above, it was found that these cells did not exhibit phosphorylation of TIGIT upon interaction with exogenous PVR, cross-linked anti-TIGIT monoclonal antibody 10A7, or with pervanadate treatment. Additionally, 10A7 treatment of these cells resulted in no significant effect on TCR signaling. These data suggested that either the ITIM motifs in the expressed TIGIT in the constructed cells were not functional or that the stable cell line lacked one or more components necessary for TIGIT activation.

To further elucidate cell-intrinsic functions for TIGIT, inhibitory RNA (RNAi) studies were performed. On-Targetplus gene-specific siRNAs and negative control siRNA were obtained from Dharmacon RNAi Technology. Human CD45RO⁺ T cells were purified from buffy coat with a MACS™ kit (Miltenyi Biotec) and labeled with CFSE. siRNAs (siRNA$_{control\ 1\ or\ siRNATIGIT}$) were transfected into these cells with Nucleofector™ technology (Amaxxa) according to the manufacturer's instructions. After 24 hours, the transfected cells were activated with plate-bound anti-CD3 (5 µg/mL) alone or plus 2 µg/mL soluble anti-CD28. Some cells were collected at day 2 or day 5 post activation for quantitative RT-PCR (qRT-PCR) or FACS analysis. T cell proliferation was determined by FACS at day 5, as described above. qRT-PCR was performed as described above in Example 3(A), and RPL-19 mRNA levels in each sample were used as internal controls. The TIGIT primers are given above; human CTLA4 and CD226 primers and problems were obtained from Applied Biosystems. The primer and probe sequences used to detect different species of murine IL-12 and IL-10 were as follows:

```
                                         (SEQ ID NO: 55)
mIL-12p40: forward primer:
5'-ACATCTACCGAAGTCCAATGCA-3';

(SEQ ID NO: 56)
reverse primer:
5'-GGAATTGTAATAGCGATCCTGAGC-3';

(SEQ ID NO: 57)
probe:  5'-TGCACGCAGACATTCCCGCCT-3';

(SEQ ID NO: 58)
mIL-12p35: forward primer:
5'-TCTGAATCATAATGGCGAGACT-3';

(SEQ ID NO: 59)
reverse primer: 5'-TCACTCTGTAAGGGTCTGCTTCT-3';

(SEQ ID NO: 60)
probe: 5'-TGCGCCAGAAACCTCCTGTGG-3';

(SEQ ID NO: 61)
mIL-10: forward primer:
5'-TGAGTTCAGAGCTCCTAAGAGAGT-3';

(SEQ ID NO: 62)
reverse primer: 5'-AAAGGATCTCCCTGGTTTCTC-3';

(SEQ ID NO: 63)
probe: 5'-TCCCAAGACCCATGAGTTTCTTCACA-3'.
```

Figure 28A:
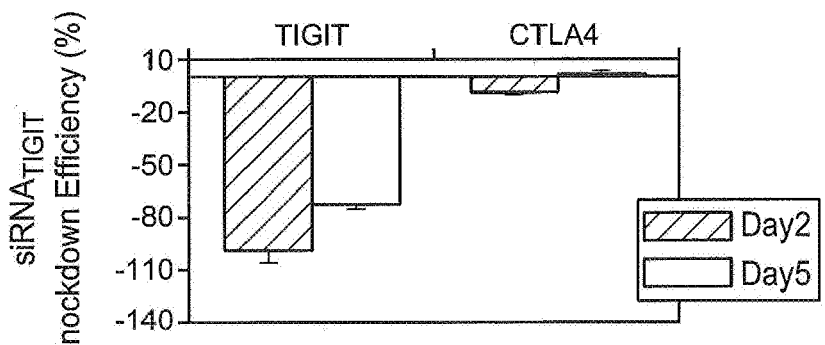
Figure 28B:
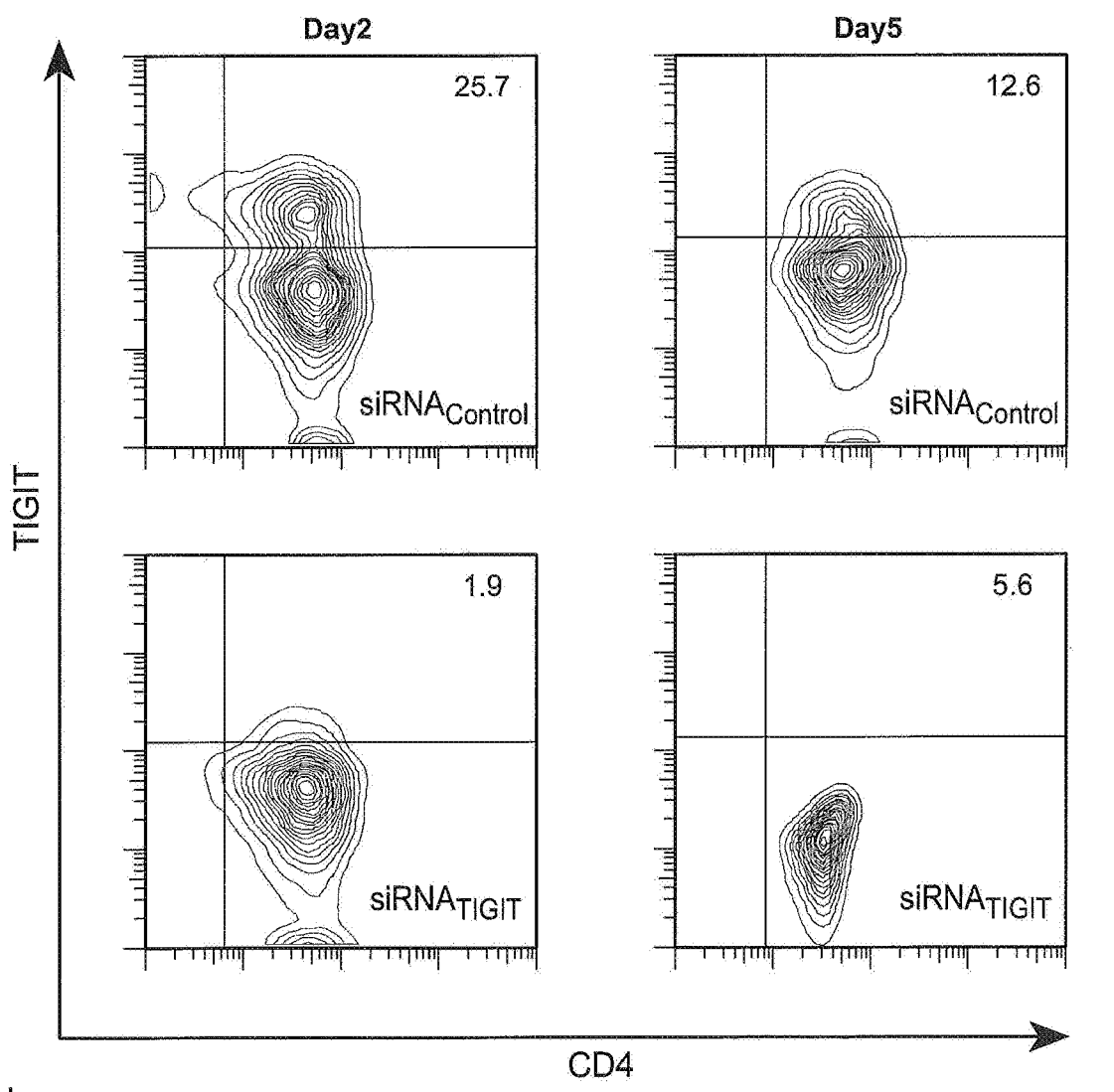
Figure 28C:
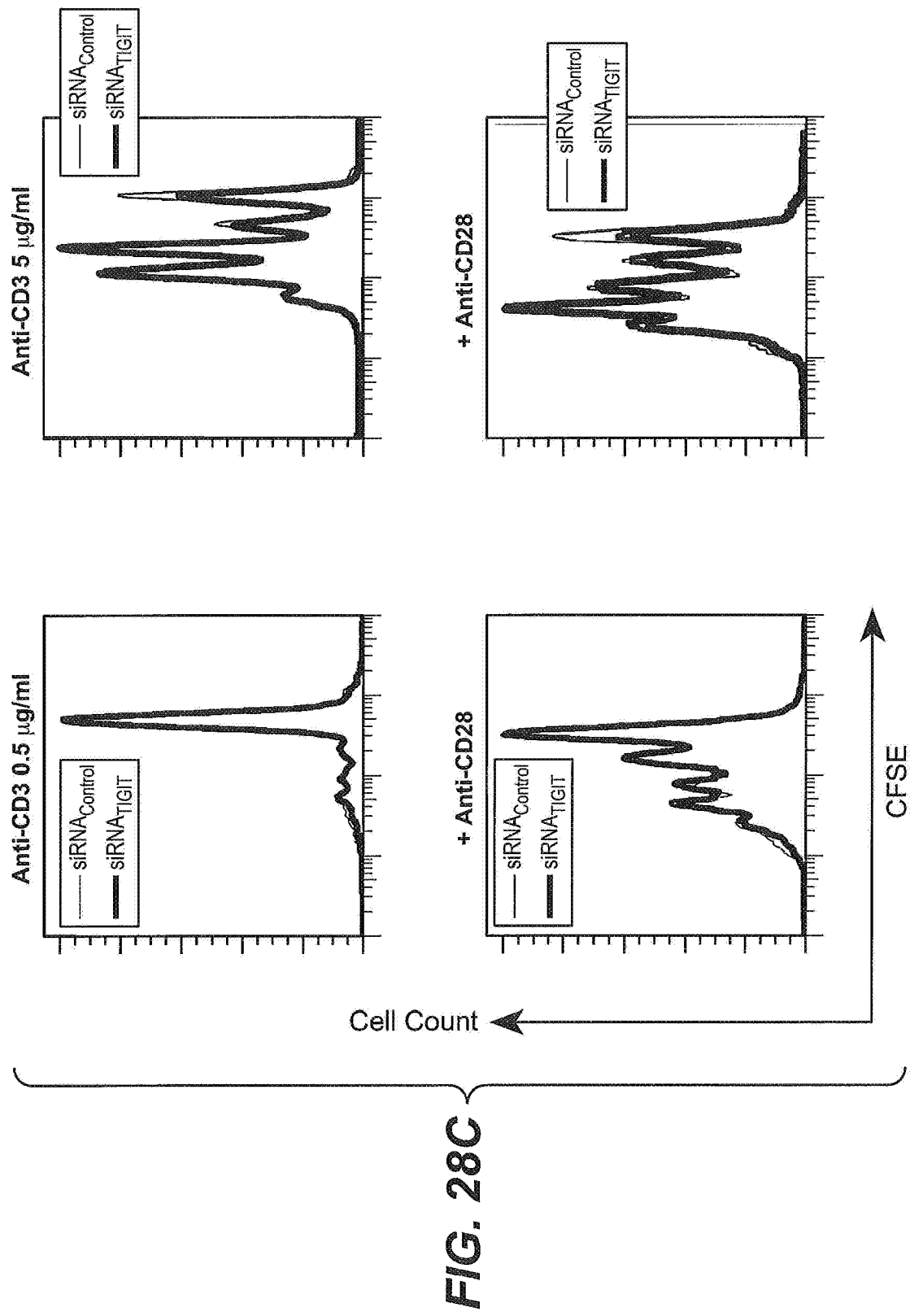
Figure 28E:
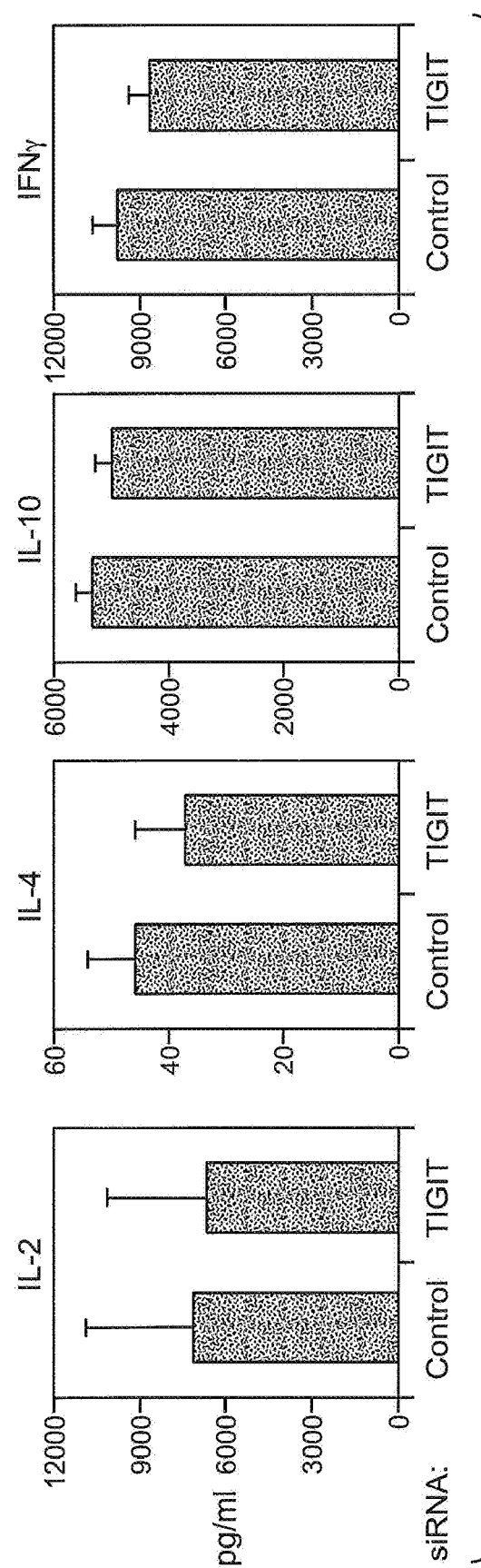

RNAi specific for TIGIT were employed to specifically knock down TIGIT expression in primary human CD45RO⁺T cells, which normally express high levels of TIGIT (FIGS. 10A-1 to 10A-2). The efficacy of TIGIT knockdown using this method was assessed by qRT-PCR and FACS analysis (FIGS. 28A, 28B, and Table 7). By the second day of treatment, TIGIT transcription was reduced by >90% by the siRNA$_{TIGIT}$ treatment as compared to a scrambled siRNA$_{control}$, while CTLA4 mRNA (a control protein) was unchanged by the treatment. The reduction in TIGIT mRNA resulted in a decrease of cell surface TIGIT from an average of 25% to <2% of the T cells (FIG. 28B). By day 5, TIGIT expression in those same cells was 70% reduced as compared to expression in control cells (FIGS. 28A and 28B, and Table 7). Knockdown of TIGIT had no significant effect on T cell proliferation in response to anti-CD3 (either at suboptimal or optimal concentrations) or to anti-CD3 plus anti-CD28 (FIG. 28C). Similarly, knockdown of TIGIT also had no observed effect on production of the cytokines IL-2, IL-4, IL-10, or IFN-γ (FIG. 28E). Furthermore, treatment of the cells with anti-TIGIT antibody 10A7 had no observed effect on activation of T cells expressing TIGIT under the same conditions as described above (FIG. 28D).

TABLE 7

TIGIT RNAi Knockdown Efficiency

| $C_T$* | siRNA$_{control}$ | | siRNA$_{TIGIT}$ | |
|---|---|---|---|---|
| | Day 2 | Day 5 | Day 2 | Day 5 |
| TIGIT mRNA | 23.3 ± 0.1 | 24.0 ± 0.0 | 31.2 ± 0.6 | 29.8 ± 0.1 |
| CTLA4 mRNA | 27.2 ± 0.4 | 24.3 ± 0.3 | 27.6 ± 0.3 | 23.8 ± 0.3 |

*$C_T$ values are given as the $C_T$ value ± standard deviation for TIGIT or CTLA4

Example 5

Effect of TIGIT on Cytokine Production

To determine whether TIGIT had a direct effect on DCs other than the above-described general effect on T cell maturation, DC maturation and function in the presence and absence of TIGIT-Fc was assessed. The result in Example 4 regarding TIGIT's ability to modulate IFNγ and IL-17 production in mixed T cell populations suggested that further studies of cytokine production by DC treated with TIGIT-Fc should be performed. Untreated T cells were purified by negative selection (CD4 T cell isolation kit, Miltenyi Biotech) to a purity of >95%. Cells were resuspended in complete RPMI 1640 medium with standard nutritional supplements. Allogenic T cells (2×10$^5$) were cultured in the absence (medium alone) or presence of iMDDCs and MDDCs at the indicated ratio in 96-well U-bottomed µplates (Nunc) in 200 µL of medium per well. Cells were cultured for 72 hours followed by an 18 hour pulse with 1 µCi (0.037 MBq) of [$^3$H]thymidine (Amersham). Cells were transferred to a Unifilter-96 plate GF/C using a cell harvester and [$^3$H]thymidine incorporation was measured in scintillation fluid using a scintillation counter (Canberra Packard Ltd.). All determinations were carried out in triplicate. Cytokine production by iMDDCs was analyzed on supernatants collected on day 5 of culture and stored at −80° C. The same MDDCs were matured in the presence or absence of indicated stimuli for 24 hours in the presence or absence of TIGIT-Fc or TIGIT-Fc-DANA. After 48 hours of stimulation, supernatants were collected and stored at −80° C. Cytokine concentrations were measured by ELISA (R&D Biosystems) according to the manufacturer's instructions, or by using LINCOplex antibody-immobilized beads (LINCO Research) with detection by a Luminex 100 instrument (Luminex) according to the manufacturer's instructions.

Figures 1, 22A:
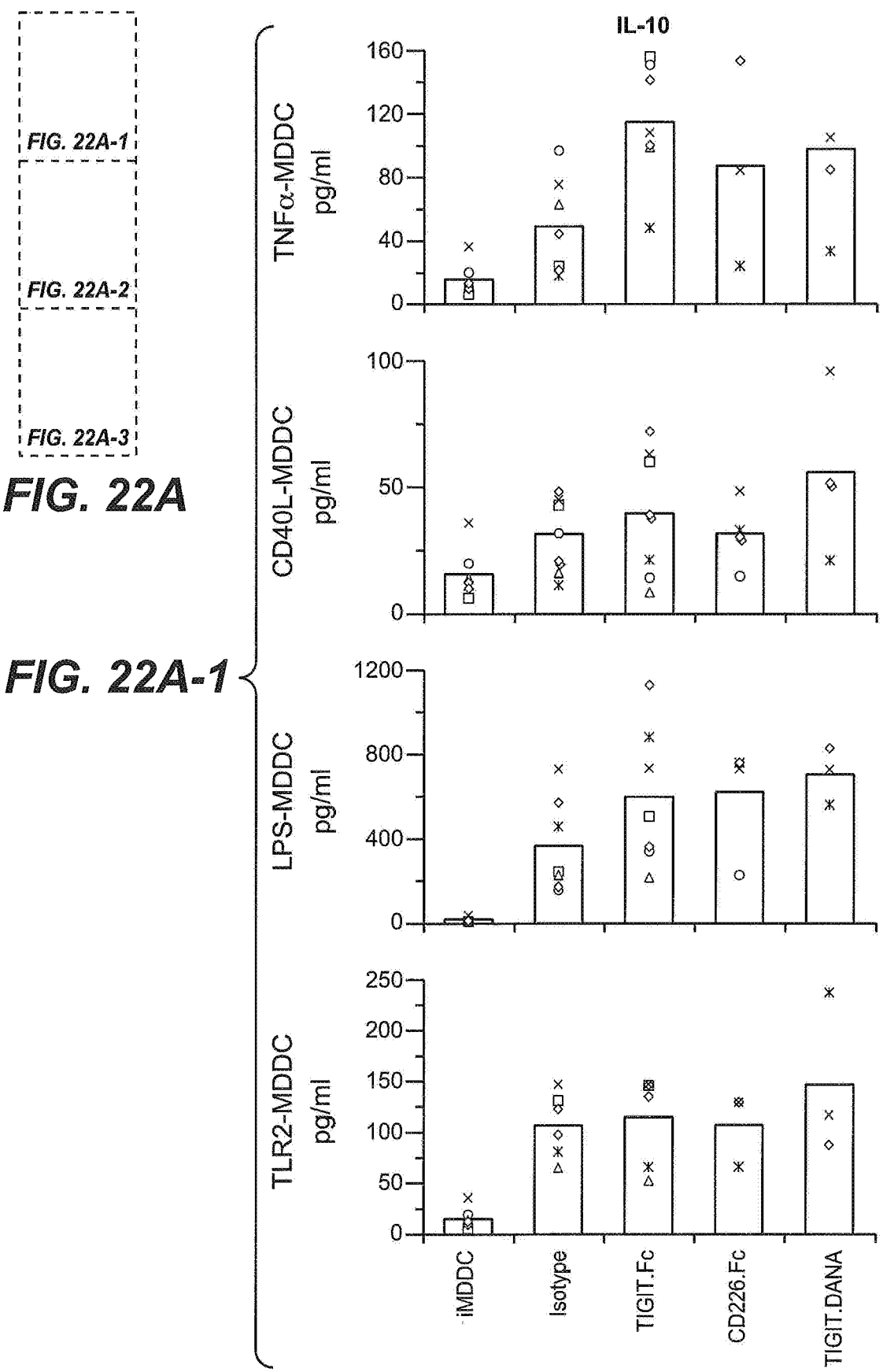
FIG. 1 depicts an alignment of human, mouse, rhesus and dog TIGIT protein sequences. Shading indicates positions containing identical amino acids in three or four species. The signal sequence is indicated by a dashed line, the immunoglobulin V-set domain is indicated by a double line, N-glycosylation sites are indicated by a thin line above the requisite position, the transmembrane domain is indicated by a thick line, and the putative extended ITIM motif is indicated by a double dashed line. Human TIGIT shares 88%, 67%, and 58% identity with rhesus, dog and mouse sequences, respectively.
FIGS. 22A-22D depict the results of experiments assessing the ability of TIGIT to modulate cytokine production in matured iMDDC and DC, as described in Example 5.
Figures 2, 22A:
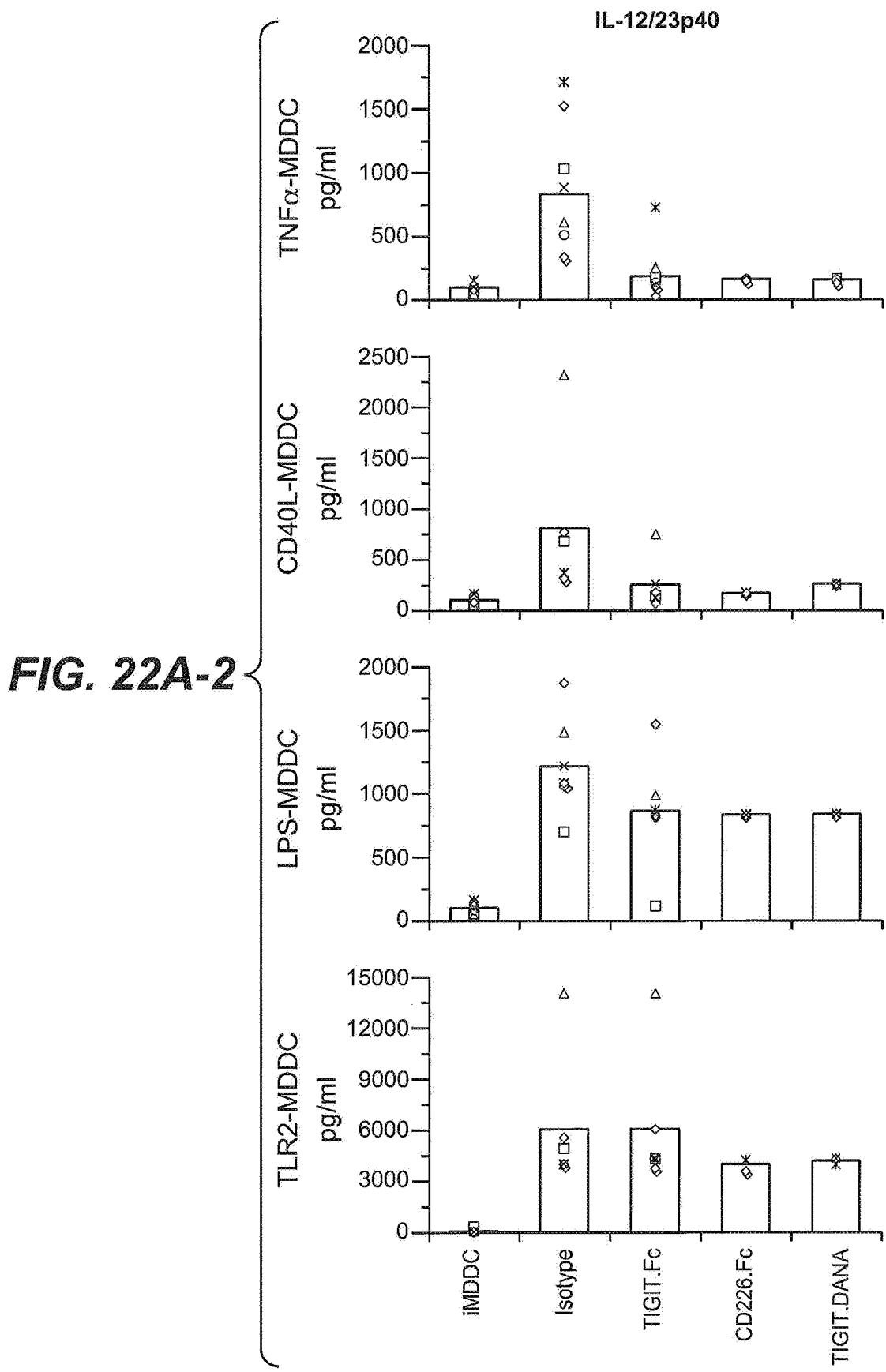
Figures 3, 22A:
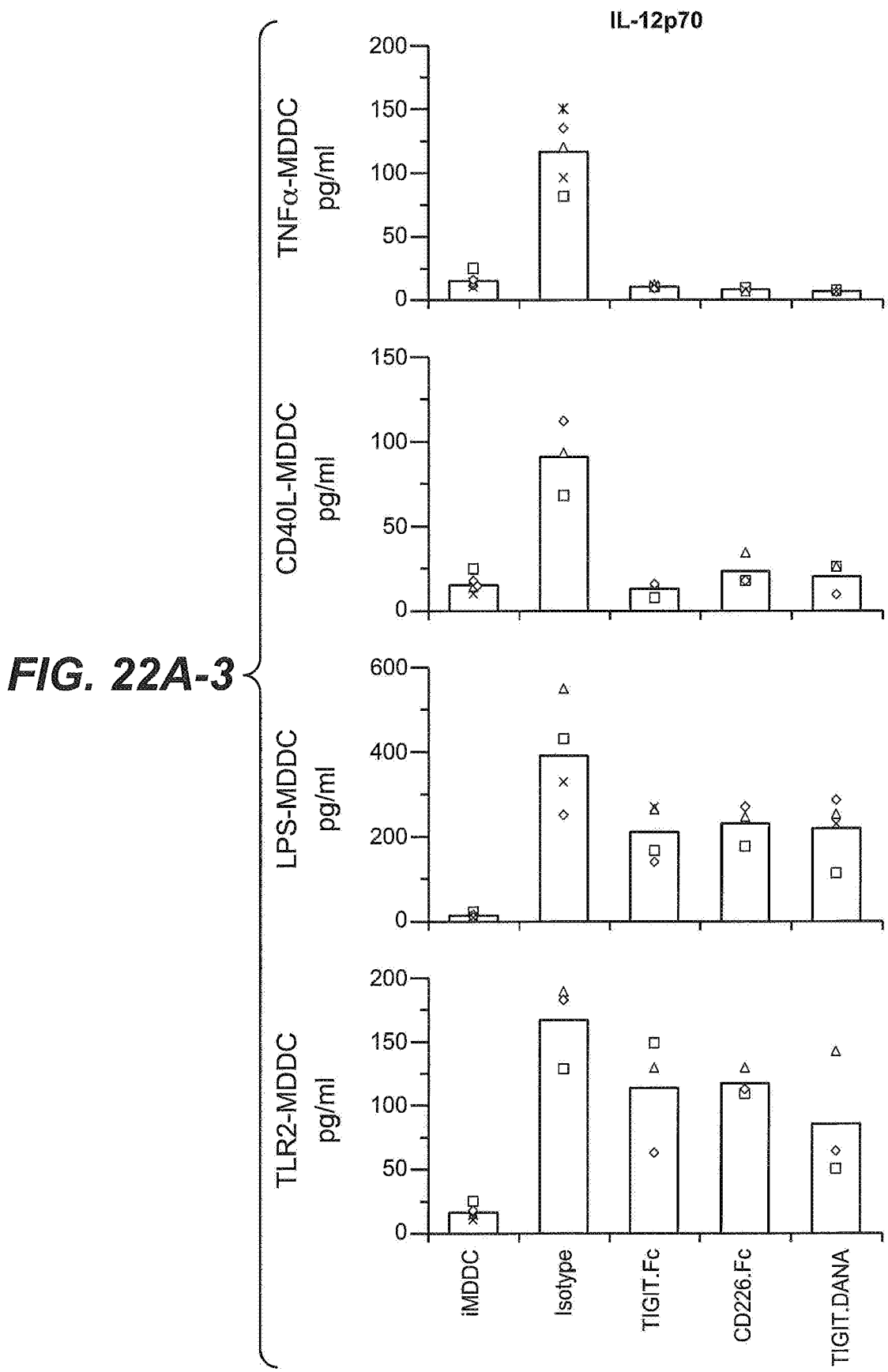
Figure 22B:
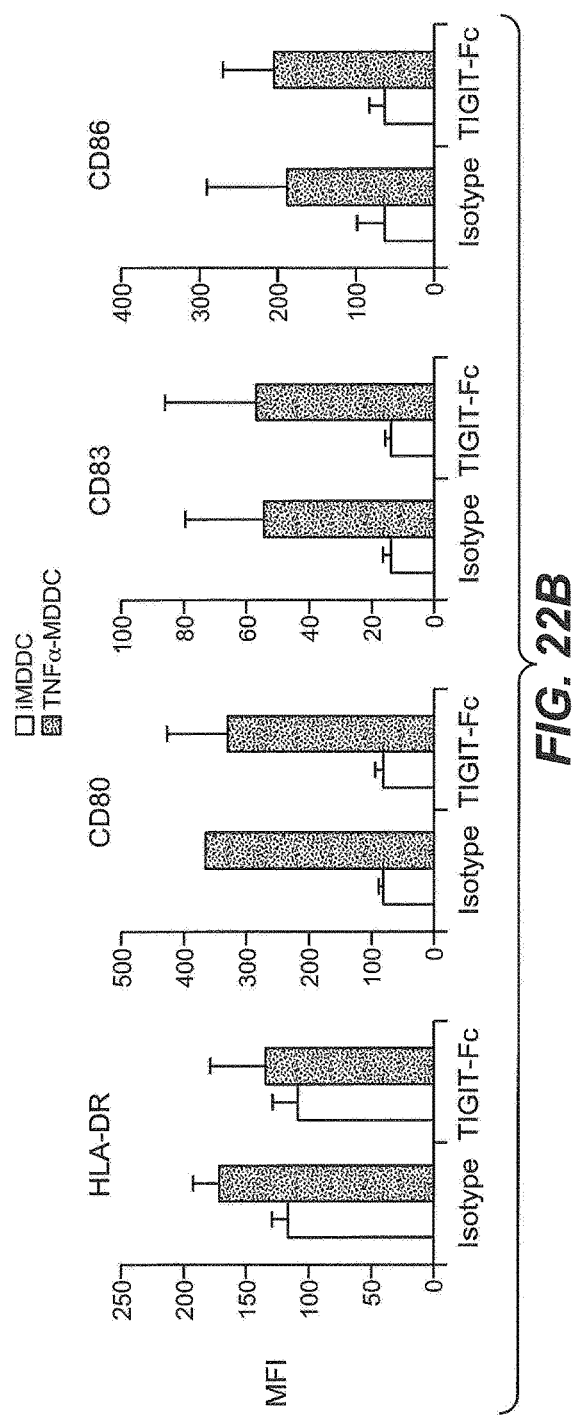

When TIGIT-Fc, TIGIT-Fc-DANA, or CD226-Fc were added to iMDDC during maturation with TNFα or soluble CD40L, IL-12/23p40 production and IL-12p70 production were significantly reduced as compared to treatment with isotype-matched control (p=0.007 and p=0.03, respectively), to levels comparable for iMDDC (FIGS. 22A-1 to 22A-3). Conversely, secreted IL-10 was increased by TIGIT-Fc, TIGIT-Fc-DANA, or CD226-Fc treatment relative to treatment with isotype-matched control (p=0.027 and p=0.18, respectively) (FIGS. 22A-1 to 22A-3). TGFβ secretion was also increased in iMDDC in response to TIGIT-Fc treatment (see FIG. 22D). TIGIT-Fc did not, however, affect the ability of iMDDC to mature to MDDC, since CD80, CD86, CD83 and HLA-DR were equivalently upregulated in isotype control cultures (FIG. 22B). Notably, the TIGIT-PVR interaction did not directly induce DC maturation.

Figure 29A:
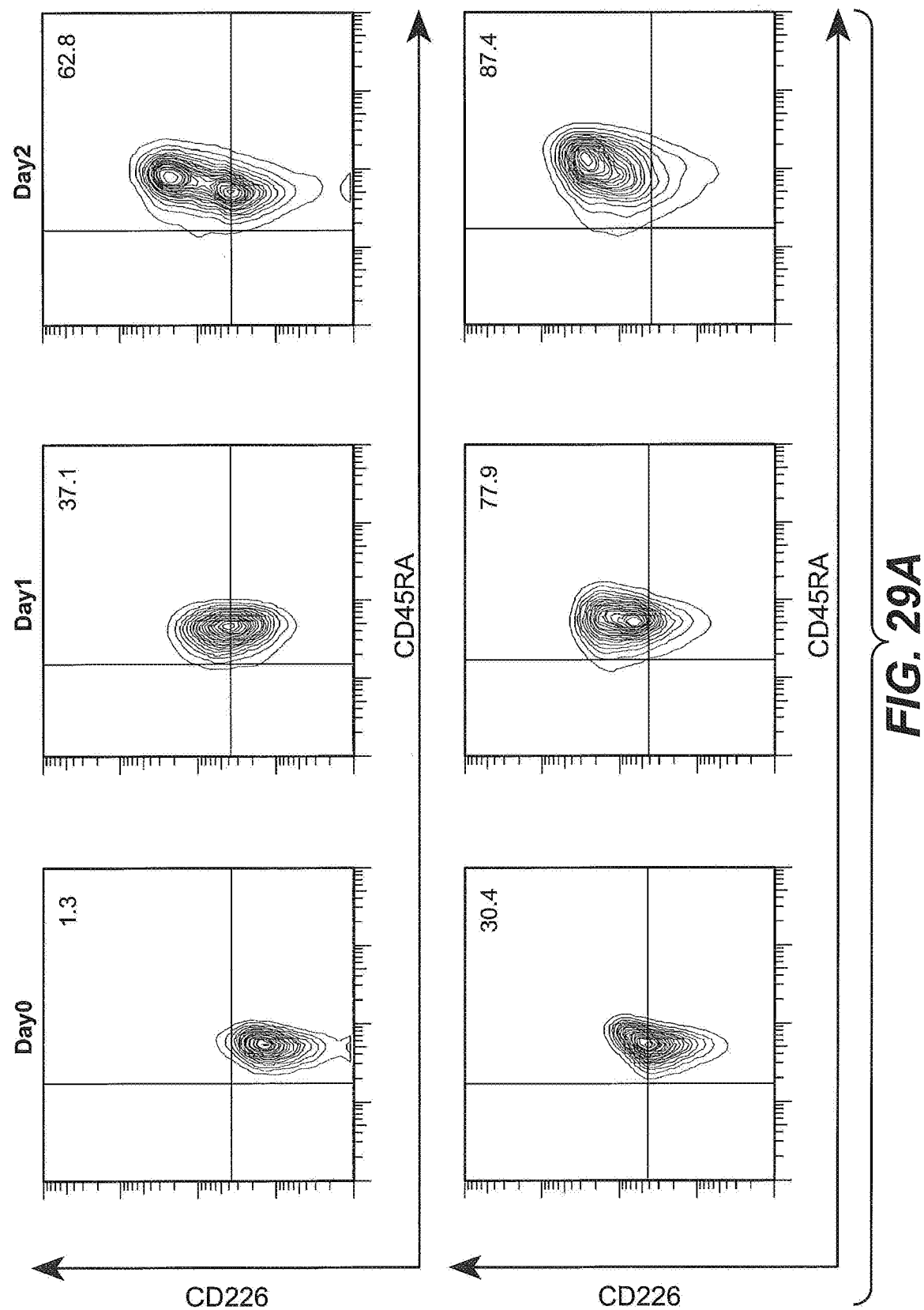
Figure 29D:
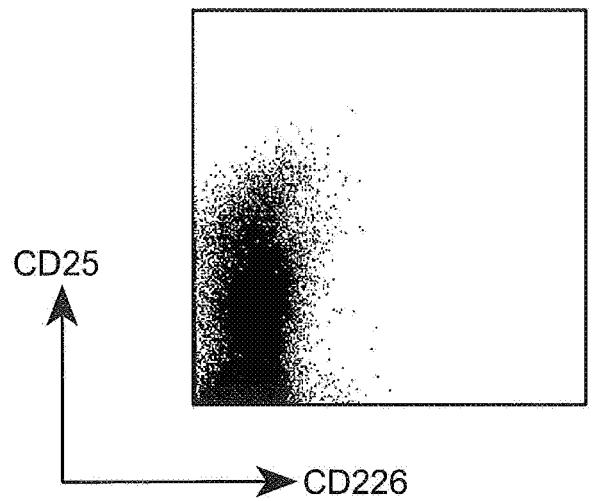
Figure 29E:
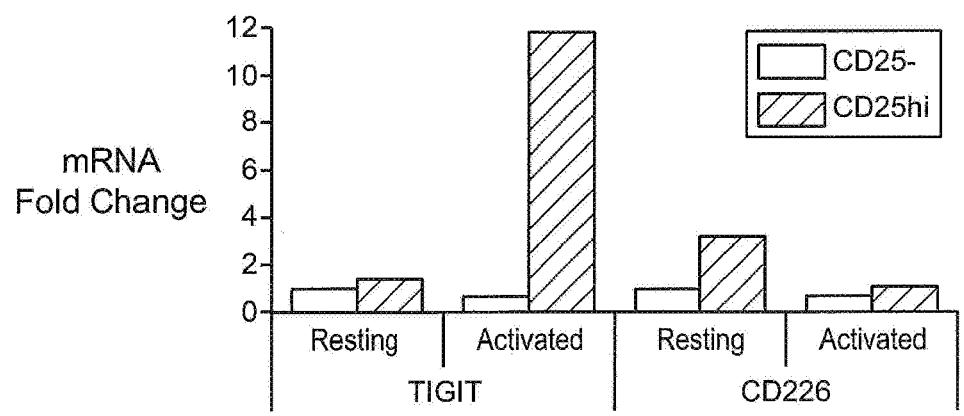

The effect of TIGIT-Fc, TIGIT-Fc-DANA and CD226-Fc on TLR-mediated DC maturation pathways was also examined. Treatment with each of the three Fc proteins exhibited similar, though less robust increase of IL-10 production from LPS (TLR4-matured MDDC (p<0.01), a decrease in IL-12/23p40 (p=0.07 to 0.18) and significant decrease in IL-12p70 production (p<0.05 for all fusion proteins) (see FIGS. 22A-1 to 22A-3), and had no effect on the TLR2 maturation pathway. This modulation of IL-10 and IL-12p40 production by TIGIT treatment of DC was similar whether TIGIT-Fc was added to monocytes during differentiation with GM-CSF and IL-4, or when only added during the maturation phase (data not shown). The effects of TIGIT-Fc on IL-10 and IL-12p40 production in iMDDC not undergoing maturation were modest, but since the observed levels of those cytokines in iMDDC were low, statistically significant effects may have been difficult to detect (FIG. 22B). Notably, CD226 functioned similarly to TIGIT in these assays, supporting a role for PVR in MDDC. Given that CD226 has an ITAM motif and may act to enhance TCR signals (Dalhardon et al. J. Immunol. 175: 1558-1565 (2005)), the degree of expression of TIGIT and/or CD226 on different subsets of T cells may contribute to differential regulation of local inflammatory responses in vivo (FIG. 10, FIG. 29).

Figure 22C:
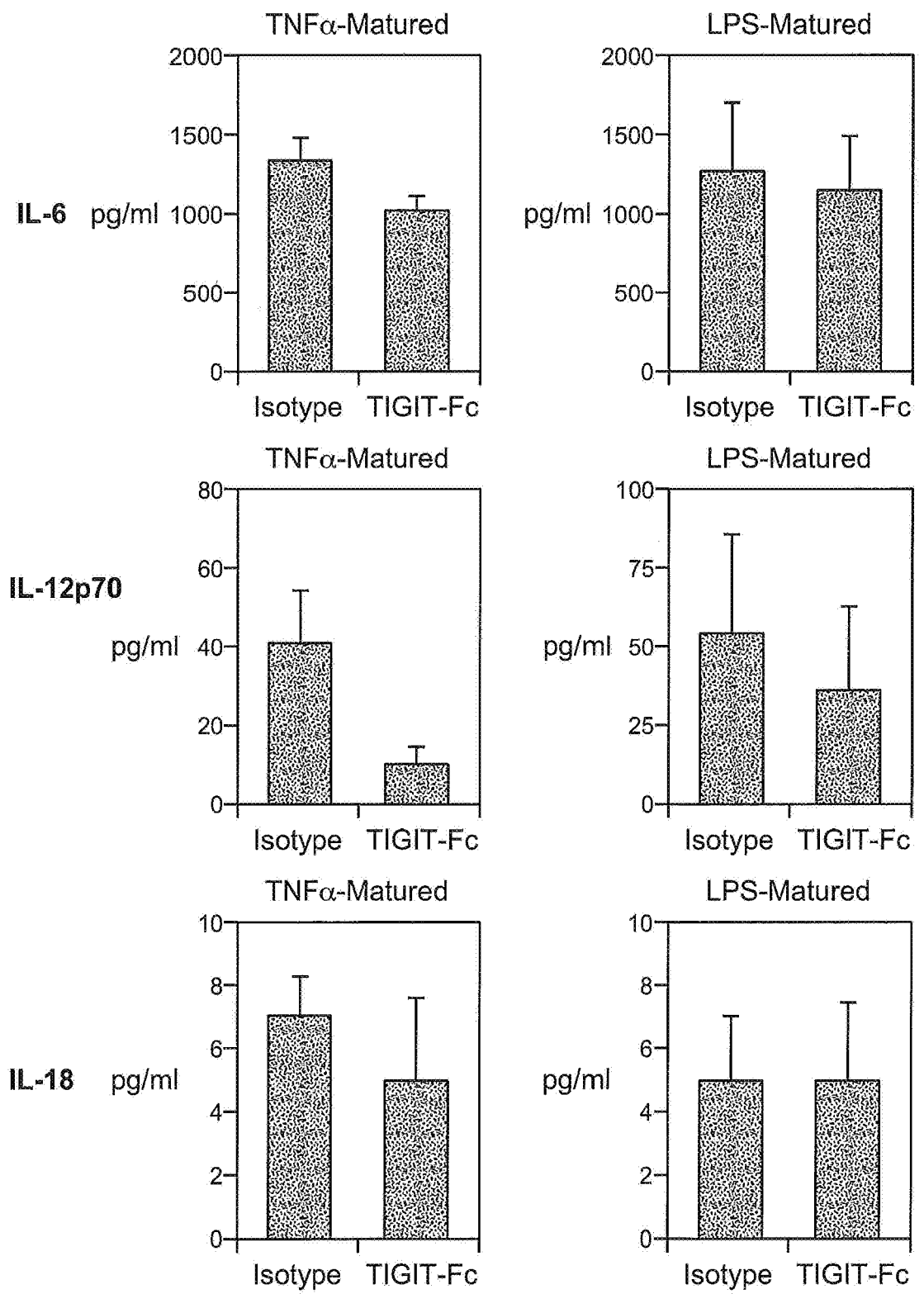
Figure 22D:
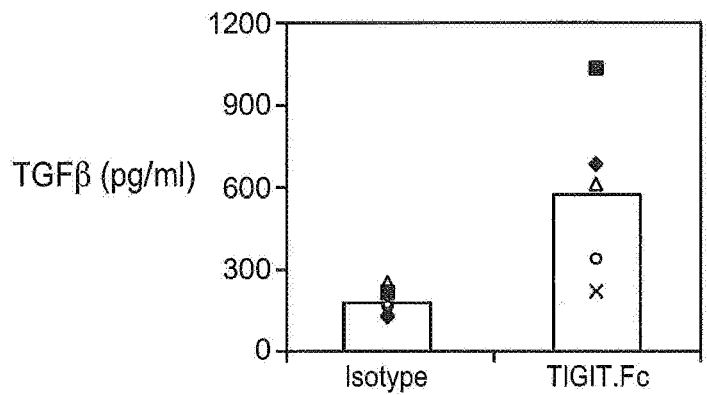

The levels of production of other proinflammatory cytokines by DC treated with TIGIT-Fc were also determined. Both IL-6 and IL-18 production was significantly reduced by TIGIT-Fc treatment in all matured MDDC populations. IL-12p40 is a known subunit of both IL-12p70 and IL-23, so the levels of production of both of those cytokines were measured in TIGIT-Fc-treated MDDC cultures. Compared to control cultures, TIGIT-Fc treatment resulted in significantly decreased IL-12p70 production by MDDC matured with TNFα or CD40L (FIG. 22C). IL-23 levels were relatively low and barely detectable under the assay conditions. TIGIT-Fc reduced both IL-6 and IL-18 under all matured MDDC conditions, but due to donor variability the observed reduction was not statistically significant. To assess whether the observed effect of TIGIT-Fc required cross-linking of PVR, an Fc-mutated version of TIGIT-Fc in which FcαR binding was completely abrogated (TIGIT-Fc-DANA, described in Example 1) was used. As shown in FIGS. 22A-1 to 22A-3, both TIGIT-Fc and TIGIT-Fc-DANA equally and significantly inhibited IL-12p40 and enhanced IL-10 production from DC matured with TNFα. This result indicated that cytokine skewing by the TIGIT fusion protein was not dependent on Fc-mediated cross-linking.

The ability of TIGIT to modify the cytokine production pattern from DC was not observed under all in vitro maturation conditions. The effect was most pronounced on TNFα, soluble CD40L and LPS (TLR4)-induced maturation pathways, whereas TLR2-mediated maturation remained unaffected. It has been shown that LPS and Pam3CSK4 activate ERK and p38 to various extents: LPS mainly activates p38 and Pam3CSK4 treatment results in high ERK kinase activity. Thus it is not surprising that TIGIT-Fc treatment of Pam3CSK4-matured DC showed little effect (see FIGS. 22A-1 to 22A-3). The differential ability of these and other stimuli such as TNFα and CD40L to regulate the ERK/p38 pathways is significant in determining the outcome of MDDC function. Not only have DC been demonstrated to expand Tregs, but DC can also break $T_{reg}$ tolerance and induce activation and IL-2 production (Fehervari, Z. & Sakaguchi, S., Curr Opin Immunol 16, 203-8 (2004)). The ability of TIGIT to modify DC under some maturation conditions but not others suggests that TIGIT modulation is one method by which $T_{reg}$ and activated T cells may fine-tune DC function.

Figure 13A:
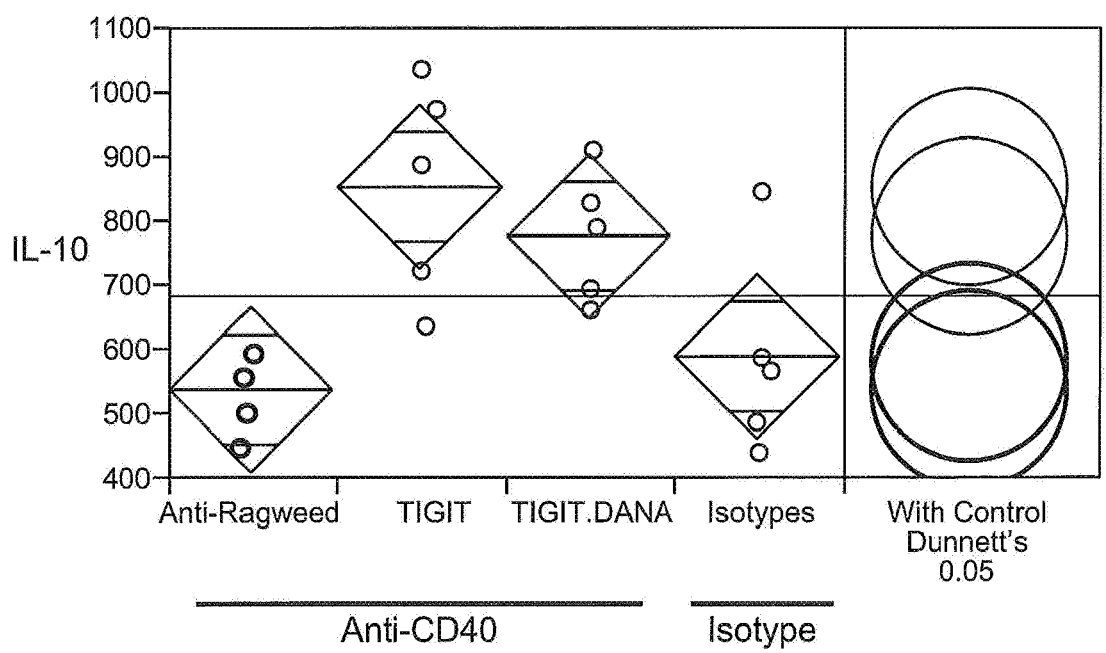
FIGS. 13A-13C show plots depicting the results of experiments assessing the ability of TIGIT to modulate IL-10, IL-12p40 and IL-12p70 production in scid mice lacking B and T cells, as described in Example 5.
Figure 13B:
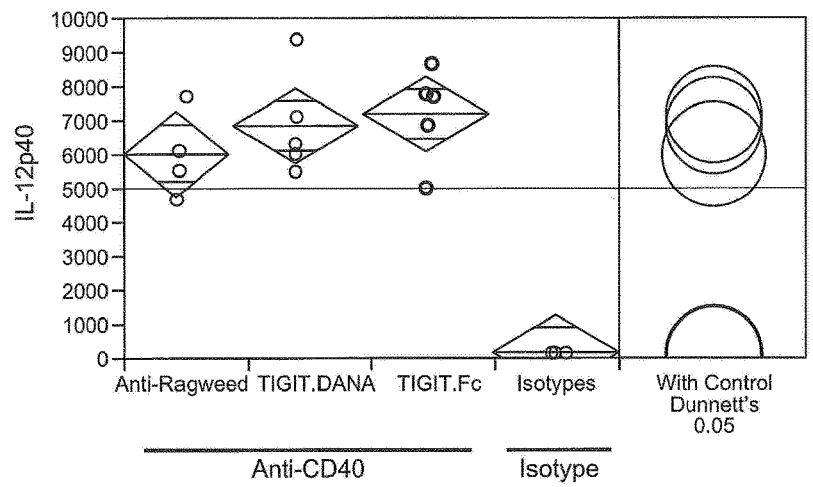
Figure 13C:
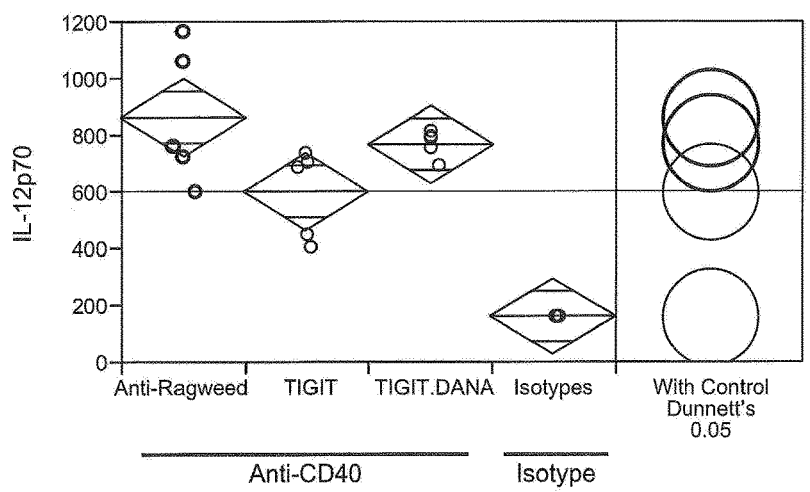

Studies of TIGIT function were also performed in a mouse model lacking B and T cells but which have macrophages and dendritic cells (scid mice). Briefly, CB17/SCID mice (6-8 weeks old) were treated once intravenously with 200 µg of TIGIT.Fc, TIGIT.DANA, or a control anti-ragweed antibody. Anti-CD40 monoclonal antibody or isotype control (200 µg/mice) was administered six hours later. Serum was collected 16 hours later to analyze levels of IL-10, MCP-1, IL-12p40 and IL-12p70 by ELISA assay. Administration of TIGIT-Fc or TIGIT-Fc-DANA in scid mice stimulated IL-10, and IL-12p40 production and decreased IL-12p70 production (FIGS. 13A-13C). This finding was consistent with the in vitro data above, and suggests that TIGIT does not require B or T cells to exert its cytokine modulatory effects.

From the preceding examples, expression of TIGIT was restricted to T cells and NK cells, with the highest expression found in $T_{regs}$. CD226, the low affinity ligand for PVR, is not expressed on $T_{regs}$ despite expression on activated T cells (Abbas, A. R. et al., Genes Immun 6, 319-31 (2005); Dardalhon, V. et al., J Immunol 175, 1558-65 (2005)). Although the balance of TIGIT and CD226 in vivo remains to be determined, the higher affinity of TIGIT for PVR suggests it plays a dominant role when both are co-expressed. Taken together, the high expression of TIGIT on activated T cells and $T_{reg}$ and interaction of TIGIT with PVR to induce IL-10 and to inhibit proinflammatory cytokine release from mature DC suggest that TIGIT provides a feedback mechanism to down-regulate immune response.

Example 6

Effect of TIGIT on PVR Signaling

Since the MAPK signaling pathway is important in regulating the IL-10 pathway (Xia, C. Q. & Kao, K. J., Scand J Immunol 58, 23-32 (2003)), the activity of several members of the
MAPK pathway was assessed in TIGIT-treated MDDC. CHO-PVR were serum-starved for three hours then treated with 50 µg/mL TIGIT-Fc or not treated for 15 minutes at 37° C. Cells were homogenized and membrane proteins were extracted using a Plasma Membrane Extraction Kit (BioVision) and subjected to sodium dodecyl sulfate-polyacrylamide gel electrophoresis (SDS-PAGE) under non-reducing conditions, followed by transfer to nitrocellulose membranes (BioRad). Membranes were blocked with 5% BSA in 50 mM Tris-HCl (pH 7.6), 150 mM NaCl, 0.1% Tween-20, and then probed with anti-phosphotyrosine-HRP (BD Bioscience), stripped with Restore Buffer (Pierce), and re-probed with anti-PVR goat polyclonal antibody (R&D Systems). Day 5 iMDDC were treated with 10 µg/mL TIGIT-Fc or control human IgG for the indicated time period at 37° C. Total cell lysates were prepared in RIPA buffer and subjected to SDS-PAGE under reducing conditions and transferred to Immobilon polyvinylidene difluoride membrane (PVDF, Millipore). After blocking with 1% BSA in 50 mM Tris-HCl pH 7.6, 150 mM NaCl, 0.1% Tween-20, followed by chemiluminescent protein detection. For reprobing, membranes were incubated in stripping buffer (62.5 mM Tris-HCl pH 6.7, 100 mM β-mercaptoethanol, 2% SDS) for 30 minutes at 50° C. with occasional agitation. Detection of phosphotyrosine, phosphor-p38MAPK, and phosphor-ERK was carried out using polyclonal antibodies specific for anti-phosphotyrosine (Upstate), anti-phospho-p38MAPK (Cell Signaling Technology), and a monoclonal anti-phospho-p44/42 MAPK (Cell Signaling Technology). As a control for protein loading, blots were re-probed with polyclonal antisera against ERK (Cell Signaling Technology), p38MAPK (Cell Signaling Technology) or β-actin (NeoMarkers), β-catenin (BD Pharmingen) or active β-catenin (Upstate).

Figure 23C:
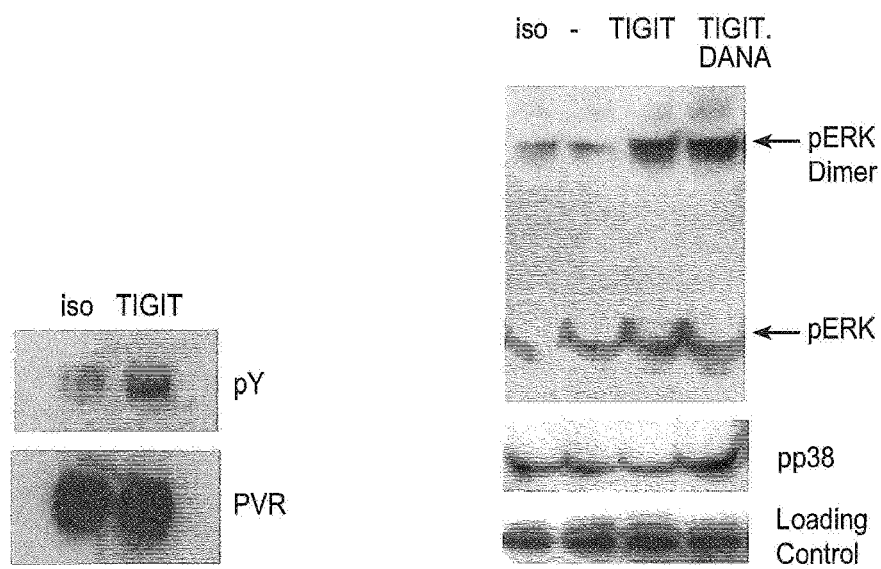
Figure 23C:
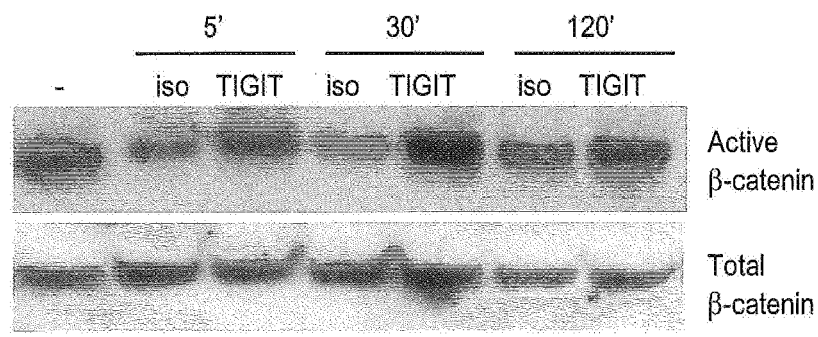

The data shown in FIG. 23A demonstrate that PVR is phosphorylated upon binding to TIGIT (compare faint phosphorylated tyrosine band observed in isotype-matched control versus TIGIT-treated cells, while overall amounts of PVR remained constant as indicated by the equivalently dark bands in the lower portion of the figure). This suggested that TIGIT binding initiates a signaling function mediated by PVR. Increased phosphorylation of pERK dimer (91 KD) but not monomer (42KD) was observed in TIGIT-Fc and TIGIT-Fc-DANA-treated iMDDC (FIG. 23B). In contrast, p38 activity was not affected (FIG. 23B). A recent report suggested that stimulation of E-cadherin and induction of active β-catenin caused murine bone marrow-derived DC to mature into tolerogenic DC capable of inhibiting immune responses in vivo (Jiang, A. et al., Immunity 27, 610-24 (2007)). Here, when human MDDC were treated with TIGIT-Fc the active form of the β-catenin pathway was induced, an effect not observed with the isotype matched control (FIG. 23C).

Figure 24A:
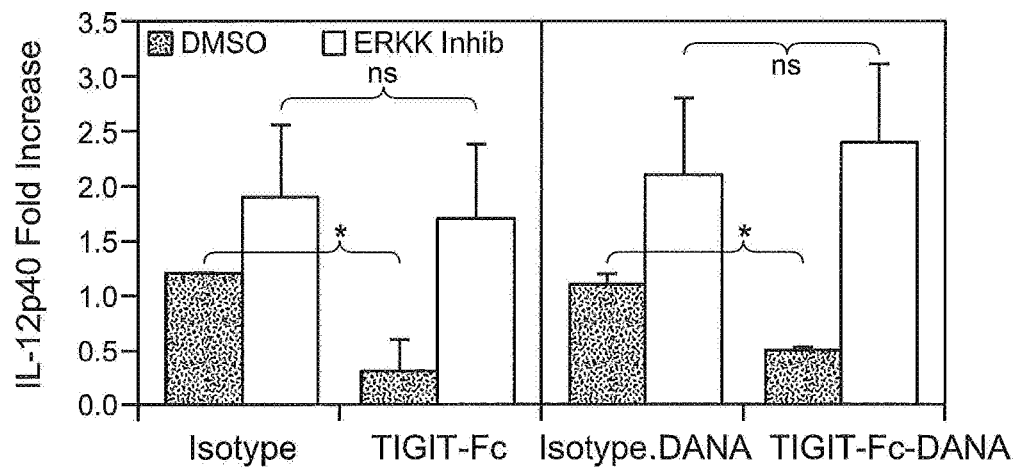
FIGS. 24A and 24B depict the results of experiments assessing the effect of blockade of various downstream signaling molecules on TIGIT-induced decreases in IL-12p40 production in TNFα-matured MDDC, as described in Example 6.
Figure 24B:
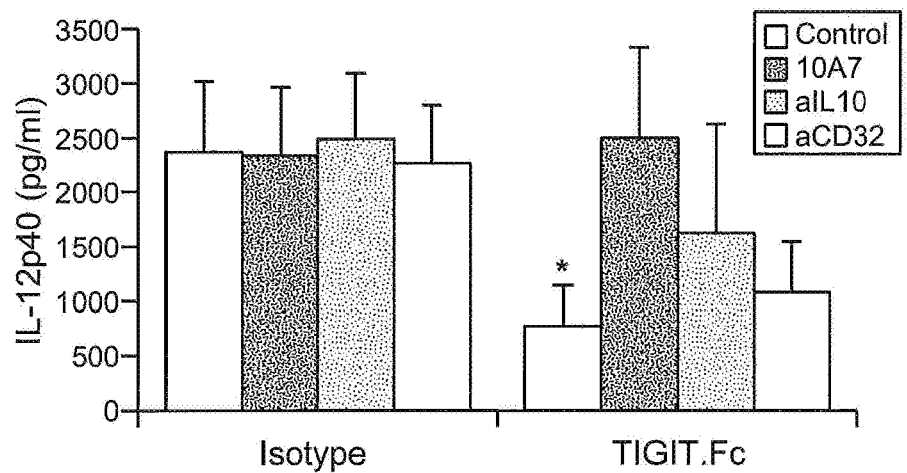

These results suggested that TIGIT, through its interaction with PVR, modulates ERK activity and thus cytokine production by MDDC. To confirm this observation, an ERK kinase specific inhibitor was added together with TIGIT-Fc to MDDC cultures, and the levels of secreted IL-12 from those cultures were determined. TIGIT-Fc-mediated down-regulation of IL-12p40 production was reversed in the presence of the ERK inhibitor (FIG. 24A). A similar effect was observed when a neutralizing anti-IL-10 antibody was included in the culture (see FIG. 24B). TIGIT-modulated cytokine production from MDDC was also blocked by anti-TIGIT antibody 10A7 or a blocking anti-PVR antibody (FIG. 24B). Together, these results indicated that TIGIT-PVR ligation affects ERK kinase activity and increases the ratio of IL-10/IL-12 cytokine production in DC relative to other produced cytokines.

Example 7

Impact of TIGIT-Modulated MDDC on T-Cell Activation

Figure 25A:
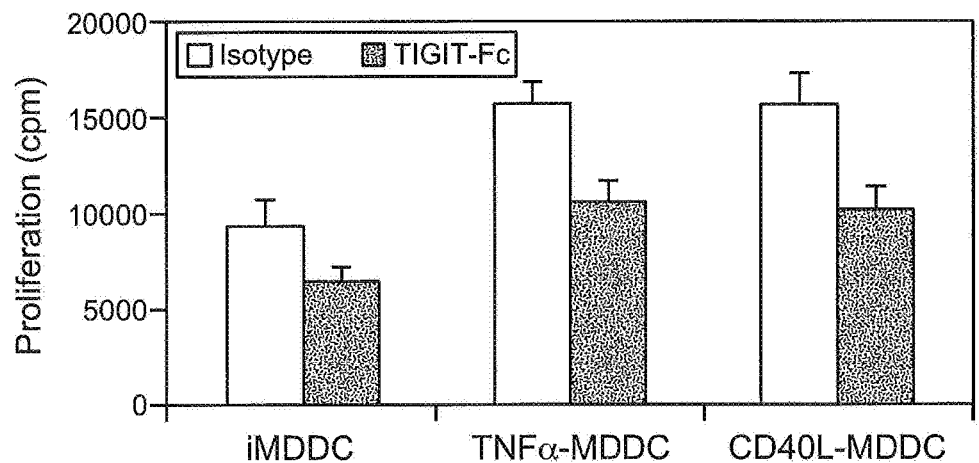
FIGS. 25A and 25B depict the results of experiments assessing the impact of TIGIT-Fc treatment on T cell activation, as described in Example 7. Graphs of data from experiments assessing the amount of T cell proliferation (FIG. 25A) or IL-2 production (FIG. 25B) induced by/in iMDDC or TNFα/CD40L-matured MDDC cultures treated with TIGIT-Fc or control antibody.
Figure 25B:
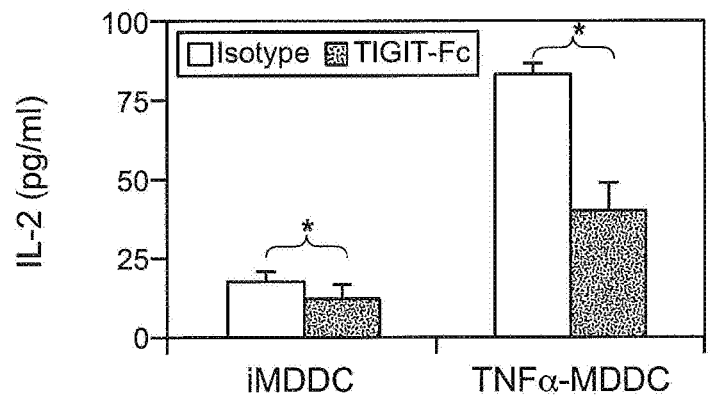

To determine if the effect of TIGIT on DC cytokine production had functional consequences, experiments were performed to assess the effect of TIGIT modulation of MDDC on T cell proliferation and cytokine production. TIGIT-Fc-treated MDDC (matured with either TNFα or sCD40L) were cultured with T cells in an MLR response as described above, and the effect on T cells was monitored. T cell proliferation was inhibited by an average of 50% (p<0.05) when cultures containing TIGIT-modified DC were compared with control DC (FIG. 25A). Additionally, IL-2 levels in the cultures were two-fold reduced (p<0.01) (FIG. 25B)). This data correlates with the decrease in IL-12 and increase in IL-10 production in DC treated with TIGIT, as described in the preceding examples. Overall, TIGIT-modified MDDC inhibited T cells, which suggests that TIGIT can regulate DC functional capabilities once DC are fully matured. Notably, addition of TIGIT-Fc to MDDC-T cell cultures inhibited proliferation of the T cells, which indicates that TIGIT-Fc does not need to be present at the initiation of DC maturation to modify the DC.

Figure 26:
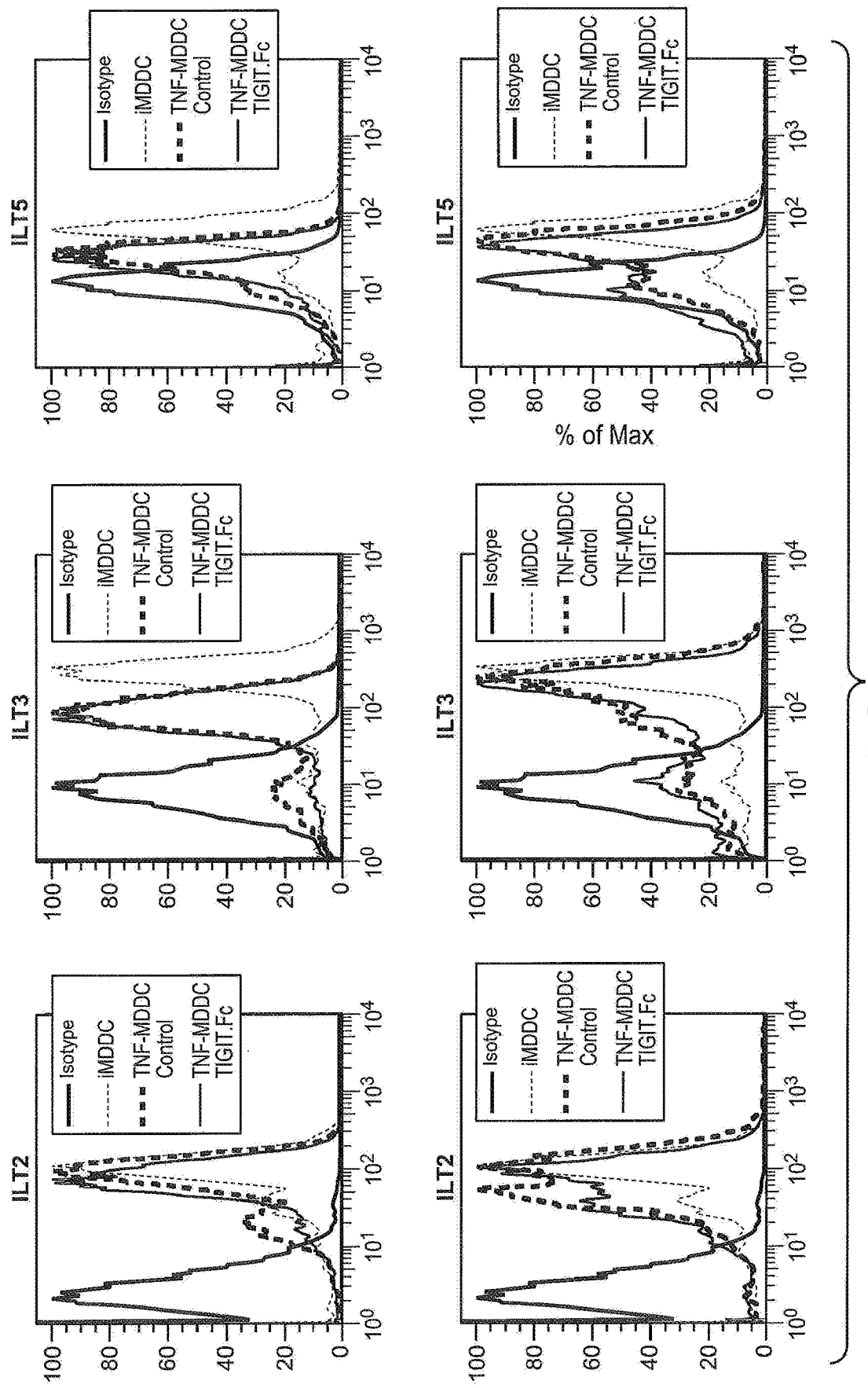
FIG. 26 depicts the results of experiments assessing the impact of TIGIT-Fc treatment on expression of ILTs in activated human MDDC, as described in Example 7.

The impact of TIGIT treatment on the expression of other cell-surface molecules in activated human MDDC was also investigated. It had been known that the expression of certain immunoglobulin-like transcripts (ILT) receptors on DC is modulated in response to activation of those cells (Velten et al., Eur. J. Immunol. 34: 2800-2811 (2004); Ju et al., Gene 331: 159-164 (2004)). For example, expression of the ILT2 and ILT3 receptors is down-regulated in CpG-DNA-activated DC, and expression of ILT2, ILT3, ILT4, and ILT5 is up-regulated in IL-10-induced DC. Given that TIGIT stimulates IL-10 production in DC, the impact of TIGIT on ILT expression in activated DC was examined. iMDDC were isolated as described above. Certain populations of iMDDC were activated with TNF or CD40L, and also treated with TIGIT-Fc or an isotype-matched control. Treated cells were sorted by FACS based on their expression of immunoglobulin-like transcript 2, 3, or 5 (ILT2, ILT3, or ILT5). As shown in FIG. 26, activation of iMDDC down-regulates ILT2, ILT3, and ILT5 expression. In contrast, activation and simultaneous treatment with TIGIT-Fc results in a decreased down-regulation of ILT2, ILT3, and ILT5 expression relative to the down-regulation seen in iMDDC activated but untreated with TIGIT-Fc. This observed effect may be due to the ability of TIGIT to stimulate IL-10 production in DC; IL-10-expressing DC are known to be tolerogenic and to express higher levels of ILTs. However, down-regulation of ILTs such as ILT2, 3, and 5 may also be a direct effect of TIGIT, and provide another method by which TIGIT induces tolerance.

To determine whether the observed in vitro effects of TIGIT treatment on T cell activation could be translated to an in vivo situation, the effects of TIGIT-Fc treatment were compared to those of CTLA4-Fc, a well-documented inhibitor of T cell response (Linsley, P. S. et al., *Science* 257, 792-5 (1992)) in a delayed-type hypersensitivity (DTH) response. Briefly, 8-10 week old C57BL/6 mice were immunized subcutaneously in the base of the tail with 100 keyhole limpet hemocyanin (KLH) (Sigma) in 100 μL CFA (Difco Laboratories). One cohort of animals (n=10) was treated on days 1, 4 and 6 with 100 μg of murine TIGIT-Fc, TIGIT-Fc-DANA, CTLA-4-Fc or negative isotype control anti-ragweed IgG2a by intraperitoneal injection. On day 6, right and left ear thickness was measured. The right ear was then injected with 25 μL, saline and the left ear was challenged with 30 μg KLH in 25 μL saline. On day 7, right and left ear thicknesses were again measured, and the difference between day 7 and day 6 ear thicknesses was defined as ear swelling. Ear swelling in ears injected with saline alone was less than 0.02 mm for each treatment group. After ear swelling measurement, mice were euthanized and spleens harvested. Single-cell suspensions were prepared and cultured in 96-well flat-bottom plates at a density of $1\times10^6$ cells/ml (200 μL/well) in DMEM containing 10% FBS, 2 mM glutamine, penicillin (100 U/ml) and streptomycin (100 μg/mL). Cells were cultured in medium alone or in the presence of various concentrations of KLH. As a positive control for T cell activation, cells were cultured on wells precoated with 5 μg/mL anti-CD3 (BD Biosciences) with 2 μg/mL soluble anti-CD28 (BD Biosciences). For proliferation analysis, 1 μCi [$^3$H]thymidine (Perkin Elmer) was added to each well in a volume of 50 μL for the last 18 hours of a four-day culture, cells were harvested and incorporation of [$^3$H]thymidine was measured by liquid scintillation counting.

Figure 27A:
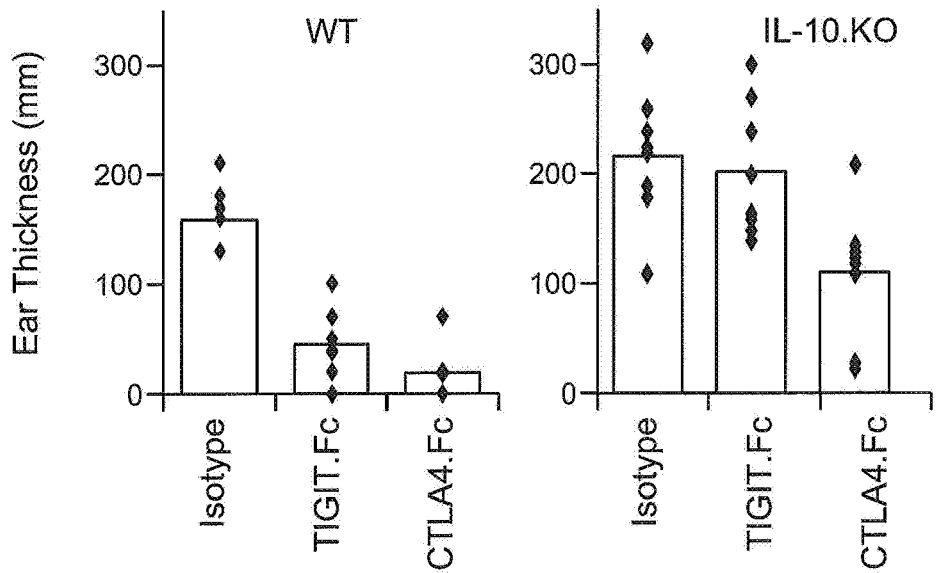
FIGS. 27A-27H depict the results of experiments assessing the effect of TIGIT treatment on delayed type hypersensitivity responses in mice, as described in Example 7.
Figure 27B:
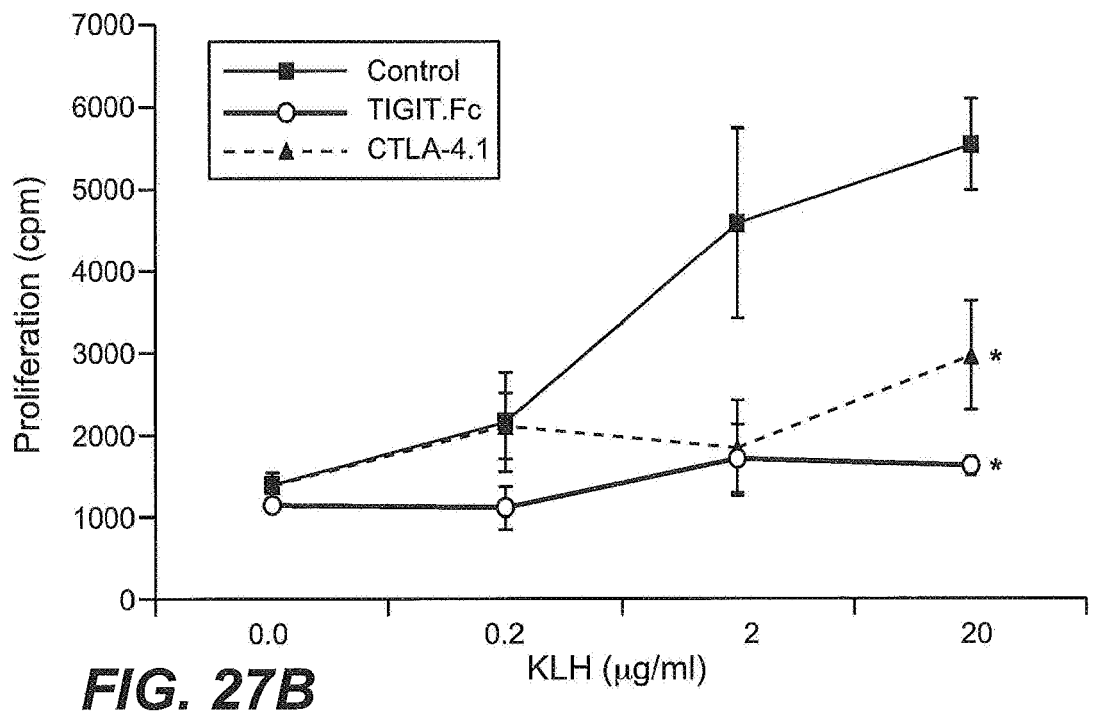
Figure 27C:
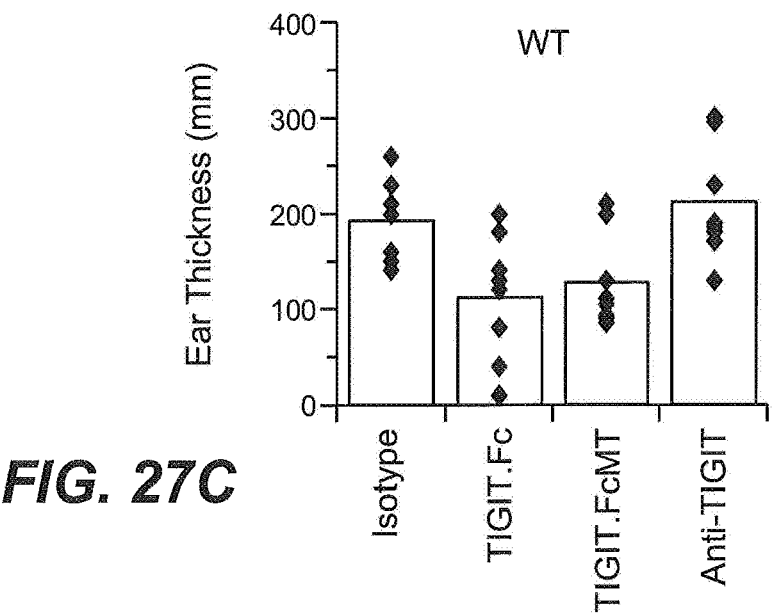
Figure 27D:
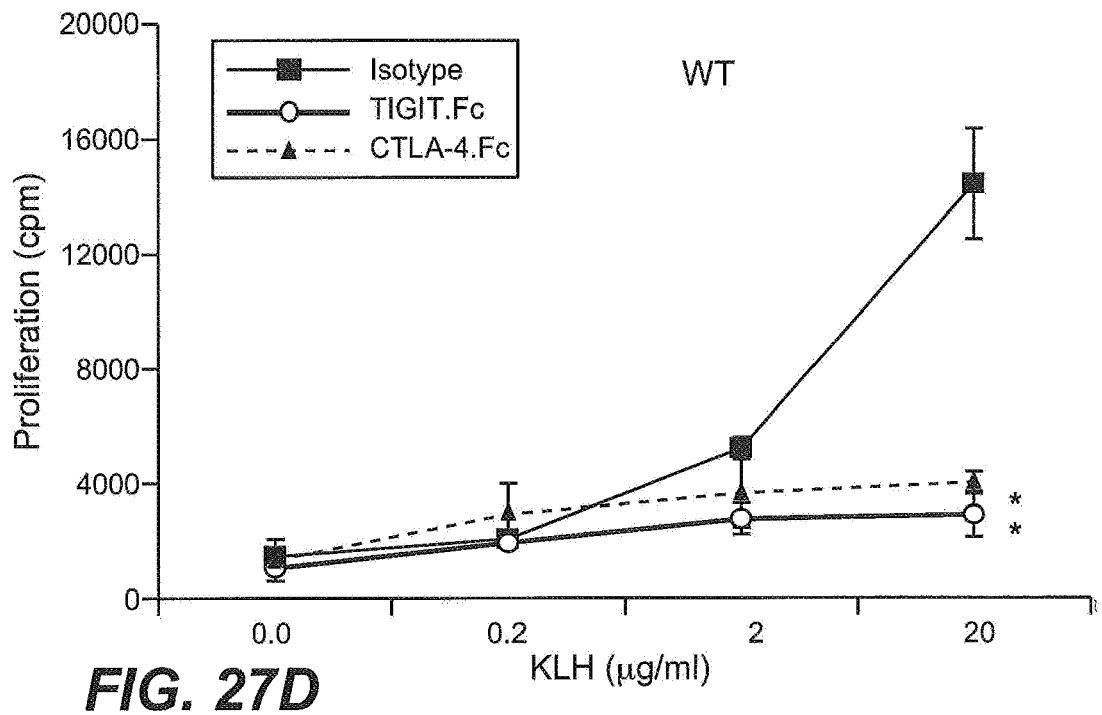
Figure 27E:
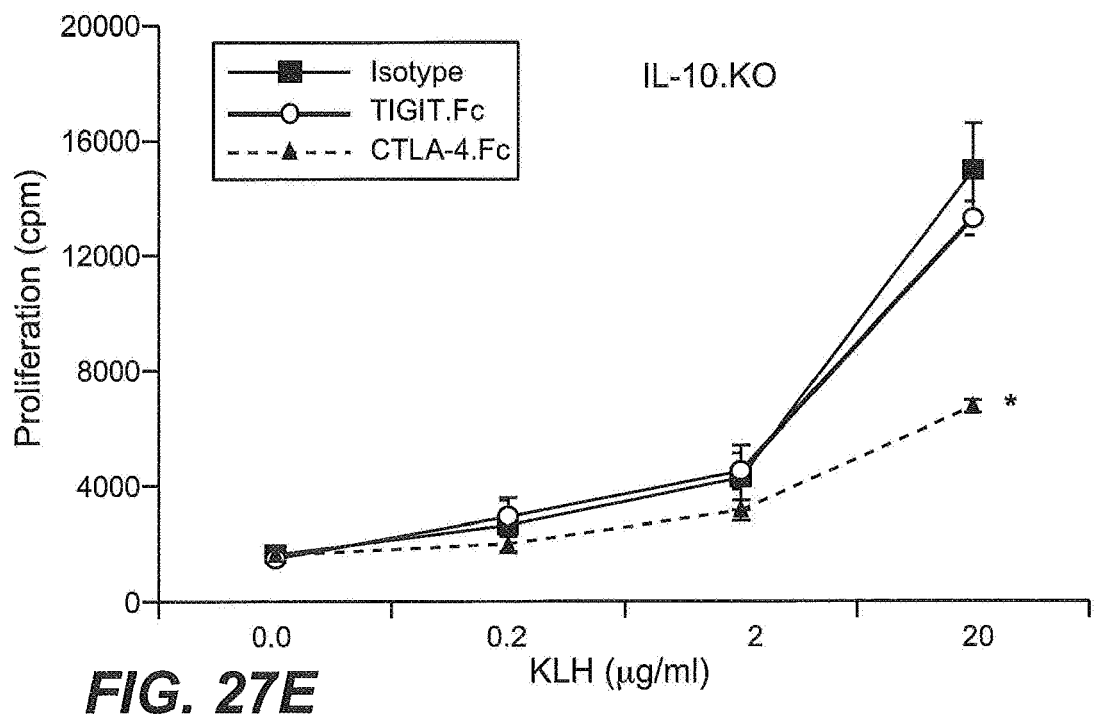
Figure 27F:
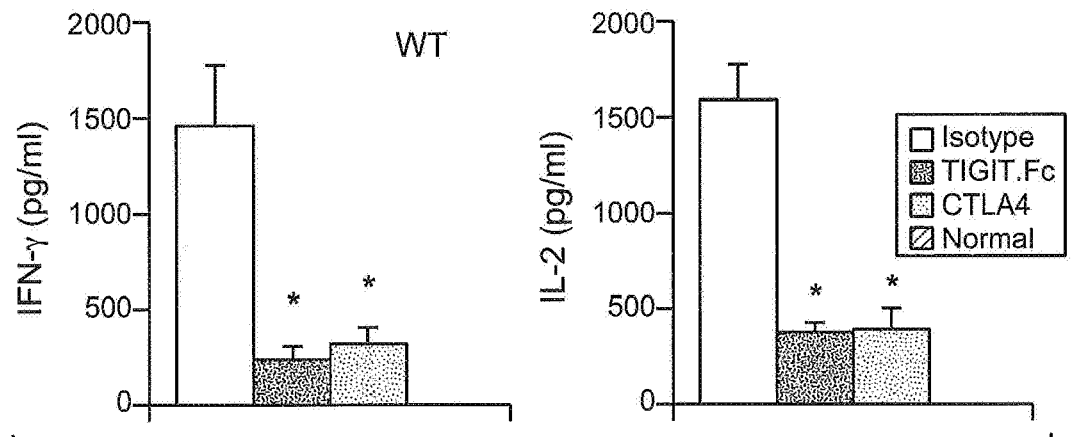
Figure 27G:
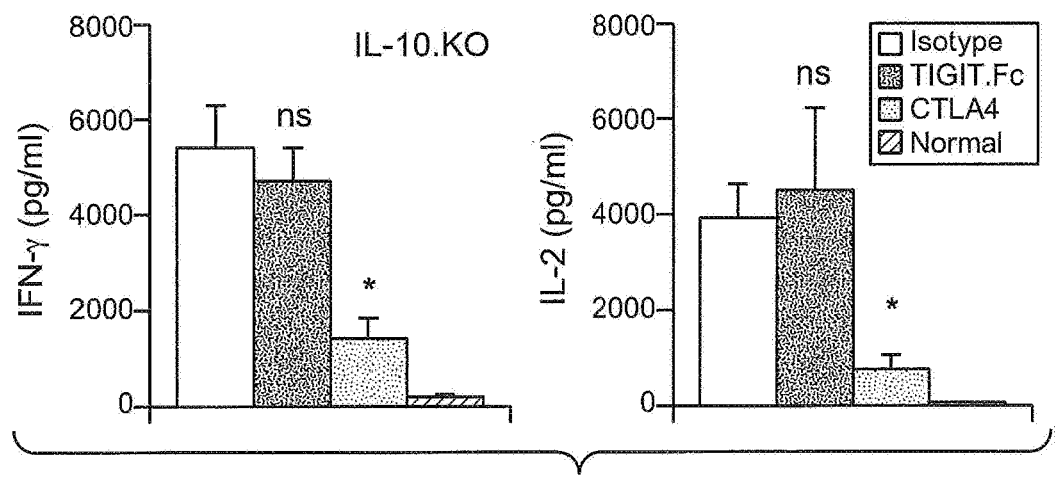

Significantly lower ear swelling was measured in TIGIT-Fc and CTLA4-Fc-treated mice as compared to the control treatment, and potency was similar for both treatment groups ($p<0.0001$ for both groups) (FIG. 27A). There was no statistical difference between TIGIT-Fc and CTLA4-Fc ($p=0.07$). Significantly, in IL-10 deficient mice, TIGIT-Fc had no effect on DTH responses, in spite of inhibition of DTH with CTLA4-Fc ($p=0.004$), supporting the role of IL-10 in TIGIT-PVR function. TIGIT-Fc-DANA was similar in its effects at inhibition of DTH as TIGIT-Fc, demonstrating that TIGIT-Fc did not require Fc-mediated cross-linking of PVR. Anti-TIGIT had no effect on DTH (FIG. 27C). Assays were performed to determine in vitro recall responses to KLH in treated mice and demonstrated that proliferation, IL-2 and IFNγ cytokine production was significantly decreased in TIGIT-Fc-treated wild type but not IL-10-deficient mice (FIGS. 27D-27G).

Figure 27H:
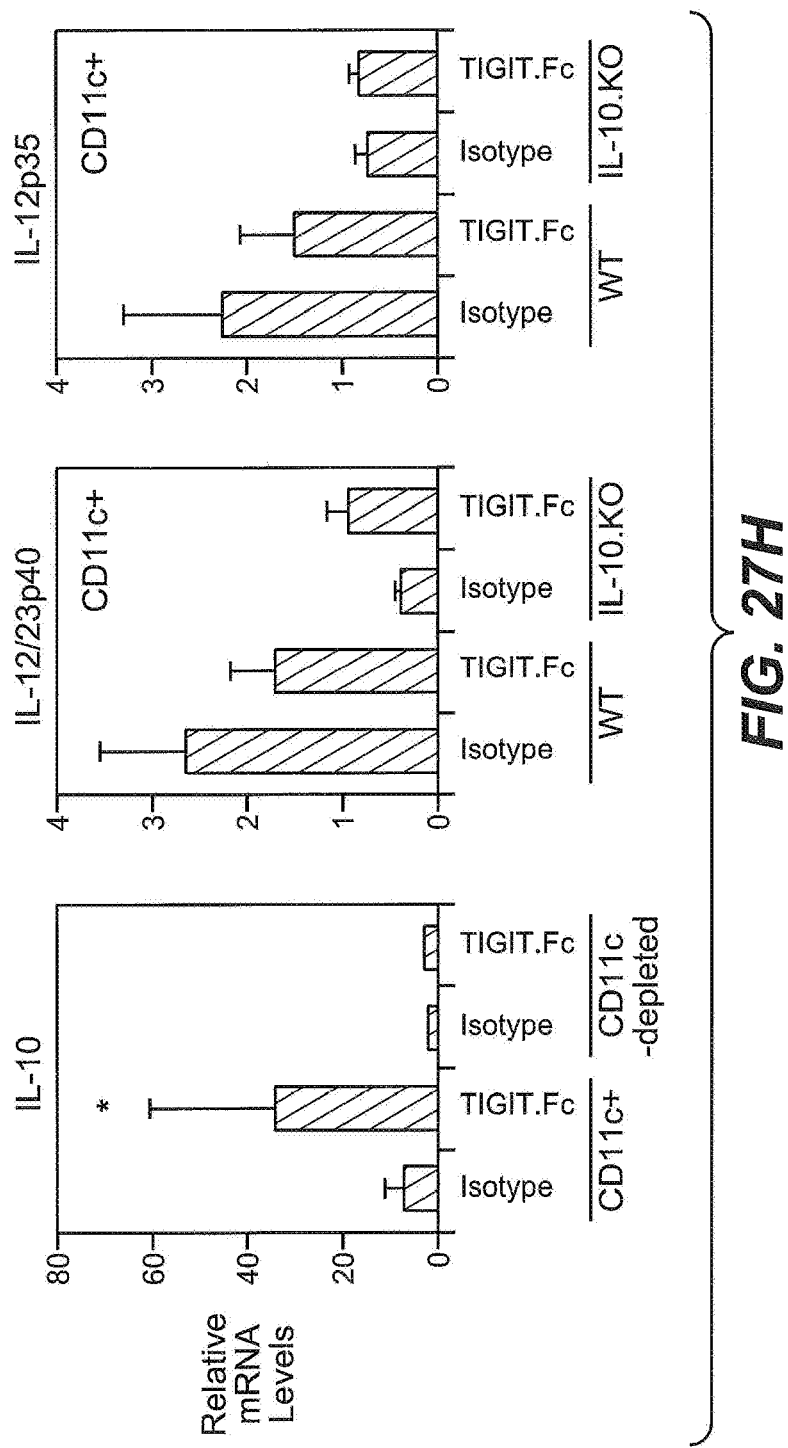

CD11c$^+$DC were isolated from spleens in the DTH mice at study termination (day 7) and the effect of TIGIT-Fc on DC proliferation and cytokine profiles was assessed by qRT-PCR, as described above. Splenic T cells isolated from TIGIT-Fc and CTLA4-Fc-treated animals did not proliferate in response to KLH in recall assays as compared to isotype-treated control animals ($p<0.001$ for both treatment groups) (FIG. 27B). This result indicates that TIGIT may be important during both T-cell priming and the effector phase of T-cell driven immune responses. Similar to the in vitro data obtained above from the MDDC studies, CD11c$^+$cells isolated from TIGIT-Fc-treated mice had increased IL-10 mRNA ($p<0.05$) and decreased IL-12/23p40 and IL-12p35 mRNA, although these latter measurements did not reach statistical significance ($p=0.07$ and $0.08$, respectively) (FIG. 27H). However, the TIGIT-Fc treatment had only a minor effect on IL-12p40/p35 transcription in CD11c$^+$cells derived from IL-10 KO mice, indicating that TIGIT-mediated down-regulation of IL-12p40/p35 mRNA levels is specific and TIGIT-mediated upregulation of IL-10 is required for down-regulation of proinflammatory cytokine IL-12 in this model.

Example 8

TIGIT Deficient Mice

TIGIT knockout mice were generated using standard techniques. To confirm the absence of a functional TIGIT gene in these mice, total T cells were isolated from spleens of knockout or wild-type mice, and subsequently incubated with anti-CD3 antibodies and anti-CD28 antibodies for three days. Total RNA was isolated from the cells using an RNeasy kit (Qiagen) and subjected to real-time RT-PCR to measure TIGIT mRNA. CD96 mRNA levels were also assessed as a control. The results of the study demonstrated that the knockout mice were deficient in TIGIT expression.

Immune cell populations from mesenteric lymph nodes were examined in 9 month-old TIGIT knockout mice in comparison with wild-type mice, using FACS analyses as described in Example 3A. The TIGIT knockout mice displayed increased numbers of memory CD4$^+$ T cells, mDC, pDC, monocytes, CD11c$^+$ PVR$^{hi}$ T cells, and overall B cells as compared to wildtype mice. The populations of naïve and mature CD4$^+$ cells were similar between the knockout and wildtype mice. The knockout mice were also found to have increased numbers of MZB (B220+CD21$^{hi}$), NKT (DX5+ CD4+ or DX5+CD8+), and memory CD8+ T cells in spleen, relative to wildtype mice. This increased level of memory CD8+ T cells was also observed in mesenteric lymph nodes and Peyer's patch cells in the knockout mice. The increase in pDC and monocyte cell numbers observed in the mesenteric lymph node of the knockout mice was also observed in spleen and Peyer's patches of those mice, though the difference in levels relative to those in wildtype mice was less pronounced than in the mesenteric lymph node.

The activity of T cells isolated from the TIGIT deficient mice was also investigated. Briefly, total splenocytes were isolated from 9-month-old TIGIT-deficient mice and wild-type littermates. $10^6$ cells from each type of mice were seeded onto flat-bottom 96-well plates and stimulated with plate-bound anti-CD3 (10 µg/mL) plus anti-CD28 (2 µg/mL). On the second day, supernatants were collected and cytokine production was analyzed by Luminex. Cells were collected and subjected to FACS, sorting by the presence of intracellular IFNγ and IL-4. Cell proliferation was measured by $^3$H-thymidine incorporation, as described in Example 3A. MLR assays were performed generally according to the methods described in Example 4A. Specifically, CD4+ T cells were isolated from spleens of TIGIT-deficient mice or wild-type littermates by negative isolation (MACS). T-cell-depleted Balb/C splenocytes were irradiated at 3000 rad and used as antigen presenting cells. $2\times10^5$CD4+ T cells were stimulated with 1 µg/mL soluble anti-CD3 (T cells only) or mixed with allogenic antigen presenting cells at a 1:2 ratio. Proliferation was measured on the third day by $^3$H-thymidine incorporation, as described in Example 3A. In a second experiment, the MLR assay was performed identically, but the CD4+ T cells were isolated from Balb/c mice and the antigen presenting cells were prepared from TIGIT-deficient mice or from wild-type mice.

Figure 30A:
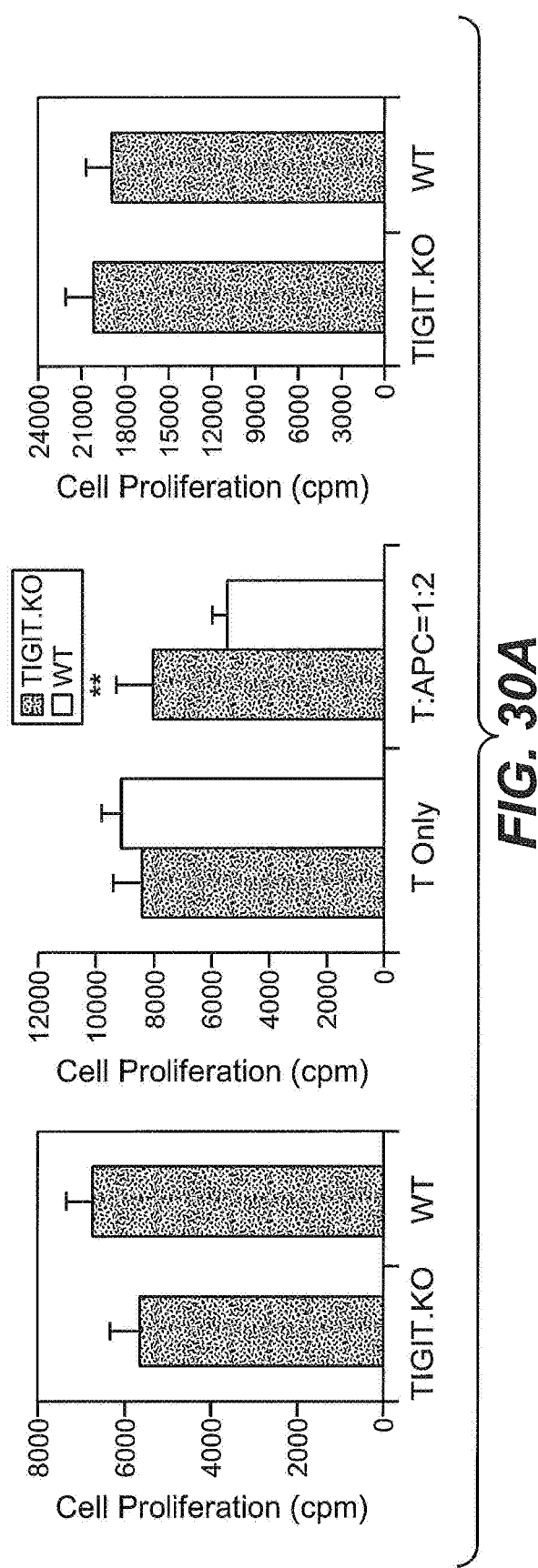
FIGS. 30A-30C depict the results of experiments assessing immune cell functionality in TIGIT-deficient mice, as described in Example 8.
Figure 30B:
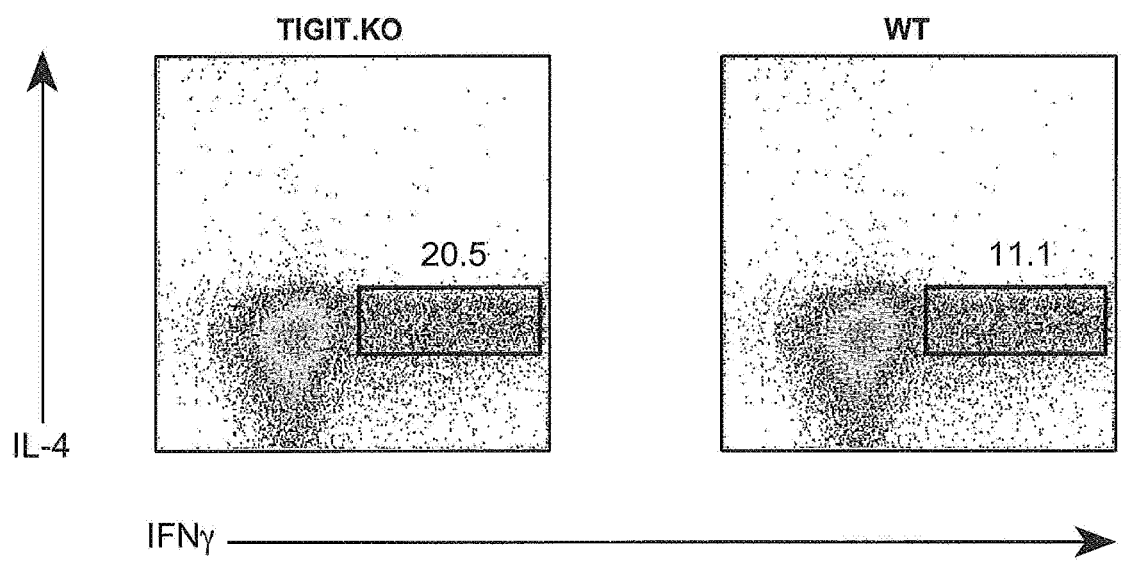
Figure 30C:
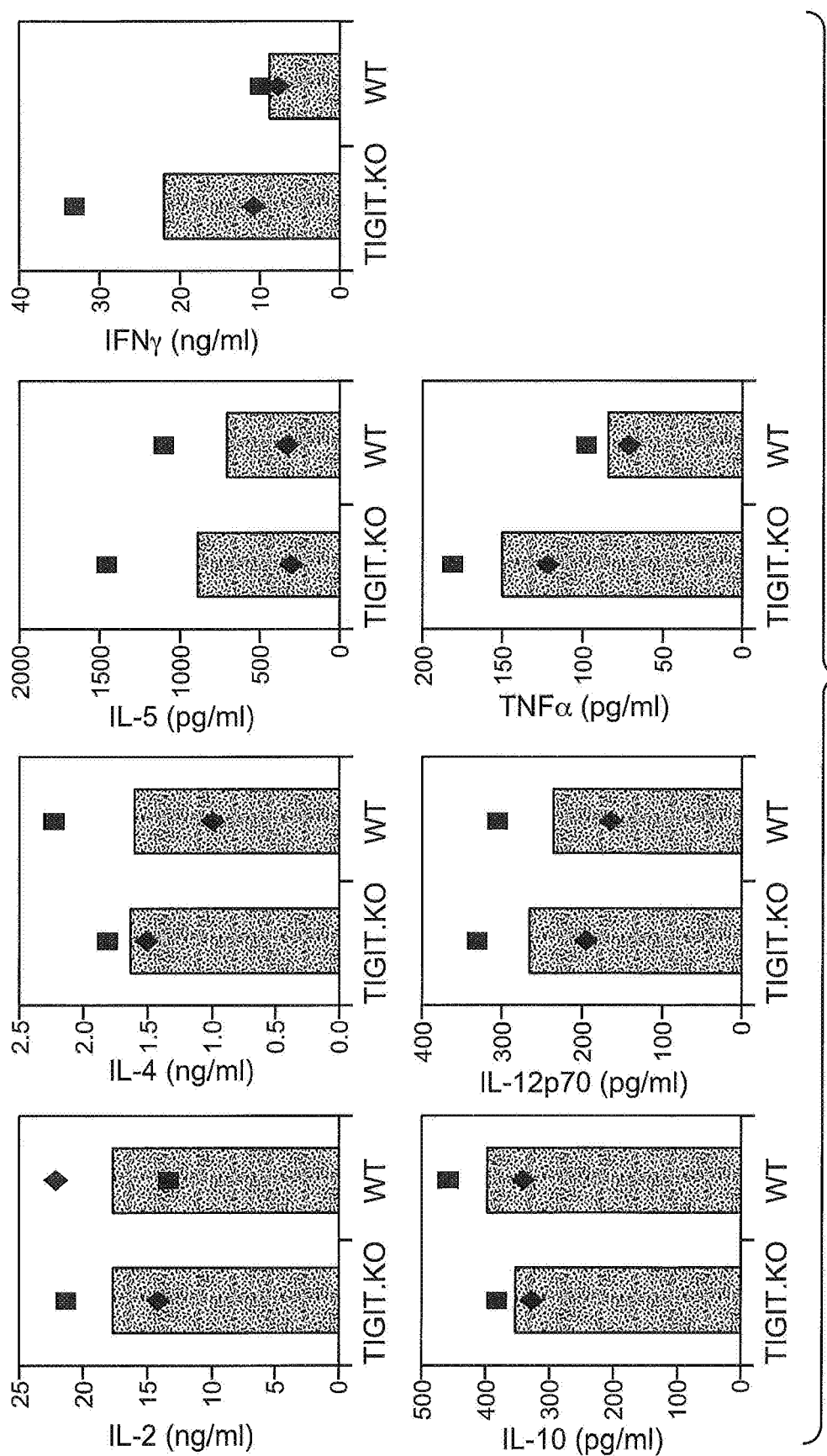

The TIGIT-deficient mouse T cells proliferated similarly to T cells from wild-type mice in a standard proliferation assay (FIG. 30A, left panel). However, in the presence of antigen presenting cells, TIGIT-deficient T cells had increased proliferation relative to wild-type T cells (FIG. 30A, middle panel). Notably, antigen-presenting cells from TIGIT-deficient mouse spleen stimulated proliferation of wild-type T cells to the same extent as antigen presenting cells taken from wild-type mice (FIG. 30A, right panel). Combined, this data suggests that T cells are downregulated in proliferation by a mechanism involving TIGIT expressed on those T cells, rather than on antigen-presenting cells, and further confirms the activity of TIGIT in the down-regulation of T cell response. A greater proportion of the TIGIT-deficient mouse T cells had high intracellular IFNγ levels than the wild-type mouse T cells (FIG. 30B). Cytokine production analyses of supernates from TIGIT-deficient and wild-type T cells showed that IFNγ and TNFα production/secretion was increased in the TIGIT-deficient T cells relative to the wild-type T cells, while IL-2, IL-4, IL-5, IL-10, and IL-12p70 levels remained consistent between the two cell populations.

What is claimed is:

1. A method of identifying or detecting a TIGIT polypeptide, wherein the method comprises:
   (i) contacting a putative TIGIT polypeptide with an anti-TIGIT antibody, or antigen-binding fragment thereof; and
   (ii) determining the binding of the anti-TIGIT antibody, or antigen-binding fragment thereof, to the putative TIGIT polypeptide, wherein the antibody, or antigen-binding fragment thereof, comprises:
   (a) a light chain comprising an HVR-L1 comprising SEQ ID NO: 23, an HVR-L2 comprising SEQ ID NO: 24, and an HVR-L3 comprising SEQ ID NO: 25, and a heavy chain comprising an HVR-H1 comprising SEQ ID NO: 26, an HVR-H2 comprising SEQ ID NO: 27, and an HVR-H3 comprising SEQ ID NO: 28; or
   (b) a light chain comprising an HVR-L1 comprising SEQ ID NO: 31, an HVR-L2 comprising SEQ ID NO: 32, and an HVR-L3 comprising SEQ ID NO: 33, and a heavy chain comprising an HVR-H1 comprising SEQ ID NO: 34, an HVR-H2 comprising SEQ ID NO: 35, and an HVR-H3 comprising SEQ ID NO: 36.

2. The method of claim 1, wherein the anti-TIGIT antibody, or antigen-binding fragment thereof, comprises a light chain comprising an amino acid sequence at least 90% identical to the amino acid sequence set forth in SEQ ID NO: 21.

3. The method of claim 2, wherein the anti-TIGIT antibody, or antigen-binding fragment thereof, comprises a heavy chain comprising an amino acid sequence at least 90% identical to the amino acid sequence set forth in SEQ ID NO: 22.

4. The method of claim 3, wherein the light chain comprises the amino acid sequence set forth in SEQ ID NO: 21 and the heavy chain comprises the amino acid sequence set forth in SEQ ID NO: 22.

5. The method of claim 1, wherein the anti-TIGIT antibody, or antigen-binding fragment thereof, comprises a heavy chain comprising an amino acid sequence at least 90% identical to the amino acid sequence set forth in SEQ ID NO: 22.

6. The method of claim 1, wherein the anti-TIGIT antibody, or antigen-binding fragment thereof, comprises a light chain comprising an amino acid sequence at least 90% identical to the amino acid sequence set forth in SEQ ID NO: 29.

7. The method of claim 6, wherein the anti-TIGIT antibody, or antigen-binding fragment thereof, comprises a heavy chain comprising an amino acid sequence at least 90% identical to the amino acid sequence set forth in SEQ ID NO: 30.

8. The method of claim 7, wherein the light chain comprises the amino acid sequence set forth in SEQ ID NO: 29 and the heavy chain comprises the amino acid sequence set forth in SEQ ID NO: 30.

9. The method of claim 1, wherein the anti-TIGIT antibody, or antigen-binding fragment thereof, comprises a heavy chain comprising an amino acid sequence at least 90% identical to the amino acid sequence set forth in SEQ ID NO: 30.

10. The method of claim 1, wherein the anti-TIGIT antibody is a humanized antibody, a chimeric antibody, a bispecific antibody, or a heteroconjugate antibody.

11. A method of determining whether a test Treg, memory T cell, NK cell, or TFh cell is an activated Treg, memory T cell, NK cell, or TFh cell, wherein the method comprises:
   (i) assessing a level of expression of TIGIT in the test Treg, memory T cell, NK cell, or TFh cell by contacting the test Treg, memory T cell, NK cell, or TFh cell with an anti-TIGIT antibody, or antigen-binding fragment thereof, wherein the anti-TIGIT antibody, or antigen-binding fragment thereof, comprises
   (a) a light chain comprising an HVR-L1 comprising SEQ ID NO: 23, an HVR-L2 comprising SEQ ID NO: 24, and an HVR-L3 comprising SEQ ID NO: 25, and a heavy chain comprising an HVR-H1 comprising SEQ ID NO: 26, an HVR-H2 comprising SEQ ID NO: 27, and an HVR-H3 comprising SEQ ID NO: 28; or
   (b) a light chain comprising an HVR-L1 comprising SEQ ID NO: 31, an HVR-L2 comprising SEQ ID NO: 32, and an HVR-L3 comprising SEQ ID NO: 33, and a heavy chain comprising an HVR-H1 comprising SEQ ID NO: 34, an HVR-H2 comprising SEQ ID NO: 35, and an HVR-H3 comprising SEQ ID NO: 36; and
   (ii) comparing the level of expression of TIGIT in the test Treg, memory T cell, NK cell, or TFh cell to the level of expression of TIGIT in a known activated Treg, memory T cell, NK cell, or TFh cell, or comparing the level of expression of TIGIT in the test immune cell to known standard TIGIT expression value(s).

12. The method of claim 11, wherein the anti-TIGIT antibody, or antigen-binding fragment thereof, comprises a light chain comprising an amino acid sequence at least 90% identical to the amino acid sequence set forth in SEQ ID NO: 21.

13. The method of claim 12, wherein the anti-TIGIT antibody, or antigen-binding fragment thereof, comprises a heavy chain comprising an amino acid sequence at least 90% identical to the amino acid sequence set forth in SEQ ID NO: 22.

14. The method of claim 13, wherein the light chain comprises the amino acid sequence set forth in SEQ ID NO: 21 and the heavy chain comprises the amino acid sequence set forth in SEQ ID NO: 22.

15. The method of claim 11, wherein the anti-TIGIT antibody, or antigen-binding fragment thereof, comprises a heavy chain comprising an amino acid sequence at least 90% identical to the amino acid sequence set forth in SEQ ID NO: 22.

16. The method of claim 11, wherein the anti-TIGIT antibody, or antigen-binding fragment thereof, comprises a light chain comprising an amino acid sequence at least 90% identical to the amino acid sequence set forth in SEQ ID NO: 29.

17. The method of claim 16, wherein the anti-TIGIT antibody, or antigen-binding fragment thereof, comprises a heavy chain comprising an amino acid sequence at least 90% identical to the amino acid sequence set forth in SEQ ID NO: 30.

18. The method of claim 17, wherein the light chain comprises the amino acid sequence set forth in SEQ ID NO: 29 and the heavy chain comprises the amino acid sequence set forth in SEQ ID NO: 30.

19. The method of claim 11, wherein the anti-TIGIT antibody, or antigen-binding fragment thereof, comprises a heavy chain comprising an amino acid sequence at least 90% identical to the amino acid sequence set forth in SEQ ID NO: 30.

20. The method of claim 11, wherein the anti-TIGIT antibody is a humanized antibody, a chimeric antibody, a bispecific antibody, or a heteroconjugate antibody.

* * * * *

SEQUENCE LISTING

<160> NUMBER OF SEQ ID NOS: 64

<210> SEQ ID NO 1
<211> LENGTH: 244
<212> TYPE: PRT
<213> ORGANISM: Homo sapiens

<400> SEQUENCE: 1

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175
```

```
Gly Asp Leu Arg Arg Lys Ser Ala Gly Gln Glu Trp Ser Pro Ser
            180                 185                 190
Ala Pro Ser Pro Gly Ser Cys Val Gln Ala Glu Ala Pro Ala
        195                 200                 205
Gly Leu Cys Gly Glu Gln Arg Gly Glu Asp Cys Ala Glu Leu His Asp
    210                 215                 220
Tyr Phe Asn Val Leu Ser Tyr Arg Ser Leu Gly Asn Cys Ser Phe Phe
225                 230                 235                 240
Thr Glu Thr Gly

<210> SEQ ID NO 2
<211> LENGTH: 245
<212> TYPE: PRT
<213> ORGANISM: Macaca mulatta

<400> SEQUENCE: 2

Met Arg Trp Cys Leu Phe Leu Ile Trp Ala Gln Gly Leu Arg Gln Ala
1               5                   10                  15
Pro Leu Ala Ser Gly Met Met Thr Gly Thr Ile Glu Thr Thr Gly Asn
            20                  25                  30
Ile Ser Ala Lys Lys Gly Gly Ser Val Ile Leu Gln Cys His Leu Ser
        35                  40                  45
Ser Thr Met Ala Gln Val Thr Gln Val Asn Trp Glu Gln His Asp His
    50                  55                  60
Ser Leu Leu Ala Ile Arg Asn Ala Glu Leu Gly Trp His Ile Tyr Pro
65                  70                  75                  80
Ala Phe Lys Asp Arg Val Ala Pro Gly Pro Gly Leu Gly Leu Thr Leu
                85                  90                  95
Gln Ser Leu Thr Met Asn Asp Thr Gly Glu Tyr Phe Cys Thr Tyr His
            100                 105                 110
Thr Tyr Pro Asp Gly Thr Tyr Arg Gly Arg Ile Phe Leu Glu Val Leu
        115                 120                 125
Glu Ser Ser Val Ala Glu His Ser Ala Arg Phe Gln Ile Pro Leu Leu
130                 135                 140
Gly Ala Met Ala Met Met Leu Val Val Ile Cys Ile Ala Val Ile Val
145                 150                 155                 160
Val Val Val Leu Ala Arg Lys Lys Lys Ser Leu Arg Ile His Ser Val
                165                 170                 175
Glu Ser Gly Leu Gln Arg Lys Ser Thr Gly Gln Glu Glu Gln Ile Pro
            180                 185                 190
Ser Ala Pro Ser Pro Gly Ser Cys Val Gln Ala Glu Ala Ala Pro
        195                 200                 205
Ala Gly Leu Cys Gly Glu Gln Gln Gly Asp Asp Cys Ala Glu Leu His
    210                 215                 220
Asp Tyr Phe Asn Val Leu Ser Tyr Arg Ser Leu Gly Ser Cys Ser Phe
225                 230                 235                 240
Phe Thr Glu Thr Gly
                245

<210> SEQ ID NO 3
<211> LENGTH: 245
<212> TYPE: PRT
<213> ORGANISM: Canis familiaris

<400> SEQUENCE: 3
```

```
Met Gln Trp Tyr Leu Leu Ile Trp Ala Gln Gly Leu Gly Gln Ala
1               5                   10                  15

Pro Leu Pro Thr Ser Gly Ala Val Ser Gly Arg Ile Met Thr Met Gly
            20                  25                  30

Asn Ile Ser Ala Lys Glu Gly Gly Ser Val Thr Leu Gln Cys His Leu
            35                  40                  45

Ser Ser Thr Thr Ala Asn Val Thr Gln Val Asn Trp Glu Lys Gln Asp
50                  55                  60

Gln Leu Leu Ala Val His His Thr Asp Leu Gly Trp His Ile Tyr Pro
65                  70                  75                  80

Ala Phe Arg Glu Arg Val Ala Pro Gly Pro Asn Leu Gly Leu Thr Leu
                85                  90                  95

Gln Ser Leu Thr Arg Asn Asp Thr Gly Glu Tyr Leu Cys Thr Tyr His
            100                 105                 110

Thr Tyr Pro Asp Gly Ile Tyr Arg Gly Thr Phe Phe Leu Glu Val Leu
            115                 120                 125

Gln Ser Ser Val Ala Glu Arg Ser Ala Ala Phe Gln Ile Pro Leu Leu
            130                 135                 140

Gly Ala Met Ala Ser Val Leu Ala Val Ile Cys Val Ala Val Ile Leu
145                 150                 155                 160

Gly Gly Leu Trp Thr Arg Lys Lys Lys Cys Arg Arg Val His Cys Gly
                165                 170                 175

Glu Ser Gly Leu Arg Thr Met Thr Tyr Glu Gln Glu Glu Gln Ser Pro
            180                 185                 190

Cys Ile Leu Ser Ser Thr Gly Arg Ala Ile Gln Val Glu Met Val Pro
            195                 200                 205

Val Gly Leu Tyr Thr Glu Gln Arg Ala Asp Asp Tyr Ala Glu Pro His
            210                 215                 220

Asp Tyr Phe Asn Val Leu Ser Tyr Arg Ser Leu Gly Ser Phe Ser Phe
225                 230                 235                 240

Leu Ala Glu Thr Gly
                245

<210> SEQ ID NO 4
<211> LENGTH: 241
<212> TYPE: PRT
<213> ORGANISM: Mus musculus

<400> SEQUENCE: 4

Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
            35                  40                  45

Ser Ser Asp Thr Ala Glu Val Thr Gln Val Asp Trp Lys Gln Gln Asp
50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
            115                 120                 125
```

-continued

```
Glu Ser Ser Val Ala Gln Phe Gln Thr Ala Pro Leu Gly Gly Thr Met
            130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Gly Tyr Phe Asn
    210                 215                 220

Val Leu Ser Tyr Arg Ser Leu Glu Ser Phe Ile Ala Val Ser Lys Thr
225                 230                 235                 240

Gly
```

<210> SEQ ID NO 5
<211> LENGTH: 112
<212> TYPE: PRT
<213> ORGANISM: Homo sapiens

<400> SEQUENCE: 5

```
Leu Ala Ser Gly Met Met Thr Gly Thr Ile Glu Thr Thr Gly Asn Ile
1               5                   10                  15

Ser Ala Glu Lys Gly Gly Ser Ile Ile Leu Gln Cys His Leu Ser Ser
            20                  25                  30

Thr Thr Ala Gln Val Thr Gln Val Asn Trp Glu Gln Gln Asp Gln Leu
        35                  40                  45

Leu Ala Ile Cys Asn Ala Asp Leu Gly Trp His Ile Ser Pro Ser Phe
    50                  55                  60

Lys Asp Arg Val Ala Pro Gly Pro Gly Leu Gly Leu Thr Leu Gln Ser
65                  70                  75                  80

Leu Thr Val Asn Asp Thr Gly Glu Tyr Phe Cys Ile Tyr His Thr Tyr
                85                  90                  95

Pro Asp Gly Ala Tyr Thr Gly Arg Ile Phe Leu Glu Val Leu Glu Ser
            100                 105                 110
```

<210> SEQ ID NO 6
<211> LENGTH: 132
<212> TYPE: PRT
<213> ORGANISM: Homo sapiens

<400> SEQUENCE: 6

```
Pro Pro Pro Gly Thr Gly Asp Val Val Gln Ala Pro Thr Gln Val
1               5                   10                  15

Pro Gly Phe Leu Gly Asp Ser Val Thr Leu Pro Cys Tyr Leu Gln Val
            20                  25                  30

Pro Asn Met Glu Val Thr His Val Ser Gln Leu Thr Trp Ala Arg His
        35                  40                  45

Gly Glu Ser Gly Ser Met Ala Val Phe His Gln Thr Gln Gly Pro Ser
    50                  55                  60

Tyr Ser Glu Ser Lys Arg Leu Glu Phe Val Ala Ala Arg Leu Gly Ala
65                  70                  75                  80

Glu Leu Arg Asn Ala Ser Leu Arg Met Phe Gly Leu Arg Val Glu Asp
                85                  90                  95
```

Glu Gly Asn Tyr Thr Cys Leu Phe Val Thr Phe Pro Gln Gly Ser Arg
                100                 105                 110

Ser Val Asp Ile Trp Leu Arg Val Leu Ala Lys Pro Gln Asn Thr Ala
        115                 120                 125

Glu Val Gln Lys
    130

<210> SEQ ID NO 7
<211> LENGTH: 131
<212> TYPE: PRT
<213> ORGANISM: Homo sapiens

<400> SEQUENCE: 7

Phe Val Lys Gly Val Trp Glu Lys Thr Val Asn Thr Glu Glu Asn Val
1               5                   10                  15

Tyr Ala Thr Leu Gly Ser Asp Val Asn Leu Thr Cys Gln Thr Gln Thr
            20                  25                  30

Val Gly Phe Phe Val Gln Met Gln Trp Ser Lys Val Thr Asn Lys Ile
        35                  40                  45

Asp Leu Ile Ala Val Tyr His Pro Gln Tyr Gly Phe Tyr Cys Ala Tyr
    50                  55                  60

Gly Arg Pro Cys Glu Ser Leu Val Thr Phe Thr Glu Thr Pro Glu Asn
65                  70                  75                  80

Gly Ser Lys Trp Thr Leu His Leu Arg Asn Met Ser Cys Ser Val Ser
                85                  90                  95

Gly Arg Tyr Glu Cys Met Leu Val Leu Tyr Pro Glu Gly Ile Gln Thr
            100                 105                 110

Lys Ile Tyr Asn Leu Leu Ile Gln Thr His Val Thr Ala Asp Glu Trp
        115                 120                 125

Asn Ser Asn
    130

<210> SEQ ID NO 8
<211> LENGTH: 144
<212> TYPE: PRT
<213> ORGANISM: Homo sapiens

<400> SEQUENCE: 8

Leu Glu Thr Gly Ala Gln Asp Val Arg Val Gln Val Leu Pro Glu Val
1               5                   10                  15

Arg Gly Gln Leu Gly Gly Thr Val Glu Leu Pro Cys His Leu Leu Pro
            20                  25                  30

Pro Val Pro Gly Leu Tyr Ile Ser Leu Val Thr Trp Gln Arg Pro Asp
        35                  40                  45

Ala Pro Ala Asn His Gln Asn Val Ala Ala Phe His Pro Lys Met Gly
    50                  55                  60

Pro Ser Phe Pro Ser Pro Lys Pro Gly Ser Glu Arg Leu Ser Phe Val
65                  70                  75                  80

Ser Ala Lys Gln Ser Thr Gly Gln Asp Thr Glu Ala Glu Leu Gln Asp
                85                  90                  95

Ala Thr Leu Ala Leu His Gly Leu Thr Val Glu Asp Glu Gly Asn Tyr
            100                 105                 110

Thr Cys Glu Phe Ala Thr Phe Pro Lys Gly Ser Val Arg Gly Met Thr
        115                 120                 125

Trp Leu Arg Val Ile Ala Lys Pro Lys Asn Gln Ala Glu Ala Gln Lys
    130                 135                 140

<210> SEQ ID NO 9
<211> LENGTH: 131
<212> TYPE: PRT
<213> ORGANISM: Homo sapiens

<400> SEQUENCE: 9

Phe Leu Pro Gly Val His Ser Gln Val Val Gln Val Asn Asp Ser Met
1               5                   10                  15

Tyr Gly Phe Ile Gly Thr Asp Val Val Leu His Cys Ser Phe Ala Asn
            20                  25                  30

Pro Leu Pro Ser Val Lys Ile Thr Gln Val Thr Trp Gln Lys Ser Thr
        35                  40                  45

Asn Gly Ser Lys Gln Asn Val Ala Ile Tyr Asn Pro Ser Met Gly Val
    50                  55                  60

Ser Val Leu Ala Pro Tyr Arg Glu Arg Val Glu Phe Leu Arg Pro Ser
65                  70                  75                  80

Phe Thr Asp Gly Thr Ile Arg Leu Ser Arg Leu Glu Leu Glu Asp Glu
                85                  90                  95

Gly Val Tyr Ile Cys Glu Phe Ala Thr Phe Pro Thr Gly Asn Arg Glu
            100                 105                 110

Ser Gln Leu Asn Leu Thr Val Met Ala Lys Pro Thr Asn Trp Ile Glu
        115                 120                 125

Gly Thr Gln
        130

<210> SEQ ID NO 10
<211> LENGTH: 128
<212> TYPE: PRT
<213> ORGANISM: Homo sapiens

<400> SEQUENCE: 10

Arg Leu Cys Gly Ala Leu Ala Gly Pro Ile Ile Val Glu Pro His Val
1               5                   10                  15

Thr Ala Val Trp Gly Lys Asn Val Ser Leu Lys Cys Leu Ile Glu Val
            20                  25                  30

Asn Glu Thr Ile Thr Gln Ile Ser Trp Glu Lys Ile His Gly Lys Ser
        35                  40                  45

Ser Gln Thr Val Ala Val His His Pro Gln Tyr Gly Phe Ser Val Gln
    50                  55                  60

Gly Glu Tyr Gln Gly Arg Val Leu Phe Lys Asn Tyr Ser Leu Asn Asp
65                  70                  75                  80

Ala Thr Ile Thr Leu His Asn Ile Gly Phe Ser Asp Ser Gly Lys Tyr
                85                  90                  95

Ile Cys Lys Ala Val Thr Phe Pro Leu Gly Asn Ala Gln Ser Ser Thr
            100                 105                 110

Thr Val Thr Val Leu Val Glu Pro Thr Val Ser Leu Ile Lys Gly Pro
        115                 120                 125

<210> SEQ ID NO 11
<211> LENGTH: 133
<212> TYPE: PRT
<213> ORGANISM: Homo sapiens

<400> SEQUENCE: 11

Phe Thr Gly Arg Cys Pro Ala Gly Glu Leu Gly Thr Ser Asp Val Val
1               5                   10                  15

Thr Val Val Leu Gly Gln Asp Ala Lys Leu Pro Cys Phe Tyr Arg Gly

```
                 20                  25                  30

Asp Ser Gly Glu Gln Val Gly Gln Val Ala Trp Ala Arg Val Asp Ala
            35                  40                  45

Gly Glu Gly Ala Gln Glu Leu Ala Leu Leu His Ser Lys Tyr Gly Leu
        50                  55                  60

His Val Ser Pro Ala Tyr Glu Gly Arg Val Glu Gln Pro Pro Pro Pro
65                  70                  75                  80

Arg Asn Pro Leu Asp Gly Ser Val Leu Arg Asn Ala Val Gln Ala
                85                  90                  95

Asp Glu Gly Glu Tyr Glu Cys Arg Val Ser Thr Phe Pro Ala Gly Ser
            100                 105                 110

Phe Gln Ala Arg Leu Arg Leu Arg Val Leu Val Pro Pro Leu Pro Ser
        115                 120                 125

Leu Asn Pro Gly Pro
        130

<210> SEQ ID NO 12
<211> LENGTH: 128
<212> TYPE: PRT
<213> ORGANISM: Homo sapiens

<400> SEQUENCE: 12

Leu Leu His Val Tyr Arg Ala Leu Cys Glu Glu Val Leu Trp His Thr
1               5                   10                  15

Ser Val Pro Phe Ala Glu Asn Met Ser Leu Glu Cys Val Tyr Pro Ser
            20                  25                  30

Met Gly Ile Leu Thr Gln Val Glu Trp Phe Lys Ile Gly Thr Gln Gln
        35                  40                  45

Asp Ser Ile Ala Ile Phe Ser Pro Thr His Gly Met Val Ile Arg Lys
    50                  55                  60

Pro Tyr Ala Glu Arg Val Tyr Phe Leu Asn Ser Thr Met Ala Ser Asn
65                  70                  75                  80

Asn Met Thr Leu Phe Phe Arg Asn Ala Ser Glu Asp Asp Val Gly Tyr
                85                  90                  95

Tyr Ser Cys Ser Leu Tyr Thr Tyr Pro Gln Gly Thr Trp Gln Lys Val
            100                 105                 110

Ile Gln Val Val Gln Ser Asp Ser Phe Glu Ala Ala Val Pro Ser Asn
        115                 120                 125

<210> SEQ ID NO 13
<211> LENGTH: 131
<212> TYPE: PRT
<213> ORGANISM: Homo sapiens

<400> SEQUENCE: 13

Cys Leu Ser Gly Leu Ala Val Glu Val Lys Val Pro Thr Glu Pro Leu
1               5                   10                  15

Ser Thr Pro Leu Gly Lys Thr Ala Glu Leu Thr Cys Thr Tyr Ser Thr
            20                  25                  30

Ser Val Gly Asp Ser Phe Ala Leu Glu Trp Ser Phe Val Gln Pro Gly
        35                  40                  45

Lys Pro Ile Ser Glu Ser His Pro Ile Leu Tyr Phe Thr Asn Gly His
    50                  55                  60

Leu Tyr Pro Thr Gly Ser Lys Ser Lys Arg Val Ser Leu Leu Gln Asn
65                  70                  75                  80

Pro Pro Thr Val Gly Val Ala Thr Leu Lys Leu Thr Asp Val His Pro
```

```
                    85                  90                  95
Ser Asp Thr Gly Thr Tyr Leu Cys Gln Val Asn Asn Pro Pro Asp Phe
                100                 105                 110
Tyr Thr Asn Gly Leu Gly Leu Ile Asn Leu Thr Val Leu Val Pro Pro
                115                 120                 125
Ser Asn Pro
        130

<210> SEQ ID NO 14
<211> LENGTH: 136
<212> TYPE: PRT
<213> ORGANISM: Homo sapiens

<400> SEQUENCE: 14

Thr Gly Val Ala Ala Ser Leu Glu Val Ser Glu Ser Pro Gly Ser Ile
1               5                   10                  15
Gln Val Ala Arg Gly Gln Thr Ala Val Leu Pro Cys Thr Phe Thr Thr
                20                  25                  30
Ser Ala Ala Leu Ile Asn Leu Asn Val Ile Trp Met Val Thr Pro Leu
            35                  40                  45
Ser Asn Ala Asn Gln Pro Glu Gln Val Ile Leu Tyr Gln Gly Gly Gln
        50                  55                  60
Met Phe Asp Gly Ala Pro Arg Phe His Gly Arg Val Gly Phe Thr Gly
65                  70                  75                  80
Thr Met Pro Ala Thr Asn Val Ser Ile Phe Ile Asn Asn Thr Gln Leu
                85                  90                  95
Ser Asp Thr Gly Thr Tyr Gln Cys Leu Val Asn Asn Leu Pro Asp Ile
                100                 105                 110
Gly Gly Arg Asn Ile Gly Val Thr Gly Leu Thr Val Leu Val Pro Pro
                115                 120                 125
Ser Ala Pro His Cys Gln Ile Gln
        130                 135

<210> SEQ ID NO 15
<211> LENGTH: 119
<212> TYPE: PRT
<213> ORGANISM: Homo sapiens

<400> SEQUENCE: 15

Leu Gly Leu Glu Gly Gln Gly Ile Val Gly Ser Leu Pro Glu Val Leu
1               5                   10                  15
Gln Ala Pro Val Gly Ser Ser Ile Leu Val Gln Cys His Tyr Arg Leu
                20                  25                  30
Gln Asp Val Lys Ala Gln Lys Val Trp Cys Arg Phe Leu Pro Glu Gly
            35                  40                  45
Cys Gln Pro Leu Val Ser Ser Ala Val Asp Arg Arg Ala Pro Ala Gly
        50                  55                  60
Arg Arg Thr Phe Leu Thr Asp Leu Gly Gly Gly Leu Leu Gln Val Glu
65                  70                  75                  80
Met Val Thr Leu Gln Glu Glu Asp Ala Gly Glu Tyr Gly Cys Met Val
                85                  90                  95
Asp Gly Ala Arg Gly Pro Gln Ile Leu His Arg Val Ser Leu Asn Ile
                100                 105                 110
Leu Pro Pro Glu Glu Glu Glu
        115
```

```
<210> SEQ ID NO 16
<211> LENGTH: 124
<212> TYPE: PRT
<213> ORGANISM: Homo sapiens

<400> SEQUENCE: 16

Asn Phe Trp Asn Leu Pro Ile Thr Ala Gln Val Thr Ile Glu Ala Leu
1               5                   10                  15

Pro Pro Lys Val Ser Glu Gly Lys Asp Val Leu Leu Leu Val His Asn
            20                  25                  30

Leu Pro Gln Asn Leu Ala Gly Tyr Ile Trp Tyr Lys Gly Gln Leu Met
        35                  40                  45

Asp Leu Tyr His Tyr Ile Thr Ser Tyr Val Val Asp Gly Gln Ile Asn
    50                  55                  60

Ile Tyr Gly Pro Ala Tyr Thr Gly Arg Glu Thr Val Tyr Ser Asn Ala
65                  70                  75                  80

Ser Leu Leu Ile Gln Asn Val Thr Arg Glu Asp Ala Gly Ser Tyr Thr
                85                  90                  95

Leu His Ile Ile Lys Arg Gly Asp Arg Thr Arg Gly Val Thr Gly Tyr
            100                 105                 110

Phe Thr Phe Asn Leu Tyr Leu Lys Leu Pro Lys Pro
        115                 120

<210> SEQ ID NO 17
<211> LENGTH: 136
<212> TYPE: PRT
<213> ORGANISM: Homo sapiens

<400> SEQUENCE: 17

Ser Ala Cys Gly Gly Cys Val Glu Val Asp Ser Glu Thr Glu Ala Val
1               5                   10                  15

Tyr Gly Met Thr Phe Lys Ile Leu Cys Ile Ser Cys Lys Arg Arg Ser
            20                  25                  30

Glu Thr Asn Ala Glu Thr Phe Thr Glu Trp Thr Phe Arg Gln Lys Gly
        35                  40                  45

Thr Glu Glu Phe Val Lys Ile Leu Arg Tyr Glu Asn Glu Val Leu Gln
    50                  55                  60

Leu Glu Glu Asp Glu Arg Phe Glu Gly Arg Val Val Trp Asn Gly Ser
65                  70                  75                  80

Arg Gly Thr Lys Asp Leu Gln Asp Leu Ser Ile Phe Ile Thr Asn Val
                85                  90                  95

Thr Tyr Asn His Ser Gly Asp Tyr Glu Cys His Val Tyr Arg Leu Leu
            100                 105                 110

Phe Phe Glu Asn Tyr Glu His Asn Thr Ser Val Val Lys Lys Ile His
        115                 120                 125

Ile Glu Val Val Asp Lys Gly Glu
    130                 135

<210> SEQ ID NO 18
<211> LENGTH: 134
<212> TYPE: PRT
<213> ORGANISM: Homo sapiens

<400> SEQUENCE: 18

Ile Gly Phe Gly Ile Ser Gly Arg His Ser Ile Thr Val Thr Thr Val
1               5                   10                  15

Ala Ser Ala Gly Asn Ile Gly Glu Asp Gly Ile Gln Ser Cys Thr Phe
            20                  25                  30
```

Glu Pro Asp Ile Lys Leu Ser Asp Ile Val Ile Gln Trp Leu Lys Glu
                35                  40                  45

Gly Val Leu Gly Leu Val His Glu Phe Lys Glu Gly Lys Asp Glu Leu
 50                  55                  60

Ser Glu Gln Asp Glu Met Phe Arg Gly Arg Thr Ala Val Phe Ala Asp
 65                  70                  75                  80

Gln Val Ile Val Gly Asn Ala Ser Leu Arg Leu Lys Asn Val Gln Leu
                    85                  90                  95

Thr Asp Ala Gly Thr Tyr Lys Cys Tyr Ile Ile Thr Ser Lys Gly Lys
                100                 105                 110

Gly Asn Ala Asn Leu Glu Tyr Lys Thr Gly Ala Phe Ser Met Pro Glu
                115                 120                 125

Val Asn Val Asp Tyr Asn
                130

<210> SEQ ID NO 19
<211> LENGTH: 25
<212> TYPE: PRT
<213> ORGANISM: Artificial sequence
<220> FEATURE:
<223> OTHER INFORMATION: sequence is synthesized

<400> SEQUENCE: 19

Met Gly Gly Thr Ala Ala Arg Leu Gly Ala Val Ile Leu Phe Val Val
 1               5                  10                  15

Ile Val Gly Leu His Gly Val Arg Gly
            20                  25

<210> SEQ ID NO 20
<211> LENGTH: 25
<212> TYPE: PRT
<213> ORGANISM: Artificial sequence
<220> FEATURE:
<223> OTHER INFORMATION: sequence is synthesized

<400> SEQUENCE: 20

Lys Tyr Ala Leu Ala Asp Ala Ser Leu Lys Met Ala Asp Pro Asn Arg
 1               5                  10                  15

Phe Arg Gly Lys Asp Leu Pro Val Leu
            20                  25

<210> SEQ ID NO 21
<211> LENGTH: 114
<212> TYPE: PRT
<213> ORGANISM: Artificial sequence
<220> FEATURE:
<223> OTHER INFORMATION: sequence is synthesized

<400> SEQUENCE: 21

Asp Ile Val Met Thr Gln Ser Pro Ser Ser Leu Ala Val Ser Pro Gly
 1               5                  10                  15

Glu Lys Val Thr Met Thr Cys Lys Ser Ser Gln Ser Leu Tyr Tyr Ser
                20                  25                  30

Gly Val Lys Glu Asn Leu Leu Ala Trp Tyr Gln Gln Lys Pro Gly Gln
                35                  40                  45

Ser Pro Lys Leu Leu Ile Tyr Tyr Ala Ser Ile Arg Phe Thr Gly Val
             50                  55                  60

Pro Asp Arg Phe Thr Gly Ser Gly Ser Gly Thr Asp Tyr Thr Leu Thr
 65                  70                  75                  80

```
Ile Thr Ser Val Gln Ala Glu Asp Met Gly Gln Tyr Phe Cys Gln Gln
                    85                  90                  95

Gly Ile Asn Asn Pro Leu Thr Phe Gly Asp Gly Thr Lys Leu Glu Ile
                100                 105                 110

Lys Arg

<210> SEQ ID NO 22
<211> LENGTH: 119
<212> TYPE: PRT
<213> ORGANISM: Artificial sequence
<220> FEATURE:
<223> OTHER INFORMATION: sequence is synthesized

<400> SEQUENCE: 22

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
                20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
                100                 105                 110

Thr Leu Val Thr Val Ser Ser
        115

<210> SEQ ID NO 23
<211> LENGTH: 17
<212> TYPE: PRT
<213> ORGANISM: Artificial sequence
<220> FEATURE:
<223> OTHER INFORMATION: sequence is synthesized

<400> SEQUENCE: 23

Lys Ser Ser Gln Ser Leu Tyr Tyr Ser Gly Val Lys Glu Asn Leu Leu
1               5                   10                  15

Ala

<210> SEQ ID NO 24
<211> LENGTH: 6
<212> TYPE: PRT
<213> ORGANISM: Artificial sequence
<220> FEATURE:
<223> OTHER INFORMATION: sequence is synthesized

<400> SEQUENCE: 24

Ala Ser Ile Arg Phe Thr
1               5

<210> SEQ ID NO 25
<211> LENGTH: 9
<212> TYPE: PRT
<213> ORGANISM: Artificial sequence
<220> FEATURE:
<223> OTHER INFORMATION: sequence is synthesized

<400> SEQUENCE: 25
```

```
Gln Gln Gly Ile Asn Asn Pro Leu Thr
1               5

<210> SEQ ID NO 26
<211> LENGTH: 10
<212> TYPE: PRT
<213> ORGANISM: Artificial sequence
<220> FEATURE:
<223> OTHER INFORMATION: sequence is synthesized

<400> SEQUENCE: 26

Gly Phe Thr Phe Ser Ser Phe Thr Met His
1               5                   10

<210> SEQ ID NO 27
<211> LENGTH: 17
<212> TYPE: PRT
<213> ORGANISM: Artificial sequence
<220> FEATURE:
<223> OTHER INFORMATION: sequence is synthesized

<400> SEQUENCE: 27

Phe Ile Arg Ser Gly Ser Gly Ile Val Phe Tyr Ala Asp Ala Val Arg
1               5                   10                  15

Gly

<210> SEQ ID NO 28
<211> LENGTH: 10
<212> TYPE: PRT
<213> ORGANISM: Artificial sequence
<220> FEATURE:
<223> OTHER INFORMATION: sequence is synthesized

<400> SEQUENCE: 28

Arg Pro Leu Gly His Asn Thr Phe Asp Ser
1               5                   10

<210> SEQ ID NO 29
<211> LENGTH: 112
<212> TYPE: PRT
<213> ORGANISM: Artificial sequence
<220> FEATURE:
<223> OTHER INFORMATION: sequence is synthesized

<400> SEQUENCE: 29

Asp Val Val Leu Thr Gln Thr Pro Leu Ser Leu Ser Val Ser Phe Gly
1               5                   10                  15

Asp Gln Val Ser Ile Ser Cys Arg Ser Ser Gln Ser Leu Val Asn Ser
            20                  25                  30

Tyr Gly Asn Thr Phe Leu Ser Trp Tyr Leu His Lys Pro Gly Gln Ser
        35                  40                  45

Pro Gln Leu Leu Ile Phe Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Pro Thr Phe Gly Pro Gly Thr Lys Leu Glu Val Lys
            100                 105                 110

<210> SEQ ID NO 30
<211> LENGTH: 119
```

```
<212> TYPE: PRT
<213> ORGANISM: Artificial sequence
<220> FEATURE:
<223> OTHER INFORMATION: sequence is synthesized

<400> SEQUENCE: 30

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly His
            20                  25                  30

Leu Met Asn Trp Val Lys Gln Ser His Gly Lys Asn Leu Glu Trp Ile
        35                  40                  45

Gly Leu Ile Ile Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Asp Asp Ser Ala Val Tyr Phe Cys
                85                  90                  95

Ser Arg Gly Leu Arg Gly Phe Tyr Ala Met Asp Tyr Trp Gly Gln Gly
            100                 105                 110

Thr Ser Val Thr Val Ser Ser
        115

<210> SEQ ID NO 31
<211> LENGTH: 16
<212> TYPE: PRT
<213> ORGANISM: Artificial sequence
<220> FEATURE:
<223> OTHER INFORMATION: sequence is synthesized

<400> SEQUENCE: 31

Arg Ser Ser Gln Ser Leu Val Asn Ser Tyr Gly Asn Thr Phe Leu Ser
1               5                   10                  15

<210> SEQ ID NO 32
<211> LENGTH: 7
<212> TYPE: PRT
<213> ORGANISM: Artificial sequence
<220> FEATURE:
<223> OTHER INFORMATION: sequence is synthesized

<400> SEQUENCE: 32

Gly Ile Ser Asn Arg Phe Ser
1               5

<210> SEQ ID NO 33
<211> LENGTH: 9
<212> TYPE: PRT
<213> ORGANISM: Artificial sequence
<220> FEATURE:
<223> OTHER INFORMATION: sequence is synthesized

<400> SEQUENCE: 33

Leu Gln Gly Thr His Gln Pro Pro Thr
1               5

<210> SEQ ID NO 34
<211> LENGTH: 10
<212> TYPE: PRT
<213> ORGANISM: Artificial sequence
<220> FEATURE:
<223> OTHER INFORMATION: sequence is synthesized

<400> SEQUENCE: 34
```

```
Gly Tyr Ser Phe Thr Gly His Leu Met Asn
1               5                   10
```

<210> SEQ ID NO 35
<211> LENGTH: 17
<212> TYPE: PRT
<213> ORGANISM: Artificial sequence
<220> FEATURE:
<223> OTHER INFORMATION: sequence is synthesized

<400> SEQUENCE: 35

```
Leu Ile Ile Pro Tyr Asn Gly Gly Thr Ser Tyr Asn Gln Lys Phe Lys
1               5                   10                  15

Gly
```

<210> SEQ ID NO 36
<211> LENGTH: 10
<212> TYPE: PRT
<213> ORGANISM: Artificial sequence
<220> FEATURE:
<223> OTHER INFORMATION: sequence is synthesized

<400> SEQUENCE: 36

```
Gly Leu Arg Gly Phe Tyr Ala Met Asp Tyr
1               5                   10
```

<210> SEQ ID NO 37
<211> LENGTH: 23
<212> TYPE: DNA
<213> ORGANISM: Artificial sequence
<220> FEATURE:
<223> OTHER INFORMATION: sequence is synthesized

<400> SEQUENCE: 37
tttyttgtcc accktggtgc tgc                                          23

<210> SEQ ID NO 38
<211> LENGTH: 22
<212> TYPE: DNA
<213> ORGANISM: Artificial sequence
<220> FEATURE:
<223> OTHER INFORMATION: sequence is synthesized

<400> SEQUENCE: 38
ctggacaggg atccagagtt cc                                           22

<210> SEQ ID NO 39
<211> LENGTH: 22
<212> TYPE: DNA
<213> ORGANISM: Artificial sequence
<220> FEATURE:
<223> OTHER INFORMATION: sequence is synthesized

<400> SEQUENCE: 39
cargtcamdg tcactgrctc ag                                           22

<210> SEQ ID NO 40
<211> LENGTH: 19
<212> TYPE: DNA
<213> ORGANISM: Artificial sequence
<220> FEATURE:
<223> OTHER INFORMATION: sequence is synthesized

<400> SEQUENCE: 40
gtagaagttg ttcaagaag                                               19

<210> SEQ ID NO 41
<211> LENGTH: 21
<212> TYPE: DNA
<213> ORGANISM: Artificial sequence
<220> FEATURE:
<223> OTHER INFORMATION: sequence is synthesized

<400> SEQUENCE: 41
gaggcacctc cagatgttaa c                                              21

<210> SEQ ID NO 42
<211> LENGTH: 22
<212> TYPE: DNA
<213> ORGANISM: Artificial sequence
<220> FEATURE:
<223> OTHER INFORMATION: sequence is synthesized

<400> SEQUENCE: 42
ctgctcactg gatggtggga ag                                             22

<210> SEQ ID NO 43
<211> LENGTH: 21
<212> TYPE: DNA
<213> ORGANISM: Artificial sequence
<220> FEATURE:
<223> OTHER INFORMATION: sequence is synthesized

<400> SEQUENCE: 43
gaagatggat acagttggtg c                                              21

<210> SEQ ID NO 44
<211> LENGTH: 66
<212> TYPE: DNA
<213> ORGANISM: Artificial sequence
<220> FEATURE:
<223> OTHER INFORMATION: sequence is synthesized
<220> FEATURE:
<221> NAME/KEY: d
<222> LOCATION: (66)..(66)
<223> OTHER INFORMATION: d = A, G or T
<220> FEATURE:
<221> NAME/KEY: n
<222> LOCATION: (66)..(66)
<223> OTHER INFORMATION: n = A, G, C or T
<220> FEATURE:
<221> NAME/KEY: misc_feature
<222> LOCATION: (66)..(66)
<223> OTHER INFORMATION: n is a, c, g, or t

<400> SEQUENCE: 44
gattcaaatc tcaattatat aatccgaata tgtttaccgg ctcgctcatg gaccccccccc    60 ccccdn                                                               66

<210> SEQ ID NO 45
<211> LENGTH: 19
<212> TYPE: DNA
<213> ORGANISM: Artificial sequence
<220> FEATURE:
<223> OTHER INFORMATION: sequence is synthesized

<400> SEQUENCE: 45
gaattccccc cccccccccc                                                19

<210> SEQ ID NO 46
<211> LENGTH: 20
<212> TYPE: DNA

<213> ORGANISM: Artificial sequence
<220> FEATURE:
<223> OTHER INFORMATION: sequence is synthesized

<400> SEQUENCE: 46
ctcatggacc cccccccccc                                              20

<210> SEQ ID NO 47
<211> LENGTH: 24
<212> TYPE: DNA
<213> ORGANISM: Artificial sequence
<220> FEATURE:
<223> OTHER INFORMATION: sequence is synthesized

<400> SEQUENCE: 47
aaatataata cccccccccc cccc                                         24

<210> SEQ ID NO 48
<211> LENGTH: 17
<212> TYPE: DNA
<213> ORGANISM: Artificial sequence
<220> FEATURE:
<223> OTHER INFORMATION: sequence is synthesized

<400> SEQUENCE: 48
aaatataata ccccccc                                                 17

<210> SEQ ID NO 49
<211> LENGTH: 15
<212> TYPE: DNA
<213> ORGANISM: Artificial sequence
<220> FEATURE:
<223> OTHER INFORMATION: sequence is synthesized

<400> SEQUENCE: 49
ctcatggacc ccccc                                                   15

<210> SEQ ID NO 50
<211> LENGTH: 336
<212> TYPE: DNA
<213> ORGANISM: Artificial sequence
<220> FEATURE:
<223> OTHER INFORMATION: sequence is synthesized

<400> SEQUENCE: 50
gatgttgtgt tgactcaaac tccactctcc ctgtctgtca gctttggaga tcaagtttct    60
atctcttgca ggtctagtca gagtcttgta aacagttatg gaacaccctt tttgtcttgg   120
tacctgcaca agcctggcca gtctccacag ctcctcatct ttgggatttc caacagattt   180
tctggggtgc cagacaggtt cagtggcagt ggttcaggga cagatttcac actcaagatc   240
agcacaataa agcctgagga cttgggaatg tattactgct tacaaggtac gcatcagcct   300
cccacgttcg gtcctgggac caagctggag gtgaaa                             336

<210> SEQ ID NO 51
<211> LENGTH: 357
<212> TYPE: DNA
<213> ORGANISM: Artificial sequence
<220> FEATURE:
<223> OTHER INFORMATION: sequence is synthesized

<400> SEQUENCE: 51
gaggtccagc tgcaacagtc tggacctgag ctggtgaagc ctggaacttc aatgaagata    60
tcctgcaagg cttctggtta ctcattcact ggccatctta tgaactgggt gaagcagagc   120

```
catggaaaga accttgagtg gattggactt attattcctt acaatggtgg tacaagctat    180
aaccagaagt tcaagggcaa ggccacattg actgtagaca agtcatccag cacagcctac    240
atggagctcc tcagtctgac ttctgatgac tctgcagtct atttctgttc aagaggcctt    300 agggcttct atgctatgga ctactgggt caaggaacct cagtcaccgt ctcctca        357
```

<210> SEQ ID NO 52
<211> LENGTH: 19
<212> TYPE: DNA
<213> ORGANISM: Artificial sequence
<220> FEATURE:
<223> OTHER INFORMATION: sequence is synthesized

<400> SEQUENCE: 52

```
tgccaggttc cagattcca                                                  19
```

<210> SEQ ID NO 53
<211> LENGTH: 21
<212> TYPE: DNA
<213> ORGANISM: Artificial sequence
<220> FEATURE:
<223> OTHER INFORMATION: sequence is synthesized

<400> SEQUENCE: 53

```
acgatgactg ctgtgcagat g                                               21
```

<210> SEQ ID NO 54
<211> LENGTH: 18
<212> TYPE: DNA
<213> ORGANISM: Artificial sequence
<220> FEATURE:
<223> OTHER INFORMATION: sequence is synthesized

<400> SEQUENCE: 54

```
agccatggcc gcgacgct                                                   18
```

<210> SEQ ID NO 55
<211> LENGTH: 22
<212> TYPE: DNA
<213> ORGANISM: Artificial sequence
<220> FEATURE:
<223> OTHER INFORMATION: sequence is synthesized

<400> SEQUENCE: 55

```
acatctaccg aagtccaatg ca                                              22
```

<210> SEQ ID NO 56
<211> LENGTH: 24
<212> TYPE: DNA
<213> ORGANISM: Artificial sequence
<220> FEATURE:
<223> OTHER INFORMATION: sequence is synthesized

<400> SEQUENCE: 56

```
ggaattgtaa tagcgatcct gagc                                            24
```

<210> SEQ ID NO 57
<211> LENGTH: 21
<212> TYPE: DNA
<213> ORGANISM: Artificial sequence
<220> FEATURE:
<223> OTHER INFORMATION: sequence is synthesized

<400> SEQUENCE: 57
tgcacgcaga cattcccgcc t                                        21

<210> SEQ ID NO 58
<211> LENGTH: 22
<212> TYPE: DNA
<213> ORGANISM: Artificial sequence
<220> FEATURE:
<223> OTHER INFORMATION: sequence is synthesized

<400> SEQUENCE: 58
tctgaatcat aatggcgaga ct                                       22

<210> SEQ ID NO 59
<211> LENGTH: 23
<212> TYPE: DNA
<213> ORGANISM: Artificial sequence
<220> FEATURE:
<223> OTHER INFORMATION: sequence is synthesized

<400> SEQUENCE: 59
tcactctgta agggtctgct tct                                      23

<210> SEQ ID NO 60
<211> LENGTH: 21
<212> TYPE: DNA
<213> ORGANISM: Artificial sequence
<220> FEATURE:
<223> OTHER INFORMATION: sequence is synthesized

<400> SEQUENCE: 60
tgcgccagaa acctcctgtg g                                        21

<210> SEQ ID NO 61
<211> LENGTH: 24
<212> TYPE: DNA
<213> ORGANISM: Artificial sequence
<220> FEATURE:
<223> OTHER INFORMATION: sequence is synthesized

<400> SEQUENCE: 61
tgagttcaga gctcctaaga gagt                                     24

<210> SEQ ID NO 62
<211> LENGTH: 21
<212> TYPE: DNA
<213> ORGANISM: Artificial sequence
<220> FEATURE:
<223> OTHER INFORMATION: sequence is synthesized

<400> SEQUENCE: 62
aaaggatctc cctggtttct c                                        21

<210> SEQ ID NO 63
<211> LENGTH: 26
<212> TYPE: DNA
<213> ORGANISM: Artificial sequence
<220> FEATURE:
<223> OTHER INFORMATION: sequence is synthesized

<400> SEQUENCE: 63
tcccaagacc catgagtttc ttcaca                                   26

<210> SEQ ID NO 64
<211> LENGTH: 20
<212> TYPE: DNA
<213> ORGANISM: Artificial sequence

```
<220> FEATURE:
<223> OTHER INFORMATION: sequence is synthesized

<400> SEQUENCE: 64
gaartarccc ttgaccaggc                                              20
```

UNITED STATES PATENT AND TRADEMARK OFFICE
CERTIFICATE OF CORRECTION

| | |
|---|---|
| PATENT NO. | : 11,390,678 B2 |
| APPLICATION NO. | : 16/537280 |
| DATED | : July 19, 2022 |
| INVENTOR(S) | : Clark et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 193 days.

Signed and Sealed this
Fourteenth Day of January, 2025

Derrick Brent
*Acting Director of the United States Patent and Trademark Office*